United States Patent
Christians et al.

(10) Patent No.: US 9,976,181 B2
(45) Date of Patent: May 22, 2018

(54) SYNTHETIC NUCLEIC ACID SPIKE-INS

(71) Applicant: Karius, Inc., Menlo Park, CA (US)

(72) Inventors: Fred C. Christians, Los Altos Hills, CA (US); Igor D. Vilfan, East Palo Alto, CA (US); Michael Kertesz, Menlo Park, CA (US); Timothy A. Blauwkamp, Palo Alto, CA (US); Shivkumar Venkatasubrahmanyam, San Jose, CA (US); Michael Rosen, Palo Alto, CA (US); Rene Sit, Sunnyvale, CA (US)

(73) Assignee: KARIUS, INC., Redwood City, CA (US)

( * ) Notice: Subject to any disclaimer, the term of this patent is extended or adjusted under 35 U.S.C. 154(b) by 0 days. days.

(21) Appl. No.: 15/469,474

(22) Filed: Mar. 24, 2017

(65) Prior Publication Data

US 2017/0275691 A1 Sep. 28, 2017

Related U.S. Application Data

(60) Provisional application No. 62/313,668, filed on Mar. 25, 2016, provisional application No. 62/397,873, filed on Sep. 21, 2016, provisional application No. 62/451,363, filed on Jan. 27, 2017.

(51) Int. Cl.
*C12Q 1/68* (2018.01)
*C12N 15/10* (2006.01)
*G06F 19/22* (2011.01)

(52) U.S. Cl.
CPC ....... *C12Q 1/6874* (2013.01); *C12N 15/1065* (2013.01); *C12Q 1/689* (2013.01); *G06F 19/22* (2013.01); *C12Q 2600/166* (2013.01)

(58) Field of Classification Search
None
See application file for complete search history.

(56) References Cited

U.S. PATENT DOCUMENTS

| | | |
|---|---|---|
| 6,753,137 B2 | 6/2004 | Lo et al. |
| RE39,920 E | 11/2007 | Umansky et al. |
| 7,803,929 B2 | 9/2010 | Melkonyan et al. |
| 7,914,982 B2 | 3/2011 | Melkonyan et al. |
| 7,973,154 B2 | 7/2011 | Melkonyan et al. |
| 8,682,592 B2 | 3/2014 | Rabinowitz et al. |
| 8,703,652 B2 | 4/2014 | Quake et al. |
| 8,715,967 B2 * | 5/2014 | Casbon ................ C12Q 1/6855 435/6.1 |
| 2004/0209299 A1 | 10/2004 | Pinter et al. |
| 2005/0202414 A1 | 9/2005 | Jia et al. |
| 2006/0073506 A1 | 4/2006 | Christians et al. |
| 2007/0111233 A1 | 5/2007 | Bianchi et al. |
| 2010/0068711 A1 | 3/2010 | Umansky et al. |
| 2011/0160290 A1 * | 6/2011 | Tewari ................ C12Q 1/6809 514/44 R |
| 2012/0021412 A1 | 1/2012 | Melkonyan et al. |
| 2012/0021919 A1 | 1/2012 | Scholl et al. |
| 2012/0077185 A1 | 3/2012 | Oliphant et al. |
| 2012/0190663 A1 | 7/2012 | Gornik et al. |
| 2012/0295810 A1 | 11/2012 | Quake et al. |
| 2013/0024127 A1 | 1/2013 | Stuelpnagel et al. |
| 2013/0178544 A1 | 7/2013 | Melkonyan et al. |
| 2013/0237431 A1 | 9/2013 | Lo et al. |
| 2013/0245961 A1 | 9/2013 | Lo et al. |
| 2013/0252835 A1 | 9/2013 | Koh et al. |
| 2014/0066317 A1 | 3/2014 | Talasaz |
| 2014/0147851 A1 | 5/2014 | Qian |
| 2014/0155274 A1 * | 6/2014 | Xie ................ C12Q 1/6853 506/2 |
| 2014/0242582 A1 | 8/2014 | Oliphant et al. |
| 2014/0274740 A1 | 9/2014 | Srinivasan et al. |
| 2016/0017420 A1 | 1/2016 | Koh et al. |
| 2016/0251704 A1 | 9/2016 | Talasaz et al. |
| 2016/0304953 A1 | 10/2016 | Chen et al. |
| 2016/0326572 A1 * | 11/2016 | Schupp ................ C12Q 1/686 |
| 2017/0145507 A1 | 5/2017 | Koh et al. |
| 2017/0145508 A1 | 5/2017 | Koh et al. |
| 2017/0145509 A1 | 5/2017 | Koh et al. |

FOREIGN PATENT DOCUMENTS

| | | |
|---|---|---|
| EP | 1856295 A2 | 11/2007 |
| EP | 1885877 A2 | 2/2008 |
| EP | 2351857 A1 | 8/2011 |

(Continued)

OTHER PUBLICATIONS

Fu et al. (Molecular indexing enables quantitative targeted RNA sequencing and reveals poor efficiencies in standard library preparations, Proc Natl Acad Sci U S A. Feb. 4, 2014;111(5):1891-6. Epub Jan. 21, 2014) (Year: 2014).*
Quail et al., SASI-Seq: sample assurance Spike-Ins, and highly differentiating 384 barcoding for Illumina sequencing, BMC Genomics. Feb. 7, 2014;15:110. doi: 10.1186/1471-2164-15-110.*
Kim et al., Characterizing noise structure in single-cell RNA-seq distinguishes genuine from technical stochastic allelic expression, Nat Commun. Oct. 22, 2015;6:8687.*
International Search Report and Written Opinion dated Jul. 26, 2017 for International PCT Patent Application No. PCT/US2017/024176.
Islam, et al. Quantitative single-cell RNA-seq with unique molecular identifiers. Nat Methods. Feb. 2014;11(2):163-6.
Matranga, et al. Enhanced methods for unbiased deep sequencing of Lassa and Ebola RNA viruses from clinical and biological samples. Genome Biol. 2014;15(11):519.
Zook, et al. Synthetic spike-in standards improve run-specific systematic error analysis for DNA and RNA sequencing. PLoS One. 2012;7(7):e41356.

(Continued)

*Primary Examiner* — Aaron A Priest
(74) *Attorney, Agent, or Firm* — Wilson Sonsini Goodrich & Rosati

(57) ABSTRACT

This disclosure provides methods for determining relative abundance of one or more non-host species in a sample from a host. Also provided are methods involving addition of known concentrations of synthetic nucleic acids to a sample and performing sequencing assays to identify non-host species such as pathogens. Also provided are methods of tracking samples, tracking reagents, and tracking diversity loss in sequencing assays.

30 Claims, 27 Drawing Sheets

(56) References Cited

FOREIGN PATENT DOCUMENTS

| | | | |
|---|---|---|---|
| WO | WO-2011156795 A2 | 12/2011 | |
| WO | WO-2012129363 A2 | 9/2012 | |
| WO | WO-2012159023 A2 | 11/2012 | |
| WO | WO-2012168815 A2 | 12/2012 | |
| WO | WO-2013052907 A2 | 4/2013 | |
| WO | WO-2013109981 A1 | 7/2013 | |
| WO | WO-2013132305 A1 | 9/2013 | |
| WO | WO-2013156627 A1 | 10/2013 | |
| WO | WO-2013159035 A2 | 10/2013 | |
| WO | WO-2013188846 A1 | 12/2013 | |
| WO | WO-2014039556 A1 | 3/2014 | |
| WO | WO-2014068075 A1 | 5/2014 | |
| WO | WO-2014082032 A1 * | 5/2014 | ............ C40B 20/04 |
| WO | WO-2014149134 A2 | 9/2014 | |
| WO | WO-2014165596 A1 | 10/2014 | |
| WO | WO-2015089333 A1 | 6/2015 | |
| WO | WO-2016094947 A1 * | 6/2016 | ........... C12Q 1/6869 |

OTHER PUBLICATIONS

Abril, et al. Diagnosis of Capnocytophaga canimorsus Sepsis by Whole-Genome Next-Generation Sequencing. Open Forum Infect Dis. Sep. 2016; 3(3): ofw144. Published online Jul. 12, 2016. DOI:10.1093/ofid/ofw144.

Chen, et al. The overlooked fact: fundamental need of spike-in controls for virtually all genome-wide analyses. Manuscript posted online Dec. 28, 2015. Mol. Cell. Biol. American Society for Microbiology, doi:10.1128/MCB.00970-14. 20 pages.

Deveson, et al. Representing genetic variation with synthetic DNA standards. Nature Methods. vol. 13, pp. 784-791. Accepted Jun. 28, 2016. Published online Aug. 8, 2016. DOI:doi:10.1038/nmeth.3957.

Heger, Monica. Garvan Team Uses Synthetic DNA to Create Spike-In Method for NGS Assay Validation. Genomeweb. Aug. 8, 2016. 4 pages.

Highlander, Sarah K., High throughput sequencing methods for microbiome profiling: application to food animal systems, Animal Health Research Reviews, Jun. 2012, vol. 13(1); pp. 40-53.

Jiang, et al. Synthetic spike-in standards for RNA-seq experiments. Genome Res. Sep. 2011;21(9):1543-51. doi: 10.1101/gr.121095. 111. Epub Aug. 4, 2011.

Locati, et al. Improving small RNA-seq by using a synthetic spike-in set for size-range quality control together with a set for data normalization. Nucleic Acids Res. Aug. 18, 2015;43(14):e89. doi: 10.1093/nar/gkv303. Epub Apr. 13, 2015.

Quail, et al. SASI-Seq: sample assurance Spike-Ins, and highly differentiating 384 barcoding for Illumina sequencing. BMC Genomics. Feb. 7, 2014;15:110. doi: 10.1186/1471-2164-15-110.

Saukkonen, et al. Cell-free plasma DNA as a predictor of outcome in severe sepsis and septic shock. Clin Chem. Jun. 2008;54(6):1000-7. doi: 10.1373/clinchem.2007.101030. Epub Apr. 17, 2008.

Xia, et al. Accurate genome relative abundance estimation based on shotgun metagenomic reads. PLoS One. 2011;6(12):e27992. doi: 10.1371/journal.pone.0027992. Epub Dec. 6, 2011.

Yu, et al. Normalization of human RNA-seq experiments using chimpanzee RNA as a spike-in standard. Sci Rep. Aug. 24, 2016;6:31923. doi: 10.1038/srep31923.

* cited by examiner

SYNTHETIC NUCLEIC ACID SPIKE-INS

CROSS-REFERENCE

The application claims the benefit of U.S. Provisional Patent Application 62/313,668, filed on Mar. 25, 2016, U.S. Provisional Patent Application 62/397,873, filed Sep. 21, 2016, and U.S. Provisional Patent Application 62/451,363, filed Jan. 27, 2017, which are herein incorporated by reference in their entireties.

SEQUENCE LISTING

The instant application contains a Sequence Listing which has been submitted electronically in ASCII format and is hereby incorporated by reference in its entirety. Said ASCII copy, created on Apr. 11, 2017, is named 47697-705_201_SL.txt and is 57,941 bytes in size.

BACKGROUND

Next generation sequencing can be used to gather massive amounts of data about the genetic content of a sample. It can be particularly useful for analyzing nucleic acids in complex samples, such as clinical samples and for the sequencing of whole genomes. However, there is a need in the art for more efficient and accurate methods for detecting and quantifying nucleic acids, particularly low abundance nucleic acids or nucleic acids in patient samples.

SUMMARY

Provided herein are methods and compositions for improved identification or quantification of nucleic acids in next generation sequencing assays and other assays, using spike-in synthetic nucleic acids. In some cases, the spike-in synthetic nucleic acids have special features such as specific sequences, lengths, GC content, degrees of degeneracy, degrees of diversity, and/or known starting concentrations. The methods provided herein are particularly useful for detection of pathogen nucleic acids in a clinical sample such as plasma, but can also be used to detect other types of targets.

In one aspect, provided herein is a method for determining abundance of nucleic acids in an initial sample comprising target nucleic acids, the method comprising: (a) adding a starting quantity of at least 1000 synthetic nucleic acids to the sample, wherein each of the at least 1000 synthetic nucleic acids comprises a unique variable region; (b) performing a sequencing assay on a portion of the target nucleic acids and on a portion of the at least 1000 synthetic nucleic acids in the sample, thereby obtaining target and synthetic nucleic acid sequence reads, wherein the synthetic nucleic acid sequence reads include unique variable region sequences; (c) detecting diversity loss of the at least 1000 synthetic nucleic acids by (i) quantifying a number of different variable region sequences within the synthetic nucleic acid sequence reads to obtain a unique sequenced value; and (ii) comparing the starting quantity of the at least 1,000 synthetic nucleic acids with the unique sequenced value in order to obtain the diversity loss of the at least 1,000 synthetic nucleic acids; and (d) using the diversity loss of the at least 1000 synthetic nucleic acids to calculate an abundance of the target nucleic acids in the initial sample. In some cases, the starting quantity that is compared is a starting concentration.

In some embodiments, the target nucleic acids comprise pathogen nucleic acids. In some cases, the target nucleic acids comprise pathogen nucleic acids from at least five different pathogens. In some cases, the target nucleic acids comprise pathogen nucleic acids from at least two different pathogens. In some cases, the target nucleic acids comprise pathogen nucleic acids from at least ten different pathogens.

In some cases, the at least 1,000 synthetic nucleic acids comprise DNA. In some cases, the at least 1,000 synthetic nucleic acids comprise RNA, ssRNA, dsDNA, ssDNA, or some combination thereof. In some cases, each of the at least 1,000 synthetic nucleic acids is less than 500 base pairs or nucleotides in length. In some cases, the each of the at least 1,000 synthetic nucleic acids is less than 200 base pairs or nucleotides in length. In some cases, the each of the at least 1,000 synthetic nucleic acids is less than 100 base pairs or nucleotides in length. In some cases, the sample is blood, plasma, serum, cerebrospinal fluid, synovial fluid, bronchial-alveolar lavage, urine, stool, saliva, or a nasal sample. In some cases, the sample is from a human subject. In some cases, the sample is a sample of isolated nucleic acids.

In some cases, the method further comprises generating a sequencing library from the sample, wherein the at least 1,000 synthetic nucleic acids are added to the sample before the generating the sequencing library. In some cases, the diversity loss of the at least 1,000 synthetic nucleic acids indicates a loss of one or more nucleic acids during sample processing of the sample.

In some cases, each of the at least 1,000 synthetic nucleic acids comprises an identifying tag sequence. In some cases, the quantifying the number of unique variable region sequences comprises detecting sequences containing the tag sequence. In some cases, the quantifying the at least 1,000 unique sequences within the first sequence reads comprises determining a reads count of the unique sequences within the first sequence reads. In some cases, the at least 1,000 unique synthetic nucleic acids comprise at least $10^4$ unique synthetic nucleic acids.

In some cases, the method further comprises adding additional synthetic nucleic acids with at least three different lengths. In some cases, the method further comprises adding a first group of additional synthetic nucleic acids with a first length, a second group of additional synthetic nucleic acids with a second length, and a third group of additional synthetic nucleic acids with a third length, wherein the first, second and third groups of additional synthetic nucleic acids each comprises synthetic nucleic acids with at least three different GC contents. In some cases, the method further comprises using the additional synthetic nucleic acids to calculate the absolute abundance value of the target nucleic acids in the sample. In some cases, the method further comprises using the additional synthetic nucleic acids to calculate the absolute or relative abundance of the target nucleic acids in the sample based on lengths, GC contents, or both lengths and GC contents of the additional synthetic nucleic acids.

In some cases, the at least 1,000 synthetic nucleic acids are added to the sample at a first sample processing step. In some cases, the method further comprises adding an additional pool of at least 1,000 unique synthetic nucleic acids to the sample at a second sample processing step, wherein the second sample processing step is different from the first sample processing step. In some cases, the method further comprises calculating diversity loss for the additional pool of at least 1,000 synthetic nucleic acids. In some cases, the method further comprises identifying a sample processing step with relatively high diversity loss by comparing the diversity loss for the at least 1,000 synthetic nucleic acids with the diversity loss for the additional pool of at least 1,000 synthetic nucleic acids.

In some cases, each of the unique synthetic nucleic acids in the additional pool of at least 1,000 unique synthetic nucleic acids comprises a domain identifying the synthetic nucleic acid as a member of the additional pool of at least 1,000 synthetic nucleic acids. In some cases, the method further comprises adding a sample identifier nucleic acid to the sample. In some cases, (a) above further comprises adding non-unique synthetic nucleic acids to the sample.

In some embodiments, the calculated abundance is a relative abundance. In some embodiments, calculated abundance is absolute abundance.

In another aspect, provided herein is a method of determining a relative abundance or an initial abundance of a pathogen nucleic acids in a sample, the method comprising: (a) obtaining the sample from a subject infected by, or suspected of being infected by, a pathogen, wherein the sample comprises a plurality of pathogen nucleic acids; (b) adding a plurality of synthetic nucleic acids to the sample such that the sample comprises a known initial abundance of the synthetic nucleic acids, wherein (i) the synthetic nucleic acids are less than 500 base pairs in length; (ii) the synthetic nucleic acids comprise synthetic nucleic acids with a first length, synthetic nucleic acids with a second length, and synthetic nucleic acids with a third length, wherein the first, second and third lengths are different; and (iii) the synthetic nucleic acids with the first lengths comprise synthetic nucleic acids with at least three different GC contents; (c) performing a sequencing assay on the sample comprising the plurality of synthetic nucleic acids, thereby determining a final abundance of the synthetic nucleic acids and a final abundance of the plurality of pathogen nucleic acids; (d) comparing the final abundance and the known initial abundance of synthetic nucleic acids in order to produce a recovery profile for the synthetic nucleic acids; and (e) using the recovery profile for the synthetic nucleic acids to normalize the final abundance of the plurality of pathogen nucleic acids by comparing the pathogen nucleic acids to the synthetic nucleic acids with the closest GC content and length, thereby determining the relative abundance or the initial abundance of the plurality of pathogen nucleic acids.

In some cases, the at least three different GC contents comprise a first GC content that is between 10% and 40%, a second GC content that is between 40% and 60%, and a third GC content that is between 60% and 90%. In some cases, the at least three different GC contents are each between 10% and 50%. In some cases, the at least three different GC contents are each between 5% and 40%. In some cases, the synthetic nucleic acids are less than 200 base pairs or nucleotides in length. In some cases, the synthetic nucleic acids are less than 100 base pairs or nucleotides in length. In some cases, the at least three different GC contents is at least 4 different, at least 5 different, at least 6 different, at least 7 different or at least 8 different GC contents. In some cases, the synthetic nucleic acids have at least a fourth length, at least a fifth length, at least a sixth length, at least a seventh length, at least a ninth length, at least a tenth length, at least a $12^{th}$ length or at least a $15^{th}$ length. In some embodiments, each length comprises synthetic nucleic acids with at least 3, 4, 5, 6, 7, 8, 9, 10 different GC contents, or no more than 50 different GC contents.

In some cases, the synthetic nucleic acids comprise double-stranded DNA. In some cases, the method further comprises monitoring denaturation of the pathogen nucleic acids using the synthetic nucleic acids. In some cases, the method further comprises normalizing the relative abundance or initial abundance of the pathogen nucleic acid by using a weighting factor. In some cases, the weighting factor is obtained by analyzing a raw measurement of a first synthetic nucleic acid of the plurality of synthetic nucleic acids and a raw measurement of a second synthetic nucleic acid of the plurality of synthetic nucleic acids in comparison with a known concentration of the first synthetic acid and a known concentration of the second synthetic acid.

In another aspect, provided herein is a method for detecting a nucleic acid from a pathogen, the method comprising: (a) obtaining a first sample comprising a first pathogen nucleic acid, wherein the first sample is obtained from a first subject infected by the first pathogen; (b) obtaining a second sample from a second subject; (c) obtaining a first and second sample identifier, each comprising a different synthetic nucleic acid that is not capable of hybridizing to the first pathogen nucleic acid and assigning the first sample identifier to the first sample and the second sample identifier to the second sample; (d) adding the first sample identifier to the first sample and the second sample identifier to the second sample; (e) performing a sequencing assay on the first sample comprising the first sample identifier and on the second sample comprising the second sample identifier, thereby obtaining sequence results for the first and second samples; (f) detecting a presence or absence of the first sample identifier, the second sample identifier, and the first pathogen nucleic acid in the sequence results for the first sample; and (g) determining that the detected first pathogen nucleic acid is originally present in the first sample when the sequencing assay detects in the first sample: (i) the first sample identifier; (ii) the first pathogen nucleic acid; and (iii) no second sample identifier or second sample identifier below a threshold level.

In another aspect, provided herein is a method for detecting a nucleic acid, the method comprising: (a) obtaining a first nucleic acid sample comprising a first nucleic acid; (b) obtaining a first control nucleic acid sample comprising a first positive control nucleic acid; (c) adding to the first control nucleic acids a first sample identifier comprising a synthetic nucleic acid that is not capable of hybridizing to the first nucleic acid; (d) performing a sequencing assay on the first nucleic acid sample and the first control nucleic acid sample comprising the first sample identifier, thereby obtaining sequence reads for the first and control nucleic acid samples; (e) aligning the sequence reads for the first nucleic acid sample with a reference sequence in order to detect a presence or absence of the first sample identifier in the sequence reads for the first nucleic acids sample; and (f) based on the aligning of the sequence reads, determining whether the first positive control nucleic acid is present in the first nucleic acids sample.

In some cases, the synthetic nucleic acid of the first sample identifier is less than 150 base pairs or nucleotides in length. In some cases, the first positive control nucleic acid is a pathogen nucleic acid. In some cases, the first sample identifier comprises a modified nucleic acid. In some cases, the first sample identifier comprises DNA. In some cases, the sample comprises a cell-free body fluid. In some cases, the sample is from a subject infected by a pathogen.

In another aspect, provided herein is a method for detecting a reagent in a sample, the method comprising: (a) adding a first synthetic nucleic acid to the reagent, wherein the first synthetic nucleic acid comprises a unique sequence; (b) adding the reagent comprising the first synthetic nucleic acid to a nucleic acid sample; (c) preparing the nucleic acid sample for a sequencing assay; (d) performing the sequencing assay on the nucleic acid sample, thereby obtaining sequence results for the nucleic acid sample; and (e) based on the sequence results for the nucleic acid sample, detecting the reagent in the sample by determining a presence or absence of the first synthetic nucleic acid in the sample.

In some cases, the first synthetic nucleic acid is less than 150 base pairs or nucleotides in length. In some cases, the first synthetic nucleic acid is added a first reagent lot and further comprising adding a second synthetic nucleic acid to a second reagent lot. In some cases, detecting the reagent in the sample comprises detecting a specific lot of reagent. In some cases, the synthetic nucleic acids are not degradable by a nuclease. In some cases, the reagent comprises an aqueous buffer. In some cases, the reagent comprises an extraction reagent, an enzyme, a ligase, a polymerase, or dNTPs.

In another aspect, provided herein is a method of generating a sequencing library, the method comprising: (a) obtaining a sample comprising: (i) target nucleic acids; (ii) sequencing adapters; and (iii) at least one synthetic nucleic acid, wherein the at least one synthetic nucleic acid comprises DNA and resists ligation to a nucleic acid; and (b) conducting a ligation reaction on the sample such that the sequencing adapters preferentially ligate to the target nucleic acids over the at least one synthetic nucleic acid.

In another aspect, provided herein is a method for generating a sequencing library, the method comprising: (a) obtaining a sample comprising target nucleic acids and at least one synthetic nucleic acid; and (b) removing the at least one synthetic nucleic acid from the sample, thereby obtaining a sequencing sample comprising the target nucleic acids and not the at least one synthetic nucleic acid; and (c) attaching sequencing adapters to the target nucleic acids within the sequencing sample.

In another aspect, provided herein is a method of generating a sequencing library, the method comprising: (a) obtaining a sample comprising target nucleic acids and at least one synthetic nucleic acid, wherein the at least one synthetic nucleic acid comprises: (i) single-stranded DNA; (ii) a nucleotide modification inhibiting amplification of the synthetic nucleic acid; (iii) an immobilization tag; (iv) a DNA-RNA hybrid; (v) a nucleic acid with a length longer than a length of the target nucleic acids; or (vi) any combination thereof; and (b) generating a sequencing library from the sample for a sequencing reaction, wherein at least a portion of the at least one synthetic nucleic acid is not sequenced in the sequencing reaction.

In another aspect, provided herein is a method of generating a sequencing library, the method comprising: (a) obtaining a sample comprising: (i) target nucleic acids; (ii) sequencing adapters; and (iii) at least one synthetic nucleic acid, wherein the at least one synthetic nucleic acid comprises DNA and resists end-repair; and (b) conducting an end-repair reaction on the sample such that target nucleic acids are preferentially end-repaired over the at least one synthetic nucleic acid.

In another aspect, provided herein is a kit for generating a sequencing library, the kit comprising (a) a sequencing adapter; and (b) at least one synthetic nucleic acid, wherein the at least one synthetic nucleic acid comprises DNA and resists end-repair to a nucleic acid.

In one aspect, provided herein is a method for determining absolute or relative abundance of nucleic acids in an initial sample comprising target nucleic acids, the method comprising: (a) adding a starting quantity of at least 1000 unique synthetic nucleic acids to the sample, wherein each of the at least 1000 unique synthetic nucleic acids comprises (i) an identifying tag and (ii) a variable region; (b) performing a sequencing assay on a portion of the target nucleic acids and on a portion of the at least 1000 unique synthetic nucleic acids in the sample, thereby obtaining target and synthetic nucleic acid sequence reads, wherein the synthetic nucleic acid sequence reads include identifying tag sequences and variable region sequences; (c) detecting diversity loss of the at least 1000 unique synthetic nucleic acids by (i) detecting the sequence reads corresponding to at least a portion of the identifying tag sequences in order to obtain a set of first sequence reads; (ii) quantifying a number of different variable region sequences within the first sequence reads to obtain a unique sequenced value; and (iii) comparing the starting quantity of the at least 1,000 unique synthetic nucleic acids with the unique sequenced value in order to obtain the diversity loss of the at least 1,000 unique synthetic nucleic acids; and (d) using the diversity loss of the at least 1000 unique synthetic nucleic acids to calculate an absolute or relative abundance value of the target nucleic acids in the initial sample. In some cases, the starting quantity that is compared is a starting concentration.

In some cases, the target nucleic acids comprise pathogen nucleic acids. In some cases, the target nucleic acids comprise pathogen nucleic acids from at least five different pathogens. In some cases, wherein the at least 1,000 unique synthetic nucleic acids comprise DNA.

In some cases, each of the at least 1,000 unique synthetic nucleic acids is less than 500 base pairs or nucleotides in length. In some cases, the each of the at least 1,000 unique synthetic nucleic acids is less than 200 base pairs or nucleotides in length. In some cases, the each of the at least 1,000 unique synthetic nucleic acids is less than 100 base pairs or nucleotides in length.

In some cases, the sample is blood, plasma, serum, cerebrospinal fluid, synovial fluid, bronchial-alveolar lavage, urine, stool, saliva, or a nasal sample. In some cases, the sample is a sample of isolated nucleic acids. In some cases, the sample is from a human subject.

In some cases, the method further comprises generating a sequencing library from the sample, wherein the at least 1,000 unique synthetic nucleic acids are added to the sample before the generating the sequencing library. In some cases, the diversity loss of the at least 1,000 unique synthetic nucleic acids indicates a loss of one or more nucleic acids during sample processing of the sample. In some cases, the identifying tags comprise a common sequence. In some cases, the quantifying the at least 1,000 unique sequences within the first sequence reads comprises determining a reads count of the unique sequences within the first sequence reads.

In some cases, the at least 1,000 unique synthetic nucleic acids comprise at least $10^4$ unique synthetic nucleic acids. In some cases, the at least 1,000 unique synthetic nucleic acids comprise at least $10^5$ unique synthetic nucleic acids. In some cases, the method further comprises adding additional synthetic nucleic acids with at least three different lengths.

In some cases, the method further comprises adding a first group of additional synthetic nucleic acids with a first length, a second group of additional synthetic nucleic acids with a second length, and a third group of additional synthetic nucleic acids with a third length, wherein the first, second and third groups of additional synthetic nucleic acids each comprises synthetic nucleic acids with at least three different GC contents. In some cases, the method further comprises using the additional synthetic nucleic acids to calculate the absolute or relative abundance value of the target nucleic acids in the sample. In some cases, the method further comprises using the additional synthetic nucleic acids to calculate the absolute or relative abundance value of the target nucleic acids in the sample based on lengths, GC contents, or both lengths and GC contents of the additional synthetic nucleic acids.

In some cases, the at least 1,000 unique synthetic nucleic acids are added to the sample at a first sample processing step. In some cases, the method further comprises adding an additional pool of at least 1,000 unique synthetic nucleic acids to the sample at a second sample processing step, wherein the second sample processing step is different from the first sample processing step. In some cases, the method further comprises calculating diversity loss for the additional pool of at least 1,000 unique synthetic nucleic acids. In some cases, the method further comprises identifying a sample processing step with relatively high diversity loss by comparing the diversity loss for the at least 1,000 unique synthetic nucleic acids with the diversity loss for the additional pool of at least 1,000 unique synthetic nucleic acids.

In some cases, each of the unique synthetic nucleic acids in the additional pool of at least 1,000 unique synthetic nucleic acids comprises a domain identifying the synthetic nucleic acid as a member of the additional pool of at least 1,000 unique synthetic nucleic acids. In some cases, the method further comprises adding a sample identifier nucleic acid to the sample. In some cases, (a) above further comprises adding non-unique synthetic nucleic acids to the sample. In some cases, the variable sequence reads are detected by aligning with a reference sequence. In some cases, the number of different variable sequence reads is quantified by aligning the variable sequence reads with each other and throwing out duplicate sequence reads.

Provided herein are methods of determining relative abundance or concentration of a pathogen nucleic acid in a sample of nucleic acids. In some cases, the method may comprise: obtaining a sample from a subject infected by, or suspected of being infected by, a pathogen, wherein the sample comprises two or more pathogen nucleic acids, wherein the two or more pathogen nucleic acids comprise first and second pathogen nucleic acids having lengths that are different; adding a known concentration of two or more synthetic nucleic acids to the sample, wherein the two or more synthetic nucleic acids comprise a first synthetic nucleic acid with a length between 65% and 135%, between 75% and 125%, or between 85% and 115%, of the first pathogen nucleic acid and a second synthetic nucleic acid with a length between 65% and 135%, between 75% and 125%, or between 85% and 115%, of the second pathogen nucleic acid and wherein the two or more synthetic nucleic acids do not hybridize to the first or second pathogen nucleic acid; performing a sequencing assay on the sample, thereby obtaining raw measurements for the two or more synthetic nucleic acids, the first pathogen nucleic acid, and the second pathogen nucleic acid; comparing the raw measurement of the first synthetic nucleic acid with the known concentration of the first synthetic nucleic acid in order to produce a recovery profile for the first synthetic nucleic acid; and using the recovery profile for the first synthetic nucleic acid to normalize the raw measurement for the first pathogen nucleic acid, thereby determining the relative abundance or starting concentration of the first pathogen nucleic acid.

In some cases, the first and second pathogen nucleic acids are derived from a same pathogen. In some cases, the first and second pathogen nucleic acids are derived from different pathogens. In some cases, a method described herein further comprises normalizing the relative abundance or starting concentration of the first pathogen nucleic acid by using a weighting factor. In some cases, the weighting factor is obtained by analyzing the raw measurement of the first synthetic nucleic acid and the raw measurement of the second synthetic nucleic acid in comparison with the known concentration of the first synthetic acid and the known concentration of the second synthetic acid.

Provided herein is a method of determining relative abundance or starting concentration of a nucleic acid in a sample, the method comprising: (a) obtaining a nucleic acid sample from a subject, wherein the nucleic acid sample comprises first and second nucleic acids having lengths that are different; adding a known concentration of two or more synthetic nucleic acids to the sample, wherein: (i) the two or more synthetic nucleic acids comprise a first synthetic nucleic acid with a length between 65% and 135%, between 75% and 125%, or between 85% and 115% of the length of the first nucleic acid and a second synthetic nucleic acid with a length between 65% and 135%, between 75% and 125%, or between 85% and 115% of the length of the second nucleic acid; (ii) the first synthetic nucleic acid comprises a load domain of a specific length and an identifier domain with a unique sequence coded to identify the specific length of the load domain; and (iii) the two or more synthetic nucleic acids are not capable of hybridizing to the first nucleic acid or the second nucleic acid; (b) performing a sequencing assay on the sample, thereby obtaining raw measurements for the two or more synthetic nucleic acids, the first nucleic acid, and the second nucleic acid; (c) comparing the raw measurement of the first synthetic nucleic acid with the known concentration of the first synthetic nucleic acid in order to produce a recovery profile; and (d) using the recovery profile to normalize the raw measurement for the first nucleic acid, thereby determining the relative abundance or starting concentration of the first nucleic acid.

In some cases, the first nucleic acid is a pathogen nucleic acid. In some cases, the known concentration of the two or more synthetic nucleic acids comprises 2 or more; 3 or more; 5 or more; 10 or more; 50 or more; 100 or more; or 1,000 or more different concentrations. In some cases, the known concentration of the two or more synthetic nucleic acids is an equimolar concentration. In some cases, the two or more synthetic nucleic acids comprise DNA or modified DNA. In some cases, the two or more synthetic nucleic acids comprise RNA or modified RNA. In some cases, the two or more synthetic nucleic acids comprise nucleic acids of 2 or more; 3 or more; 5 or more; 8 or more; 10 or more; 50 or more; 100 or more; or 1,000 or more different lengths. In some cases, the two or more synthetic nucleic acids comprise nucleic acids of 2 or more; 3 or more; 5 or more; 8 or more; 10 or more; 50 or more; 100 or more; or 1,000 or more different sequences. In some cases, the two or more synthetic nucleic acids are up to 50, up to 100, up to 200, up to 300, up to 350, up to 400, up to 450, up to 500, up to 750, or up to 1,000 nucleotides in length. In some cases, the two or more synthetic nucleic acids are at least 10, at least 20, or at least 30, at least 50, at least 100, or at least 150 nucleotides in length. In some cases, the two or more synthetic nucleic acids comprise a nucleic acid sequence that identifies the two or more synthetic nucleic acids as synthetic. In some cases, the nucleic acid sequence that identifies the two or more synthetic nucleic acids as synthetic is up to 10, up to 20, up to 30, up to 40, up to 50, up to 100, up to 200, or up to 500 nucleotides in length. In some cases, the two or more synthetic nucleic acids comprise a nucleic acid sequence that identifies the length of the synthetic nucleic acid. In some cases, the nucleic acid sequence that identifies the length of the synthetic nucleic acid is up to 10, up to 20, up to 30, up to 40, up to 50, up to 100, up to 200, or up to 500 nucleotides in length.

In some cases, the sample is selected from the group consisting of blood, plasma, serum, cerebrospinal fluid, synovial fluid, bronchio-alveolar lavage, urine, stool, saliva, nasal swab, and any combination thereof. In some cases, the sample comprises cell-free nucleic acids. In some cases, the sample comprises circulating cell-free nucleic acids. In some cases, the subject is human. In some cases, the pathogen is a bacterium, virus, fungus, or parasite. In some cases, the subject has or is suspected of having sepsis. In some cases, the pathogen is associated with sepsis. In some cases, the two or more pathogen nucleic acids comprise 3 or more; 5 or more; 10 or more; 50 or more; 100 or more; 1,000 or more; 2,000 or more; 5,000 or more; 8,000 or more; 10,000 or more; 15,000 or more; or 20,000 or more pathogen nucleic acid sequences.

In some cases, the determining relative abundance of the first pathogen nucleic acid comprises generating one or more genome copies. In some cases, the generating one or more genome copies is expressed as genome copies per volume. In some cases, a method described herein further comprises extracting nucleic acids from the sample. In some cases, the extracting nucleic acids from the sample is performed using magnetic beads. In some cases, a method described herein further comprises removing low-quality sequencing reads. In some cases, a method described herein further comprises removing sequencing reads aligned or mapped to a reference sequence of a species of the subject. In some cases, a method described herein further comprises determining relative efficiency of recovering nucleic acids of one or more different lengths. In some cases, a method described herein further comprises determining measured concentrations of one or more synthetic nucleic acids. In some cases, a method described herein further comprises comparing the measured concentrations of the one or more synthetic nucleic acids to the known concentration. In some cases, a method described herein further comprises detecting one or more; 2 or more; 3 or more; 5 or more; 10 or more; 50 or more; 100 or more; 1,000 or more; 2,000 or more; 5,000 or more; 8,000 or more; 10,000 or more; 15,000 or more; or 20,000 or more pathogen nucleic acids in the sequencing assay. In some cases, a method described herein further comprises detecting one or more; 2 or more; 3 or more; 5 or more; 10 or more; 50 or more; 100 or more; 1,000 or more; 2,000 or more; 5,000 or more; 8,000 or more; 10,000 or more; 15,000 or more; or 20,000 or more pathogen nucleic acids indicating antimicrobial, antibacterial, antiviral, or antifungal resistance in the sequencing assay. In some cases, a method described herein further comprises identifying co-incidence of 2 or more; 3 or more; 5 or more; 10 or more; 50 or more; or 100 or more pathogens within the sample.

In some cases, the two or more synthetic nucleic acids are added to the sample prior to or during extraction of the nucleic acids from the sample. In some cases, the two or more synthetic nucleic acids are added to the sample after extraction of the nucleic acids from the sample and prior to library preparation of the nucleic acids. In some cases, the lengths of the two or more synthetic nucleic acids differ by at least about 20 base pairs. In some cases, the two or more synthetic nucleic acids comprise three or more, five or more, eight or more, 10 or more, 20 or more, or 50 or more synthetic nucleic acids. In some cases, the two or more synthetic nucleic acids are selected from the group consisting of SEQ ID NO: 111-SEQ ID NO: 118, and any combination thereof. In some cases, the two or more synthetic nucleic acids share a common forward sequence. In some cases, the common forward sequence is up to about 20 base pairs in length. In some cases, the two or more synthetic nucleic acids share a common reverse sequence. In some cases, the common reverse sequence is up to about 20 base pairs in length.

In some cases, a method described herein further comprises: comparing the raw measurement of the second synthetic nucleic acid with the known concentration of the second synthetic nucleic acid in order to produce a recovery profile for the second synthetic nucleic acid; and using the recovery profile for the second synthetic nucleic acid to normalize the raw measurement for the second pathogen nucleic acid, thereby determining the relative abundance or starting concentration of the second pathogen nucleic acid.

In some cases, the two or more pathogen nucleic acids comprise five or more pathogen nucleic acids having lengths that are different; the two or more synthetic nucleic acids comprise one or more synthetic nucleic acids with a length between 65% and 135%, between 75% and 125%, or between 85% and 115% of the length of each of the five or more pathogen nucleic acids and wherein the two or more synthetic nucleic acids do not hybridize to the five or more pathogen nucleic acids; the performing a sequencing assay on the sample obtains raw measurements for the two or more synthetic nucleic acids and the five or more pathogen nucleic acids; the comparing the raw measurement comprises comparing the raw measurement with the known concentration of each synthetic nucleic acid in order to produce a recovery profile for each synthetic nucleic acid; and/or the using the recovery profile comprises using the recovery profile for each synthetic nucleic acid to normalize the raw measurement for each of the five or more pathogen nucleic acids, thereby determining the relative abundance or starting concentration of each of the five or more pathogen nucleic acids. In some cases, the five or more pathogen nucleic acids comprise 10 or more, 50 or more; 100 or more; 1,000 or more; 2,000 or more; 5,000 or more; 8,000 or more; 10,000 or more; 15,000 or more; or 20,000 or more pathogen nucleic acids. In some cases, a method described herein further comprises extracting or purifying the nucleic acids in the sample of nucleic acids and the two or more synthetic nucleic acids. In some cases, the extracting or purifying the nucleic acids in the sample of nucleic acids and the two or more synthetic nucleic acids changes a relative concentration of the nucleic acids in the sample of nucleic acids or the two or more synthetic nucleic acids. In some cases, the raw measurements are read counts.

Provided herein is a method for detecting a nucleic acid from a pathogen, the method comprising: (a) obtaining a first nucleic acid sample comprising a first pathogen nucleic acid, wherein the first nucleic acid sample is obtained from a first subject infected by the first pathogen, or suspected of being infected by the first pathogen; (b) obtaining a second nucleic acid sample comprising a second pathogen nucleic acid, wherein the second nucleic acid sample is obtained from a second subject infected by the second pathogen, or suspected of being infected by the second pathogen; (c) obtaining a first and second sample identifier, each comprising a different synthetic nucleic acid that is not capable of hybridizing to the pathogen nucleic acid and assigning the first sample identifier to the first nucleic acid sample and the second sample identifier to the second nucleic acid sample; (d) adding the first sample identifier to the first nucleic acid sample and the second sample identifier to the second nucleic acid sample; (e) performing a sequencing assay on the first nucleic acid sample comprising the first sample-identifier and on the second nucleic acid sample comprising the second sample identifier, thereby obtaining sequence results for the first and second samples; (f) detecting a presence or absence of the first sample identifier, the second sample identifier, and the pathogen nucleic acids in the sequence results; and (g) determining that a target nucleic acid is originally present in the first sample when the sequencing assay detects the first sample identifier and the target nucleic acid but not the second sample identifier.

In some cases, the synthetic nucleic acids are up to about 500 base pairs in length. In some cases, the synthetic nucleic acids are up to about 100 base pairs in length. In some cases, the synthetic nucleic acids are at least about 50 base pairs in length. In some cases, the synthetic nucleic acids are at least about 100 base pairs in length. In some cases, the synthetic nucleic acids comprise DNA or modified DNA. In some cases, the synthetic nucleic acids comprise RNA or modified RNA. In some cases, the synthetic nucleic acids are modified nucleic acids. In some cases, the synthetic nucleic acids comprise a sequence selected from the group consisting of SEQ ID NO: 1-SEQ ID NO: 110, and any combination thereof. In some cases, the first sample comprises a cell-free body fluid.

Provided herein is a method for detecting a reagent in a sample, the method comprising: adding a first synthetic nucleic acid to the reagent, wherein the first synthetic nucleic acid comprises a unique sequence; adding the reagent comprising the first synthetic nucleic acid to a nucleic acid sample; preparing the nucleic acid sample for a sequencing assay; performing the sequencing assay on the nucleic acid sample, thereby obtaining sequence results for the nucleic acid sample; and based on the sequence results for the nucleic acid sample, detecting the reagent in the sample by determining a presence or absence of the first synthetic nucleic acid in the sample.

In some cases, the adding the first synthetic nucleic acid to the reagent in step a comprises adding the first synthetic nucleic acid to a specific lot of the reagent. In some cases, a method described herein further comprises detecting the specific lot of the reagent based on the sequence results for the nucleic acid sample. In some cases, the first synthetic nucleic acid does not hybridize to nucleic acids from a pathogen. In some cases, a method described herein further comprises adding a second synthetic nucleic acid to a different lot of the reagent, wherein the second synthetic nucleic acid uniquely identifies the different lot of the reagent. In some cases, a method described herein further comprises detecting a target nucleic acid based on results from the sequencing assay of the nucleic acid sample. In some cases, a method described herein further comprises: (i) using the specific lot of the reagent in future sequencing assays if the target nucleic acid is accurately detected; or (ii) refraining from using the specific lot of the reagent in future sequencing assays if the target nucleic acid is not accurately detected. In some cases, the reagent comprises an aqueous solution. In some cases, the synthetic nucleic acid is between about 50 to about 500 base pairs in length. In some cases, the synthetic nucleic acid comprises DNA or modified DNA. In some cases, the synthetic nucleic acid comprises RNA or modified RNA. In some cases, the synthetic nucleic acid is selected from the group consisting of SEQ ID NO: 1-SEQ ID NO: 110, and any combination thereof. In some cases, the synthetic nucleic acid is not capable of being degraded by DNase.

Provided herein is a method for determining diversity loss or abundance of nucleic acids in a sample, the method comprising: adding known concentrations of 1,000 unique synthetic nucleic acids to a sample comprising target nucleic acids; performing a sequencing assay on the sample, thereby obtaining sequence read counts of target nucleic acids and of at least a portion of the 1,000 unique synthetic nucleic acids; detecting diversity loss of the 1,000 unique synthetic nucleic acids by aligning the sequence read counts of the at least a portion of the 1,000 unique synthetic nucleic acids with sequences of the 1,000 unique nucleic acids added to the sample comprising target nucleic acids in step a and comparing diversity of the aligned sequence read counts with diversity of the 1,000 or more unique synthetic nucleic acids; and using the diversity loss of the 1,000 unique synthetic nucleic acids to calculate diversity loss in, or abundance of, the target nucleic acids in the sample.

In some cases, the 1,000 unique synthetic nucleic acids are up to about 500 base pairs in length or up to about 100 base pairs in length. In some cases, the 1,000 unique synthetic nucleic acids are added in equimolar concentrations. In some cases, the 1,000 unique synthetic nucleic acids have a diversity of at least about $1 \times 10^6$. In some cases, the 1,000 unique synthetic nucleic acids have a diversity of at least about $1 \times 10^7$. In some cases, the 1,000 unique synthetic nucleic acids have a diversity of at least about $1 \times 10^8$. In some cases, the 1,000 unique synthetic nucleic acids have a randomized section. In some cases, the 1,000 unique synthetic nucleic acids comprise DNA, modified DNA, RNA or modified RNA. In some cases, the 1,000 unique synthetic nucleic acids comprise sequences identified in SEQ ID NO: 119 and SEQ ID NO: 120. In some cases, the 1,000 unique synthetic nucleic acids are added to the sample at a first sample processing step. In some cases, a method described herein further comprises adding an additional pool of 1,000 unique synthetic nucleic acids to the sample at a second sample processing step, wherein the second sample processing step is different from the first sample processing step. In some cases, diversity loss is calculated for the additional pool of 1,000 unique synthetic nucleic acids. In some cases, a method described herein comprises identifying a sample processing step with relatively high diversity loss by comparing the diversity loss for the 1,000 unique synthetic nucleic acids with the diversity loss for the additional pool of 1,000 unique synthetic nucleic acids. In some cases, the 1,000 unique synthetic nucleic acids comprise domains identifying the synthetic nucleic acids as members of a pool comprising the 1,000 unique synthetic nucleic acids. In some cases, the additional pool of 1,000 unique synthetic nucleic acids comprises domains identifying the synthetic nucleic acids as members of the additional pool of 1,000 unique synthetic nucleic acids. In some cases, the 1,000 unique synthetic nucleic acids are added to the sample prior to extraction of the target nucleic acids. In some cases, the 1,000 unique synthetic nucleic acids are added to the sample prior to library preparation of the target nucleic acids. In some cases, a method described herein further comprises adding known concentrations of 5,000 unique synthetic nucleic acids to the sample comprising the target nucleic acids.

Further disclosed herein are methods and compositions for analyzing molecules. In one aspect, disclosed herein is a method for generating a sequencing library, the method comprising: a) obtaining a sample comprising: (i) target nucleic acids; (ii) sequencing adapters; and (iii) at least one synthetic nucleic acid, wherein the at least one synthetic nucleic acid comprises DNA and resists ligation to a nucleic acid; and b) conducting a ligation reaction on the sample such that the sequencing adapters preferentially ligate to the target nucleic acids over the at least one synthetic nucleic acid.

In some cases, the at least one synthetic nucleic acid resists ligation to the nucleic acid via a phosphodiester bond. In some cases, the at least one synthetic nucleic acid resists ligation to the sequencing adapters. In another aspect, disclosed herein is a method for generating a sequencing library, the method comprising: a) obtaining a sample comprising target nucleic acids and at least one synthetic nucleic acid; b) removing the at least one synthetic nucleic acid from the sample, thereby obtaining a sequencing sample comprising the target nucleic acids and not the at least one synthetic nucleic acid; and c) attaching sequencing adapters to the target nucleic acids within the sequencing sample. In some cases, the removing the at least one synthetic nucleic acid is not performed by endonuclease digestion. In some cases, the at least one synthetic nucleic acid removed from the sample is not attached to another synthetic nucleic acid. In some cases, the at least one synthetic nucleic acid resists end-repair.

In another aspect, disclosed herein is a method for generating a sequencing library, the method comprising: a) obtaining a sample comprising target nucleic acids and at least one synthetic nucleic acid; b) attaching sequencing adapters to the target nucleic acids within the sample, thereby obtaining a sequencing sample; and c) removing the at least one synthetic nucleic acid from the sequencing sample by affinity-based depletion, RNA-guided DNase digestion, or a combination thereof, wherein the removing the at least one synthetic nucleic acid from the sequencing sample comprises preferentially removing the at least one synthetic nucleic acid over the sequencing adapters and over multimers of the sequencing adapters.

In some cases, the methods further comprise removing the at least one synthetic nucleic acids by endonuclease digestion, size-based depletion, or a combination thereof. In some cases, the sequencing adapters are nucleic acids. In some cases, the removing the at least one synthetic acid is performed by affinity-based depletion, and the at least one synthetic nucleic acid comprises an immobilization tag. In some cases, the removing the at least one synthetic nucleic acid is performed by RNA-guided DNase digestion. In some cases, the RNA-guided DNase comprises a CRISPR-associated protein. In some cases, the removing the at least one synthetic nucleic acid is performed by endonuclease digestion. In some cases, the removing the at least one synthetic acid is performed by size-based depletion, and the at least one synthetic nucleic acid has a length greater than a length of the target nucleic acids. In some cases, the removing the at least one synthetic acid is performed with RNase and the at least one synthetic nucleic acid is a DNA-RNA hybrid. In some cases, the attaching the sequencing adapters to the target nucleic acids comprises ligating the sequencing adapters to the target nucleic acids. In some cases, the attaching the sequencing adapters to the target nucleic acids comprises ligating the sequencing adapters to the target nucleic acids.

In another aspect, disclosed herein is a method of generating a sequencing library, the method comprising: a) obtaining a sample comprising target nucleic acids and at least one synthetic nucleic acid, wherein the at least one synthetic nucleic acid comprises: (i) single-stranded DNA; (ii) a nucleotide modification inhibiting amplification of the synthetic nucleic acid; (iii) an immobilization tag; (iv) a DNA-RNA hybrid; (v) a nucleic acid with a length longer than a length of the target nucleic acids; or (vi) any combination thereof and b) generating a sequencing library from the sample for a sequencing reaction, wherein at least a portion of the at least one synthetic nucleic acid is not sequenced in the sequencing reaction.

In some cases, the at least one synthetic nucleic acid further comprises an endonuclease recognition site. In some cases, the obtaining the sample comprises extracting the target nucleic acids from a test sample, and further comprises adding the at least one synthetic nucleic acid to the test sample after the extracting the target nucleic acids from the test sample. In some cases, the obtaining the sample comprises extracting the target nucleic acids from a test sample, and further comprises adding the at least one synthetic nucleic acid to the test sample prior to the extracting the target nucleic acids from the test sample. In some cases, wherein the at least one synthetic nucleic acid comprises a blocking group inhibiting a ligation reaction, and the blocking group comprises a modified nucleotide. In some cases, the modified nucleotide comprises an inverted deoxy-sugar. In some cases, the inverted deoxy-base comprises a 3' inverted deoxy-sugar. In some cases, the modified nucleotide comprises an inverted thymidine, an inverted adenosine, an inverted guanosine, or an inverted cytidine. In some cases, the modified nucleotide comprises an inverted dideoxy-sugar. In some cases, the inverted dideoxy-sugar comprises a 5' inverted dideoxy-sugar. In some cases, the modified nucleotide comprises an inverted dideoxy-thymidine, an inverted dideoxy-adenosine, an inverted dideoxy-guanosine, or an inverted dideoxy-cytidine. In some cases, the modified nucleotide is dideoxy-cytidine. In some cases, the at least one synthetic nucleic acid comprises a blocking group inhibiting a ligation reaction, and the blocking group comprises a spacer. In some cases, the spacer comprises a C3 spacer or spacer 18. In some cases, the at least one synthetic nucleic acid comprises a blocking group inhibiting a ligation reaction, and the blocking group comprises a hairpin structure. In some cases, the synthetic nucleic acid comprises a nucleotide modification inhibiting amplification of the at least one synthetic nucleic acid, and the nucleotide modification comprises at least one abasic site. In some cases, the at least one abasic site is at least one internal abasic site. In some cases, the nucleotide modification comprises 8 to 10 abasic sites. In some cases, the at least one abasic site is a single abasic site. In some cases, the at least one abasic site is on a modified ribose. In some cases, the at least one abasic site comprises 1',2'-dideoxyribose, locked nucleic acid, bridged nucleic acid, or twisted intercalating nucleic acid. In some cases, the at least one synthetic nucleic acid comprises an immobilization tag, and the immobilization tag comprises biotin, digoxigenin, polyhistidine, or Ni-Nitrilotriacetic acid. In some cases, the at least one synthetic nucleic acid comprises DNA and is labeled with internal uracil. In some cases, the at least one synthetic nucleic acid is removed from the sequencing sample with a Uracil-Specific Excision Reagent enzyme.

In some cases, the test sample is a biological sample. In some cases, the biological sample is whole blood, plasma, serum, or urine. In some cases, the target nucleic acids are cell-free nucleic acids. In some cases, the cell-free nucleic acids are cell-free DNA. In some cases, the cell-free nucleic acids are pathogen nucleic acids. In some cases, the cell-free nucleic acids are circulating cell-free nucleic acids. In some cases, the at least one synthetic nucleic acid comprises a double-stranded nucleic acid. In some cases, the at least one synthetic nucleic acid comprises a single-stranded nucleic acid. In some cases, the at least one synthetic nucleic acid comprises DNA, RNA, DNA-RNA hybrid, or any analog thereof.

In some cases, the methods further comprise one or more of: (a) extracting the target nucleic acids from the sample; (b) purifying the target nucleic acids from the sample; (c) end-repairing the target nucleic acids; (d) fragmenting the target nuclei acids; (e) amplifying the target nucleic acids; (f) attaching a sequencing adapter to the target nucleic acids; and (g) sequencing the target nucleic acids. In some cases, the methods comprise attaching the sequencing adapter to the target nucleic acids, and further comprise treating the sequencing sample with an endonuclease before the attaching the sequencing adapter to the target nucleic acids. In some cases, the methods comprise attaching the sequencing adapter to the target nucleic acids, and further comprise treating the sequencing sample with an endonuclease after the attaching the sequencing adapter to the target nucleic acids. In some cases, the methods comprise end-repairing the target nucleic acids, wherein the at least one synthetic nucleic acid is added to the sample before the end-repairing the target nucleic acids. In some cases, the methods comprise end-repairing the target nucleic acids, wherein the at least one synthetic nucleic acid is added to the sample after the end-repairing the target nucleic acids. In some cases, the methods comprise attaching the sequencing adapter to the target nucleic acids, and the at least one synthetic nucleic acid is added to the sample prior to the attaching the sequencing adapter to the target nucleic acids. In some cases, a ratio of a concentration of the at least one synthetic nucleic acid in the sample to a concentration of the target nucleic acids in the sample is from 1:1 to 1000:1.

In some cases, difference between a size of the at least one synthetic nucleic acid and a size of the target nucleic acid allows size-based separation of the at least one synthetic nucleic acid from the target nucleic acid. In some cases, the synthetic nucleic acid comprises a blocking group inhibiting a ligation reaction, and a nucleotide modification inhibiting an amplification reaction. In some cases, the blocking group inhibiting the ligation reaction comprises 3' inverted deoxy-T, and the nucleotide modification inhibiting the amplification reaction comprises an internal abasic site. In some cases, the blocking group further comprises 5' inverted dideoxy-T. In some cases, the methods further comprise incubating the sample with endonuclease VIII. In some cases, the sample is incubated with the endonuclease VIII for no greater than one hour. In some cases, the methods comprise the extracting the target nucleic acids from the sample, and the extracting the target nucleic acids has a higher yield compared to extracting the target nucleic acids from a sample not containing the at least one synthetic nucleic acid. In some cases, the methods comprise the end-repairing the target nucleic acids, and the end-repairing the target nucleic acids has a higher efficiency compared to end-repairing the target nucleic acids in a sample not containing the at least one synthetic nucleic acid. In some cases, the target nucleic acids comprise naturally occurring nucleic acids or copies thereof. In some cases, the methods further comprise obtaining sequence information of at least one of the target nucleic acids using a computer.

In another aspect, disclosed herein is a method of generating a sequencing library, the method comprising: (a) obtaining a sample comprising: (i) target nucleic acids; (ii) sequencing adapters; and (iii) at least one synthetic nucleic acid, wherein the at least one synthetic nucleic acid comprises DNA and resists end-repair; and b) conducting an end-repair reaction on the sample such that target nucleic acids are preferentially end-repaired over the at least one synthetic nucleic acid.

In some embodiments, any of the preceding methods may comprise reporting a result of the method to a patient, caregiver, or other person.

In another aspect, disclosed herein is a kit for generating a sequencing library, the kit comprising: a) a sequencing adapter; and b) at least one synthetic nucleic acid, wherein the at least one synthetic nucleic acid comprises DNA and resists end-repair to a nucleic acid. In some cases, the ratio of an amount of the at least one synthetic nucleic acid to an amount of the sequencing adapter is no greater than 1:1.

BRIEF DESCRIPTION OF THE DRAWINGS

The novel features of the disclosed subject matter are set forth with particularity in the appended claims. A better understanding of the features and advantages of the present disclosed subject matter will be obtained by reference to the following detailed description that sets forth illustrative embodiments, in which the principles of the disclosed subject matter are utilized, and the accompanying drawings of which:

FIG. 6 depicts a design of an exemplary Spank spike-in.

INCORPORATION BY REFERENCE

Figure 1:
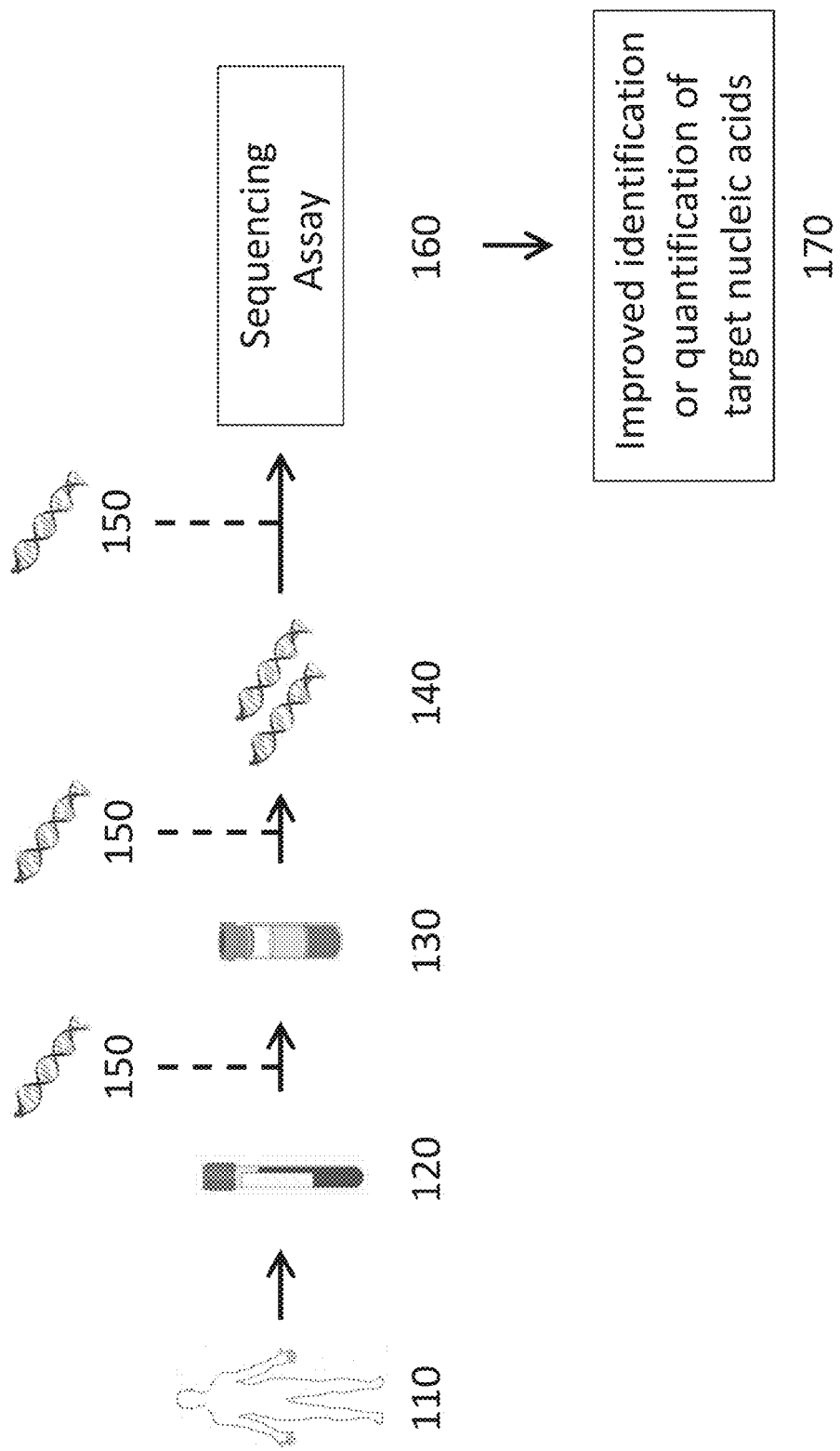
FIG. 1 shows a schematic of a basic method of this disclosure.

All publications, patents, and patent applications mentioned in this specification are herein incorporated by reference in their entireties to the same extent as if each individual publication, patent, or patent application was specifically and individually indicated to be incorporated by reference.

DETAILED DESCRIPTION

Overview

This disclosure provides multiple methods and approaches for improved identification or quantification of nucleic acids in next generation sequencing assays and other assays. Generally, the methods provided herein involve the use of spike-in synthetic nucleic acids that have special features such as specific sequences, lengths, GC content, degrees of degeneracy, degrees of diversity, and/or known starting concentrations. The use of such spike-in synthetic nucleic acids may enable and improve absolute abundance determination, relative abundance determination, abundance normalization, universal quantification, bias control, sample identification, cross-contamination detection, information transfer efficiency, reagent tracking, loss-of-diversity normalization, absolute or relative loss determination, quality control and many other applications. The spike-in synthetic nucleic acids provided herein also include specially-designed carrier nucleic acids that may increase the total concentration of nucleic acids in the sample, yet have the ability to evade detection by sequencing or other assays.

In preferred embodiments, this disclosure provides sets of species of spike-in synthetic nucleic acids, wherein the length and/or GC content of each species is designed to match or closely-approximate the expected or observable lengths and/or GC contents of the set of target nucleic acids to be analyzed. For example, the lengths of the spike-in synthetic nucleic acids may approximate the lengths of disease-specific or pathogen-specific cell-free nucleic acids in a sample (e.g., plasma) obtained from a human patient infected by such pathogen. In other preferred embodiments, this disclosure provides spike-in synthetic nucleic acids comprising sequences to uniquely identify a sample, reagent, or reagent lot. In still other preferred embodiments, this disclosure provides pools comprising large numbers of spike-in synthetic nucleic acids with unique sequences (e.g., $10^4$, $10^5$, $10^6$, $10^7$, $10^8$, $10^9$ or $10^{10}$ unique spike-in synthetic nucleic acids) that can be used to track absolute nucleic acid loss in a sample through the decrease in diversity of the unique spike-in sequences during the course of a high-throughput sequencing assay, particularly sample processing steps such as nucleic acid extraction and/or library preparation.

The ability to track absolute nucleic acid loss may permit the determination of the absolute abundance of a target nucleic acid in an initial sample. For example, absolute amount of a pathogen in a clinical sample can be determined based on the number of sequencing reads attributed to that pathogen. Medical treatment can be monitored or adjusted by determining the absolute abundance of the pathogen in clinical samples taken over time, such as before, during, and after treatment with an antibiotic or pharmaceutical composition. In addition to determining whether a specific pathogen is present, degrees or stages of infection or illness can also be determined.

The methods may involve adding the spike-in synthetic nucleic acids to a variety of different samples including, but not limited to, clinical samples, processed samples (e.g., extracted nucleic acids, extracted cell-free DNA, extracted cell-free RNA, plasma, serum), unprocessed samples (e.g., whole blood) and any other type of sample, particularly a sample that comprises nucleic acids. The methods may, in some instances, involve addition of the spike-in synthetic nucleic acids to reagents, particularly laboratory reagents (or specific reagent lots) used at any stage of analysis of a sample by sequencing (e.g., next generation sequencing). In preferred embodiments, the methods may comprise introducing known concentrations of synthetic nucleic acids into reagents and samples. The methods may be especially helpful for increasing the accuracy and efficiency of assays designed to detect, identify, monitor, or quantify low-abundance pathogens or nucleic acids derived from pathogens in clinical samples. The methods may also reduce the undesirable outcomes that occur with errors in sample tracking; from unequal loss of nucleic acid sequences during sample preparation, nucleic acid purification, or sequencing library preparation; or from a lack of internal normalization standards when comparing analyses of different target nucleic acids or different samples.

FIG. 1 provides a general overview of the steps of many of the methods provided herein, particularly as they relate to abundance normalization. The methods may involve obtaining a sample from a subject 110, such as a human patient. In some particular embodiments, the subject has an infectious disease or is otherwise suspected of being infected with a pathogen. The sample may be a blood sample 120 or plasma sample 130, as depicted, or any other type of biological sample, especially a biological sample containing a bodily fluid, tissue, and/or cells, or a cell-free biological sample.

Nucleic acids (e.g., cell-free nucleic acids) from a sample 140 may be extracted and used in an assay, such as a sequencing assay (e.g., next generation sequencing assay). One or more types of synthetic nucleic acids 150 may be added (or spiked-in) at one or more steps in the method, for example to the blood sample 120, to the plasma sample 130, or to the sample nucleic acids 140. The synthetic nucleic acids may have lengths designed to approximate the lengths of the set of target nucleic acids to be analyzed and/or GC-contents designed to approximate the GC-contents of the set of target nucleic acids to be analyzed. Generally, the synthetic nucleic acids also have known starting concentrations. The sample comprising the synthetic nucleic acids may then be analyzed by a sequencing assay 160 such as a next generation sequencing assay. In some cases, the quantity of synthetic nucleic acids identified by the sequencing assay is compared with the known starting concentration of the synthetic nucleic acids in order to correlate the read count with the known starting concentration. As a result, target nucleic acids within the sample nucleic acids can be identified or quantified, particularly by comparing the abundance of the detected target nucleic acid with that of the synthetic nucleic acids closest in length and/or GC-content to such target nucleic acids 170. By use of such methods, and others provided herein, a condition of the subject can be identified with a higher accuracy and level of certainty. In some particular embodiments, the sequencing assay (e.g., next generation sequencing assay) detects pathogen nucleic acids within a sample of cell-free nucleic acids (e.g., DNA) derived from a human patient.

The steps may be performed in any order and in any combination. In some cases, certain steps are repeated several times. In some cases, certain steps are not performed. In some cases, new steps are added to, or interspersed between, the depicted steps.

Figure 2:
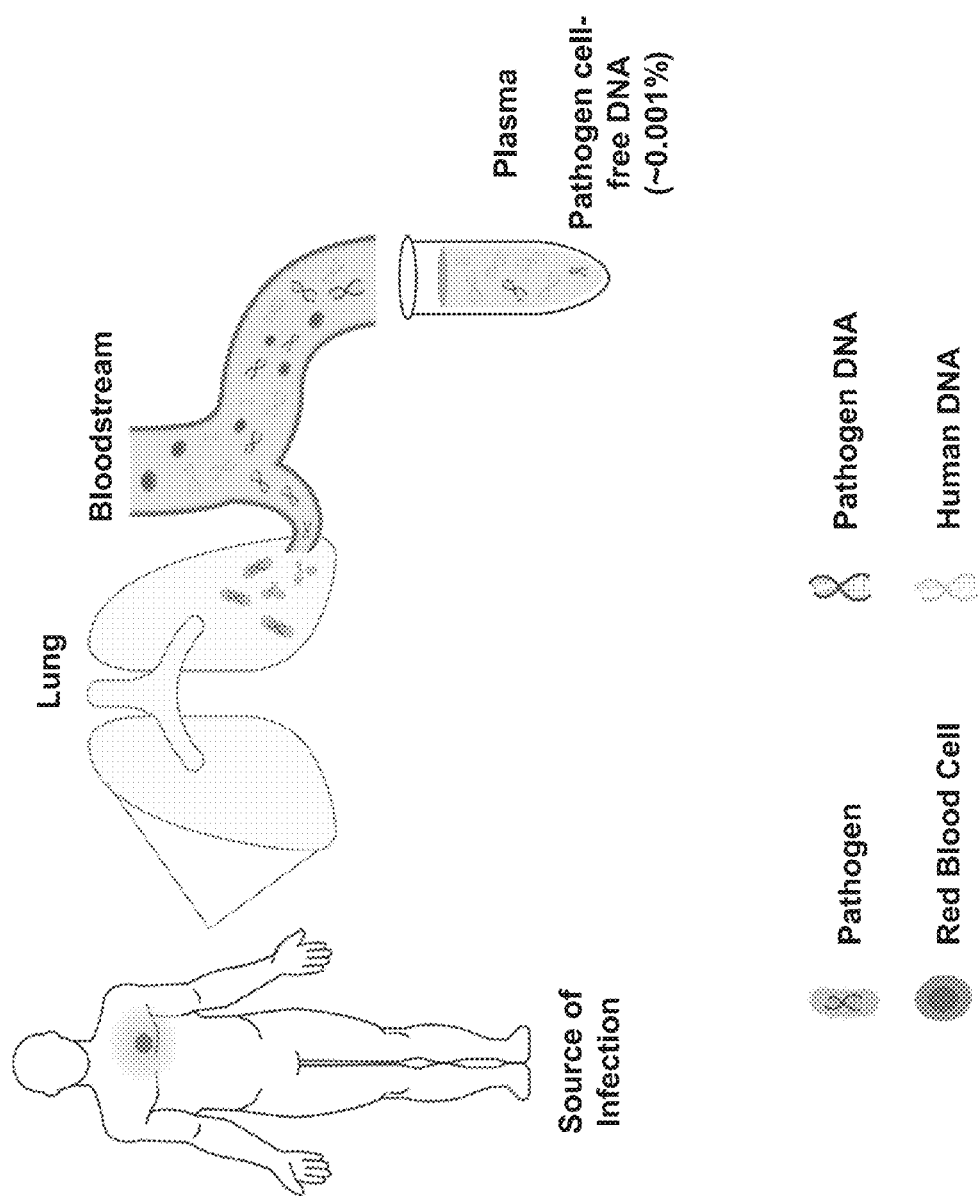
FIG. 2 shows a schematic of an exemplary infection.

FIG. 2 provides a schematic of an exemplary infection. A source of a pathogen infection may be, for example in the lung. Cell-free nucleic acids, such as cell-free DNA, derived from the pathogen may travel through the bloodstream and can be collected in a plasma sample for analysis. The nucleic acids in the sample may then be analyzed by a sequencing assay as shown in FIG. 1.

Figure 3:
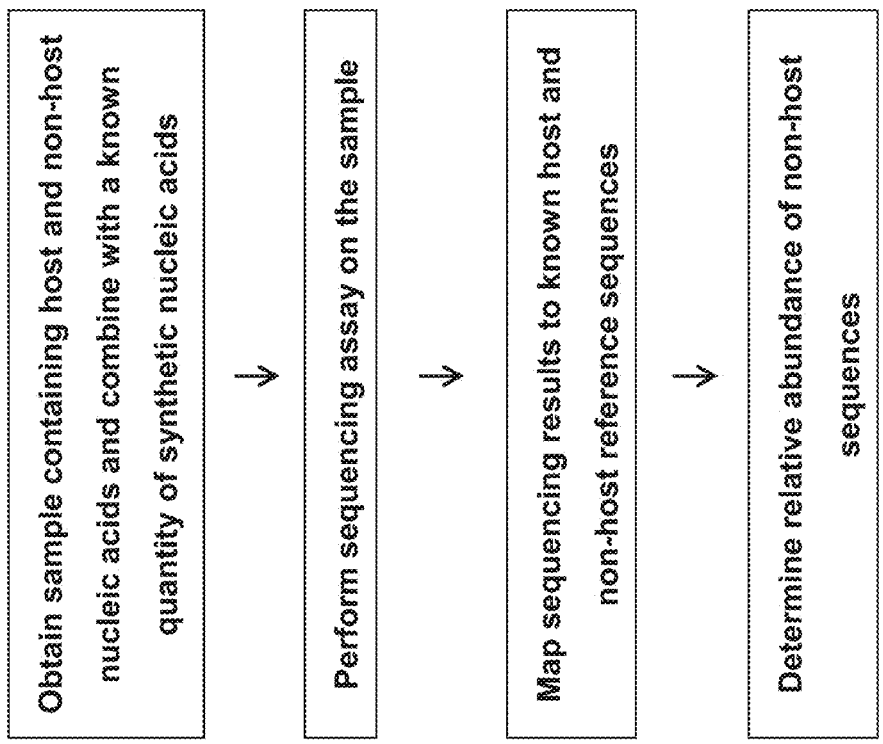
FIG. 3 depicts a general scheme of some of the methods provided herein.

FIG. 3 depicts a general scheme of some of the methods provided herein. The methods may involve obtaining a sample containing host (e.g., human) and non-host (e.g., pathogen) nucleic acids. The sample may be obtained from a subject, such as a patient. In some particular embodiments, the subject has an infectious disease or is otherwise suspected of being infected with a pathogen. The sample may be a blood sample or plasma sample, or any other type of biological sample, especially a biological sample containing a bodily fluid, tissue, and/or cells. Nucleic acids (e.g., cell-free nucleic acids) from the sample may be combined with a known quantity of synthetic nucleic acids. The sample comprising the synthetic nucleic acids may then be analyzed by a sequencing assay such as a next generation sequencing assay. The sequencing results can be mapped to known host and non-host reference sequences. In some cases, the quantity of synthetic nucleic acids identified by the sequencing assay is compared with the known starting concentration of the synthetic nucleic acids in order to correlate the read count with the known starting concentration. As a result, the relative abundance of non-host sequences can be determined. The steps may be performed in any order and in any combination. In some cases, certain steps are repeated several times. In some cases, certain steps are not performed. In some cases, new steps are added to, or interspersed between, the depicted steps.

The methods provided herein may enable improved identification or quantification of target nucleic acids by next generation sequencing, particularly when the target nucleic acids are present in low abundance in the sample or when multiple samples or multiple target nucleic acids are compared or tracked. For example, accurate detection and quantification of target pathogens, tumor cells or oncogenomic markers in clinical samples by next generation sequencing may be undermined or negatively impacted if the samples are improperly tracked or if target nucleic acids are inaccurately normalized or quantified. The methods provided herein thus may help avoid the pitfalls that arise from errors in sample tracking or identification or in nucleic acid quantification or otherwise cloud analysis of sequencing data.

The methods and compositions provided herein may be used for adding and/or removing synthetic nucleic acids during sequencing library preparation to increase the yield, quality, or efficiency of the sequencing library, particularly when the starting sample has relatively low amounts of nucleic acids. Generally, in some cases, the synthetic nucleic acids may act as carrier nucleic acids in these applications to raise the concentration of total nucleic acids during a sample preparation process. Adding the synthetic nucleic acids to a sample may increase the yield and/or efficiency of one or more steps of sequencing library generation. The one or more steps may be nucleic acid concentration sensitive. For example, the yield and/or efficiency of the steps may depend on the nucleic acid concentration in the sample. Such steps may include nucleic acid extraction, purification, ligation, and end-repairing. In some cases, the synthetic nucleic acids may be removed from the sequencing library. The synthetic nucleic acids may comprise certain features that prevent them from participating in one or more steps in the sequencing library generation. Thus, the synthetic nucleic acids may not be sequenced in the sequencing step.

The methods and compositions may be used to analyze samples (e.g., generating a sequencing library from target nucleic acids in the sample) from multiple subjects. The concentrations of target nucleic acids in these samples may vary among the subjects. Adding the synthetic nucleic acids herein to these samples may reduce the concentration variation among the samples, thus improving the accuracy of the analysis.

The methods and compositions may be used for preparing a sequencing library from a sample by adding at least one synthetic nucleic acid. The synthetic nucleic acids may have one or more characteristics so that they are not sequenced in a sequencing reaction. In some cases, the synthetic nucleic acids comprise modifications that inhibit one or more reactions in sequencing library generation, e.g., adapter ligation and nucleic acid amplification. For example, the nucleic acids may comprise inverted sugars at one or both ends, and/or one or more abasic sites.

In some cases, the synthetic nucleic acids may be removed from the sequencing library before sequencing. In some cases, the synthetic nucleic acids may be removed by enzyme digestion. For example, the synthetic nucleic acids may comprise a restriction enzyme recognition site, and may be degraded by the restriction enzyme. In some cases, the synthetic nucleic acids may be removed by affinity-based depletion. For example, the synthetic nucleic acids may comprise one or more immobilization tags, and may be removed by affinity-based depletion. In certain cases, the synthetic nucleic acids may be removed by size-based depletion. The synthetic nucleic acids may also have a size different from other molecules in the sequencing library, so that the synthetic nucleic acids may be removed by size-based depletion. In some cases, the synthetic nucleic acids may comprise a combination of the characteristics and/or modifications herein, so that they do not participate in one or more steps of sequence library generation and can also be removed before sequencing.

Samples

The methods provided herein may enable improved analysis of a wide variety of samples. The synthetic nucleic acids provided herein may be used to analyze such samples, which may involve directly adding the synthetic nucleic acids to the sample or to a processed version of the sample, e.g., extracted cell-free nucleic acids from a clinical plasma sample.

The samples analyzed in the methods provided herein are preferably any type of clinical sample. In some cases, the samples contain cells, tissue, or a bodily fluid. In preferred embodiments, the sample is a liquid or fluid sample. In some cases, the sample contains a body fluid such as whole blood, plasma, serum, urine, stool, saliva, lymph, spinal fluid, synovial fluid, bronchoalveolar lavage, nasal swab, respiratory secretions, vaginal fluid, amniotic fluid, semen or menses. In some cases, the sample is made up of, in whole or in part, cells or tissue. In some cases, cells, cell fragments, or exosomes are removed from the sample, such as by centrifugation or filtrations. The samples herein may be biological samples.

A sample may comprise any concentration of nucleic acids. The compositions and methods herein may be useful for samples with low concentration of total nucleic acids. In some cases, a sample has a total concentration of nucleic acid of at most 100 ng/μL, 50 ng/μL, 10 ng/μL, 5 ng/μL, 2 ng/μL, 1.5 ng/μL, 1.2 ng/μL, 1 ng/μL, 0.8 ng/μL, 0.4 ng/μL, 0.2 ng/μL, 0.1 ng/μL, 0.05 ng/μL, 0.01 ng/μL, 10 ng/mL, 5 ng/mL, 2 ng/mL, 1 ng/mL, 0.8 ng/mL, 0.6 ng/mL, 0.5 ng/mL, or 0.1 ng/mL. In some cases, a sample comprises a total concentration of nucleic acid of at least 0.1 ng/mL, 0.5 ng/mL, 0.6 ng/mL, 0.8 ng/mL, 1 ng/mL, 2 ng/mL, 5 ng/mL, 10 ng/mL, 0.01 ng/μL, 0.05 ng/μL, 0.1 ng/μL, 0.2 ng/μL, 0.4 ng/μL, 0.8 ng/μL, 1 ng/μL, 1.2 ng/μL, 1.5 ng/μL, 2 ng/μL, 5 ng/μL, 10 ng/μL, 50 ng/μL, or 100 ng/μL. In some cases, a sample has a total concentration of nucleic acid within the range from about 0.1 ng/mL to about 10,000 ng/mL (i.e., from about 0.1 ng/mL to about 10 ng/μL).

A sample may comprise one or more controls. In some cases, a sample comprises one or more negative controls. Exemplary negative controls include samples (e.g., plasma-minus samples) prepared to identify contaminants, plasma from healthy subjects, and low-diversity samples (e.g., samples collected from apparently healthy subjects). In some cases, a sample comprises one or more positive controls. Exemplary positive controls include samples (e.g., plasma samples) from healthy subject with genomic DNA from known pathogens. The genomic DNA from known pathogens may be intact genomic DNA. In some cases, the genomic DNA from known pathogens may be sheared, e.g., to various average lengths. The shearing may be performed by mechanical shearing (e.g. ultrasound, hydrodynamic shearing forces), enzymatic shearing (e.g. endonuclease), thermal fragmentation (e.g. incubation at high temperatures), chemical fragmentation (e.g. alkaline solutions, divalent ions).

A sample may comprise target nucleic acids. The target nucleic acids may refer to the nucleic acids to be analyzed in the sample. For example, the target nucleic acids may be originally in the sample, e.g., natural nucleic acids. A sample may further comprise one or more synthetic nucleic acids disclosed herein. In some cases, the target nucleic acids are cell-free nucleic acids described herein. For example, the target nucleic acids may be cell-free DNA, cell-free RNA (e.g., cell-free mRNA, cell-free miRNA, cell-free siRNA), or any combination thereof. In certain cases, the cell-free nucleic acids are pathogen nucleic acids, e.g., nucleic acids from pathogens. The cell-free nucleic acids may be circulating nucleic acids, e.g., circulating tumor DNA or circulating fetal DNA. A sample may comprise nucleic acid from pathogens, e.g., viruses, bacteria, fungi, and/or eukaryotic parasites.

In certain cases, a sample also comprises adapters. An adapter may be a nucleic acid with known or unknown sequence. An adapter may be attached to the 3'end, 5'end, or both ends of a nucleic acid. An adapter may comprise known sequences and/or unknown sequences. An adapter may be double-stranded or single-stranded. In some cases, an adapter is a sequencing adapter. A sequencing adapter may attach to a target nucleic acid and help the sequencing of the target nucleic acid. For example, a sequencing adapter may comprise one or more of: a sequencing primer binding site, a unique identifier sequence, a non-unique identifier sequence, and a sequence for immobilizing the target nucleic acid on a solid support. A target nucleic acid attached with the sequencing adapter may be immobilized on a solid support on a sequencer. A sequencing primer may hybridize to the adapter and be extended using the target nucleic acid as a template in a sequencing reaction. In some cases, the identifiers in the adapter are used to label the sequence reads of different target sequences, thus allowing high-throughput sequencing of a plurality of target nucleic acids.

The term "attach" and its grammatical equivalents may refer to connecting two molecules using any mode of attachment. For example, attaching may refer to connecting two molecules by chemical bonds or other method to generate a new molecule. Attaching an adapter to a nucleic acid may refer to forming a chemical bond between the adapter and the nucleic acid. In some cases, attaching is performed by ligation, e.g., using a ligase. For example, a nucleic acid adapter may be attached to a target nucleic acid by ligation, via forming a phosphodiester bond catalyzed by a ligase.

A sequencing library may be generated from a sample using the methods and compositions provided herein. A sequencing library may comprise a plurality of nucleic acids that are compatible with a sequencing system to be used. For example, nucleic acids in a sequencing library may comprise a target nucleic acid attached with one or more adapters. Steps for preparing a sequencing library may include one or more of: extracting target nucleic acids from a sample, fragmenting the target nucleic acids, attaching adapters to the target nucleic acids, amplifying the target nucleic acid-adapter complexes and sequencing the amplified target nucleic acid-adapter complexes.

The sample (particularly cellular samples or tissue biopsies) may be from any part or region of the body. Exemplary samples may be obtained from, e.g., the blood, the central nervous system, the brain, spinal cord, bone marrow, pancreas, thyroid, gall bladder, liver, heart, spleen, colon, rectum, lung, respiratory system, throat, nasal cavity, stomach, esophagus, ears, eyes, skin, limbs, uterus, prostate, reproductive organ, or any other organ or region of the body.

Generally, the samples are from a human subject, especially human patients. But the samples may also be from any other type of subject including any mammal, non-human mammal, non-human primate, domesticated animal (e.g., laboratory animals, household pets, or livestock), or non-domesticated animal (e.g., wildlife). In some particular embodiments, the subject is a dog, cat, rodent, mouse, hamster, cow, bird, chicken, pig, horse, goat, sheep, rabbit, ape, monkey, or chimpanzee.

In preferred embodiments, the subject is a host organism (e.g., a human) infected with a pathogen, at risk of infection by a pathogen, or suspected of having a pathogenic infection. In some cases, the subject is suspected of having a particular infection, e.g., suspected having tuberculosis. In other cases, the subject is suspected of having an infection of unknown origin. In some cases, a host or subject is infected (e.g., with one or more microbes, pathogens, bacteria, viruses, fungi, or parasites). In some cases, a host or subject has been diagnosed with or is at risk for developing one or more types of cancer. In some cases, a host or subject is not infected (e.g., with one or more microbes, pathogens, bacteria, viruses, fungi, or parasites). In some cases, a host or subject is healthy. In some cases, a host or subject is susceptible or at risk of an infection.

In some cases, the subject may have been treated or may be treated with an antimicrobial, antibacterial, antiviral, or antiparasitic drug. The subject may have an actual infection (e.g., with one or more microbes, pathogens, bacteria, viruses, fungi, or parasites). In some cases, the subject is not infected (e.g., with one or more microbes, pathogens, bacteria, viruses, fungi, or parasites). In some cases, the subject is healthy. In some cases, the subject is susceptible or at risk of an infection (e.g., patient is immunocompromised). The subject may have or be at risk of having another disease or disorder. For example, the subject may have, be at risk of having, or be suspected of having a disease such as cancer (e.g., breast cancer, lung cancer, pancreatic cancer, hematological cancer, etc.).

The sample may be a nucleic acid sample; in some cases, the sample contains a certain amount of nucleic acids. Nucleic acids within a sample may include double-stranded (ds) nucleic acids, single stranded (ss) nucleic acids, DNA, RNA, cDNA, mRNA, cRNA, tRNA, ribosomal RNA, dsDNA, ssDNA, miRNA, siRNA, circulating nucleic acids, circulating cell-free nucleic acids, circulating DNA, circulating RNA, cell-free nucleic acids, cell-free DNA, cell-free RNA, circulating cell-free DNA, cell-free dsDNA, cell-free ssDNA, circulating cell-free RNA, genomic DNA, exosomes, cell-free pathogen nucleic acids, circulating pathogen nucleic acids, mitochondrial nucleic acids, non-mitochondrial nucleic acids, nuclear DNA, nuclear RNA, chromosomal DNA, circulating tumor DNA, circulating tumor RNA, circular nucleic acids, circular DNA, circular RNA, circular single-stranded DNA, circular double-stranded DNA, plasmids, or any combination thereof. In some cases, sample nucleic acids may include synthetic nucleic acids. In some cases, synthetic nucleic acids include any types of nucleic acids disclosed herein, e.g., DNA, RNA, DNA-RNA hybrid. For example, a synthetic nucleic acid may be DNA.

In some cases, different types of nucleic acids may be present in a sample. For example, the sample may comprise cell-free RNA and cell-free DNA. Likewise, a method provided herein may include a method where both the RNA and the DNA present in a sample are analyzed, singly or in combination.

As used herein, the term "cell-free" refers to the condition of the nucleic acid as it appeared in the body before the sample is obtained from the body. For example, circulating cell-free nucleic acids in a sample may have originated as cell-free nucleic acids circulating in the bloodstream of the human body. In contrast, nucleic acids that are extracted from a solid tissue, such as a biopsy, are generally not considered to be "cell-free."

In some cases, the sample may be an unprocessed sample (e.g., whole blood) or a processed sample (e.g., serum, plasma) that contains cell-free or cell-associated nucleic acids. In some cases, the sample has been enriched for a certain type of nucleic acid, e.g., DNA, RNA, cell-free DNA, cell-free RNA, cell-free circulating DNA, cell-free circulating RNA, etc. In some cases, a sample has been processed in some way to isolate nucleic acids or to separate nucleic acids from other components within the sample. In some cases, the sample has been enriched for pathogen-specific nucleic acids.

Often, the sample is a fresh sample. In some cases, the sample is a frozen sample. In some cases, the sample is fixed, e.g., with a chemical fixative such as formalin-fixed paraffin-embedded tissue.

Target Nucleic Acids

The methods provided herein may be used to detect any number of target nucleic acids. The target nucleic acids include but are not limited to: whole or partial genomes, exomes, genetic loci, genes, exons, introns, modified nucleic acids (e.g., methylated nucleic acids), and/or mitochondrial nucleic acids. Often, the methods provided herein can be used to detect pathogen target nucleic acids; in some cases, the pathogen target nucleic acids are present in complex clinical sample containing nucleic acids from the subject. The pathogen target nucleic acid may be associated with an infectious disease, such as influenza, tuberculosis, or any other known infectious disease or disorder, including those described further herein. In some cases, a target nucleic acid described herein may be a target nucleic acid.

In some cases, the pathogen target nucleic acid is present in a tissue sample, such as a tissue sample from a site of infection. In other cases, the pathogen target nucleic acid has migrated from the site of infection; for example, it may be obtained from a sample containing circulating cell-free nucleic acids (e.g., DNA).

In some cases, the target nucleic acid derives from cancer tissue. The target nucleic acid may be obtained directly from the tissue or tumor. In some cases, the target cancer nucleic acid is obtained from circulating cell-free nucleic acids or from circulating tumor cells (CTCs).

In some cases, the target nucleic acid may make up only a very small portion of the entire sample, e.g., less than 1%, less than 0.5%, less than 0.1%, less than 0.01%, less than 0.001%, less than 0.0001%, less than 0.00001%, less than 0.000001%, or less than 0.0000001% of the total nucleic acids in a sample. In some cases, the target nucleic acid may make up from about 0.00001% to about 0.5% of the total nucleic acids in a sample. Often, the total nucleic acids in an original sample may vary. For example, total cell-free nucleic acids (e.g., DNA, mRNA, RNA) may be in a range of 1-100 ng/ml, e.g., (about 1, 5, 10, 20, 30, 40, 50, 80, 100 ng/ml). In some cases, the total concentration of cell-free nucleic acids in a sample is outside of this range (e.g., less than 1 ng/ml; in other cases, the total concentration is greater than 100 ng/ml). This may be the case with cell-free nucleic acid (e.g., DNA) samples that are predominantly made up of human DNA and/or RNA. In such samples, pathogen target nucleic acids or cancer target nucleic acids may have scant presence compared to the human or healthy nucleic acids, for example with a sample from a subject undergoing chemotherapy. For example, pathogen target nucleic acids may make up less than 0.001% of total nucleic acids in a sample, and cancer target nucleic acids may make up less than 1% of total nucleic acids in a sample.

The length of target nucleic acids can vary. In some cases, target nucleic acids may be about or at least about 20, 30, 40, 50, 60, 70, 80, 90, 100, 110, 120, 130, 140, 150, 160, 170, 180, 190, 200, 250, 300, 350, 400, 450, 500, 750, 1000, 1500, 2000, 3000, 4000, 5000, 10000, 15000, 20000, 25000, or 50000 nucleotides (or base pairs) in length. In some cases, target nucleic acids may be up to about 20, 30, 40, 50, 60, 70, 80, 90, 100, 110, 120, 130, 140, 150, 160, 170, 180, 190, 200, 250, 300, 350, 400, 450, 500, 750, 1000, 1500, 2000, 3000, 4000, 5000, 10000, 15000, 20000, 25000, or 50000 nucleotides (or base pairs) in length. In some particular embodiments, the target nucleic acids are relatively short, e.g., less than 500 base pairs (or nucleotides) or less than 1000 base pairs (or nucleotides) in length. In some cases, the target nucleic acids are relatively long, e.g., greater than 1000, greater than 1500, greater than 2000, greater than 2500, greater than 3000, or greater than 5000 base pairs (or nucleotides) in length. In some cases, target nucleic acids may be in the range from about 20 to about 120 base pairs. In some cases, target nucleic acids may be in the range from about 40 to about 100 base pairs.

As is the case with the sample nucleic acids, the target nucleic acids may be any type of nucleic acid including: double-stranded (ds) nucleic acids, single stranded (ss) nucleic acids, DNA, RNA, cDNA, mRNA, cRNA, tRNA, ribosomal RNA, dsDNA, ssDNA, miRNA, siRNA, circulating nucleic acids, circulating cell-free nucleic acids, circulating DNA, circulating RNA, cell-free nucleic acids, cell-free DNA, cell-free RNA, circulating cell-free DNA, cell-free dsDNA, cell-free ssDNA, circulating cell-free RNA, genomic DNA, exosomes, cell-free pathogen nucleic acids, circulating pathogen nucleic acids, mitochondrial nucleic acids, non-mitochondrial nucleic acids, nuclear DNA, nuclear RNA, chromosomal DNA, circulating tumor DNA, circulating tumor RNA, circular nucleic acids, circular DNA, circular RNA, circular single-stranded DNA, circular double-stranded DNA, plasmids, or any combination thereof. The target nucleic acids are preferably nucleic acids derived from pathogens including but not limited to viruses, bacteria, fungi, parasites and any other microbe, particularly an infectious microbe. The target nucleic acids may be nucleic acids derived from a particular organ or tissue. In some cases, the target nucleic acids are derived directly from the subject, as opposed to a pathogen.

Spike-In Synthetic Nucleic Acids

This disclosure describes single synthetic nucleic acids and sets of synthetic nucleic acids for use in a variety of applications, particularly related to high-throughput or next generation sequencing assays. In some cases, when used in the described methods, the spike-in synthetic nucleic acids may allow efficient normalization of nucleic acids (e.g., disease-specific nucleic acids, pathogen nucleic acids) across samples, e.g., independent of the individual from which it was derived, the pre-analytical sample handling conditions, the method of nucleic acid extraction, the nucleic acid manipulations with molecular biology tools and methods, the methods of nucleic acid purification, the act of the measurement itself, the storage conditions, and the passage of time. In some cases, this disclosure provides pools or sets of synthetic nucleic acids having particular characteristics, such as high numbers of unique sequences. The sets of synthetic nucleic acids may be used to monitor diversity loss during the course of sample analysis, which can, in turn, be used to determine the abundance of starting nucleic acids. The synthetic nucleic acids provided herein may also be used to track samples, to monitor cross-contamination between samples, to track reagents, to track reagent lots, and numerous other applications. Often, the design, length, quantity, concentration, diversity level, and sequence of the synthetic nucleic acids may be tailored for a particular application. In some cases, spike-in synthetic nucleic acids include carrier synthetic nucleic acids (e.g., carrier synthetic nucleic acids) described herein.

Collections (or sets) of synthetic nucleic acids provided herein may contain several species of synthetic nucleic acids. In some cases, the lengths, concentrations, and/or sequences of the species may be the same or similar. In some cases, the lengths, concentrations, and/or sequences of the species may differ.

In preferred embodiments, the species of synthetic nucleic acids differ in length. For example, the collection of synthetic nucleic acid species may collectively span the observable range of lengths of certain target nucleic acids in a sample, or at least a portion of such observable range. For example, the species may collectively span the lengths of disease-specific or pathogen-specific nucleic acids in a sample, particularly a sample obtained from a subject that is infected by, or suspected of being infected by, a pathogen. In some cases, the lengths of disease-specific or pathogen-specific nucleic acids in a sample may be in the range from about 40 to about 100 base pairs. In some cases, the species may collectively span the lengths of a variety of different disease-specific or pathogen-specific nucleic acids in a sample. The species may, in some instances, collectively span the lengths of particular pathogen-specific nucleic acids, such as nucleic acids within a particular pathogen genome. In some cases, the nucleic acids may be specific nucleic acids within a pathogen genome, such as nucleic acids within a virulence region of the pathogen, antibiotic-resistance region of the pathogen, or other region or specific nucleic acid or gene. In some cases, the lengths or nucleic acids may be specific to a particular type of infection (e.g., acute, chronic, active, or latent). In other examples, the species may collectively span the lengths of certain subject nucleic acids in a sample (e.g., from an infected subject) and/or pathogen nucleic acids.

The lengths of the species of synthetic nucleic acids within a collection may exactly match the lengths of particular target nucleic acids (e.g., observable range of pathogen- or disease-specific nucleic acids in a sample). In other cases, the lengths of the species of synthetic nucleic acids within a collection of synthetic nucleic acids may closely match the lengths of target nucleic acids, or substantially match such lengths. For example, the lengths of the species of synthetic nucleic acids may be within 50%-150% of the length of the target nucleic acids, within 55%-145% of the length of the target nucleic acids, within 60%-140% of the length of the target nucleic acids, within 65%-135% of the length of the target nucleic acids, within 70%-130% of the length of the target nucleic acids, within 75%-125% of the length of the target nucleic acids, within 80%-120% of the length of the target nucleic acids, within 85%-115% of the length of the target nucleic acids, within 90%-110% of the length of the target nucleic acids, within 95%-105% of the length of the target nucleic acids, within 96%-104% of the length of the target nucleic acids, within 99%-101% of the length of the target nucleic acids, or within 99.5%-100.5% of the length of the target nucleic acids. In some cases, the lengths of the species of synthetic nucleic acids may be within 50%-150% of the length of the target nucleic acids. In some cases, the lengths of the species of synthetic nucleic acids may be up to twice, three times, four times, or five times the length of the target nucleic acids. In some cases, the lengths of the species of synthetic nucleic acids may be within 1, 2, 3, 4, 5, 10, 20, 30, 40, 50, 60, 70, 80, 90, 100, 125, 150, or 200 nucleotides of the length of the target nucleic acids. In some cases, a species of synthetic nucleic acids within the collection is greater than 65%, 75%, 80%, 85%, 90%, 92%, 95%, 97%, or 99% of the length of the most closely-matched target nucleic acids.

Each or most nucleic acid "species" within a collection (or pool) of synthetic nucleic acids disclosed herein may contain one or more domains or regions of interest. In some cases, the domain or region of interest is a length identifier sequence. The length identifier sequence may contain a code pre-determined to indicate or signify a particular length; often such length identifier may be a short sequence, e.g., 10 base pairs (bp), 9 bp, 8 bp, 7 bp, 6 bp, 5 bp, 4 bp, or 3 bp; less than 9 bp, less than 8 bp, less than 7 bp, or less than 6 bp; or from 6-15 bp, 5-10 bp, 4-8 bp, or 6-9 bp. The species may contain 1, 2, or more length identifier sequences. In some cases, the length identifier is present as a forward and/or reverse sequence.

In some cases, the domain within the nucleic acid species within the collection of synthetic nucleic acids may be a load sequence of a particular length, generally corresponding to the length coded by the length-identifying sequence in the synthetic nucleic acids, if present. The length of a spike-in nucleic acid or load can vary. In some cases, the entire spike-in nucleic acid may be about or at least about 20, 30, 40, 50, 60, 70, 80, 90, 100, 110, 120, 130, 140, 150, 160, 170, 180, 190, 200, 250, 300, 350, 400, 450, or 500 nucleotides in length. In some cases, a spike-in nucleic acid may be up to about 20, 30, 40, 50, 60, 70, 80, 90, 100, 110, 120, 130, 140, 150, 160, 170, 180, 190, 200, 250, 300, 350, 400, 450, or 500 nucleotides in length. In some cases, a spike-in nucleic acid may be in the range from about 20 to about 200 base pairs, such as from about 20 to about 120 base pairs. In some cases, the length of the load sequence domain within the spike-in nucleic acid may be about or at least about 20, 30, 40, 50, 60, 70, 80, 90, 100, 110, 120, 130, 140, 150, 160, 170, 180, 190, 200, 250, 300, 350, 400, 450, or 500 nucleotides in length. In some cases, the length of the load sequence domain within the spike-in nucleic acid may be up to about 20, 30, 40, 50, 60, 70, 80, 90, 100, 110, 120, 130, 140, 150, 160, 170, 180, 190, 200, 250, 300, 350, 400, 450, or 500 nucleotides in length. In some cases, the length of the load sequence domain within the spike-in nucleic acid may be within the range from 0 to about 200 bp.

The domain within a nucleic acids species within a collection of synthetic nucleic acids may be a synthetic nucleic acid identifying sequence (e.g., Spark-identifying sequence, Spank-identifying sequence) that comprises a unique code signifying that the nucleic acid is a spike-in as opposed to part of the original sample. Generally, the unique code is a code not present in the original sample or in the pool of target nucleic acids. The synthetic-nucleic acid identifying sequence may comprise a specific number of bps, e.g., 25 bp, 20 bp, 19 bp, 18 bp, 16 bp, 15 bp, 12 bp, 10 bp, or other length. The species may contain 1, 2, or more synthetic-nucleic acid identifying sequences or domains. In some cases, the synthetic-nucleic acid identifying sequence is present as a forward and/or reverse sequence.

In some cases, a domain within a nucleic acid species within a collection of synthetic nucleic acids may be a "diversity code" associated with the overall pool or collection of synthetic acids. The diversity code domain may be a unique code signifying the amount of diversity within the pool of synthetic nucleic acids. In such cases, every synthetic nucleic acid within the diversity pool may be coded with a sequence signifying the degree of diversity (e.g., $10^8$ unique sequences) of the pool. In some cases, such as when two or more diversity pools are used on the same sample, the diversity codes may be used to identify diversity loss in the two or more pools.

In some cases, the domain within a nucleic acid species within a collection of synthetic nucleic acids may be a feature domain associated with one or features of the sample, or the reagent, depending on the applications. For example, the feature domain may comprise a sequence coded to signify a particular reagent; a particular reagent lot; or a particular sample (e.g., sample number, patient number, patient name, patient age, patient gender, patient race, location where sample was obtained from patient).

The domains or regions of interest may be present in any combination and number. For example, the synthetic nucleic acids may comprise: one or more length-identifier sequences, one or more load sequences, one or more synthetic nucleic acid-identifier sequences, one or more diversity codes, and/or one or more feature domains in any combination or ratio. For example, in some cases the synthetic nucleic acid contains a length-identifier sequence and a load sequence. In some cases, the synthetic nucleic acid contains a synthetic nucleic acid-identifier sequence and a feature domain sequence. In some cases, the synthetic nucleic acid contains a synthetic nucleic acid identifier sequence, while in other cases, it does not contain such sequence.

The synthetic nucleic acids may, in some instances, contain a domain with an overlapping purpose. For example, in some cases, the synthetic nucleic acid contains one or more length-identifier sequences that also serve as the load sequence. In some cases, the length identifier sequence and/or the load sequence serve also as synthetic nucleic acid identifier sequences.

Synthetic or spike-in nucleic acids may be selected or designed to be compatible with a nucleic acid library. In some cases, synthetic nucleic acids or spike-ins can contain adapters, common sequences, random sequences, poly-(A) tails, blunt ends, or ragged ends, or any combination thereof. In some cases, synthetic nucleic acids or spike-ins are designed to mimic nucleic acids in a sample in one or more of these or other characteristics.

The synthetic nucleic acids provided here (e.g., spike-in synthetic nucleic acids) may contain any type of nucleic acid or a combination of nucleic acid types. In preferred embodiments, a synthetic or spike-in nucleic acid is DNA. In some cases, a synthetic or spike-in nucleic acid is single-stranded DNA. In some cases, a synthetic or spike-in nucleic acid is double-stranded DNA. In some cases, a synthetic or spike-in nucleic acid is RNA. In some cases, a synthetic or spike-in nucleic acid can contain modified bases or artificial bases. A double-stranded synthetic or spike-in nucleic acid can have blunt ends or recessed ends. A synthetic or spike-in nucleic acid can have phosphorylated or dephosphorylated ends. In some cases, the synthetic nucleic acids may contain double-stranded (ds) nucleic acids, single stranded (ss) nucleic acids, DNA, RNA, cDNA, mRNA, cRNA, tRNA, ribosomal RNA, dsDNA, ssDNA, snRNA, genomic DNA, oligonucleotides, duplex oligonucleotides, longer assembled duplex DNA (e.g., gBlocks from Integrated DNA Technologies), plasmids, PCR products, transcripts synthesized in vitro, viral particles, fragmented or unfragmented genomic DNA, circular nucleic acids, circular DNA, circular RNA, circular single-stranded DNA, circular double-stranded DNA, plasmids, or any combination thereof. The synthetic nucleic acids often may comprise nucleobases, such as adenine (A), cytosine (C), guanine (G), thymine (T) and/or uracil (U).

Synthetic nucleic acids may be or may comprise any synthetic nucleic acid or nucleic acid analogue. The synthetic nucleic acids may comprise a modified or altered phosphate backbone; modified pentose sugar (e.g., modified ribose or deoxyribose); or a modified or altered nucleobase (e.g., modified adenine (A), cytosine (C), guanine (G), thymine (T), uracil (U)). In some cases, the synthetic nucleic acid may comprise one or more modified bases such as 5-methylcytosine (m5C), pseudouridine (T), dihydrouridine (D), inosine (I), and/or 7-methylguanosine (m7G). In some cases, the synthetic nucleic acid may comprise peptide nucleic acid (PNA), bridged nucleic acid (BNA), analog nucleic acid, glycerol nucleic acid (GNA), threose nucleic acid (TNA), locked nucleic acid (LNA), 2'-O-methyl-substituted RNA, morpholino, or other synthetic polymers with nucleotide side chains. In some cases, synthetic nucleic acids may comprise DNA, RNA, PNA, LNA, BNA, or any combination thereof. In some cases, the synthetic nucleic acids may comprise a double helix or triple helix or other structure.

Synthetic nucleic acids may comprise any combination of any nucleotides. The nucleotides may be naturally occurring or synthetic. In some cases, the nucleotides may be oxidized or methylated. The nucleotides may include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate.

A synthetic or spike-in nucleic acid can refer to any molecule that is added to a sample and is not limited to molecules that are synthesized chemically, e.g., on a column. In some cases, a synthetic or spike-in nucleic acid can be synthesized, for example, by PCR amplification, in vitro transcription, or other template-based replications. In some cases, the synthetic or spike-in nucleic acid is or comprises sheared or otherwise fragmented nucleic acids. The sheared or fragmented nucleic acids may comprise genomic nucleic acids such as human or pathogen genomic nucleic acids. In some cases, the synthetic nucleic acids contain no human nucleic acids. In some cases, the synthetic nucleic acids contain no nucleic acids that can be found in nature. In some cases, the synthetic nucleic acids contain no sample nucleic acids.

The guanine-cytosine content (GC-content) of a spike-in or synthetic nucleic acid can vary. In some cases, GC-content of a spike-in or synthetic nucleic acid can be about or at least about 0%, 5%, 10%, 15%, 20%, 25%, 30%, 35%, 40%, 45%, 50%, 55%, 60%, 65%, 70%, 75%, 80%, 85%, 90%, 95%, or 100%. In some cases, GC-content can be up to about 5%, 10%, 15%, 20%, 25%, 30%, 35%, 40%, 45%, 50%, 55%, 60%, 65%, 70%, 75%, 80%, 85%, 90%, 95%, or 100%. In some cases, GC-content of a spike-in or synthetic nucleic acid can be within the range from about 15% to about 85%, such as from about 20% to about 80%. The GC-contents of the species of synthetic nucleic acids within a collection may exactly match the GC-contents of particular target nucleic acids (e.g., observable range of pathogen- or disease-specific nucleic acids in a sample). In other cases, the GC-contents of the species of synthetic nucleic acids within a collection of synthetic nucleic acids may closely match the GC-contents of target nucleic acids, or substantially match such GC-contents. For example, the GC-contents of the species of synthetic nucleic acids may be within 75%-125% of the GC-contents of the target nucleic acids, within 80%-120% of the GC-contents of the target nucleic acids, within 85%-115% of the GC-contents of the target nucleic acids, within 90%-110% of the GC-contents of the target nucleic acids, within 95%-105% of the GC-contents of the target nucleic acids, within 96%-104% of the GC-contents of the target nucleic acids, within 99%-101% of the GC-contents of the target nucleic acids, or within 99.5%-100.5% of the GC-contents of the target nucleic acids.

A spike-in nucleic acid may be attached, ligated or conjugated to a different molecule such as a bead, a fluorophore, a polymer. Examples of fluorophores include but are not limited to a fluorescent protein, Green Fluorescent Protein (GFP), Alexa dye, fluorescein, Red Fluorescent Protein (RFP), and Yellow Fluorescent Protein (YFP). A spike-in nucleic acid can be associated with a protein (e.g., histone, nucleic acid binding protein, DNA-binding protein, RNA-binding protein). In other cases, the spike-in nucleic acid is not associated with a protein. A spike-in nucleic acid can be particle-protected (e.g., similar to a nucleic acid in a virion). In some cases, a spike-in nucleic acid is encapsulated in or associated with a particle. In some cases, the particle comprises protein, lipids, metal, metal oxide, plastic, polymer, biopolymer, ceramics, or composite materials.

Spike-in nucleic acids can have sequences that differ from sequences potentially found in a sample or host. In some cases, spike-in nucleic acid sequences are naturally occurring. In some cases, spike-in nucleic acid sequences are not naturally occurring. In some cases, spike-in nucleic acid sequences are derived from a host. In some cases, spike-in nucleic acid sequences are not derived from a host. In some cases, the spike-in or synthetic nucleic acids are not capable of hybridizing (or are not complementary) to one or more target nucleic acids (e.g., pathogen nucleic acids, disease-specific nucleic acids) and/or to one or more sample nucleic acids.

The concentration of a spike-in nucleic acid in a sample can vary. Spike-ins can be added in a wide range of concentrations, which can be useful for determining sensitivity and sample loss. In some cases, about or at least about 0.1 million, 0.5 million, 1 million, 2 million, 3 million, 4 million, 5 million, 6 million, 7 million, 8 million, 9 million, 10 million, 20 million, 30 million, 40 million, 50 million, 60 million, 70 million, 80 million, 90 million, 100 million, 500 million, or 1,000 million (a billion) molecules of each spike-in nucleic acid are added to each mL of plasma or sample. In some cases, from about 10 million to about 1000 million molecules of each spike-in nucleic acid are added to each mL of plasma or sample. In some cases, the synthetic nucleic acids are spiked in at equimolar concentrations. In other cases, the synthetic nucleic acids are spiked in to the sample in different concentrations.

The number of different spike-in nucleic acids added to a sample can vary. Multiple spike-in nucleic acids can be added to a sample or reagent. In some cases, about or at least about 1, 2, 3, 4, 5, 6, 7, 8, 9, or 10 spike-in nucleic acids are added to a sample or reagent. In some cases, up to about 1, 2, 3, 4, 5, 6, 7, 8, 9, or 10 spike-in nucleic acids are added to a sample or reagent. In some cases, the spike-in nucleic acids added to a sample or reagent are the same length. In some cases, the spike-in nucleic acids added to a sample or reagent are different lengths. In some cases, the spike-in nucleic acids are selected from the group consisting of SEQ ID NOs 1-120 and any combination thereof.

The level of uniqueness of spike-in nucleic acids can vary. An essentially unlimited number of spike-ins (e.g., ID Spikes) can be designed or used.

The step in the process in which spike-in nucleic acids are added can vary. For sample tracking, earlier addition of spike-in nucleic acids may be better and reduce the subsequent likelihood of operator or system error. In some cases, the tube to which a sample (e.g., blood) is first added may already contain spike-in nucleic acids. Manufacturing of these tubes can be more systematically controlled and tested compared to adding the spike-in nucleic acids to the samples in a clinic or lab, thereby reducing the chance of sample mix-up. In some cases, an ID Spike may replace all external labels ("white label").

In some cases, identifying nucleic acid markers can be added to each nucleic acid fragment in a sample, so that every sequence read contains the identifying marker. This method would enable differentiating initial vs. downstream cross-contamination. If the tagging of fragments is complete enough, it could also allow intentionally multiplexing samples as soon as the barcodes are added to the sample fragments. Methods for incorporating the tags include, but are not limited to, transposons, terminal transferases, cutting at methylated sites, and cutting at demethylated sites.

For other applications, including but not limited to those involving process quality control or development work, spike-in nucleic acids can be added at different steps in the process. For example, for an RNA analysis, multiple RNA spike-ins, each at a different concentration, length, sequence, and/or GC content can be added at the beginning of sample preparation, and DNA spike-ins can be added after the RNA has been converted to DNA. For DNA libraries, different forms of DNA can be added at different steps of the library generation process. For example, to test an end repair step, DNA spike-ins with non-blunt ends, with +/−5'-phosphate, and with +/−3'-adenine extension can be used. To test a step that ligates adapters to end-repaired fragments, +/− pre-adapted spike-ins can be used. Sequencing or qPCR can quantify sample loss at individual steps. qPCR of spike-ins can also be used alongside other library quantification methods for final library assessment before sequencing.

The terms "spike-in", "spike-in synthetic nucleic acid," "spike," and "synthetic nucleic acid," are used interchangeably herein and should be interpreted as such, except in cases where context dictates a different interpretation. The term "ID Spikes" or "tracer" is generally used herein to refer to identification spikes that can be used, e.g., for sample identification tracking, for cross-contamination detection, for reagent tracking, or reagent lot tracking. The term "Sparks" is generally used herein to refer to nucleic acids that are size or length markers, which may be used for abundance normalization, development and/or analysis purposes, and other purposes. The term "Spanks" is generally used herein to refer to degenerate pools, or pools of nucleic acids with diverse sequences, and may often be used for diversity assessment and abundance calculation.

Universal Normalization of Nucleic Acid Measurements

This disclosure describes sets of synthetic nucleic acids, that when used in the described methods, may allow efficient and improved normalization of the amounts of disease-specific nucleic acids, pathogen-specific nucleic acids, or other target nucleic acids in a sample. The sets of spiked nucleic acids may contain several "species" of nucleic acids that differ in length, such that the collection of spiked nucleic acid species collectively spans the observable range of lengths in the pathogen nucleic acids, disease-specific nucleic acids or other target nucleic acids to be measured.

The spike-in synthetic nucleic acids may be used to normalize the sample in a number of different ways. Often, the normalization may be across samples, independent of the subject from which the sample was derived, the pre-analytical sample handling conditions, the method of nucleic acid extraction, the nucleic acid manipulations with molecular biology tools and methods, the methods of nucleic acid purification, the act of the measurement itself, the storage conditions, and/or the passage of time.

In some preferred embodiments, the spike-in nucleic acids may normalize across all samples and all methods of measuring disease-specific nucleic acids, pathogen-specific nucleic acids or other target nucleic acids. In some cases, the spike-ins may be used to determine relative abundance of a pathogen nucleic acid (or disease-specific nucleic acid or target nucleic acid) in a sample compared to other pathogen nucleic acids.

Generally, the methods provided herein involve spiking-in or introducing one or more sets of synthetic nucleic acids into a sample. This spike-in step may occur at any point of the entire method including early in the process, mid-way through, or towards the end. For example, the synthetic nucleic acids may be introduced at the time, or directly after, the sample is collected from the subject, prior to or during storage of the sample, prior to transfer of the sample, before or during nucleic acid extraction, before or during library preparation, directly before the sequencing assay or any other step of the method. In some cases, the method may comprise spiking a biological sample early in the process with a known amount of unique nucleic acid molecules that are measured by the same method, but readily distinguished from pathogen-specific or disease-specific nucleic acids, or other sample nucleic acids. In some cases, the biological sample is spiked with the synthetic nucleic acids at a single step in the process, e.g., when the sample is collected from the subject, when the sample is obtained in order to conduct analysis, during sample storage, before or during nucleic acid extraction, before or during library preparation, or directly before the sequencing assay. In other cases, the same or different spike-in synthetic nucleic acids are introduced at different steps of the process. For example, unique synthetic nucleic acids may be introduced early in the process, such as at sample collection, and a different set of unique synthetic nucleic acid may be introduced later in the process such as prior to or following extraction, purification, or library preparation. The spike-in step may also be repeated at different steps of the method using identical collections of spike-in nucleic acids, or collections that differ in some aspect.

In general, a known concentration (or concentrations) of species of synthetic nucleic acids may be spiked into each sample. In many cases, the species of synthetic nucleic acids are spiked in at equimolar concentration of each species. In some cases, the concentrations of the species of synthetic nucleic acids are different.

As the sample is processed and ultimately measured, the relative abundance of the nucleic acid species may be altered due to the inherent biases of the sample handling, preparation, and measurement. After measurement, the efficiency of recovering nucleic acids of each length can be determined by comparing the measured abundance of each "species" of spiked nucleic acid to the amount spiked in originally. This can yield a "length-based recovery profile".

The "length-based recovery profile" may be used to normalize the abundance of all (or most, or some) disease-specific nucleic acids, pathogen nucleic acids, or other target nucleic acids by normalizing the disease-specific nucleic acid abundances (or the abundances of the pathogen nucleic acids or other target nucleic acids) to the spiked molecule of the closest length, or to a function fitted to the spiked molecules of different lengths. This process may be applied to the disease-specific nucleic acids, and may result in an estimate of the "original length distribution of all disease-specific nucleic acids" at the time of spiking the sample. Similarly, this process may be applied to other target nucleic acids such as the pathogen-specific nucleic acids, and may result in an estimate of the "original length distribution of all pathogen-specific nucleic acids" at the time of spiking the sample. The "original length distribution of all target nucleic acids" may show the length distribution profile for the target nucleic acids (e.g., disease-specific nucleic acids, pathogen-specific nucleic acids) at the time of spiking the sample. It is this length distribution that the spiked nucleic acids can seek to recapitulate in order to achieve perfect or near-perfect abundance normalization.

As it may not be possible to spike a sample with a mixture of known nucleic acids that exactly recapitulates the relative abundance profile of disease-specific nucleic acids, pathogen nucleic acids, or other target nucleic acids in that specific sample, in part because the sample may have been used up or time may have changed the relative abundance profile, each "species" of spike-in can be weighted in proportion to its relative abundance within the "original length distribution of all disease-specific nucleic acids". The sum of all "weighting factors" can equal 1.0.

Normalization can involve a single step or a series of steps. In some cases, the abundance of disease-specific nucleic acids (or pathogen nucleic acids or other target nucleic acids) may be normalized using the raw measurement of the closest sized spiked nucleic acid abundance to yield the "Normalized disease-specific nucleic acid (or pathogen nucleic acids or other target nucleic acid) abundance". Then, the "Normalized disease-specific nucleic acid abundance" (or pathogen nucleic acids or other target nucleic acid abundance) may be multiplied by the "weighting factor" to adjust for the relative importance of recovering that length, yielding the "Weighted normalized disease-specific (or pathogen-specific or other target) nucleic acid abundance". One advantage of this method of normalization may be that it allows comparable measurements of target nucleic acid (e.g., disease-specific nucleic acid, pathogen nucleic acid) abundance across all (or most) methods of measuring disease-specific nucleic acid abundance, regardless of method.

The measurement of target nucleic acid abundance, or relative abundance may be especially useful for detection, prediction, monitoring and diagnostic assays. Such assays may involve measuring the amount of target nucleic acids (e.g., disease-specific nucleic acids) in biological samples (e.g., plasma) to detect the presence of a pathogen or identify disease states. The methods described herein can make these measurements comparable across samples, times of measurement, methods of nucleic acid extraction, methods of nucleic acid manipulation, methods of nucleic acid measurement, and/or a variety of sample handling conditions.

The exact sequence of the spiked molecules, the exact number of "species", the length range of the "species", the concentration of the spiked molecules, the relative amount of each molecule, the actual amount of each molecule spiked, and the stage at which the molecules are spiked can be optimized or tailored based on sample. Length can be replaced or analyzed with GC content, nucleic acid structure, DNA damage, or DNA modification status.

In some cases, the methods provided herein may comprise use of spiked nucleic acids containing a single length of nucleic acid, often with a largely fixed sequence composition (except for some short randomized portions in some methods). This method may work well when the disease-specific nucleic acids, pathogen-specific nucleic acids, or other target nucleic acids are of nearly identical length as the spiked nucleic acid.

Single-length nucleic acids may be used in isolation, or the method may be combined with another method involving use of multi-length nucleic acids. For example, a pool of multi-length nucleic acids may be spiked into a sample when the sample is obtained or prior to extraction of nucleic acids, and a pool of single-length nucleic acids may be spiked into the sample at a different point in the process such as following extraction of nucleic acids and prior to library preparation. When single-length and/or multi-length nucleic acids are used, the amount of disease-specific nucleic acids, pathogen nucleic acids, or other target nucleic acids may be normalized to the amount of spiked nucleic acid measured at the end of the method.

In many cases, use of synthetic nucleic acids with multiple lengths, as described herein, may be preferable to using a method involving use of synthetic nucleic acids of a single length. The methods provided herein are particularly useful when the target nucleic acids have multiple lengths. For example, disease-specific (or pathogen-specific) nucleic acids may be widely varied in length. As such, use of spike-in nucleic acids that span the observable lengths of the disease-specific nucleic acids may particularly helpful. Furthermore, the length of the measured disease-specific nucleic acids may also dramatically be affected by a number of factors, including the metabolism of the individual from which it was derived, the pre-analytical sample handling conditions, the method of nucleic acid extraction, the nucleic acid manipulations with molecular biology tools and methods, the methods of nucleic acid purification, the act of the measurement itself, the storage conditions, and the passage of time. These factors have differential effects on nucleic acids of different lengths, and therefore a single spiked nucleic acid may not adequately reflect the overall efficiency of a process performed on nucleic acids of mixed lengths.

Calculation of "Genome Copies Per Volume"

The methods and synthetic nucleic acids provided herein may be used to assist with certain calculations, including determining genome copies per volume of a microbe or pathogen in a sample from next generation sequencing results. In general, genome copies per volume may refer to an absolute measure of the amount of target nucleic acid (e.g., target nucleic acids derived from a specific pathogen) per 1 ml of fluid (e.g., plasma, urine, buffer, etc.) and may often be used as an expression to indicate the abundances, or relative abundance, of individual pathogens. The total number of reads and/or the magnitudes of the pathogen abundances may vary from sample to sample. It can be desirable to report a value that corresponds to the biological level of the infection and that can be useful for sample-to-sample comparisons.

In particular examples, the methods may be used to determine genome copies per volume of pathogen nucleic acids in a sample, especially a sample obtained from a subject infected by a pathogen, or suspected of being infected by a pathogen. The genome copies per volume may be determined or estimated using a statistical framework. The statistical framework can be used to estimate what the relative abundances are of one or more genomes that give rise to a collection of non-human reads (e.g., pathogen reads) in the sequencing results from a sample.

Using the spike-in synthetic nucleic acids provided herein, an estimate can be computed of the number of "genome copies per volume" of one or more pathogens/organisms in the sample. Generally, nucleic acids of various lengths may be spiked into the sample at known concentrations. In some cases, the fraction of information from the sample that is actually observed in the sequencing data can be observed for each spike-in length (e.g., by comparing observed reads with reads associated with the spiked nucleic acids, or by dividing the observed reads by the spike reads). The original numbers of non-host or pathogen molecules at each length can be back-calculated as well (e.g., inferred in part from the number of spike-in reads at each length). When the genome length of each pathogen is known, this load can be converted into a "genome copies per volume" measure.

In many cases, the methods for detecting genome copies per volume (as well as other methods provided herein) may involve removal or sequestration of low-quality reads. Removal of low-quality reads may improve the accuracy and reliability of the methods provided herein. In some cases, the method may comprise removal or sequestration of (in any combination): un-mappable reads, reads resulting from PCR duplicates, low-quality reads, adapter dimer reads, sequencing adapter reads, non-unique mapped reads, and/or reads mapping to an uninformative sequence.

In some cases, the sequence reads are mapped to a reference genome, and the reads not mapped to such reference genome are mapped to the target or pathogen genome or genomes. The reads, in some instances, may be mapped to a human reference genome (e.g., hg19), while remaining reads are mapped to a curated reference database of viral, bacterial, fungal, and other eukaryotic pathogens (e.g., fungi, protozoa, parasites).

In some particular examples, the method may comprise spiking a sample (e.g., plasma sample) with a known concentration of synthetic nucleic acids (e.g., DNA) prior to DNA extraction (e.g., cell-free DNA extraction, cell-free RNA extraction) or at a different stage of the assay (e.g., after extraction, before library preparation, before sequencing, during storage of the sample). The synthetic nucleic acids may also be added to negative and/or positive control samples. The control samples may, in some cases, be processed alongside the sample. The method may further comprise producing sequencing libraries for the samples (e.g., plasma sample, positive control, negative control). The libraries may be multiplexed and sequenced on a sequencing device known in the art, particularly a device capable of next generation sequencing. The method may further comprise discarding low quality reads and removing human reads by aligning to a human reference sequence (e.g., hg19). Remaining reads may be then aligned to a database of pathogen sequences. In some cases, reads corresponding to target sequences of interest (e.g., pathogen sequences) are quantified from NGS read sets. From this information, relative abundance of target nucleic acids (e.g., pathogen nucleic acids) may be expressed as genome copies per volume. The genome copies per volume value may be determined by, for example, determining the number of sequences present for each organism (e.g., pathogen) normalized to the known quantity of oligonucleotides spiked into the sample (e.g., plasma). The calculation of the genomes per volume may also take into account the relative length of the individual pathogen genome. In some cases, the genome copies per volume value may be determined by quantifying the number of sequences present for each organism (e.g., pathogen), normalizing to the known quantity of synthetic nucleic acids spiked into the sample, wherein the normalization of a pathogen sequence takes into account the synthetic nucleic acid that is closest in length to the pathogen sequence. Similarly, the normalization may involve use of a collection of spike-in synthetic nucleic acids of different lengths (e.g., 2, 3, 4, 5, 6, 10, 15, 20 or more different lengths), wherein the pathogen nucleic acids are normalized in relation to the respective closest-in-length spike-in nucleic acid within the collection of spike-ins.

Spike-Ins for Sample Tracking and/or Analysis

Molecules can be spiked into samples to provide unique identifiers and tracers. These molecules may become part of the sample and can be read by an appropriate measurement device, a concept analogous to the 1D or 2D barcodes on the outside of sample tubes that are read by laser scanners. Optical, radioactive, and other tracers are possible, but for analyzing nucleic acid samples, nucleic acid tracers can be the most appropriate choice because the identity of the spike-ins can be revealed in the same process (e.g., DNA or RNA sequencing) that assesses the nucleic acids of the sample.

Externally derived nucleic acids can include, but are not limited to, oligonucleotides, duplex oligonucleotides, longer assembled duplex DNA (e.g., gBlocks from Integrated DNA Technologies), plasmids, PCR products, transcripts synthesized in vitro, viral particles, and fragmented or unfragmented genomic DNA, and they can be added to a sample such as a body fluid from a subject. Advantages to using spike-ins include, but are not limited to, the ability to tailor the nucleic acid sequence, length, diversity, and concentration for a sample or application.

Applications include, but are not limited to, sample tracking (e.g., ID Spikes can be used in addition to, or potentially instead of, traditional label barcodes), sample cross-contamination (e.g., if the ID Spikes are not found naturally in any of the samples and if different ID Spikes are added to different samples, mixing of samples can be determined), reagent tracking (e.g., ID Spikes can also be added to reagents. For example, every reagent lot can be tracked for every sample for which it is used, providing a less error-prone reagent-tracking molecular laboratory information management system (LIMS)), quality control or development work (e.g., different spike-ins can be added at various times in the sample handling process to monitor library complexity (e.g., PCR duplicates), sample loss, or sensitivity), normalization or yield (e.g., comparing a known input with a measured output of the spike-ins can enable inferences of unknown input (e.g., in the sample) with its measured output. These measurements and calculations can inform pathogen load of samples, for example), and increasing nucleic acid concentrations (e.g., if the barcodes are nucleic acids, they can be used in high concentrations for samples whose nucleic acid concentration is limiting, which can improve sample recoveries).

In some preferred embodiments, the spike-ins can be used to estimate the likelihood that a particular nucleic acid sequence of interest originated from the sample in which it was observed, or whether its presence in the observed sample could be a result of cross-contamination or carry-over from a different sample. By introducing unique spike-in molecules into each sample at a concentration that is higher than the concentration reasonably expected for molecules from a particular pathogen (or other sequence class of interest), it is likely that any pathogen sequence (or other sequence class of interest) accidentally introduced by cross-contamination or carry-over will be accompanied by an even greater number of spike-in molecules from the source of the contaminating or carry-over sequences. Therefore, the ratio of pathogen sequence count (or other class of sequences) to cross-contaminating or carry-over spike-in molecule counts can be used to identify any pathogen sequences that could be a result of sample-to-sample cross-contamination or carry-over. In some cases, the absence of a cross-contaminating or carry-over spike-in molecule, or its presence at a level below a threshold level, is used to indicate that the sample has not been contaminated.

For some applications, the genotype of the subject from which the sample is derived can be used, particularly for sample-tracking. In some cases, the genotype can be determined during the analysis procedure or by removing an aliquot and doing a separate genotyping process. In some cases, the sample's genotype is already known. The sequencing output of the subject's DNA can be compared to the independently derived genotype. An advantage of using genotype is that it is already part of and intrinsic to the sample. An exemplary orthogonal genotyping method is short tandem repeat (STR) analysis, see, e.g., ATCC's testing service.

In some cases, phenotypic characteristics can aid in sample identification. For example, a subject's eye color, blood type, gender, race, and other traits could provide clues to the genotype.

ID Spikes

Unique sample identifiers can be completely scrambled (e.g., randomers of A, C, G, and T for DNA or A, C, G, and U for RNA) or they can have some regions of shared sequence. For example, a shared region on each end may reduce sequence biases in ligation events. In some cases, a shared region is about or at least about 1, 2, 3, 4, 5, 6, 7, 8, 9, 10, 15, or 20 common base pairs. In some cases, a shared region is up to about 1, 2, 3, 4, 5, 6, 7, 8, 9, 10, 15, or 20 common base pairs. See Table 1 for exemplary sequences.

Combinations of ID Spikes can be added to increase diversity without having to use an overwhelming number of ID Spikes. For example, ID Spikes can be used as identifiers for well position in a microtiter plate (e.g., 96 different ID Spikes for a 96-well plate), and another ID Spike can be used as an identifier for a plate number (e.g., 24 different ID Spikes for 24 different plates), giving 96×24=2,304 combinations using only 96+24=120 sequences. Using 3 or more ID Spikes per sample can increase the achievable diversity even more dramatically.

TABLE 1

Exemplary ID Spike sequences

| SEQ ID NO | Name | Sequence |
| --- | --- | --- |
| SEQ ID NO: 1 | ID_028_100 bp | ACGTTGTCTGCGAGTCAGCTAATCCTATCCTGGTGCAT GCTTGACTTGTCACCGAGGTAATCATCGAATCCTGGAT GAGGACGCAAGAGATGTATGGTCA |
| SEQ ID NO: 2 | ID_029_100 bp | ACGTCGAATCCTACGCGACTGCGCGTGACTAGGTGAA GGTGAACTTAGAGGCTCTCAACCTCATCCACTCGGTAT CATCCTGTGTGTATCAAGAGAGTCA |
| SEQ ID NO: 3 | ID_030_100 bp | ACGTGAGTGAGAGTACTCAATCAATCTTCTCCGCACCG TGAATGCGTGAGTGTGGCCAATGCCGCCATCAACGATT CTACTGAGCGAGTGCTCGCAGTCA |
| SEQ ID NO: 4 | ID_031_100 bp | ACGTTGGTCTCAATGCCTGTGACGGACATAACGCATTA AGGACCGATATGGTAGAACTGTTCCTCATGTGACTAGG AGGTAATCCTGGCGCATAACGTCA |
| SEQ ID NO: 5 | ID_032_100 bp | ACGTACAACTATGGTATGTCCACTGAGCGGCAACCAG GTTCTCATCATCGCTGCGGAGAAGTCACGTAATATTCT GAAGGTAGTGGCGTGTAGACGGTCA |
| SEQ ID NO: 6 | ID_033_100 bp | ACGTCGTATGCAACGTATATGGAATTATCTGTGTACGT GCATACGTGACCAACAACCAGACGGCACCGATCATCT TAGTCGCCGAGAGATCTAATTGTCA |
| SEQ ID NO: 7 | ID_034_100 bp | ACGTACGGCATTGTTCTCAGGAACGTGTGTTCATACGA TCTTCGACTCTAGCATATCCAACGTCGAAGTTATCATT ACCGAGCCGGAACAACGTCGGTCA |
| SEQ ID NO: 8 | ID_035_100 bp | ACGTACCGTTAAGTGCTGTTGAAGAATATGAGTCTATA GGTTCCGGACCTGTTGCGACGTGCGATGGCTACTTACG CATTAACCAGTGTTGTATAGGTCA |

TABLE 1-continued

Exemplary ID Spike sequences

| SEQ ID NO | Name | Sequence |
|---|---|---|
| SEQ ID NO: 9 | ID_036_100 bp | ACGTTGACCAAGAGGACGATACTTGGATAAGTTCTTGC TATATGAGCGCGGTCAACGTGAAGGCCGATATCGCGC CAATCTTCACGATGGAGCTTCGTCA |
| SEQ ID NO: 10 | ID_037_100 bp | ACGTCCTGAATCATCGACTGAACCGGCTTACTAGGAAT TAGTCAGCGCATAATATACTCCAATGAATGTTCTGAGC TCGACGCTCTTGCCGGAGTGGTCA |
| SEQ ID NO: 11 | ID_038_100 bp | ACGTTCTGTCTATACGTATATGCTAAGCGCAATATGAT TCAATGGTAGTCACTTCGTCCGACGGCGAGTAACGCAC CACGTGTCCATTCTCTGGAGGTCA |
| SEQ ID NO: 12 | ID_039_100 bp | ACGTTACTGGTGACGGATGCCTCTCCTGACCGAGTATC TAGGCACCACACGGACGTTGACAGGCATGCTTAATCC GGTGATGAACGGATCGGTCCTGTCA |
| SEQ ID NO: 13 | ID_040_100 bp | ACGTGAGGCGTCTCGCGATGTCAAGTGAATATGATGC AGTTCTGACTGCACACCACACGAGGTCGCTTGAAGTCG ATGACTCCGCATAGTCATTCAGTCA |
| SEQ ID NO: 14 | ID_041_100 bp | ACGTCGCACGTATGACGTGCGAGGTTAGAGTTGGCCT ACTACTTAGATAATCTTGCCGCATGCTTATTAACTAGA ACGGTTGCCGAATTGCACCTGGTCA |
| SEQ ID NO: 15 | ID_042_100 bp | ACGTCACTTATGCACGACTCAACTTGAGGTAAGCGTGT AGAGAAGCCTTGATAGTCTTGTCGTCGCGGCGGAGAT CTCCGTTACCTTCACACTTGGGTCA |
| SEQ ID NO: 16 | ID_043_100 bp | ACGTTCCGATAGATAAGCACAAGTCAGCGAAGCCTTG TCCGCTGTGTAACATATATCATCGAATGCGATAGTCGG TTGGAACGCGATCTGACGTACGTCA |
| SEQ ID NO: 17 | ID_044_100 bp | ACGTCCAGCATTCAATAAGCATCGACTCTTAGTGCGGT GTGGAGTGTACTTCCATGTGACAACTCGAGTAGACCG ATTAGGCTGCTGACAAGTTAGGTCA |
| SEQ ID NO: 18 | ID_045_100 bp | ACGTGGAATAGAGATGGTAAGCCACCGGCTTCGGTGC CTTGGCACGTGAGACCTATAGCTTAGTGCTCATCCATC GTTATCTACGACGAACATCGCGTCA |
| SEQ ID NO: 19 | ID_046_100 bp | ACGTGCCGCGTGTTGTGTACCGTACAGTGTTCTAGAAG TCTATTGGATTGGCTAGCTAGCGAGATTACCGACGCTA CTCAACAGAGTGGAGCTCATGTCA |
| SEQ ID NO: 20 | ID_047_100 bp | ACGTAACTAGCGATCGCAGAGGCTAAGGCGTACAGTT CGTGGTTCGCGTCCACGTAGGCCGTTATCTGCTTACTT CCGTAGGTACTGAGAGATTCAGTCA |
| SEQ ID NO: 21 | ID_048_100 bp | ACGTAGGCCGGATGTGACTGATGATTCATCTCAGCAGC ATAGCCTTCACGTGTAGCGGCTTATCACGCTGAGTTCG TTCCAACAGCTGGATAGTAGGTCA |
| SEQ ID NO: 22 | ID_049_100 bp | ACGTTATGTACACGTGAAGCTGGCGCGTGCGCGCTACT TATATTACGGAGGTTAGTTCATCAATATCAGAGAAGTT CCTCATGTATACATGAATTCGTCA |
| SEQ ID NO: 23 | ID_050_100 bp | ACGTCTGGTACAGACGGATGCTGCTTGTCCAATTATGG TGACTAACTCCTAATCATCAGCAATCGCGAGTCCGGTA AGCGTCCGCGACTGATCGCCGTCA |
| SEQ ID NO: 24 | ID_051_100 bp | ACGTGTTATACCGTACCGGTAGGAACACAAGTGTACCT GGTGAGATAGGTTCCATGCTTCTGGCGACCTGACAATC TACAGCAGACTAGTATGCGGGTCA |
| SEQ ID NO: 25 | ID_052_100 bp | ACGTTGCGGCCAGGACAATCATATCGCAATGATCATG ACTGTGATTCAACGGACTCGCGTCATGAGATGAATCTG CCAGAGTATGTCGGCTCTGGAGTCA |
| SEQ ID NO: 26 | ID_053_100 bp | ACGTTGAGAGATAATTGAGCGATACTGTTATCGCGGCT ATACATAGCTCTCACCTCATGGACAGCGTAGGATTGTG AATAGCTGCTCCACTCGTCCGTCA |
| SEQ ID NO: 27 | ID_054_100 bp | ACGTACGGAAGACGGCAAGTTCTTGATCTTCACGCATC TGCCGCTATTGCAATATGTGGTATGACGTGATAACTAG CCGGCGTCCGACGTAACATGGTCA |

TABLE 1-continued

Exemplary ID Spike sequences

| SEQ ID NO | Name | Sequence |
|---|---|---|
| SEQ ID NO: 28 | ID_055_100 bp | ACGTCATCGATCGTAGGCGCTTCCGGCAAGGACCTAGT AGACTTCCAGATTGGACTTCTACGGCTCGGATATTATA CCGTCTCAAGGAACGGTGCTGTCA |
| SEQ ID NO: 29 | ID_056_100 bp | ACGTCCTGCGCCTTAAGGCGCATCGCTTGTTACCAGGA TTAAGGATACGTCGTCGAATGCGCAGGTCTAGGATTGT TGTTGCTATAGAACTAATACGTCA |
| SEQ ID NO: 30 | ID_057_100 bp | ACGTCAGGCGTACATCGAACTGCTTACTCTCACGTCTG TCCGTATCAGGTTGACCTAACGCGTCTGGTGGCAAGCT AATACTGAGCATAGCAGTAGGTCA |
| SEQ ID NO: 31 | ID_058_100 bp | ACGTTACGCAATGTGTCATACGCGCATCTGAGTTCAGA CTGCAATCACGCTGACGCACGACTATATGGTTGCCTCC GAGTACTTGGTACTAGGTCGGTCA |
| SEQ ID NO: 32 | ID_059_100 bp | ACGTTTGACAGCGCGCTAGCAATCTGATGCAGTTGACG TGTTCCGTATTCCTAGTTGACACATACAACGTCCTCAC GTGTCGAAGACCGTATTCGTGTCA |
| SEQ ID NO: 33 | ID_060_100 bp | ACGTTTCTGCCTCTTAAGCTGTGAAGCAAGCCGCTTAG TCAGGACTGTATTCCAACTGTTCCAGCTTCCGGTTGAA CACTGTATCAGGCAACGAGCGTCA |
| SEQ ID NO: 34 | ID_061_100 bp | ACGTACTACTCACCAATTGGCCAATACAGTTAGTATCA GCTGGAGCCGTGAGACTTATGCTTCGGATGACTTCAGT TGGCTAATTGGAGGCGACCAGTCA |
| SEQ ID NO: 35 | ID_062_100 bp | ACGTGATTAGATAATGAGTCCACACGCATCTTGTGTTG GACTGCAGCGTTAACAATGACGATGCCTTGCGTTACGG CGCTATCTTCATTAGGACTCGTCA |
| SEQ ID NO: 36 | ID_063_100 bp | ACGTGAGATACGCGCCTGACGGATACCGTGACCGTAT ATGTCCAGGTTATGAGAGAACATGACTTGAGAGAGTC TGGCACTTCCTTGACGTGTCCGGTCA |
| SEQ ID NO: 37 | ID_064_100 bp | ACGTCAGCGGCGTTGGTCACACGTCAACACCTCTCGTA GAATCTGCTGCAGCTCCTGTCGTTCAGTAGGCTAAGCA CTGAGGTAGTAAGGCTCAGTGTCA |
| SEQ ID NO: 38 | ID_065_100 bp | ACGTACTTCCTACTCCTTCGTGTGAGGAAGGTGCCACG GTGATGTGTCACGTAGTCTCGGAATATATGGCCACACT ACTTCCATGCAACTGCGGATGTCA |
| SEQ ID NO: 39 | ID_066_100 bp | ACGTGTGGCCTCTAGGAAGGAAGGTGCAACCAGCTAC TTGATAGACGTCGACTAGCATACTACTCCTCACGTGTG CTGTGCGAGTATGAGTTCCTAGTCA |
| SEQ ID NO: 40 | ID_067_100 bp | ACGTATTCGAATTGATGCGGACTACCACTAGCAACGCC GTTGATAATAGCAAGATGGAACGTACTTGTACCTTGCC TGAGGCGCTCGATTAACGCGGTCA |
| SEQ ID NO: 41 | ID_068_100 bp | ACGTAGCAACGTGTTAAGACTTGCGACAACGGTCCTG CGGAAGGTACTGATACTTACATTATTAGACTGCAGTTG ACTACCGTGTAAGTGGACGTCGTCA |
| SEQ ID NO: 42 | ID_069_100 bp | ACGTAATTCGAGCAGGCTACACTGGCTTAAGTAGGCT GTGTTCAGTAGCGTACACATTCTACAACGTCCGAGCCA CATCGATATGTGCCTAAGTCGGTCA |
| SEQ ID NO: 43 | ID_070_100 bp | ACGTTAGGAATTGGCTGTGGTTCATTCGGCTGAATCTC GCCAACAACTCTCGATTGTTAAGGCACTTAAGAAGCA GAGTCGGCCGCCAATCTGGTAGTCA |
| SEQ ID NO: 44 | ID_071_100 bp | ACGTTCTTGAACCAGTGAGAAGTCAGCATAGTAACTCT CTGGTCAATTAACATAGACCATCGTCTCGGATTGCGTG GTCGACGCCTGCCAGAATGAGTCA |
| SEQ ID NO: 45 | ID_072_100 bp | ACGTGGAATGAGGAATAGGATGCTAAGACAGGACAGA ACTCTGACCATAGGCTCCTCATTGTGGCTTGAGATCTT CTTCCACGAACCGTCCGGCACGTCA |
| SEQ ID NO: 46 | ID_073_100 bp | ACGTCTGACGACTACTGAGATCACCTAGTTCGGATGAA TGCGCCATTCATGCGGAGGTATACGAGCTTACGTCGGA TCCTAGCGCGTACTGACGTGGTCA |

TABLE 1-continued

Exemplary ID Spike sequences

| SEQ ID NO | Name | Sequence |
|---|---|---|
| SEQ ID NO: 47 | ID_074_100 bp | ACGTAGGCACTATTCTAACTATTCTTAAGGCAGAGGCG AACGGTTAGTTATCCGCGCTCAGATAAGCCTCCTTACA GATCCGATATCAATGCTGGCGTCA |
| SEQ ID NO: 48 | ID_075_100 bp | ACGTCGCTTCATGGACAATTAGTTACTGCTTACAGCCA GCACAGTGGTACTAACGATCGCCGTTAGCGCAACGCC TGAGATTATCGTAGTTGAATGGTCA |
| SEQ ID NO: 49 | ID_076_100 bp | ACGTGAGTCAGTAGTCTCCAGTCATCACGAGCGAATC GAGCTCGGTGAACAGTCGTGAACAATATACCTGGTTC AGATACGTATATAGTCAGTGCCGTCA |
| SEQ ID NO: 50 | ID_077_100 bp | ACGTAGAATTCCACGTTACTGATGACCGGTAGATGAA GTTAGAGAGTAGCGCTCACTGTCGAACATCGACGCAA TTGTACTGTGTAACGTGCCATGGTCA |
| SEQ ID NO: 51 | ID_078_100 bp | ACGTCTCTTGCGCCGATATCCACTCTAAGATGTGCCAC GCGTAATCTAATAGAAGGAGCCGGAGCCGTAGTGGTA CCATCAACTTGACTGGTACTAGTCA |
| SEQ ID NO: 52 | ID_079_100 bp | ACGTCCTAAGTGCGGAAGTCCTAATTGTTGGTACGGTA TGCAAGCTTGTACGACCTTCTGCTACCTTATATAGAAG TACACAGTCGGAAGCGTCGGGTCA |
| SEQ ID NO: 53 | ID_080_100 bp | ACGTGTGAACAAGATGATCCGGTATCCAGTAGGACCG TCATAAGATCACGAGTTACCACGTAGAGTCAATTGGAT AGTCCTGGCGGTTATGCTAGTGTCA |
| SEQ ID NO: 54 | ID_081_100 bp | ACGTCGGCCGTAATCGCTTGTATCTGCTACAGTGCATT GTGGCGCACTAGAGTAATACGGATATAGGTTCTCACA CATGCGCATCCAGGCGCATGGGTCA |
| SEQ ID NO: 55 | ID_082_100 bp | ACGTGGCAACTACCGACCTGTAATTGCTAGTCGACGCA TACGGTGTCCGTGCTGGTTCTTGGTGCGATCATATCAC CAGTTGAAGCAGTGATCTGAGTCA |
| SEQ ID NO: 56 | ID_083_100 bp | ACGTCAATCGTACCGCTCTAAGTCCACGTGAACTTGCT CTCCACAATGTAATAAGAAGTTCGCCGCTGCGGACGG AGAAGGTTGCTAGATTAGGCTGTCA |
| SEQ ID NO: 57 | ID_084_100 bp | ACGTCAGCCTTATTAGCAACATACACATCGCTCGCGAT ATGTAAGAATGGTACTCTTGCTCCAAGGTGGAGCGTGT AAGAACCGTTGGTTGCTGACGTCA |
| SEQ ID NO: 58 | ID_085_100 bp | ACGTGCTCCTTGGAGGAGCATGATATAGTAACCTTCAG TTCTAACAGTCTTATACCGCTTCGAGCTAGCTCGCAAT GGCAACAACTTCATCGGAAGGTCA |
| SEQ ID NO: 59 | ID_086_100 bp | ACGTAGCTGGTAACGTGGTTAGCCACCAGATCTCGCA GGAGCCATAGGTGTATTCGCATATGAATCTTCGGCGAC ATACGTCGGATATGCAGAGTCGTCA |
| SEQ ID NO: 60 | ID_087_100 bp | ACGTCATAGCTGCCGATCACCTATGGCATAACTCATTC TACCAATTAGTCGGCAGGTGGCATGTACGCAGTGTGAT GCTCCAATGGCTTCTGAGTGGTCA |
| SEQ ID NO: 61 | ID_088_100 bp | ACGTCAAGCGAGTGTTAACTGTCTACTCCACCGATGCA TGAGTCAACAAGCCATCCTGTCTGCGCTGGTGATTACT CTTAAGAGTCCATAGGCGAGGTCA |
| SEQ ID NO: 62 | ID_089_100 bp | ACGTCCATATAGCGCGCTGCGAAGCTACACTACAGCG CATGATTGAATCAGGCCTTCTTAATTCAGGAGTCAGAT ATTCAGTGGCGCGGCGAGGACGTCA |
| SEQ ID NO: 63 | ID_090_100 bp | ACGTGATCAGCGGTATCTCGTCATACGAATATCGTGAA CGTTACGCCTAATTCCATGGTAGACTCGATGGCGCAAG AAGCGACCGAGTATCTGTTCGTCA |
| SEQ ID NO: 64 | ID_091_100 bp | ACGTTCTTGTTAATGGTTGATAGCAACAAGGCGAGTAG TCCGAATAGCTCCGGAATCACACTGTTCTCCACGACGG TAGCCATCTTGCGTCTTAGCGTCA |
| SEQ ID NO: 65 | ID_092_100 bp | ACGTAGCTGGAGAGACAACTAGATCGGCGTCAATATC TGAGCGGTATAATATGCTTGGAATGCTAGCTGTATTGG CTCTCTCTCAATCTGGTAGTGGTCA |

TABLE 1-continued

Exemplary ID Spike sequences

| SEQ ID NO | Name | Sequence |
|---|---|---|
| SEQ ID NO: 66 | ID_093_100 bp | ACGTTCATCAACAGAAGGAGAGACTGATACGATTAGC GCCATCCTGTTAGTGGCTCTTAACAGGCCGGTAGCGAT TCTGGCCATGGTATTCCGATGGTCA |
| SEQ ID NO: 67 | ID_094_100 bp | ACGTGTGTGCTTAGCACTACGTGTCGTGAGTCCGTGAT AGTCCGTTGGTATGTCACTCACTTGGCTAACGCCAAGA TACGTTCAGCATTAATCCAAGTCA |
| SEQ ID NO: 68 | ID_095_100 bp | ACGTGAAGGCACTCTTATGGTAGTCGCAGCGTGATATT GTCCGACCATTGTGAGGATCGCACGGTACTCATCTTAC TGCCAATAGTGCTCCAGTAGGTCA |
| SEQ ID NO: 69 | ID_096_100 bp | ACGTGAATCTCTGCAACGCGGAGACTGCCTCGGTTGTA AGCTACCACGTAGTCAGAACTCCGCGTCGCATATTGGC TATGATATTACGGAAGACCGGTCA |
| SEQ ID NO: 70 | ID_097_100 bp | ACGTTGTAGCACCGTCCGTCCAACTAGAGTTATACGAA GTGCTCGCCAGTTCATGATCGCTGCACTGCCAGGCTGT CACCTGTAGCTACAGTGCTTGTCA |
| SEQ ID NO: 71 | ID_098_100 bp | ACGTACTGTATCTGTAGCTGCGGTAGTGCTGACATTGT ACAAGAGCGTCCGTGCCACAGATACATCGACACGCAT GCGTTCGCCAGGTTAAGCGTGGTCA |
| SEQ ID NO: 72 | ID_099_100 bp | ACGTCGCGTCTCGTCGTAGGTAGTCAATCCTTGCAACC GCGCATAAGGACAGCATGAGGTGTCTATCTTATAAGA TAGACTAGAGGTTACGTGAGAGTCA |
| SEQ ID NO: 73 | ID_100_100 bp | ACGTTGCGGCAAGCAAGTAGCATTGAGACTGTTCACA GGACGACTACAGATGGCTCGTACACCTCCATACCTGGT TGCCGTTAGCTTGGACAGCGTGTCA |
| SEQ ID NO: 74 | ID_101_100 bp | ACGTGATGTGCGTCATCCGGAACCAACGCATTGTATGA TAACATACGGCTTGCGACCAGACGTTATCTCATAGACG TCGCGGCCTCCGCAAGGTAGGTCA |
| SEQ ID NO: 75 | ID_102_100 bp | ACGTACCAGGTGTTGACCGGAGTACGGCAACTCGCGC AGGTGTGCACGTACCTATCACGGTAGTAATACTAGTAA CACGTCGATACTGTATAGATCGTCA |
| SEQ ID NO: 76 | ID_103_100 bp | ACGTATACACTCTGCGCGCACCACGATACGGCTAACGT GCGATATCAGTCCATGTCACAACTCTGGCGTGGTAATG TAGCTTCTTGGAGTCGCTTAGTCA |
| SEQ ID NO: 77 | ID_104_100 bp | ACGTAACATCGTGGACGTGTCTAAGCTCCTGGAGAAT AGACTCGTTATTGGCATCACGTCACTTGCACGCGTATAT TCCGTCTGCCGATATGGTCCTGTCA |
| SEQ ID NO: 78 | ID_105_100 bp | ACGTCTAGCGTGTAGTTGTCGGCTCCTCAAGTACTCAA GACCGCCTCTGGTGCGTCGAGAGCTCACTGCGTAGGA CATATGCTGACACGTTAGTTAGTCA |
| SEQ ID NO: 79 | ID_106_100 bp | ACGTAGATAAGTCCGTACTAAGCGTATTCTCACTGGAT TCATGCTGAACGTAGAACTGCTATAGTCCACGTGCTAC GCCGTTGACCGACGTACGAAGTCA |
| SEQ ID NO: 80 | ID_107_100 bp | ACGTCTCTGTCGATCACACGCCGGACGCACTGTTACTT GACTGGAGGTGACCTTCGCACCAATAACGTTGAAGAG CTAGATTAGATGGTAGAACGAGTCA |
| SEQ ID NO: 81 | ID_108_100 bp | ACGTGGACCTGCTCGCCATAACGCGGATCGGTCCTGCG ATGTATCAACTGATGATTGACACACAGCGCAAGTATG ACCGTTAGATAATTCAGCTCGGTCA |
| SEQ ID NO: 82 | ID_109_100 bp | ACGTACCAACCACGCGTCGGTGAGCCGTGATACTCGA TCTACCTAGGATATTGCACTTCCTGGCGGTATGCGACC GATCTTCGTGTTCAAGGAATCGTCA |
| SEQ ID NO: 83 | ID_110_100 bp | ACGTTACTAACGTGGCCGAGGCAACTTCATGGTGAATT GCTCTAGGCCTACTATGTACCGCCAGTGACTCGGCAGA CCGACAGAACCGCAATACGGGTCA |
| SEQ ID NO: 84 | ID_111_100 bp | ACGTAGACCAGCTGGCGCGACGTCTGCGAGCAGTCTC CTGAGAGGTGTGTGTCTCACTACTCAAGTACTCTGGCA CAGGCCGCATTAATTGGATTGGTCA |

TABLE 1-continued

Exemplary ID Spike sequences

| SEQ ID NO | Name | Sequence |
|---|---|---|
| SEQ ID NO: 85 | ID_112_100 bp | ACGTTACTATGCTTGCCGTACGGTTGTCGATGAGGTCG GTACAGCAGAATCGACTAGGTATAAGACCGACATGCT CAATTAGTCTGTCACCTCATAGTCA |
| SEQ ID NO: 86 | ID_113_100 bp | ACGTTACTAGGAGACCGTAATTAGTAGTGTAACCTAGC GACAGCCGCGTACCGCAACTTCACTTGGTATTGCTGCT ATCCATTAGGTGTCACGCGAGTCA |
| SEQ ID NO: 87 | ID_114_100 bp | ACGTCTAAGTCCGCCGAAGGCATATGTGAATTCACCTG GAGACTGCCATTCACTCCGTTGAAGTACTAGTTACGGA GCTGCTAGTGCACAGAGGAAGTCA |
| SEQ ID NO: 88 | ID_115_100 bp | ACGTCACAGACCGGATTACGGTATTAGTTGCTGGAGG CGCACGCACGTCGCCGTATCAGTAAGGTGATTCCTGCG TATACTGGCCGGAAGCAGAATGTCA |
| SEQ ID NO: 89 | ID_116_100 bp | ACGTGCAGTCGCGATGACGGCTCGATCGCGAACTAAT TCTGAGCTGTAGACCGATGATCTGGTGGTAAGGCTATC ACTGTCAGTGCATCGAGCACTGTCA |
| SEQ ID NO: 90 | ID_117_100 bp | ACGTATTGGATATACAAGGATTATTGGCACGTAGTCAT ACGCACAGTGCCATGGCAAGTTGGCTTCTTACCACCTG GCCACCGTCGATCAGTGCAAGTCA |
| SEQ ID NO: 91 | ID_118_100 bp | ACGTCGCCGTCAAGGAATATGGCCATTCATGACAGAC GGAACTCGTCGCATCTGTGTTCATAAGGAGGACGAAT CTGCATCGACGTGGTCCTCGCAGTCA |
| SEQ ID NO: 92 | ID_119_100 bp | ACGTACAGCGCTGACAGGACTGGCGCAACTAGGAATG TCAGCACCTGGATCGGCTTAGAGGTGTGTCGATGTATC TGCTGCTAGTGTAACTCCTCTGTCA |
| SEQ ID NO: 93 | ID_120_100 bp | ACGTGCGGCCTGTGCGATTAGTCTTAAGCGGATCGAGT TATCCGCAAGCAGATTACAAGAAGCGTTCCTACATGA GTATTCCTGCATCGTATGGTAGTCA |
| SEQ ID NO: 94 | ID_121_100 bp | ACGTTGTATTCACTCGAGCTCCGCTGCACCTTCGGAAT TGAGAGAGTGGCAATCTCATGGACAGTCGTCGTCGTG CGCTAAGGTACAGTATTAGACGTCA |
| SEQ ID NO: 95 | ID_122_100 bp | ACGTAGTGCCGAACATGCGTGAGCTCGCCTCGGAATT AGGCCTTGGCTAAGAACTACTAAGGTATAGGCACTAA TACGCGGCTGTGGCAACATGATGTCA |
| SEQ ID NO: 96 | ID_123_100 bp | ACGTAAGGCGGCATCATTCCTCTGAGGTGACTCAAGTG CCAACCTCATTGTATAGTGGCTTAAGTTCATGCGGCAC TCTGAGAGGAACACGTATAAGTCA |
| SEQ ID NO: 97 | ID_124_100 bp | ACGTGTCATATGACGAGGATTCGCACGGTCGGTACAC ATGCCGTCTCTCCAGGTTACATTATTCGAAGTGTGTCC ATGCGGAAGACGGATGTCTCCGTCA |
| SEQ ID NO: 98 | ID_125_100 bp | ACGTTTGGACAGTGACGGAACTAATAGTTATGTCGCGT AACTCTCCGCTGATAATACATGCTAACGAGCCACGAGT TCTTGGCGAGGTCCACAAGGGTCA |
| SEQ ID NO: 99 | ID_126_100 bp | ACGTAGAGCCACTCTCCATATCGATCTCCTCTATAGTC GTAGGTCGGCTACTGTGAGCAGGTGGAGTGACTGAAG CTTGCAAGGACGAGATTCATAGTCA |
| SEQ ID NO: 100 | ID_127_100 bp | ACGTAAGCGATAGGATAGCAGTATCCGACCAGCCTAG CGTGGCACATTCCGCATTCTCAGGCAGTTACCATGTAT ATCTCTCAAGAATGCGGTTGAGTCA |
| SEQ ID NO: 101 | ID_128_100 bp | ACGTTGGTACATAGGAGGTTGACGCGCGACCATCTGC AGTTACCACTCCGACTGTATGTTCTGTCGGCGGCAATG CGGAATGTACATGCGGATGATGTCA |
| SEQ ID NO: 102 | ID_129_100 bp | ACGTAGTGTTGTTGTTCTGGCCTCTAGGAGAAGATTCA TACTTGCAAGACCGTACTACTAGACGAGTTACAGTCAT CCAGTAATCGGCGTGCCACAGTCA |
| SEQ ID NO: 103 | ID_130_100 bp | ACGTCTTCCTAGGAGTCGAGGTATGAGTTGTCCAGTTC GTTCTAGATCCTCAAGGTCCTATAAGGCTCCAACGACC GAGCAGCGGAATATGACCGTGTCA |

TABLE 1-continued

Exemplary ID Spike sequences

| SEQ ID NO | Name | Sequence |
|---|---|---|
| SEQ ID NO: 104 | ID_131_100 bp | ACGTGGCTCTATCGAGTTGTCGACTACAAGAATGCGAC TTGGTATCGGCCTACGAGACTCAACGTGGAAGTAAGG AGCCACAAGGTATCACTCGTAGTCA |
| SEQ ID NO: 105 | ID_132_100 bp | ACGTTATGAGATATAACGTCGCAGCGTGCTTCCGCATC GCGCAGACCATTAATGGTAATCCTAGACCTGGTACTTA GTCCGCAGGTTGTGTGAATAGTCA |
| SEQ ID NO: 106 | ID_133_100 bp | ACGTCCAGGAGGACCTTATGTGTCGAATATGGTCTGTA GGAGCATCCGTCCACATCTGATACTGAGTTAGCGCCAA CATCGGCCGGCGATCTAGACGTCA |
| SEQ ID NO: 107 | ID_134_100 bp | ACGTGTCTAACTGATCAGAGGAGGTGTAGTGCTCGTGT CCTAACCGCACCACACGATTCGGTGCCAGCACGTAGA TCGGACGTGTCGGTACATATAGTCA |
| SEQ ID NO: 108 | ID_135_100 bp | ACGTGATTGCTGATAACGAGTTCTCACAAGGACAGTTA TATGGCGAACTGTCTGTCGTCACTCAGTCGGCATTGAA CTCGCGCATCGGCGTAAGACGTCA |
| SEQ ID NO: 109 | ID_136_100 bp | ACGTGAGGACACTAGTGTACGTGCTCGTACCATTCCTG TTAGGTGATGCCTAATAACCTGTAATGCAGATAGAGTT ACAGCTTCTACCGCCGACAAGTCA |
| SEQ ID NO: 110 | ID_137_100 bp | ACGTCGTTCCTGACCGTACATAGAGCGGCTACCGAGCT CACTGTTGGTAGCATAGTAGTCCAGTAATGTCGAGCGG ATCGCATAACAAGGCTTGATGTCA |

Spark Bias Control Spike-Ins

A set of nucleic acid sequences spanning multiple lengths ("Sparks") can act as size markers. These sequences can be spiked into samples and processed (e.g., extraction, purification, sequencing) along with the sample nucleic acids. Certain processes may differentially affect nucleic acids of different lengths. For example, nucleic acid purification using silica membrane columns may be biased toward longer length sequences or optimized to retain sequences of specific lengths. As nucleic acid sequencing typically occurs after nucleic acids are extracted from a sample, the prevalence or distribution of lengths in sequencing results may not be representative of the original sample. By spiking in known quantities and lengths of Spark sequences, the effect of processing and sequencing on sample nucleic acids of different lengths can be monitored and quantified. In addition, relative and/or absolute quantities of sample nucleic acids of different lengths in the original sample can be estimated by measuring the final number of sequencing reads for the sample nucleic acids and the Spark size set nucleic acids and normalizing against the known quantity of Spark size set nucleic acids spiked into the original sample.

In some cases, a Spark size set can include about or at least about 3, 4, 5, 6, 7, 8, 9, 10, 11, 12, 13, 14, 15, 20, 25, 30, 35, 40, 45, 50, 100, 200, 250, 300, 350, 400, 500, 600, 700, 800, 1000 or more nucleic acids. In some cases, a Spark size set can include up to about 3, 4, 5, 6, 7, 8, 9, 10, 11, 12, 13, 14, 15, 20, 25, 30, 35, 40, 45, 50, 100, or 200 nucleic acids. In some cases, a Spark size set includes from about 3 to about 50 nucleic acids, such as from about 3 to about 30 nucleic acids. In some cases, the nucleic acids in a Spark size set have one or more different properties, such as different lengths, different GC contents, and/or different sequences.

The Spark nucleic acids may comprise any of the features of the synthetic spike-in nucleic acids described herein, including length-identifying sequences, load sequences, synthetic nucleic acid identifying sequences (which, here would be Spark-identifying sequences), and feature domains. In some cases, the nucleic acids in a Spark size set contain a fixed forward sequence and/or a fixed reverse sequence. The fixed forward sequence and/or fixed reverse sequence can be common to all nucleic acids in the Spark size set and identify a sequence as a Spark. In some cases, the fixed forward sequence and/or fixed reverse sequence is about or at least about 5, 10, 11, 12, 13, 14, 15, 16, 17, 18, 19, 20, 25, 30, 32, 40, 50, 60, 70, 80, 90, or 100 base pairs in length. In some cases, the fixed forward sequence and/or fixed reverse sequence is up to about 5, 10, 11, 12, 13, 14, 15, 16, 17, 18, 19, 20, 25, 30, 32, 40, 50, 60, 70, 80, 90, or 100 base pairs in length. In some cases, the fixed forward sequence and/or fixed reverse sequence is within the range from about 8 bp to about 50 bp, such as from about 8 bp to about 20 bp or from about 16 bp to about 40 bp. In some cases, the Spark-identifying sequence is not naturally occurring or not found in the sample. In some cases, the fixed forward sequence is different than the fixed reverse sequence.

In some cases, the nucleic acids in a Spark size set contain a unique forward sequence and/or a unique reverse sequence. The unique forward sequence and/or unique reverse sequence can distinguish Sparks in the size set from each other. In some cases, the unique forward sequence and/or unique reverse sequence is about or at least about 0, 1, 2, 3, 4, 5, 6, 7, 8, 9, 10, 11, 12, 13, 14, 15, 16, 17, 18, 19, 20, 25, 30, 32, 40, 50, 60, 70, 80, 90, or 100 base pairs in length. In some cases, the unique forward sequence and/or unique reverse sequence is up to about 1, 2, 3, 4, 5, 6, 7, 8, 9, 10, 11, 12, 13, 14, 15, 16, 17, 18, 19, 20, 25, 30, 32, 40, 50, 60, 70, 80, 90, 100, 200, 300, 306, 400, or 500 base pairs in length. In some cases, the unique forward sequence and/or unique reverse sequence is within the range from about 4 to about 10 base pairs in length. In some cases, each nucleic acid in a Spark size set has a different unique forward sequence and/or unique reverse sequence. In some cases, each nucleic acid in a Spark size set has a unique forward sequence and/or unique reverse sequence with the same length. In some cases, each nucleic acid in a Spark size set has a unique forward sequence and/or unique reverse sequence with a different length.

In some cases, the nucleic acids in a Spark size set contain a filler sequence. In some cases, the filler sequence can distinguish Sparks in the size set from each other. In some cases, the filler sequence is about or at least about 0, 1, 2, 3, 4, 5, 6, 7, 8, 9, 10, 11, 12, 13, 14, 15, 16, 17, 18, 19, 20, 25, 30, 32, 40, 50, 60, 70, 80, 90, or 100 base pairs in length. In some cases, the filler sequence is up to about 1, 2, 3, 4, 5, 6, 7, 8, 9, 10, 11, 12, 13, 14, 15, 16, 17, 18, 19, 20, 25, 30, 32, 40, 50, 60, 70, 80, 90, 100, 200, 300, 306, 400, or 500 base pairs in length. In some cases, the filler sequence is within the range from 0 to about 350 bp. In some cases, each nucleic acid in a Spark size set has a filler sequence with a different length. In some cases, the filler sequence length is selected from the group consisting of 0, 8, 31, 56, 81, 106, 131, and 306 bp.

In some cases, the nucleic acids in a Spark size set are about or at least about 10, 20, 30, 32, 40, 50, 60, 70, 80, 90, or 100 base pairs in length. In some cases, the nucleic acids in a Spark size set are up to about 100, 200, 300, 350, 400, 500, 600, 700, 800, 900, or 1,000 base pairs in length. In some cases, the nucleic acids in a Spark size set are within the range from about 20 to about 500 base pairs in length, within the range from about 20 to about 400 base pairs in length, or within the range from about 20 to about 200 base pairs in length.

Figure 4:
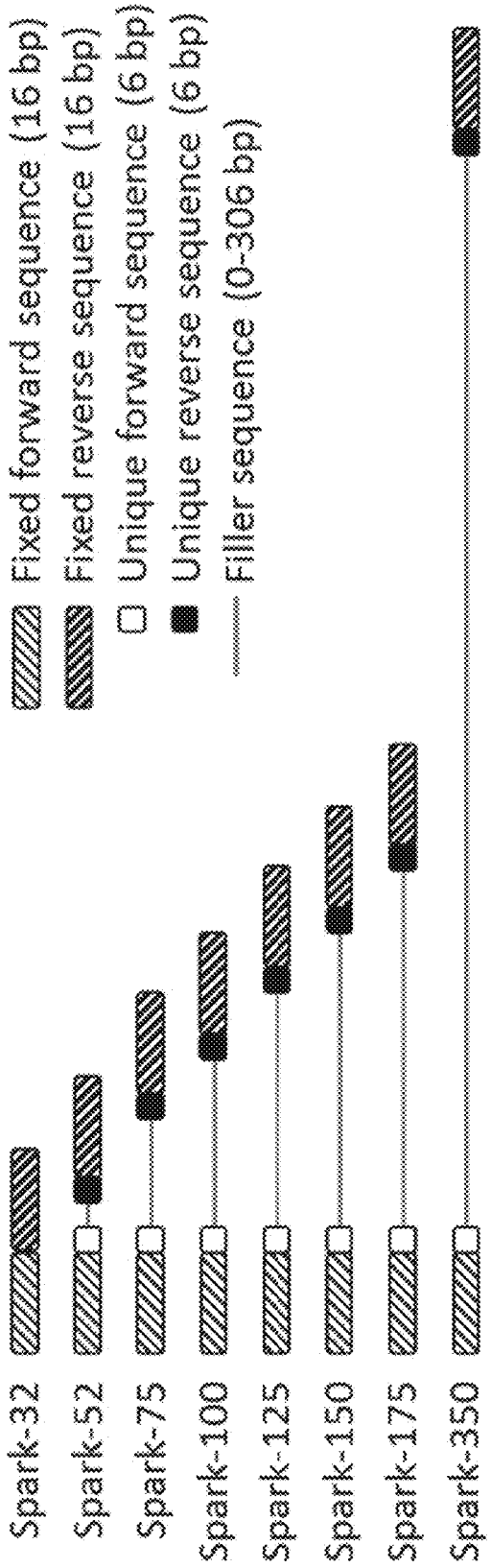
FIG. 4 depicts a design of 8 exemplary Spark size set spike-ins.

For example, a set of 8 duplex DNA sequences (SEQ ID NOs: 111-118 in Table 2, FIG. 4) can be designed with the following characteristics: a size range of 32-350 bp (e.g., fragments of 32, 52, 75, 100, 125, 150, 175, and 350 bp with filler sequence lengths of 0, 8, 31, 56, 81, 106, 131, and 306 bp, respectively), a fixed 16 bp forward sequence, a fixed 16 bp reverse sequence that is different from the forward sequence, and unique 6 bp forward and reverse sequences.

TABLE 2

Exemplary Spark size set sequences

| SEQ ID NO | Name | Length (bp) | Sequence |
|---|---|---|---|
| SEQ ID NO: 111 | Spark-032 | 32 | TAGTCAGTACAGCTGCTGCACGATACGTGTAC |
| SEQ ID NO: 112 | Spark-052 | 52 | TAGTCAGTACAGCTGCGTCTACAGTCTGCCTGCT GTTGCACGATACGTGTAC |
| SEQ ID NO: 113 | Spark-075 | 75 | TAGTCAGTACAGCTGCAGTGCAAGTCTGCCTTCA TCCTAAGTCACCGTCATTAGATGAGTGCACGATA CGTGTAC |
| SEQ ID NO: 114 | Spark-100 | 100 | TAGTCAGTACAGCTGCCGCATAAGTCTGCCTTCA TCCTAAGTCACCGTCATTAGGTTCACGTGCACTT CAGGATCTGCACTCAGTGCACGATACGTGTAC |
| SEQ ID NO: 115 | Spark-125 | 125 | TAGTCAGTACAGCTGCCTCAGTAGTCTGCCTTCA TCCTAAGTCACCGTCATTAGGTTCACGTGCACTT CAGGATCTGCTATTACAGCGCGGAAGATGCCTG CGCTGTCATGCACGATACGTGTAC |
| SEQ ID NO: 116 | Spark-150 | 150 | TAGTCAGTACAGCTGCCATCTGAGTCTGCCTTCA TCCTAAGTCACCGTCATTAGGTTCACGTGCACTT CAGGATCTGCTATTACAGCGCGGAAGATGCCTG CGACCAACGATCTAACACTTATATTGAGACATCT GCACGATACGTGTAC |
| SEQ ID NO: 117 | Spark-175 | 175 | TAGTCAGTACAGCTGCTCGCTAAGTCTGCCTTCA TCCTAAGTCACCGTCATTAGGTTCACGTGCACTT CAGGATCTGCTATTACAGCGCGGAAGATGCCTG CGACCAACGATCTAACACTTATATTGATCCGAAT CAATCATATGAGTGTTGATCTGCTTGCACGATAC GTGTAC |
| SEQ ID NO: 118 | Spark-350 | 350 | TAGTCAGTACAGCTGCGCTACAAGTCTGCCTTCA TCCTAAGTCACCGTCATTAGGTTCACGTGCACTT CAGGATCTGCTATTACAGCGCGGAAGATGCCTG CGACCAACGATCTAACACTTATATTGATCCGAAT CAATCATATGAGTGTTGACCGGACATCGGCGTGT GGTGGCCGTGGAATCACTTATTCCATGGCTCCTG CCGCGATGTATATGTCGACAGCGAGTTAGATAC GACAGATAAGTCGACGCGTGCCTTGTAGCCGTA CAACGCATATGTCTTCATTCCTGATAGAGTGTCG GTACTCATAGGAGTGAACCTATACGGTATCGTGC ACGATACGTGTAC |
| SEQ ID NO: 121 | Spark 100.3a | 100 | ACGCGGAGTGAACGCTGTATAATCCAGTGTCGT ATGATTCGTCTATCCTGTTCGGATGAAGGCACCT GCGACGAAGGTATGAAGCATTGCCACGCACATT |

TABLE 2-continued

Exemplary Spark size set sequences

| SEQ ID NO | Name | Length (bp) | Sequence |
|---|---|---|---|
| SEQ ID NO: 122 | Spark 125.3a | 125 | GTCTCCAATTAGAGGTCCTACCACGACACTTATT GGCGATCGATATAGACTGGTGACGCTGACCGGC ACCTCCAGTCCGGCTGATCAGGACTATCGTGAA GCGGTTCTAGTTCCGTAACTGTGTT |
| SEQ ID NO: 123 | Spark 150.3a | 150 | TGCTATACGGAACGGTCTCTAGGCGAACAAGTG AGGAATGTCAACAGAGACTAACATCGATATTCT CCTCGTCATTACTGTTGACGTAATTGCTCCGATG TCGCGCGCGGTCATGCCAGCTATACTGGCTAAG AGTTACTATCCATATAC |
| SEQ ID NO: 124 | Spark 175.3a | 175 | AGCTGATGGACAATATCGCCACCTGCGACTGCT AGGCATGCTGCTATAAGCGAGGCTCCTACTAAG CGCTCGCTGTACTGGTGCGGAGGACTAGGAGTT CAATACGTGCGCCATTAACGGACGTATCGAGCA GACGGAACTGCTTGGATCACCACTTCATGTTAGT TCTTGGAGA |

GC Content Spike-In Panel

Nucleic acids (e.g., DNA) spiked at known concentrations into samples and then measured after processing can provide yield and other information about the process, which can be used to infer yield and additional properties about the sample itself. For example, a nucleic acid spike-in set comprising a range of sizes can be added to a sample (e.g., plasma) and then subjected to extraction and then next-generation sequencing (NGS). The yield of each sized spike can vary depending on many factors during processing, including intentional size selection, temperature and other denaturation factors, and PCR biases. This information can be useful for developing new procedures aimed at maximizing recovery of desired size ranges, or for monitoring an existing process (e.g., quality control).

For double-stranded DNA library preparations, denaturation of relatively low melting temperature ($T_m$) DNA duplexes reduces the yield of these duplexes in inverse proportion to the $T_m$. For a given condition (e.g., salt concentration, temperature, pH, etc.), contributing factors affecting $T_m$ of a duplex include length and GC content. A size range of duplexes, each size represented with a single species with a single GC content, can provide only partial information about the $T_m$ response to different conditions.

Information on how nucleic acid length and/or GC content affects nucleic acid $T_m$ and processing can be important, for example, when using spike-ins as a surrogate to infer the recovery of short cell-free fragments from different pathogens in blood. Pathogen nucleic acids can vary dramatically in their GC content and thus may have very different $T_m$'s at short fragment lengths. Given the short length (e.g., 30, 40, 50 bp) of many cfDNA fragments, they can be susceptible to denaturation during processing for NGS, for example. A more detailed spike-in set to track recovery across a large $T_m$ range may allow better inference of the starting quantity of unknown samples.

A panel of spike-in nucleic acids that spans a range of $T_m$'s, GCs, and/or lengths can be used for absolute abundance value determination and/or to enable detailed monitoring of denaturation. For example, a panel of 28 different nucleic acids (e.g., duplexes) can be used that contains nucleic acids with 4 different lengths (e.g., 32, 42, 52, and 75 bp) and for each length 7 different GC contents (approximately 20, 30, 40, 50, 60, 70, or 80% GC), shown in Table 3. Together the panel can provide more granularity than a set with a single GC content for each size. In some cases, a panel of synthetic nucleic acids (dsDNA, ssDNA, dsRNA, ssRNA) may contain nucleic acids of at least 3 different lengths and for each length at least 2 different GC contents, at least 3 GC contents, at least 4 GC contents, at least 5 GC contents, at least 7 GC contents or at least 10 GC contents. In some cases, a panel of synthetic nucleic acids (dsDNA, ssDNA, dsRNA, ssRNA) may contain nucleic acids of at least 5 different lengths and for each length at least 2 different GC contents, at least 3 GC contents, at least 4 GC contents, at least 5 GC contents, at least 7 GC contents or at least 10 GC contents.

In some cases, a spike-in panel comprises at least 3, 5, 10, 15, 20, 25, or 30 unique nucleic acids. In some cases, a spike-in panel comprises up to 15, 20, 25, 30, 35, 40, 45, 50, or 100 unique nucleic acids.

Spike-in nucleic acids with different GC contents can be used. In some cases, a spike-in panel comprises nucleic acids with GC contents spanning the range of about 40-60% GC, about 45-65% GC, about 30-70% GC, about 25-75% GC, or about 20-80% GC. In some cases, a spike-in panel comprises nucleic acids with at least 2, 3, 4, 5, 6, 7, 8, 9, or 10 different GC contents. In some cases, a spike-in panel comprises nucleic acids with up to 3, 4, 5, 6, 7, 8, 9, 10, 15, or 20 different GC contents. In some cases, a spike-in panel comprises nucleic acids with different GC contents that differ by at least 1, 2, 3, 4, 5, 6, 7, 8, 9, 10, 15, or 20% GC. Percentage GC can be calculated by dividing the sum of the number of G and C nucleotides by the number of total nucleotides in a sequence. For example, for the sequence ACTG, the % GC would be calculated as (1+1)/4=50% GC.

Spike-in nucleic acids with different lengths can be used. In some cases, a spike-in panel comprises nucleic acids with at least 3, 4, 5, 6, 7, 8, 9, 10, or 15 different lengths. In some cases, a spike-in panel comprises nucleic acids with up to 3, 4, 5, 6, 7, 8, 9, 10, 15, 20, 25, 50, or 100 different lengths. In some cases, a spike-in panel comprises nucleic acids with lengths spanning the range of about 40-50 bp, about 35-55 bp, about 30-60 bp, about 35-60 bp, about 35-65 bp, about 35-70 bp, about 35-75 bp, about 30-70 bp, about 30-80 bp, about 30-90 bp, about 30-100 bp, about 25-150 bp, about 20-300 bp, or about 20-500 bp. In some cases, a spike-in panel comprises nucleic acids with different lengths that differ by at least 1, 2, 3, 4, 5, 6, 7, 8, 9, 10, 15, or 20 bp. In some cases, a spike-in panel comprises nucleic acids with lengths of 32, 42, 52, and 75 bp or lengths of 27, 37, 47, 57, 62, and 67 bp.

Spike-in nucleic acids with lengths and GC contents picked from a set of values can be used. For example, a set of synthetic nucleic acids can be selected from two or more lengths and two or more GC contents. The set of 28 synthetic nucleic acids in Table 3 (SEQ ID NO: 125-SEQ ID NO: 152) is formed from four different lengths (e.g., 32, 42, 52, and 75 bp) and seven different GC contents (e.g., about 20, 30, 40, 50, 60, 70, and 80% GC). A similar set of synthetic nucleic acids can be generated using different lengths (e.g., 27, 37, 47, 57, 62, and 67 bp) and different GC contents (e.g., about 15, 25, 35, 45, 55, 65, and 75% GC).

Spike-in nucleic acids with different melting temperatures ($T_m$'s) can be used. In some cases, a spike-in panel comprises nucleic acids with melting temperatures ($T_m$'s) spanning the range of about 40-50° C., about 35-55° C., about 30-60° C., about 35-60° C., about 35-65° C., about 35-70° C., about 35-75° C., or about 30-70° C. In some cases, a spike-in panel comprises nucleic acids with different melting temperatures ($T_m$'s) that differ by at least 1, 2, 3, 4, 5, 6, 7, 8, 9, 10, 15, 20, 25, or 30° C.

In some cases, $T_m$ can be calculated based on one or more parameters in addition to duplex length and GC content, such as duplex concentration, nearest-neighbor effects of the nucleotide sequence, higher-order DNA structure, monovalent and/or divalent cation concentrations, and nucleotide concentrations. In some cases, $T_m$ can be calculated empirically for a given condition, e.g., with a duplex DNA-specific dye and a gradual increase in temperature and detection of the dye signal.

Spike-in nucleic acids with different sequences can be used. Preferably, non-native or non-natural sequences are used, or sequences not capable of hybridizing to sample nucleic acids. In some cases, a spike-in panel comprises nucleic acids with at least 3, 4, 5, 6, 7, 8, 9, 10, or 15 different sequences. In some cases, a spike-in panel comprises nucleic acids with up to 3, 4, 5, 6, 7, 8, 9, 10, 15, 20, 25, 50, or 100 different sequences.

Different numbers of spike-in nucleic acids can be used. In some cases, about 1, 2, 3, 4, 5, 6, 7, 8, 9, 10, 15, 20, 25, 30, 40, or 50 nucleic acids are used. For example, a subset of the 28 sequences listed in Table 3 can be used, e.g. 32/42/52/75 bp×20/50/80% GC.

An RNA panel can be used for RNA applications. As discussed herein, an RNA panel may include identical molecules or diverse molecules that differ with respect to length, GC content, and/or other property.

The set of 8 DNA sequences (SEQ ID NOs: 111-118 in Table 2, each at approximately 50% GC) provides partial coverage of the 28-member GC panel listed in Table 3.

TABLE 3

Exemplary GC Spike sequences

| SEQ ID NO | Name | Sequence (5'-3') | Length (bp) | GC% |
| --- | --- | --- | --- | --- |
| SEQ ID NO: 125 | Spark32.20.1 | AGTCATATTATTATATTAATTTAACTATCACG | 32 | 19 |
| SEQ ID NO: 126 | Spark32.30.1 | AGTCACGTTATTTCTTTTGTAAAATACACACG | 32 | 31 |
| SEQ ID NO: 127 | Spark32.40.1 | AGTCTAAAGTCCTAACTCTTTGATCACACACG | 32 | 41 |
| SEQ ID NO: 128 | Spark32.50.1 | AGTCGGTTACTTTCTGGAGAATCCTTGGCACG | 32 | 50 |
| SEQ ID NO: 129 | Spark32.60.1 | AGTCCTTGCCAAGAGGCTCCGTAAGCACCACG | 32 | 59 |
| SEQ ID NO: 130 | Spark32.70.1 | AGTCCGGCTGAGGCTCGGGACCTTGGCTCACG | 32 | 69 |
| SEQ ID NO: 131 | Spark32.80.1 | AGTCCCACCGGCTCGGGGCGGCAGCGGCCACG | 32 | 81 |
| SEQ ID NO: 132 | Spark42.20.1 | AGTCTTATATATTAATACTATTTTCTTTTAAAGATAATCACG | 42 | 19 |
| SEQ ID NO: 133 | Spark42.30.1 | AGTCACTATATATATTTAGAGACGAATATCAAGTAAAGCACG | 42 | 31 |
| SEQ ID NO: 134 | Spark42.40.1 | AGTCTACACTACTCGGGCTTTAAACGAAATTCAACATTCACG | 42 | 41 |
| SEQ ID NO: 135 | Spark42.50.1 | AGTCTGGATACGATAACGGGAGCCCTTATTGACGGATACACG | 42 | 50 |
| SEQ ID NO: 136 | Spark42.60.1 | AGTCTGTTTAGCGGGGCGGCCCAAGAGACGTAGTCGTACACG | 42 | 59 |
| SEQ ID NO: 137 | Spark42.70.1 | AGTCCAGGGATCCACCCGTCAGGCTGCTAGCCGCCAGCCACG | 42 | 69 |
| SEQ ID NO: 138 | Spark42.80.1 | AGTCCGGTGGCTCCGCGTGCGGGCGCGGCACCGGCCACCACG | 42 | 81 |

TABLE 3-continued

Exemplary GC Spike sequences

| SEQ ID NO | Name | Sequence (5'-3') | Length (bp) | GC% |
|---|---|---|---|---|
| SEQ ID NO: 139 | Spark52.20.1 | AGTCAAATATCGATACAAATTAAAATATTTTACT ATTTTAAAGATTATCACG | 52 | 19 |
| SEQ ID NO: 140 | Spark52.30.1 | AGTCATGTTTAATTACTGAGAACGTTATGTAATA TATGTCCTGTAAATCACG | 52 | 31 |
| SEQ ID NO: 141 | Spark52.40.1 | AGTCGGTGTAGTTGTGAGTTAATCTAAGGAATAC CTTTGTTCCTATGTCACG | 52 | 41 |
| SEQ ID NO: 142 | Spark52.50.1 | AGTCTAGGCTGCTTGGCTTCTTCTAGCTCACTTG GTTATCCCGACATACACG | 52 | 50 |
| SEQ ID NO: 143 | Spark52.60.1 | AGTCTCCTAGCGGTACAGCTACTGTCATTCCTCG GGCCCTCTAGTCGCCACG | 52 | 59 |
| SEQ ID NO: 144 | Spark52.70.1 | AGTCGGCGCGCCGTTATATGGCAGAGCGGCGGT CGCCCGTCTGCGGAACACG | 52 | 69 |
| SEQ ID NO: 145 | Spark52.80.1 | AGTCGCCAACGGACTCGCGCCCCGGGGCGCGCC GCGCAGCCGGCTCGTCACG | 52 | 81 |
| SEQ ID NO: 146 | Spark75.20.1 | AGTCATTAATATATTATGGTTTATTATGAAACGA TAAAAGTATCTTTGTATAAAATTTAGAGTTTAAA TTACACG | 75 | 19 |
| SEQ ID NO: 147 | Spark75.30.1 | AGTCGAAAGCTTATTTATAAGCATACTAAAATAT TAACTTCTTGATTGGCATCGAATATATACTTTCA CAACACG | 75 | 31 |
| SEQ ID NO: 148 | Spark75.40.1 | AGTCGAAATGAAAAGGTTTAGGATGAATCCTTA AATAAATCTACCTTAGGTCGTGTACTACCGAGTG GACTCACG | 75 | 41 |
| SEQ ID NO: 149 | Spark75.50.1 | AGTCAGGAGGAAGGACAATATAGAATGCGCGTT ATCTCCTTGTCTCCAACCGGCTCAATGCTTAGTT GGCCCACG | 75 | 50 |
| SEQ ID NO: 150 | Spark75.60.1 | AGTCTCGCACTTTTGCTTCCGCTGAGATACTCGC CGCCTGGACCGATTGAGGTCGGGAGCCCACCTCT TGACACG | 75 | 59 |
| SEQ ID NO: 151 | Spark75.70.1 | AGTCTGATAGCACGCCGCCCACGGGCTCAGCCTT CCACCCGGCCGACGTTGCCGTACCTCTCCCTGCG GAGCACG | 75 | 69 |
| SEQ ID NO: 152 | Spark75.80.1 | AGTCGGGGACTCACCCGTGGCCTGCTGAGGGCC CGCGCGGCGCCCCGGCCCTCTGGCGAAGGCGGC GAGCCCACG | 75 | 81 |

Degenerate Spike-Ins: Spanks

The spike-in synthetic nucleic acids can be a degenerate pool of nucleic acids, or pool of nucleic acids with a high degree of diversity (herein at times referred to as "Spanks"). Generally, the Spanks may be used to determine absolute or relative nucleic acid loss or diversity loss that may occur during sample processing steps leading up to and/or including sequencing reactions. For unique pools of Spank sequences, a loss in sequence diversity in the pool should directly correspond to a loss in nucleic acid abundance, without needing to factor in the effects of amplification or PCR bias. For example, if $10^8$ unique Spank sequences are spiked into a sample and only $10^4$ unique Spank sequences are recovered after sequencing, the abundance of nucleic acids and the diversity of nucleic acids both decreased by a factor of $10^4$. In some case, the Spanks may be used to determine the degree of recovery of duplicate molecules. For example, after extraction and library processing, which may include PCR and potential uneven amplification of the various input molecules, sequencing and alignment of the individual Spanks can reveal the degree of recovery of duplicate molecules.

Figure 5:
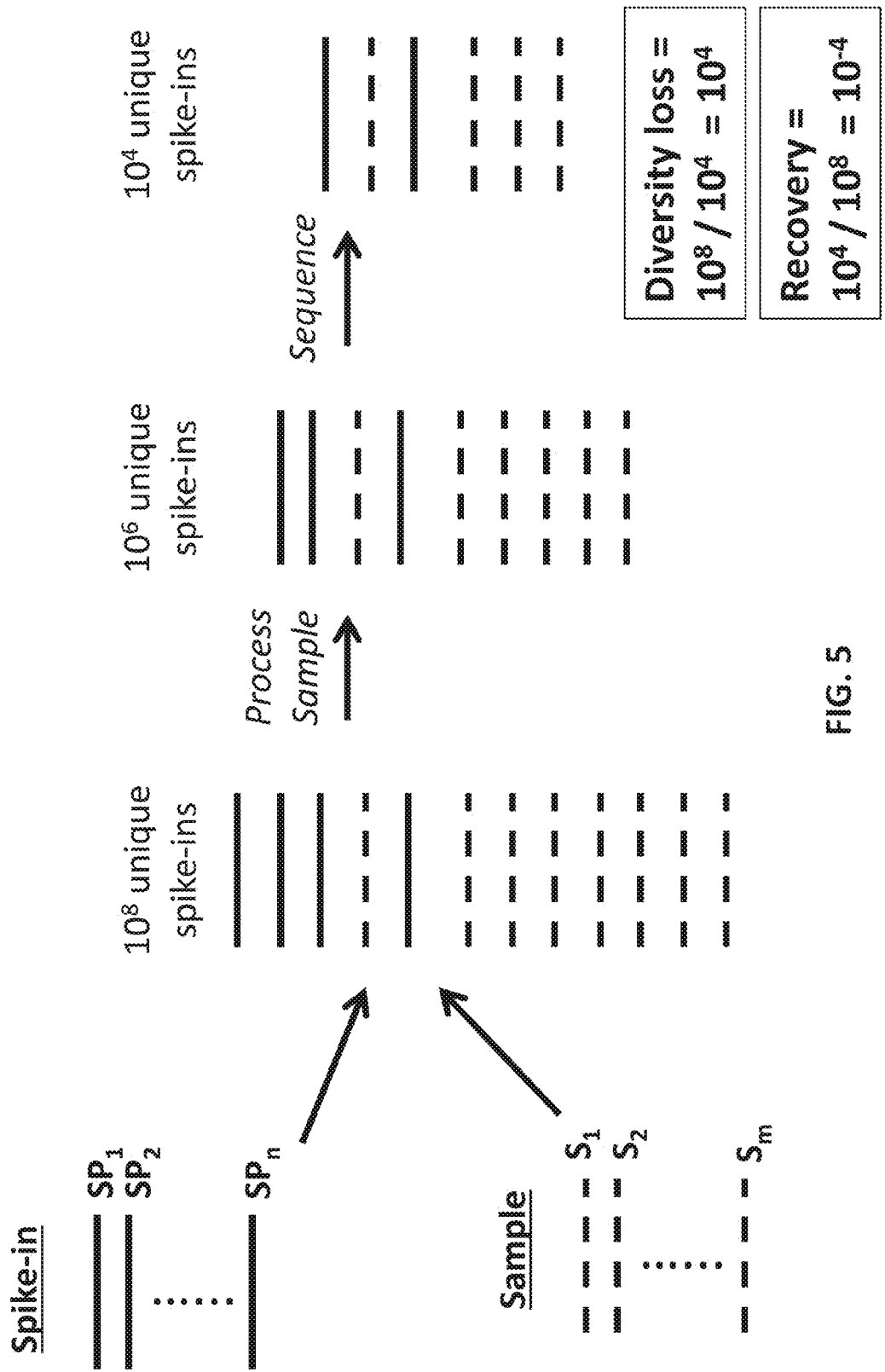
FIG. 5 depicts a general scheme of a method provided herein for determining diversity loss.

The determined diversity loss may then be used to determine absolute abundance of nucleic acids (e.g., target nucleic acids) in an initial sample prior to one or more sample processing or sequencing steps. In some cases, the determined diversity loss is used to determine relative abundance of nucleic acids in an initial sample. As shown in FIG. 5, sample nucleic acids ($S_1$, $S_2$, . . . , $S_m$) may be combined with Spank spike-in synthetic nucleic acids ($SP_1$, $SP_2$, . . . , $SP_n$) prior to one or more sample processing steps. For example, approximately $10^8$ unique Spanks can be added to a sample. During sample processing (e.g., nucleic acid extraction, purification, ligation, and/or end-repairing), a portion of the sample nucleic acids and a portion of the synthetic nucleic acids may be lost. After sample processing, approximately $10^6$ unique sequences out of the initial $10^8$ unique sequences may remain. A portion of these sequences may then be sequenced, for example $10^4$ unique sequences.

An absolute diversity loss can be calculated as the initial number of unique sequences divided by the sequenced or recovered number of unique sequences (e.g., $10^8/10^4=10^4$). Similarly, a recovery value can be calculated as the sequenced or recovered number of unique sequences divided by the initial number of unique sequences (e.g., $10^4/10^8=10^{-4}$). The calculated diversity loss can be used to determine absolute abundance of nucleic acids in an initial sample. For example, sequencing read counts for the Spank sequences and for the sample sequences can be determined from the sequencing analysis, and the initial concentration or amount of the Spank sequences spiked into the sample is known. Using the determined diversity loss, the initial concentration or amount of a nucleic acid in an initial sample (e.g., nucleic acids from a particular organism, pathogen, tumor, or organ) can be determined. The absolute quantities of sample nucleic acids in the original sample can be estimated by measuring the final number of sequencing reads for the sample nucleic acids and the Spank nucleic acids and/or the final diversity of the Spank nucleic acids and normalizing against the known quantity or diversity of Spank nucleic acids spiked into the original sample.

The number of unique sequence reads can be determined through a variety of methods. For example, sequence reads with the identifying tag can be identified. The number of unique sequences within the sequence reads with the identifying tag can then be determined by de-duplicating ("deduping") or removing duplicate sequences. For example, the sequences can be aligned to a reference database of possible sequences or to each other to determine which are duplicates and which are unique or different. As the identifying tag is typically conserved among the sequences, the randomized sequence regions embedded within each spiked molecule can be analyzed. In some cases, the Spank nucleic acid does not include an identifying tag; in such cases, the Spanks may be identified by other methods, such as by reference or alignment to a database containing known sequences.

Spank sequences can be used to monitor relative loss and/or absolute loss. In some cases, if the diversity of the Spank sequences is high enough, the Spank sequences spiked into a sample can be assumed to be essentially all unique. Therefore, any duplicate Spank sequences that are sequenced are likely due to PCR amplification and not due to multiple copies of the same Spank sequence being added into the sample and can be removed from the analysis. In addition, if each Spank sequence is unique, the total number of Spank sequences originally added to a sample is known based on the nucleic acid concentration and volume added to the sample, and the total number of unique Spank sequencing reads after sequencing is known; together these values can be used to calculate a diversity loss value or a recovery value.

The methods provided herein include methods of identifying steps during sample processing associated with a population bottleneck or loss of diversity. In some cases, when a population bottleneck is identified, correction factors can be applied to the other, originally unknown, molecules in the starting population. For example, if the input Spank molecules are essentially all unique, but the recovered Spanks are only 50% unique, this indicates a bottleneck and loss of diversity that can inform the interpretation of the diversity of the other molecules from the sample.

The collection of Spanks may be spiked-in to the sample at any step during sample processing in order to identify the step at which a bottleneck occurs. For example, a first collection of Spanks may be introduced when a sample (e.g., body fluid) is collected from a subject, a second collection of Spanks may be introduced into the sample prior to or during subsequent processing of the collected sample (e.g., removal of residual cells, storage), and/or a third collection of Spanks may be introduced prior to library preparation. In some cases, the collections of Spanks spiked-into the sample at different steps during sample processing have the same or similar composition. In some cases, a different collection of Spanks is spiked into the sample at different steps during sample processing.

In some cases, the Spank nucleic acids may each contain a randomized section with a unique sequence. The Spanks may comprise one or more different domains. In some cases, the Spanks may comprise one or more process codes, one or more diversity codes, one or more length-identifier sequences, one or more load sequences, one or more synthetic nucleic acid-identifier sequences (or Spank identifier sequences), and/or one or more feature domains. In some cases, the Spanks may comprise an identifying tag and a unique nucleic acid sequence.

When different collections of Spanks are used, each collection may be coded with a "process code" to identify the Spank collection that is introduced into the sample at a particular step (e.g., at sample collection, extraction, library processing). In such cases, Spanks with the identical process code can be grouped bioinformatically and analyzed for diversity loss. The degree of diversity loss associated with a particular step can then be determined and then compared across each sample processing step.

The Spanks may comprise a "diversity code" associated with the overall pool or collection of synthetic acids or Spanks. The diversity code domain may be a unique code signifying the amount of diversity within the pool of synthetic nucleic acids. In such cases, every synthetic nucleic acid within the diversity pool may be coded with a sequence signifying the degree of diversity (e.g., $10^8$ unique sequences) of the pool. In some cases, such as when two or more diversity pools are used on the same sample, the diversity codes may be used to identify diversity loss in the two or more pools.

In some cases, the Spanks may comprise one or more codes (e.g., process codes) that identify the Spank as a member of a particular Spank pool or collection. In some cases, the Spanks may comprise one or more Spank-identifying domains identifying the Spank as a Spank, as opposed to a nucleic acid that was initially present in the sample. The Spanks may also comprise feature domains, length-identifier domains, and load domains, as further described herein.

The Spanks may be used alone or in combination with other synthetic nucleic acids in order to calculate abundance of nucleic acids or for other applications. In some cases, Spanks may be used along with other synthetic nucleic acids. For example, in some cases, a panel of Spanks and a panel of Sparks may be added to a sample. In some cases, a sample identification nucleic acid may be added to a sample as well.

Figure 6:
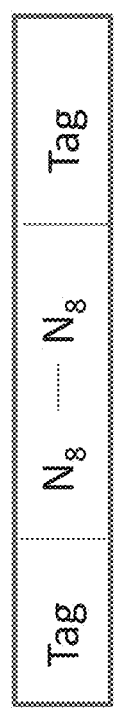

The Spank pools preferably comprise a diverse mix of nucleic acid sequences; as such, the Spanks pools may be designed in order to maximize diversity. In some cases, a Spank pool is derived from a much larger Spank pool. For example, in some cases, a 75-bp oligonucleotide can be synthesized with two 8-bp strings of N's (e.g., A/C/G/T in equal proportions). A Spank can be a synthetic nucleic acid comprising (i) one or more identifying tags and (ii) a unique nucleic acid sequence. In some cases, the unique nucleic acid sequence can be multiple degenerate or random positions, for example two groups of 8-bp strings of degenerate positions separated by one or more nucleotides, as shown in FIG. 6. Two exemplary sequences are listed in Table 4. An oligonucleotide design with two 8-bp strings of N's contains 16 total N's for a pool of $4^{16}=4.3\times10^9$ different oligonucleotides. If $1\times10^8$ molecules of this pool, for example, are spiked into 1 mL of plasma and processed as described above for the ID Spikes and Sparks, nearly all of the Spanks will be unique. For example, greater than 90%, 95%, 99% of the Spanks may be unique in such instance.

In some cases, Spank nucleic acids can be about or at least about 20, 30, 40, 50, 60, 70, 75, 80, 90, 100, 110, 120, 125, 130, 140, 150, 160, 170, 175, 180, 190, 200, 250, 300, 350, 400, 450, 500, 600, 700, 800, 900, or 1000 nucleotides in length. In some cases, Spank nucleic acids can be up to about 20, 30, 40, 50, 60, 70, 75, 80, 90, 100, 110, 120, 125, 130, 140, 150, 160, 170, 175, 180, 190, 200, 250, 300, 350, 400, 450, 500, 600, 700, 800, 900, or 1000 nucleotides in length. In some cases, Spank nucleic acids can have a length within the range from about 20 to about 175 base pairs. In some cases, the nucleic acids in a Spank set have the same length. In some cases, the nucleic acids in a Spank set have two or more different lengths (e.g., 2, 3, 4, 5, or more lengths).

In some cases, Spank nucleic acids can have about or at least about 5, 6, 7, 8, 9, 10, 11, 12, 13, 14, 15, 16, 17, 18, 19, 20, 21, 22, 23, 24, 25, 26, 27, 28, 29, or 30 degenerate positions. In some cases, Spank nucleic acids can have up to about 10, 11, 12, 13, 14, 15, 16, 17, 18, 19, 20, 21, 22, 23, 24, 25, 26, 27, 28, 29, or 30 degenerate positions. In some cases, Spank nucleic acids can have a number of degenerate positions within the range from about 5 to about 25. In some cases, the degenerate positions may be consecutive, separated, or split into two or more groups, such as two, three, four, or five groups. In some cases, where degenerate positions are split into groups, the degenerate positions may be split equally among the groups (e.g., two groups of 8-bp strings of degenerate positions for a total of 16 degenerate positions) or may be split unequally among the groups (e.g., one group of 10 degenerate positions and another group of 6 degenerate positions for a total of 16 degenerate positions). In some cases, where degenerate positions are split into groups, the groups may be separated by one or more nucleotides. In some cases, the groups are separated by about or at least about 1, 2, 3, 4, 5, 6, 7, 8, 9, 10, 15, 20, 30, 40 or 50 nucleotides. In some cases, the groups are separated by up to about 1, 2, 3, 4, 5, 6, 7, 8, 9, 10, 15, 20, 30, 40, or 50 nucleotides.

In some cases, Spank nucleic acids can have a diversity of about or at least about $1\times10^3$, $1\times10^4$, $1\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$ $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, or $1\times10^{11}$ unique sequences. In some cases, Spank nucleic acids can have a diversity of up to about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, or $1\times10^{11}$ unique sequences. In some cases, Spank nucleic acids can have a diversity within the range from about $1\times10^4$ to about $1\times10^{11}$ unique sequences.

TABLE 4

Exemplary Spank diversity sequences

| SEQ ID NO | Name | Sequence |
|---|---|---|
| SEQ ID NO: 119 | SPANK-75A | CCTGTGCTCTAGAGTAGAGTANNNNNAGCTNN NNNNNGAGCGATCTGTATAGATAGCTACACG CTGAGTGA |
| SEQ ID NO: 120 | SPANK-75B | CCTGACTCTCGATGATAGTACNNTNAGCTNN NNNNNNGTCTATAGCTCTAGCGACATACGTA CTGTGTCGT |

Tracer Sequences

Laboratory-derived nucleic acids (e.g., pathogen genomic DNA) are useful as standards for development, verification, validation, assay controls, etc. for infectious disease diagnostic testing. However, because these same organisms can be present in clinical samples (for example, in pathogen-infected samples), there is a danger that the laboratory-derived material can cross-contaminate clinical samples during testing and thus generate false positive calls, which can not only provide incorrect information to the patient and doctor but, for certain pathogen species, could also trigger required reporting to health authorities. While actual reference nucleic acids (e.g., actual pathogen genomic DNA, cancer nucleic acids, tumor nucleic acids, or other disease-associated nucleic acids) are useful or even essential as a positive control, routine or even extreme caution in handling it may be insufficient to prevent cross-contamination, especially for sensitive assays such as next-generation sequencing (NGS).

A synthetic tracer nucleic acid, not found in nature or otherwise incapable of hybridizing to sample nucleic acids, can be added to positive control nucleic acid stocks at an effective concentration at least as high as the positive control nucleic acid. The tracer and positive control nucleic acid are in forms so that they are processed and detected in the same manner. Thus the endpoint (e.g., aligned sequence reads in the case of NGS) is the same for both tracer and positive control nucleic acid, and because of its higher effective concentration the tracer is detected at least as readily as the positive control nucleic acid. In some cases, the positive control nucleic acid is pathogen genomic DNA. In some cases, the positive control nucleic acid comprises a disease-associated nucleic acid, such as an oncogene.

Tracer sequences can be varied in one or more properties, such as sequence, length, concentration, GC content, etc. The sequences shown in Table 5 and used in Example 6 have approximately 50% GC content, but tracer sequences can be varied to match the composition of the positive control or genome to which they are paired, for example 30% GC content, 35% GC content, 40% GC content, 45% GC content, 50% GC content, 55% GC content, 60% GC content, 65% GC content, or 70% GC content.

In some cases, tracer sequences can be added to positive control nucleic acids or genomic DNA after fragmentation, for example as described in Example 6. In some cases, tracer sequences can be added to positive control nucleic acid or genomic DNA before fragmentation to better represent the full processing performed on the positive control nucleic acid or sample nucleic acids. Positive control nucleic acids that are rare and found in low concentrations in clinical samples (e.g., pathogen DNA) can be labeled with tracer sequences as early as possible to minimize cross-contamination with unlabeled nucleic acids.

In some cases, more than one tracer sequence is added to each positive control nucleic acid. In some cases, the two or more, three or more, four or more, or five or more tracer sequences are added at the same concentration or at different concentrations.

Different forms of tracer sequences can be used for different applications. For example, the length of a tracer sequence can be matched to length(s) of the control sequence(s), for example to the mean or median length. In some cases, the length of a tracer sequence can be within 5%, 10%, or 20% of the mean or median length of the control sequence(s).

RNA tracer sequences can be used for RNA applications.

TABLE 5

Exemplary Tracer Sequences

| SEQ ID NO | Name | Sequence |
|---|---|---|
| SEQ ID NO: 153 | Tracer 138 | GCGTTGGCCGAGATGAAGACCTCGTGCTCA CGTTACCACGCATGAGTTAATCAGTTGGCA CGAAGGTCGGCATTA |
| SEQ ID NO: 154 | Tracer 139 | GCGCCACAGCCTGTGCTACTATGGCTAACA GCGTATGCCGTCCGGATAGTGACCTGTCCG CGTCGGATACTTGGC |
| SEQ ID NO: 155 | Tracer 140 | ACGTCGGTTGTTACATATGACGCAACGCTT GATTGAAGGCGTTGTGAATCGCGCAGTACC GTGCTCGCTCAGAGC |
| SEQ ID NO: 156 | Tracer 141 | GACAATTGAATTGTGGCCGCTTACTTCGCA CTACCGCACGCGGCAATGCTATGATGTGAG AACTTGATTCTTGGC |
| SEQ ID NO: 157 | Tracer 142 | GTAATGGAATCCTACAGACATGTGTAAGTA TGCTGATTGATCCGACTTACATCAGTCAGT CAGAGGCCGCCATAT |
| SEQ ID NO: 158 | Tracer 143 | CGCTAGTCCTCTCCTCGGTTCCGAACTTCG TCGTCACGAGGTGGCTAACCATGGCATTAG TGCTCTAAGTCCTAT |
| SEQ ID NO: 159 | Tracer 144 | CTAGATGAAGGCAGGCGAGCAACCGGATAG ATGGCTCCGTACCGCTGCGAGGTATTCTCC GATATATTGTACTCT |
| SEQ ID NO: 160 | Tracer 145 | ATGTCCTGAAGGAATAGAGAATCACTCTGC CAGCGACAAGACGGCCTGGTTCAGTAGATC TAGAGATCAGAATCT |
| SEQ ID NO: 161 | Tracer 146 | TACGAGTATGACGATTGGCGACAACGTGGC ATCTGCTTAATTATTATGTCGCCTGCGACC ACAGCACGCGAGACT |
| SEQ ID NO: 162 | Tracer 147 | AGTTGTGACTGCAGATGCCATAACAGCACC GAACCATATGTGACTGCGGTGGCGAGCGAG CTAATGCTTGCGTGG |
| SEQ ID NO: 163 | Tracer 148 | AACTGTAAGAAGAATATTCCGGCTGCCAGC CTTGAATGTCTAGCGAAGCCGAACGCATAG AGGATGCATGTGCGG |
| SEQ ID NO: 164 | Tracer 149 | GATTCCGAGGCCTAGTGCGACAGCAGCTCC GTCAACTGATATTCCACTGGCAGTCCACGA ATAGAGGTGGTGACA |
| SEQ ID NO: 165 | Tracer 150 | TTCGGTACCGAGCACGCATATGAACTCGTC GTAGATACTAGTAGATCACCGTAAGACCTT GCTGTGCGCGCCGTA |
| SEQ ID NO: 166 | Tracer 151 | AGAGCGCACTTAATGTCTCTGGAATGTTGC GTGAATCGCAGCGGCGTAAGTATGAGCAAT CGTACCTCGGACCGT |

TABLE 5-continued

Exemplary Tracer Sequences

| SEQ ID NO | Name | Sequence |
|---|---|---|
| SEQ ID NO: 167 | Tracer 152 | CTTAAGGTAGATCTTGTATCATGAATCACC AATTATGTATGCATGCGGCGCGCACCTAAG AGCCTGTGAGATGTC |
| SEQ ID NO: 168 | Tracer 153 | AGCGCTGTCGGAACACGCAACGGTGTATGT CCACTCATTGTTCCGCAGTTGCGAAGTAGA CAGGATCCTACTAAC |
| SEQ ID NO: 161 | Tracer 154 | CAGAAGCTCATGGCCTCAGTGCAGTTGCAA GGATGCGCCTGCATCTCGACTAGCAACTGT TCATACGTCATGGTC |
| SEQ ID NO: 169 | Tracer 155 | TCGCTCAATACACTTGGACCAGAATTATGT CCTATTCAGAACCTTGCCGCGCGGCAGTCG CGCAGATGGTCCTGA |

Molecular LIMS

A laboratory information management system (LIMS) is a way of tracking consumption and use of consumables, and in some cases, for ensuring that the chemicals or reagents necessary for a given experiment, and only the chemicals or reagents necessary for a given experiment, were used in that experiment. LIMS can also help to track the lot numbers of chemicals used for each repetition of the experiment. All of these functionalities (e.g., tracking lot numbers) may aid in troubleshooting a failed experiment, for example, when a single chemical decreased in quality or if incorrect reagents were used in an experiment.

LIMS systems can be designed as electronic or web applications where lab personnel enter catalogue and lot numbers for each consumable used in a process. Typically, barcoding is used to accelerate the process and increase its accuracy. However, human errors may still result in incomplete records for a given repetition of the reaction.

Provided herein are methods of molecularly labeling reagents, particularly reagents, reagent lots, aliquots, or shipments. In some cases, the methods include use of spike-in synthetic nucleic acids in order to molecularly barcode different containers various reagents. For example, adding a spike-in nucleic acid or a short nucleic acid oligomers (e.g., 50 to 100 bp) with unique sequences (e.g., non-human, non-pathogen) to each reagent, reagent lot, reagent aliquot, or reagent shipment can help track the inventory of reagents used to prepare a particular library. In some cases, one or more ID Spike, Spark, or Spank sequences can be used for molecular LIMS. The lot numbers and reagents used in the processing of each sample can then be automatically detected by sequencing and can be used for troubleshooting problematic runs, for example, by comparing against lot numbers used in the successful runs or identifying missing or extra reagents used in the processing of that sample.

Similarly, detection of spike-in nucleic acids associated with specific reagents, reagent lot numbers, aliquots, or shipments can be used to identify the lot numbers, aliquots, or shipments of reagents used in sequencing runs that are successful. In some cases, a nucleic acid or spike-in can be detected through a method other than sequencing, for example, a general polymer labeled with one or more fluorescent probe can be detected using fluorescence.

While DNA oligomers may work for many aqueous solutions, nucleic acid oligomers immune to DNase action (e.g., RNA, DNA oligomer with a modified backbone) may be designed for DNase-containing solutions. Similarly, synthetic nucleic acids resistant to RNase (e.g., DNA) may be used to track RNase-containing solutions.

Nucleic Acid Enrichment and Library Preparation

In the methods provided herein, nucleic acids can be isolated from a sample using any means known in the art. For example, nucleic acids can be extracted using liquid extraction (e.g., Trizol, DNAzol) techniques. Nucleic acids can also be extracted using commercially available kits (e.g., QIAamp Circulating Nucleic Acid Kit, Qiagen DNeasy kit, QIAamp kit, Qiagen Midi kit, QIAprep spin kit).

Nucleic acids can be concentrated or precipitated by known methods, including, by way of example only, centrifugation. Nucleic acids can be bound to a selective membrane (e.g., silica) for the purposes of purification. Nucleic acids can also be enriched for fragments of a desired length, e.g., fragments which are less than 1000, 500, 400, 300, 200 or 100 base pairs in length. Such an enrichment based on size can be performed using, e.g., PEG-induced precipitation, an electrophoretic gel or chromatography material (Huber et al. (1993) Nucleic Acids Res. 21:1061-6), gel filtration chromatography, or TSKgel (Kato et al. (1984) J. Biochem, 95:83-86), which publications are hereby incorporated by reference in their entireties for all purposes.

The nucleic acid sample can be enriched for target polynucleotides, particularly target nucleic acids associated with inflammation or infection. In some preferred cases, the target nucleic acids are pathogen nucleic acids (e.g., cell-free pathogen nucleic acids). In some preferred cases, the target nucleic acids are cell-free RNA associated with a particular organ or tissue including but not limited to uterus, heart, lung, kidney, fetal brain, liver, or cervical tissue.

Target enrichment can be by any means known in the art. For example, the nucleic acid sample may be enriched by amplifying target sequences using target-specific primers (e.g., primers specific for pathogen nucleic acids). The target amplification can occur in a digital PCR format, using any methods or systems known in the art. The nucleic acid sample may be enriched by capture of target sequences onto an array immobilized thereon target-selective oligonucleotides. The nucleic acid sample may be enriched by hybridizing to target-selective oligonucleotides free in solution or on a solid support. The oligonucleotides may comprise a capture moiety which enables capture by a capture reagent. In some embodiments, the nucleic acid sample is not enriched for target polynucleotides, e.g., represents a whole genome.

In some cases, target (e.g., pathogen, organ) nucleic acids can be enriched relative to background (e.g., subject, healthy tissue) nucleic acids in the sample, for example, by pull-down (e.g., preferentially pulling down target nucleic acids in a pull-down assay by hybridizing them to complementary oligonucleotides conjugated to a label such as a biotin tag and using, for example, avidin or streptavidin attached to a solid support), targeted PCR, or other methods. Examples of enrichment techniques include, but are not limited to: (a) self-hybridization techniques in which the major population in a sample of nucleic acids self-hybridizes more rapidly than the minor population in the sample; (b) depletion of nucleosome-associated DNA from free DNA; (c) removing and/or isolating DNA of specific length intervals; (d) exosome depletion or enrichment; and (e) strategic capture of regions of interest.

In some cases, an enriching step comprises (a) providing a sample of nucleic acids from a host, wherein the sample of nucleic acids from the host is a sample of single-stranded nucleic acids from the host and comprises host nucleic acids and non-host nucleic acids; (b) renaturing at least a portion of the single-stranded nucleic acids from the host, thereby producing a population of double-stranded nucleic acids within the sample; and (c) removing at least a portion of the double-stranded nucleic acids within the sample using a nuclease, thereby enriching non-host sequences in the sample of nucleic acids from the host. In some cases, an enriching step comprises (a) providing a sample of nucleic acids from a host, wherein the sample of nucleic acids from the host comprises host nucleic acids associated with nucleosomes and non-host nucleic acids; and (b) removing at least a portion of the host nucleic acids associated with nucleosomes, thereby enriching the non-host nucleic acids in the sample of nucleic acids from the host. In some cases, an enriching step comprises (a) providing a sample of nucleic acids from a host, wherein the sample of nucleic acids from the host comprises host nucleic acids and non-host nucleic acids; and (b) removing or isolating DNA of one or more length intervals, thereby enriching the non-host nucleic acids in the sample of nucleic acids from the host. In some cases, an enriching step comprises (a) providing a sample of nucleic acids from a host, wherein the sample of nucleic acids from the host comprises host nucleic acids, non-host nucleic acids, and exosomes; and (b) removing or isolating at least a portion of the exosomes, thereby enriching non-host sequences in the sample of nucleic acids from the host. In some cases, an enriching step comprises preferentially removing nucleic acids with lengths that are above about 300 bases in length from the sample. In some cases, an enriching step comprises preferentially amplifying or capturing non-host nucleic acids from the sample.

An enriching step can comprise preferentially removing nucleic acids from the sample that are above about 120, about 150, about 200, or about 250 bases in length. In some cases, an enriching step comprises preferentially enriching nucleic acids from the sample that are between about 10 bases and about 60 bases in length, between about 10 bases and about 120 bases in length, between about 10 bases and about 150 bases in length, between about 10 bases and about 300 bases in length between about 30 bases and about 60 bases in length, between about 30 bases and about 120 bases in length, between about 30 bases and about 150 bases in length, between about 30 bases and about 200 bases in length, or between about 30 bases and about 300 bases in length. In some cases, an enriching step comprises preferentially digesting nucleic acids derived from the host (e.g., subject). In some cases, an enriching step comprises preferentially replicating the non-host nucleic acids.

In some cases, an enriching step increases the ratio of non-host nucleic acids relative to host (e.g., subject) nucleic acids by at least 2×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 30×, at least 40×, at least 50×, at least 60×, at least 70×, at least 80×, at least 90×, at least 100×, at least 1000×, at least 5000×, or at least 10,000×. In some cases, an enriching step increases the ratio of non-host nucleic acids relative to host (e.g., subject) nucleic acids by at least 10×. In some cases, an enriching step increases the ratio of non-host nucleic acids relative to host (e.g., subject) nucleic acids within the range from about 10× to about 100×.

In some cases, a nucleic acid library is prepared. The nucleic acid library can be a single-stranded nucleic acid library or a double-stranded nucleic acid library. In some cases, a single-stranded nucleic acid library can be a single-stranded DNA library (ssDNA library) or an RNA library. In some cases, a double-stranded nucleic acid library is a double-stranded DNA library (dsDNA library). A method of preparing an ssDNA library can comprise denaturing a double stranded DNA fragment into ssDNA fragments, ligating a primer docking sequence onto one end of the ssDNA fragment, and hybridizing a primer to the primer docking sequence. The primer can comprise at least a portion of an adaptor sequence that couples to a next-generation sequencing platform. The method can further comprise extension of the hybridized primer to create a duplex, wherein the duplex comprises the original ssDNA fragment and an extended primer strand. The extended primer strand can be separated from the original ssDNA fragment. The extended primer strand can be collected, wherein the extended primer strand is a member of the ssDNA library. A method of preparing an RNA library can comprise ligating a primer docking sequence onto one end of the RNA fragment and hybridizing a primer to the primer docking sequence. The primer can comprise at least a portion of an adaptor sequence that couples to a next-generation sequencing platform. The method can further comprise extension of the hybridized primer to create a duplex, wherein the duplex comprises the original RNA fragment and an extended primer strand. The extended primer strand can be separated from the original RNA fragment. The extended primer strand can be collected, wherein the extended primer strand is a member of the RNA library. A method of preparing an dsDNA library can comprise ligating an adaptor sequence onto one or both ends of the dsDNA fragment.

In various aspects, dsDNA can be fragmented by any means known in the art or as described herein. In some cases, dsDNA can be fragmented by physical means (e.g., by mechanical shearing, nebulization, or sonication), by enzymatic means, or by chemical means.

In some embodiments, cDNA is generated from RNA. For example, cDNA may be generated using random primed reverse transcription (RNaseH+) to generate randomly sized cDNA.

The lengths of the nucleic acids may vary. The nucleic acids or nucleic acid fragments (e.g., dsDNA fragments, RNA, or randomly sized cDNA) can be less than 1000 bp, less than 800 bp, less than 700 bp, less than 600 bp, less than 500 bp, less than 400 bp, less than 300 bp, less than 200 bp, or less than 100 bp. The DNA fragments can be about 40 to about 100 bp, about 50 to about 125 bp, about 100 to about 200 bp, about 150 to about 400 bp, about 300 to about 500 bp, about 100 to about 500 bp, about 400 to about 700 bp, about 500 to about 800 bp, about 700 to about 900 bp, about 800 to about 1000 bp, or about 100 to about 1000 bp. In some cases, the nucleic acids or nucleic acid fragments (e.g., dsDNA fragments, RNA, or randomly sized cDNA) can be within the range from about 20 to about 200 bp, such as within the range from about 40 to about 100 bp.

The ends of dsDNA fragments can be polished (e.g., blunt-ended). The ends of DNA fragments can be polished by treatment with a polymerase. Polishing can involve removal of 3' overhangs, fill-in of 5' overhangs, or a combination thereof. The polymerase can be a proof-reading polymerase (e.g., comprising 3' to 5' exonuclease activity). The proofreading polymerase can be, e.g., a T4 DNA polymerase, Pol 1 Klenow fragment, or Pfu polymerase. Polishing can comprise removal of damaged nucleotides (e.g., abasic sites), using any means known in the art.

Ligation of an adaptor to a 3' end of a nucleic acid fragment can comprise formation of a bond between a 3' OH group of the fragment and a 5' phosphate of the adaptor. Therefore, removal of 5' phosphates from nucleic acid fragments can minimize aberrant ligation of two library members. Accordingly, in some embodiments, 5' phosphates are removed from nucleic acid fragments. In some embodiments, 5' phosphates are removed from at least 50%, 55%, 60%, 65%, 70%, 75%, 80%, 85%, 90%, 95%, or greater than 95% of nucleic acid fragments in a sample. In some embodiments, substantially all phosphate groups are removed from nucleic acid fragments. In some embodiments, substantially all phosphates are removed from at least 50%, 55%, 60%, 65%, 70%, 75%, 80%, 85%, 90%, 95%, or greater than 95% of nucleic acid fragments in a sample. Removal of phosphate groups from a nucleic acid sample can be by any means known in the art. Removal of phosphate groups can comprise treating the sample with heat-labile phosphatase. In some embodiments, phosphate groups are not removed from the nucleic acid sample. In some embodiments ligation of an adaptor to the 5' end of the nucleic acid fragment is performed.

Sequencing

This disclosure provides methods of analyzing nucleic acids. Such analytical methods include sequencing the nucleic acids as well as bioinformatic analysis of the sequencing results. The nucleic acids produced according the present methods may be analyzed to obtain various types of information including genomic, epigenetic (e.g., methylation), and RNA expression. Methylation analysis can be performed by, for example, conversion of methylated bases followed by DNA sequencing. RNA expression analysis can be performed by, for example, polynucleotide array hybridization, RNA sequencing techniques, or sequencing cDNA produced from RNA.

In preferred embodiments, the sequencing is performed using a next generation sequencing assay. As used herein, the term "next generation" is well-understood in the art and generally refers to any high-throughput sequencing approach including, but not limited to one or more of the following: massively-parallel signature sequencing, pyrosequencing (e.g., using a Roche 454 sequencing device), Illumina (Solexa) sequencing, sequencing by synthesis (Illumina), Ion torrent sequencing, sequencing by ligation (e.g., SOLiD sequencing), single molecule real-time (SMRT) sequencing (e.g., Pacific Bioscience), polony sequencing, DNA nanoball sequencing, heliscope single molecule sequencing (Helicos Biosciences), and nanopore sequencing (e.g., Oxford Nanopore). In some cases, the sequencing assay uses nanopore sequencing. In some cases, the sequencing assay includes some form of Sanger sequencing. In some cases, the sequencing involves shotgun sequencing; in some cases, the sequencing includes bridge PCR. In some cases, the sequencing is broad spectrum. In some cases, the sequencing is targeted.

In some cases, the sequencing assay comprises a Gilbert's sequencing method. In such approach, nucleic acids (e.g., DNA) are chemically modified and then cleaved at specific bases. In some cases, a sequencing assay comprises dideoxynucleotide chain termination or Sanger-sequencing.

A sequencing-by-synthesis approach may be used in the methods provided herein. In some cases, fluorescently-labeled reversible-terminator nucleotides are introduced to clonally-amplified DNA templates immobilized on the surface of a glass flowcell. During each sequencing cycle, a single labeled deoxynucleoside triphosphate (dNTP) may be added to the nucleic acid chain. The labeled terminator nucleotide may be imaged when added in order to identify the base and may then be enzymatically cleaved to allow incorporation of the next nucleotide. Since all four reversible terminator-bound dNTPs (A, C, T, G) are generally present as single, separate molecules, natural competition may minimize incorporation bias.

In some cases, a method called Single-molecule real-time (SMRT) is used. In such approach, nucleic acids (e.g., DNA) are synthesized in zero-mode wave-guides (ZMWs), which are small well-like containers with capturing tools located at the bottom of the well. The sequencing is performed with use of unmodified polymerase (attached to the ZMW bottom) and fluorescently labelled nucleotides flowing freely in the solution. The fluorescent label is detached from the nucleotide upon its incorporation into the DNA strand, leaving an unmodified DNA strand. A detector such as a camera may then be used to detect the light emissions; and the data may be analyzed bioinformatically to obtain sequence information.

In some cases, a sequencing by ligation approach is used to sequence the nucleic acids in a sample. One example is the next generation sequencing method of SOLiD (Sequencing by Oligonucleotide Ligation and Detection) sequencing (Life Technologies). This next generation technology may generate hundreds of millions to billions of small sequence reads at one time. The sequencing method may comprise preparing a library of DNA fragments from the sample to be sequenced. In some cases, the library is used to prepare clonal bead populations in which only one species of fragment is present on the surface of each bead (e.g., magnetic bead). The fragments attached to the magnetic beads may have a universal P1 adapter sequence attached so that the starting sequence of every fragment is both known and identical. In some cases, the method may further involve PCR or emulsion PCR. For example, the emulsion PCR may involve the use of microreactors containing reagents for PCR. The resulting PCR products attached to the beads may then be covalently bound to a glass slide. A sequencing assay such as a SOLiD sequencing assay or other sequencing by ligation assay may include a step involving the use of primers. Primers may hybridize to the P1 adapter sequence or other sequence within the library template. The method may further involve introducing four fluorescently labelled di-base probes that compete for ligation to the sequencing primer. Specificity of the di-base probe may be achieved by interrogating every first and second base in each ligation reaction. Multiple cycles of ligation, detection and cleavage may be performed with the number of cycles determining the eventual read length. In some cases, following a series of ligation cycles, the extension product is removed and the template is reset with a primer complementary to the n−1 position for a second round of ligation cycles. Multiple rounds (e.g., 5 rounds) of primer reset may be completed for each sequence tag. Through the primer reset process, each base may be interrogated in two independent ligation reactions by two different primers. For example, the base at read position 5 is assayed by primer number 2 in ligation cycle 2 and by primer number 3 in ligation cycle 1.

In any of the embodiments, the detection or quantification analysis of the oligonucleotides can be accomplished by sequencing. The subunits or entire synthesized oligonucleotides can be detected via full sequencing of all oligonucleotides by any suitable methods known in the art, e.g., Illumina HiSeq 2500, including the sequencing methods described herein.

Sequencing can be accomplished through classic Sanger sequencing methods which are well known in the art. Sequencing can also be accomplished using high-throughput systems some of which allow detection of a sequenced nucleotide immediately after or upon its incorporation into a growing strand, e.g., detection of sequence in real time or substantially real time. In some cases, high throughput sequencing generates at least 1,000, at least 5,000, at least 10,000, at least 20,000, at least 30,000, at least 40,000, at least 50,000, at least 100,000, or at least 500,000 sequence reads per hour. In some cases, each read is at least 50, at least 60, at least 70, at least 80, at least 90, at least 100, at least 120, or at least 150 bases per read. In some cases, each read is up to 2000, up to 1000, up to 900, up to 800, up to 700, up to 600, up to 500, up to 400, up to 300, up to 200, or up to 100 bases per read. Long read sequencing can include sequencing that provides a contiguous sequence read of for example, longer than 500 bases, longer than 800 bases, longer than 1000 bases, longer than 1500 bases, longer than 2000 bases, longer than 3000 bases, or longer than 4500 bases.

In some cases, high-throughput sequencing involves the use of technology available by Illumina's Genome Analyzer IIX, MiSeq personal sequencer, or HiSeq systems, such as those using HiSeq 2500, HiSeq 1500, HiSeq 2000, or HiSeq 1000. These machines use reversible terminator-based sequencing by synthesis chemistry. These machines can do 200 billion DNA or more reads in eight days. Smaller systems may be utilized for runs within 3, 2, or 1 days or less time. Short synthesis cycles may be used to minimize the time it takes to obtain sequencing results.

In some cases, high-throughput sequencing involves the use of technology available by ABI Solid System. This genetic analysis platform can enable massively parallel sequencing of clonally-amplified DNA fragments linked to beads. The sequencing methodology is based on sequential ligation with dye-labeled oligonucleotides.

The next generation sequencing can comprise ion semiconductor sequencing (e.g., using technology from Life Technologies (Ion Torrent)). Ion semiconductor sequencing can take advantage of the fact that when a nucleotide is incorporated into a strand of DNA, an ion can be released. To perform ion semiconductor sequencing, a high density array of micromachined wells can be formed. Each well can hold a single DNA template. Beneath the well can be an ion sensitive layer, and beneath the ion sensitive layer can be an ion sensor. When a nucleotide is added to a DNA, H+ can be released, which can be measured as a change in pH. The H+ ion can be converted to voltage and recorded by the semiconductor sensor. An array chip can be sequentially flooded with one nucleotide after another. No scanning, light, or cameras can be required. In some cases, an ION-PROTON™ Sequencer is used to sequence nucleic acid. In some cases, an IONPGM™ Sequencer is used. The Ion Torrent Personal Genome Machine (PGM) can do 10 million reads in two hours.

In some cases, high-throughput sequencing involves the use of technology available by Helicos BioSciences Corporation (Cambridge, Mass.) such as the Single Molecule Sequencing by Synthesis (SMSS) method. SMSS can allow for sequencing the entire human genome in up to 24 hours. SMSS, like the MIP technology, may not require a pre amplification step prior to hybridization. SMSS may not require any amplification. SMSS is described in part in US Publication Application Nos. 20060024711; 20060024678; 20060012793; 20060012784; and 20050100932.

In some cases, high-throughput sequencing involves the use of technology available by 454 Lifesciences, Inc. (Branford, Conn.) such as the Pico Titer Plate device which includes a fiber optic plate that transmits chemiluminescent signal generated by the sequencing reaction to be recorded by a CCD camera in the instrument. This use of fiber optics can allow for the detection of a minimum of 20 million base pairs in 4.5 hours.

Methods for using bead amplification followed by fiber optics detection are described in Marguiles, M., et al. "Genome sequencing in microfabricated high-density picoliter reactors", Nature, doi: 10.1038/nature03959; and well as in US Publication Application Nos. 20020012930; 20030058629; 20030100102; 20030148344; 20040248161; 20050079510, 20050124022; and 20060078909.

In some cases, high-throughput sequencing is performed using Clonal Single Molecule Array (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication Application Nos. 20040106110; 20030064398; 20030022207; and Constans, A., The Scientist 2003, 17(13):36.

In some cases, the next generation sequencing is nanopore sequencing (See e.g., Soni G V and Meller A. (2007) Clin Chem 53: 1996-2001). A nanopore can be a small hole, e.g., on the order of about one nanometer in diameter. Immersion of a nanopore in a conducting fluid and application of a potential across it can result in a slight electrical current due to conduction of ions through the nanopore. The amount of current which flows can be sensitive to the size of the nanopore. As a DNA molecule passes through a nanopore, each nucleotide on the DNA molecule can obstruct the nanopore to a different degree. Thus, the change in the current passing through the nanopore as the DNA molecule passes through the nanopore can represent a reading of the DNA sequence. The nanopore sequencing technology can be from Oxford Nanopore Technologies; e.g., a GridION system. A single nanopore can be inserted in a polymer membrane across the top of a microwell. Each microwell can have an electrode for individual sensing. The microwells can be fabricated into an array chip, with 100,000 or more microwells (e.g., more than 200,000, 300,000, 400,000, 500,000, 600,000, 700,000, 800,000, 900,000, or 1,000,000) per chip. An instrument (or node) can be used to analyze the chip. Data can be analyzed in real-time. One or more instruments can be operated at a time. The nanopore can be a protein nanopore, e.g., the protein alpha-hemolysin, a heptameric protein pore. The nanopore can be a solid-state nanopore made, e.g., a nanometer sized hole formed in a synthetic membrane (e.g., SiNx, or $SiO_2$). The nanopore can be a hybrid pore (e.g., an integration of a protein pore into a solid-state membrane). The nanopore can be a nanopore with an integrated sensors (e.g., tunneling electrode detectors, capacitive detectors, or graphene based nano-gap or edge state detectors (see e.g., Garaj et al. (2010) Nature vol. 67, doi: 10.1038/nature09379)). A nanopore can be functionalized for analyzing a specific type of molecule (e.g., DNA, RNA, or protein). Nanopore sequencing can comprise "strand sequencing" in which intact DNA polymers can be passed through a protein nanopore with sequencing in real time as the DNA translocates the pore. An enzyme can separate strands of a double stranded DNA and feed a strand through a nanopore. The DNA can have a hairpin at one end, and the system can read both strands. In some cases, nanopore sequencing is "exonuclease sequencing" in which individual nucleotides can be cleaved from a DNA strand by a processive exonuclease, and the nucleotides can be passed through a protein nanopore. The nucleotides can transiently bind to a molecule in the pore (e.g., cyclodextran). A characteristic disruption in current can be used to identify bases.

Nanopore sequencing technology from GENIA can be used. An engineered protein pore can be embedded in a lipid bilayer membrane. "Active Control" technology can be used to enable efficient nanopore-membrane assembly and control of DNA movement through the channel. In some cases, the nanopore sequencing technology is from NABsys. Genomic DNA can be fragmented into strands of average length of about 100 kb. The 100 kb fragments can be made single stranded and subsequently hybridized with a 6-mer probe. The genomic fragments with probes can be driven through a nanopore, which can create a current-versus-time tracing. The current tracing can provide the positions of the probes on each genomic fragment. The genomic fragments can be lined up to create a probe map for the genome. The process can be done in parallel for a library of probes. A genome-length probe map for each probe can be generated. Errors can be fixed with a process termed "moving window Sequencing By Hybridization (mwSBH)." In some cases, the nanopore sequencing technology is from IBM/Roche. An electron beam can be used to make a nanopore sized opening in a microchip. An electrical field can be used to pull or thread DNA through the nanopore. A DNA transistor device in the nanopore can comprise alternating nanometer sized layers of metal and dielectric. Discrete charges in the DNA backbone can get trapped by electrical fields inside the DNA nanopore. Turning off and on gate voltages can allow the DNA sequence to be read.

The next generation sequencing can comprise DNA nanoball sequencing (as performed, e.g., by Complete Genomics; see e.g., Drmanac et al. (2010) Science 327: 78-81). DNA can be isolated, fragmented, and size selected. For example, DNA can be fragmented (e.g., by sonication) to a mean length of about 500 bp. Adaptors (Ad1) can be attached to the ends of the fragments. The adaptors can be used to hybridize to anchors for sequencing reactions. DNA with adaptors bound to each end can be PCR amplified. The adaptor sequences can be modified so that complementary single strand ends bind to each other forming circular DNA. The DNA can be methylated to protect it from cleavage by a type IIS restriction enzyme used in a subsequent step. An adaptor (e.g., the right adaptor) can have a restriction recognition site, and the restriction recognition site can remain non-methylated. The non-methylated restriction recognition site in the adaptor can be recognized by a restriction enzyme (e.g., AcuI), and the DNA can be cleaved by AcuI 13 bp to the right of the right adaptor to form linear double stranded DNA. A second round of right and left adaptors (Ad2) can be ligated onto either end of the linear DNA, and all DNA with both adapters bound can be PCR amplified (e.g., by PCR). Ad2 sequences can be modified to allow them to bind each other and form circular DNA. The DNA can be methylated, but a restriction enzyme recognition site can remain non-methylated on the left Ad1 adapter. A restriction enzyme (e.g., AcuI) can be applied, and the DNA can be cleaved 13 bp to the left of the Ad1 to form a linear DNA fragment. A third round of right and left adaptor (Ad3) can be ligated to the right and left flank of the linear DNA, and the resulting fragment can be PCR amplified. The adaptors can be modified so that they can bind to each other and form circular DNA. A type III restriction enzyme (e.g., EcoP15) can be added; EcoP15 can cleave the DNA 26 bp to the left of Ad3 and 26 bp to the right of Ad2. This cleavage can remove a large segment of DNA and linearize the DNA once again. A fourth round of right and left adaptors (Ad4) can be ligated to the DNA, the DNA can be amplified (e.g., by PCR), and modified so that they bind each other and form the completed circular DNA template.

Rolling circle replication (e.g., using Phi 29 DNA polymerase) can be used to amplify small fragments of DNA. The four adaptor sequences can contain palindromic sequences that can hybridize and a single strand can fold onto itself to form a DNA nanoball (DNB™) which can be approximately 200-300 nanometers in diameter on average. A DNA nanoball can be attached (e.g., by adsorption) to a microarray (sequencing flowcell). The flow cell can be a silicon wafer coated with silicon dioxide, titanium and hexamethyldisilazane (HMDS) and a photoresist material. Sequencing can be performed by unchained sequencing by ligating fluorescent probes to the DNA. The color of the fluorescence of an interrogated position can be visualized by a high resolution camera. The identity of nucleotide sequences between adaptor sequences can be determined.

The methods provided herein may include use of a system such as a system that contains a nucleic acid sequencer (e.g., DNA sequencer, RNA sequencer) for generating DNA or RNA sequence information. The system may include a computer comprising software that performs bioinformatic analysis on the DNA or RNA sequence information. Bioinformatic analysis can include, without limitation, assembling sequence data, detecting and quantifying genetic variants in a sample, including germline variants and somatic cell variants (e.g., a genetic variation associated with cancer or pre-cancerous condition, a genetic variation associated with infection).

Sequencing data may be used to determine genetic sequence information, ploidy states, the identity of one or more genetic variants, as well as a quantitative measure of the variants, including relative and absolute relative measures.

In some cases, sequencing of the genome involves whole genome sequencing or partial genome sequencing. The sequencing may be unbiased and may involve sequencing all or substantially all (e.g., greater than 70%, 80%, 90%) of the nucleic acids in a sample. Sequencing of the genome can be selective, e.g., directed to portions of the genome of interest. For example, many genes (and mutant forms of these genes) are known to be associated with various cancers. Sequencing of select genes, or portions of genes may suffice for the analysis desired. Polynucleotides mapping to specific loci in the genome that are the subject of interest can be isolated for sequencing by, for example, sequence capture or site-specific amplification.

Applications

The methods provided herein may be used for a variety purposes, such as to diagnose or detect a condition (e.g., infection), to predict that that a condition will occur or recur, to monitor treatment, to select or modify a therapeutic regimen, or to optimize a therapy. With this approach, therapeutic and/or diagnostic regimens can be individualized and tailored according to the data obtained at different times over the course of treatment, thereby providing a regimen that is individually appropriate.

Detecting/Diagnosing/Prognosing Conditions

The methods provided herein may be used to detect, diagnose, or prognose infections or diseases in patient samples, such as human blood samples. The methods may be used to detect rare microbial nucleic acid fragments in samples that are predominantly made up of human nucleic acids. For example, cell-free DNA (cfDNA) in blood consists mostly of DNA fragments derived from the host but also contains a small amount of fragments from microbes in the body. Extraction of the cfDNA followed by deep sequencing (e.g., next-generation sequencing or NGS) can generate millions or billions of sequence reads that can be mapped against host and non-host genome databases. Likewise, the methods can also be used to detect rare populations of circulating or cell-free RNA from a particular organ. For samples in which the non-host reads are a very small proportion of the total, the methods provided herein can improve the sensitivity and specificity of the assay, which would otherwise be compromised by a lack of internal normalization standards against which to compare different target nucleic acids (e.g., derived from different microbes or organism) or to track different samples or reagents. In addition, the methods can be used in settings where the target nucleic acids make up a larger portion of the total population of nucleic acids.

The methods provided herein may be used to detect, monitor, diagnose, prognose, treat, or prevent a large variety of diseases and disorders. In particular, the methods may be used to detect one or more target nucleic acid derived from a pathogen associated with an infectious disease or disorder. Exemplary diseases and disorders include any disease or disorder associated with an infection, e.g., sepsis, pneumonia, tuberculosis, HIV infection, hepatitis infection (e.g., Hep A, B, or C), human papilloma virus (HPV) infection, chlamydial infection, syphilitic infection, Ebola infection, *staphylococcus aureus* infection, or influenza. The methods provided herein are particularly useful for detecting infections by drug-resistant microbes, including multi-drug resistant microbes, or microbes that are not readily cultured or typically tested for. Some non-limiting examples of diseases and disorders that may be detected with the present methods include: cancer, dilated cardiomyopathy, Guillain-Barre syndrome, multiple sclerosis, tuberculosis, anthrax poisoning, sleeping sickness, dysentery, toxoplasmosis, ringworm, candidiasis, histoplasmosis, ebola, *Acinetobacter* infections, Actinomycosis, African sleeping sickness (African trypanosomiasis), AIDS (Acquired immunodeficiency syndrome), HIV infection, Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis (BV), Bacteroides infection, Balantidiasis, Baylisascaris infection, BK virus infection, Black piedra, *Blastocystis hominis* infection, Blastomycosis, Bolivian hemorrhagic fever, Borrelia infection, Botulism (and Infant botulism), Brazilian hemorrhagic fever, Brucellosis, Bubonic plague, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, Chikungunya, *Chlamydia*, Chlamydophila pneumoniae infection (Taiwan acute respiratory agent or TWAR), Cholera, Chromoblastomycosis, Clonorchiasis, *Clostridium difficile* infection, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Dientamoebiasis, *Diphtheria*, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum (Sixth disease), Fasciolopsiasis, Fasciolosis, Filariasis, Food poisoning by *Clostridium perfringens*, Free-living amebic infection, *Fusobacterium* infection, Gas gangrene (*Clostridial myonecrosis*), Geotrichosis, Gerstmann-Sträussler-Scheinker syndrome (GSS), Giardiasis, Glanders, Gnathostomiasis, Gonorrhea, Granuloma inguinale (Donovanosis), Group A streptococcal infection, Group B streptococcal infection, Haemophilus influenzae infection, Hand, foot and mouth disease (HFMD), Hantavirus Pulmonary Syndrome (HPS), Heartland virus disease, Helicobacter pylori infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis (HGA), Human metapneumovirus infection, Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, *Kingella kingae* infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), *Lymphatic filariasis* (Elephantiasis), Lymphocytic choriomeningitis, Malaria, Marburg hemorrhagic fever (MHF), Measles, Middle East respiratory syndrome (MERS), Melioidosis (Whitmore's disease), Meningitis, Meningococcal disease, Metagonimiasis, Microsporidiosis, *Molluscum contagiosum* (MC), Monkeypox, Mumps, Murine typhus (Endemic typhus), *Mycoplasma pneumonia*, Mycetoma, Myiasis, Neonatal conjunctivitis (*Ophthalmia neonatorum*), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, *Pediculosis capitis* (Head lice), *Pediculosis corporis* (Body lice), *Pediculosis pubis* (Pubic lice, Crab lice), Pelvic inflammatory disease (PID), Pertussis (Whooping cough), Plague, Pneumococcal infection, *Pneumocystis pneumonia* (PCP), Pneumonia, Poliomyelitis, Prevotella infection, Primary amoebic meningoencephalitis (PAM), Progressive multifocal leukoencephalopathy, Psittacosis, Q fever, Rabies, Respiratory syncytial virus infection, Rhinosporidiosis, Rhinovirus infection, Rickettsial infection, Rickettsialpox, Rift Valley fever (RVF), Rocky Mountain spotted fever (RMSF), Rotavirus infection, Rubella, Salmonellosis, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Subacute sclerosing panencephalitis, Syphilis, Taeniasis, Tetanus (Lockjaw), *Tinea barbae* (Barber's itch), *Tinea capitis* (Ringworm of the Scalp), *Tinea corporis* (Ringworm of the Body), *Tinea cruris* (Jock itch), *Tinea manum* (Ringworm of the Hand), *Tinea nigra, Tinea pedis* (Athlete's foot), *Tinea unguium* (Onychomycosis), *Tinea versicolor* (*Pityriasis versicolor*), Toxocariasis (Ocular Larva Migrans (OLM)), Toxocariasis (Visceral Larva Migrans (VLM)), Trachoma, Trinochcliasis, Trichinlosis, Trichomoniasis, Trichuriasis (Whipworm infection), Tuberculosis, Tularemia, Typhoid Fever, Ureaplasma urealyticum infection, Valley fever, Venezuelan equine encephalitis, Venezuelan hemorrhagic fever, Viral pneumonia, West Nile Fever, White piedra (*Tinea blanca*), *Yersinia pseudotuberculosis* infection, Yersiniosis, Yellow fever, Zika virus, and Zygomycosis.

In some cases, a method described herein comprises determining if an infection is active or latent. In some cases, gene expression quantification may provide a method for detecting, predicting, diagnosing, or monitoring an active infection. In some cases, a method described herein comprises detecting an active infection. In some cases, gene expression may be quantified through detection or sequencing of one or more target nucleic acids of interest. In some cases, gene expression quantification may provide a method for detecting, predicting, diagnosing, or monitoring a latent infection. In some cases, a method described herein comprises detecting a latent infection.

The methods provided herein may be used to detect cancer, particularly in a subject that has such cancer, is at risk of having such cancer, or is otherwise suspected of having such cancer. Examples of cancers include but are not limited to: brain cancer, head and neck cancer, throat cancer, mouth cancer, breast cancer, bone cancer, blood cancer, leukemia, lymphoma, lung cancer, kidney cancer, pancreatic cancer, stomach cancer, colon cancer, rectal cancer, skin cancer, cancer of the reproductive tract, prostate cancer, etc. In some cases, the methods provided herein are particularly useful for detecting non-hematological cancers, such as cancer of a solid organ (e.g., lung cancer, breast cancer, pancreatic cancer, etc.).

The methods may also be useful for detecting any other types of diseases or conditions of the subject. Often, they are useful for detecting rare genetic variations; or nucleic acid sequences that make up only a very small portion of the total nucleic acid population in the sample.

The detection of pathogen or organ nucleic acids may involve comparing a level of pathogen or organ nucleic acids with a control or reference value in order to determine the presence or absence of the pathogen or organ nucleic acids and/or the quantity of pathogen or organ nucleic acids. The level may be a qualitative or a quantitative level. In some cases, the control or reference value is a predetermined absolute value indicating the presence or absence of the cell-free pathogen nucleic acids or cell-free organ-derived nucleic acids. For example, detecting a level of cell-free pathogen nucleic acids above the control value may indicate the presence of the pathogen or of an infection, while a level below the control value may indicate the absence of the pathogen or of an infection. The control value may be a value obtained by analyzing cell-free nucleic acid levels of a subject without an infection; in some cases, the control value may be a positive control value and may be obtained by analyzing cell-free nucleic acids from a subject with a particular infection, or with a particular infection of a specific organ.

In some cases, in order to determine whether an infection is present or not—and often to obtain a result with precision—one or more of the following methods can be applied: (i) as described in Patent WO 2015070086 A1 the totality of the reads obtained by sequencing can be aligned against a curated host genome reference database, which can be from a human, dog, cat, primate or from any other host, including for example GenBank hg19 human reference sequences; (ii) a data processor for bioinformatics analysis can subtract or sequester the host sequences so that only non-host sequences, including pathogen-related sequences, can be further analyzed; (iii) a data processor can determine the presence of one or more pathogens by aligning the non-host sequences to a curated microbial reference sequence database, including for example reference sequences from GenBank and Refseq; (iv) a statistical analysis framework can be applied to determine whether the presence of one or more pathogens is statistically significant; and/or (v) in some instances the data processor can quantify the amount of pathogen present based on the number of reads obtained for the pathogens as compared to the number of reads obtained by control molecules spiked into the sample at a known concentration before sequencing.

The control value may be a level of cell-free pathogen or organ-specific nucleic acids obtained from the subject (e.g., subject with an infection or suspected of having an infection) at a different time point, such as a time point prior to the test time point. In such cases, comparison of the level at different time points may indicate the presence of infection, presence of infection in a particular organ, improved infection, or worsening infection. For example, an increase of cell-free pathogen nucleic acids by a certain amount over time may indicate the presence of infection or of a worsening infection, e.g., an increase of pathogen or organ-specific cell-free nucleic acids of at least 5%, 10%, 20%, 25%, 30%, 50%, 75%, 100%, 200%, 300%, or 400% compared to an original value may indicate the presence of infection, or of a worsening infection. In other examples, a reduction of pathogen or organ-specific cell-free nucleic acids by at least 5%, 10%, 20%, 25%, 30%, 50%, 75%, 100%, 200%, 300%, or 400% compared to an original value may indicate the absence of infection, or of an improved infection. Often, such measurements may be taken over a particular time period, such as every day, every other day, weekly, every other week, monthly, or every other month. For example, an increase of pathogen or organ cell-free nucleic acids of at least 50% over a week may indicate the presence of infection.

Control or reference values may be measured as a concentration or as a number of sequencing reads. Control or reference values may be pathogen-dependent. For example, a control value for *Escherichia coli* may be different than a control value for *Mycoplasma homins*. A database of levels or control values may be generated based on samples obtained from one or more subjects, for one or more pathogens, for one or more organs, and/or for one or more time points. Such a database may be rurated or proprietary. Recommended treatment options may be based on different threshold levels. For instance, a low level may signify infection but treatment may not be necessary; a moderate level may lead to antibiotic treatment; and a high level may require immediate or serious intervention.

The methods provided herein may enable the generation of sequencing data with high efficiency, high accuracy, and/or high sensitivity. Often, such methods may detect a pathogen or infection that is not detected or detectable by other methods, such as plate culturing or polymerase chain reaction (PCR). The methods generally may have a very high sensitivity, e.g., a sensitivity of greater than 80%, 85%, 90%, 95%, 99%, or 99.5%. The methods generally may have a very low false positive rate, e.g., a false positive rate of less than 5%, 4%, 3%, 2%, 1%, 0.1%, 0.05%, 0.01%.

The methods provided herein may provide high specificity, high sensitivity, high positive predictive value, and/or low negative predictive value. The methods provided herein may provide a specificity (or negative percent agreement) and/or sensitivity (or positive percent agreement) that is at least 70%, 75%, 80%, 85%, 86%, 87%, 88%, 89%, 90%, 91%, 92%, 93%, 94%, 95%, 96%, 97%, 98%, 99%, or more. In some cases, the nominal specificity is greater than or equal to 70%. The nominal negative predictive value (NPV) is greater than or equal to 95%. In some cases, the NPV is at least 95%, 95.5%, 96%, 96.5%, 97%, 97.5%, 98%, 98.5%, 99%, 99.5% or more.

Sensitivity, Positive Percent Agreement (PPA), or true positive rate (TPR) may refer to an equation of TP/(TP+FN) or TP/(total number of infected subjects), where TP is the number of true positives and FN is the number of false negatives. When calculating the denominator for the previous equations, the value can reflect the total number of infection results based on a particular independent method of detecting infection (e.g., blood culture or PCR).

Specificity, Negative Percent Agreement or true negative rate may refer to an equation such as TN/(TN+FP) or TN/(total number of uninfected subjects), where TN is true negative and FP is false positive. When calculating the denominator for the previous equations, the value can reflect the total number of actual "non-infections" as determined by an independent method of detecting infection (e.g., blood culture or PCR).

In some cases, the sample is identified as infected with an accuracy of greater than 75%, 80%, 85%, 86%, 87%, 88%, 89%, 90%, 91%, 92%, 93%, 94%, 95%, 96%, 97%, 98%, 99%, 99.5% or more. In some cases, the sample is identified as infected with a sensitivity of greater than 95%. In some cases, the sample is identified as infected with a specificity of greater than 95%. In some cases, the sample is identified as infected with a sensitivity of greater than 95% and a specificity of greater than 95%. In some cases, the accuracy is calculated using a trained algorithm. The diagnosis accuracy as used herein includes specificity, sensitivity, positive predictive value, negative predictive value, and/or false discovery rate. In some cases, a method described herein has a specificity or sensitivity of greater than 70%, 75%, 80%, 85%, 86%, 87%, 88%, 89%, 90%, 91%, 92%, 93%, 94%, 95%, 96%, 97%, 98%, 99%, or 99.5%, or a positive predictive value or negative predictive value of at least 95%, 95.5%, 96%, 96.5%, 97%, 97.5%, 98%, 98.5%, 99%, 99.5% or more.

When classifying a sample for diagnosis of infection, there are typically four possible outcomes from a binary classifier. If the outcome from a prediction is p and the actual value is also p, then it is called a true positive (TP); however if the actual value is n then it is said to be a false positive (FP). Conversely, a true negative has occurred when both the prediction outcome and the actual value are n, and false negative is when the prediction outcome is n while the actual value is p. For a test that detect a disease or disorder such an infection, a false positive in this case may occur when the subject tests positive, but actually does not have the infection. A false negative, on the other hand, may occur when the subject actually does have an infection but tests negative for such infection.

The positive predictive value (PPV), or precision rate, or post-test probability of disease, is the proportion of patients with positive test results who are correctly diagnosed. It may be calculated by applying the following equation: PPV=TP/(TP+FP). The PPV may reflect the probability that a positive test reflects the underlying condition being tested for. Its value does however may depend on the prevalence of the disease, which may vary. The Negative Predictive Value (NPV) can be calculated by the following equation: TN/(TN+FN). The negative predictive value may be the proportion of patients with negative test results who are correctly diagnosed. PPV and NPV measurements can be derived using appropriate disease prevalence estimates.

In some cases, the results of the sequencing analysis of the methods described herein provide a statistical confidence level that a given diagnosis is correct. In some cases, such statistical confidence level is above 85%, 90%, 91%, 92%, 93%, 94%, 95%, 96%, 97%, 98%, 99% or 99.5%.

Monitoring and Treating

The methods may include monitoring whether a subject has an infection over time. For example, samples may be collected serially at various times in order to determine the presence or absence of an infection. In other examples, the methods may include monitoring the course of an infection over time. In such cases, samples may be collected serially at various time points during an infection or illness; in some cases, the serially-collected samples are compared to each other to determine whether the infection is improving or worsening.

The methods provided herein include methods of treating a subject, e.g., a subject with an infection or suspected of having an infection. The treatment may reduce, prevent or eliminate an infection in the subject. In some cases, the treatment may reduce, prevent or eliminate infection and/or inflammation.

The treatment may involve administering a drug or other therapy to reduce or eliminate the inflammation and/or the infection. In some cases, the subject is treated prophylactically with a drug, e.g., to prevent development of an infection or inflammation.

Any therapy (including a drug) to improve or reduce the symptoms of an infection or inflammation may be administered to the subject. Exemplary drugs include but are not limited to antibiotics, antiviral medication, ampicillin, sulbactam, penicillin, vancomycin, gentamycin, aminoglycoside, clindamycin, cephalosporin, metronidazole, timentin, ticarcillin, clavulanic acid, cefoxitin, antiretroviral drugs (e.g., highly active antiretroviral therapy (HAART), reverse transcriptase inhibitors, nucleoside/nucleotide reverse transcriptase inhibitors (NRTIs), Non-nucleoside RT inhibitors, and/or protease inhibitors), antibody-drug conjugates, and immunoglobulins.

The methods may include methods of adjusting a therapeutic regimen. For example, the subject may have a known infection and may have been administered a drug to treat the infection. The methods provided herein may be used to track or monitor the efficacy of the drug treatment. In some cases, the therapeutic regimen may be adjusted, depending on the results of such monitoring. For example, if the methods provided herein indicate that an infection is not improving as a result of the drug treatment, the therapeutic regimen may be adjusted by changing the type of drug or treatment given to the patient, discontinuing use of the previous drug, continuing use of the drug, increasing the dose of a drug treatment, or adding a new drug or other treatment to the subject's therapeutic regimen. In some cases, the therapeutic regimen may involve a particular procedure. Likewise, if the methods indicate than an infection is improving or resolved, the adjusting may involve reducing or discontinuing the drug treatment.

A method described herein may further comprise RNA sequencing (RNA-Seq) or be combined with a method comprising RNA-Seq. Tissue damage or infection may lead to release of cell-free nucleic acids from a particular organ or tissue. For example, RNA may be released by apoptotic cells in tissues. RNA-Seq of cell-free RNA can indicate the health or status of different tissues in the body.

A method comprising RNA sequencing may enable detection of a specific organ or tissue that is infected and may be used to detect or monitor the health of an organ. RNA-Seq may be used independently to investigate an organ's health or may provide increased confidence that an infection detected by a method described herein is an infection of a specific organ. The RNA-Seq test may be conducted contemporaneously with a method to detect an infection, subsequent to a method to detect an infection, or prior to a method detect and infection.

There are many potential scenarios in which a method to detect a pathogen provided herein may be combined with a method to detect the site of infection by RNA sequencing of cell-free RNA in a body fluid. For example, a method provided herein may be used to detect circulating cell-free nucleic acids from a pathogen. The method may further comprise conducting an RNA-Seq test to detect an increase in organ-specific cell-free RNA in the subject's blood. The combination of test results may indicate that the pathogen has infected the organ and may even be able to determine which organ tissue is infected.

An RNA-Seq test (or series of RNA-Seq tests) may sometimes be performed after a method described herein produces a positive test result (e.g., detection of a pathogen infection). The RNA-Seq test may be especially useful for confirming the infection or for identifying the location of the infection. For example, the methods may detect the presence of a pathogen in a subject by analyzing circulating cell-free nucleic acids, but the site of infection may be unclear. In such case, the method may further comprise sequencing cell-free RNA from the subject in order to confirm that the infection is within an organ (such as by detection of increased levels of circulating cell-free RNA derived from organ tissues). The RNA sequencing test may then be repeated over time in order to determine whether the infection is worsening or improving in a particular organ or tissue, or whether it is spreading to different organs or tissue. Likewise, the pathogen detection assay may also be repeated over time.

In some cases, a method of detecting a pathogen described herein is conducted following the performance of an RNA-Seq test. For example, an increase in plasma levels of cell-free RNA associated with an organ may indicate a disorder such as infection of the organ. In such case, the method may further comprise detecting levels of circulating cell-free nucleic acids associated with organ infection.

A method described herein may be repeated, for example, to monitor an infection or treatment over time. A method described herein may be repeated every 1, 2, 3, 4, 5, 6, 7, 8, 9, or 10 days; every 1, 2, 3, 4, 5, or 6 weeks; or every 1, 2, 3, 4, 5, 6, 7, 8, or 9 months.

In some cases, when a method described herein gives a negative test result (e.g., no pathogen is detected), a method can be repeated serially over time to monitor pathogen nucleic acids in a subject. In some cases, the RNA-Seq assay is also repeated serially over time following a negative pathogen test result or negative RNA-Seq result.

In some cases, when a method described herein gives a positive test result (e.g., detection of a pathogen), a therapeutic regimen can be administered to the subject. A therapeutic regimen can include, but is not limited to, drug administration, antibiotic administration, or antiviral administration.

In some cases, when a method described herein gives a positive test result, a method or test can be repeated serially over time to monitor the course of infection. For example, a therapeutic regimen can be adjusted depending on upward or downward course of infection. In other cases, no therapeutic regimen may be conducted initially; for example, the infection may be monitored with a "watchful waiting" or "watch and wait" approach to see if the infection clears up without additional medical intervention. In some cases, when a method described herein gives a positive test result, a drug can be administered and the course of infection can be monitored to detect how well the drug is working or when to stop drug treatment. In some cases, the therapy can be altered as needed.

Computer Control Systems

Figure 7:
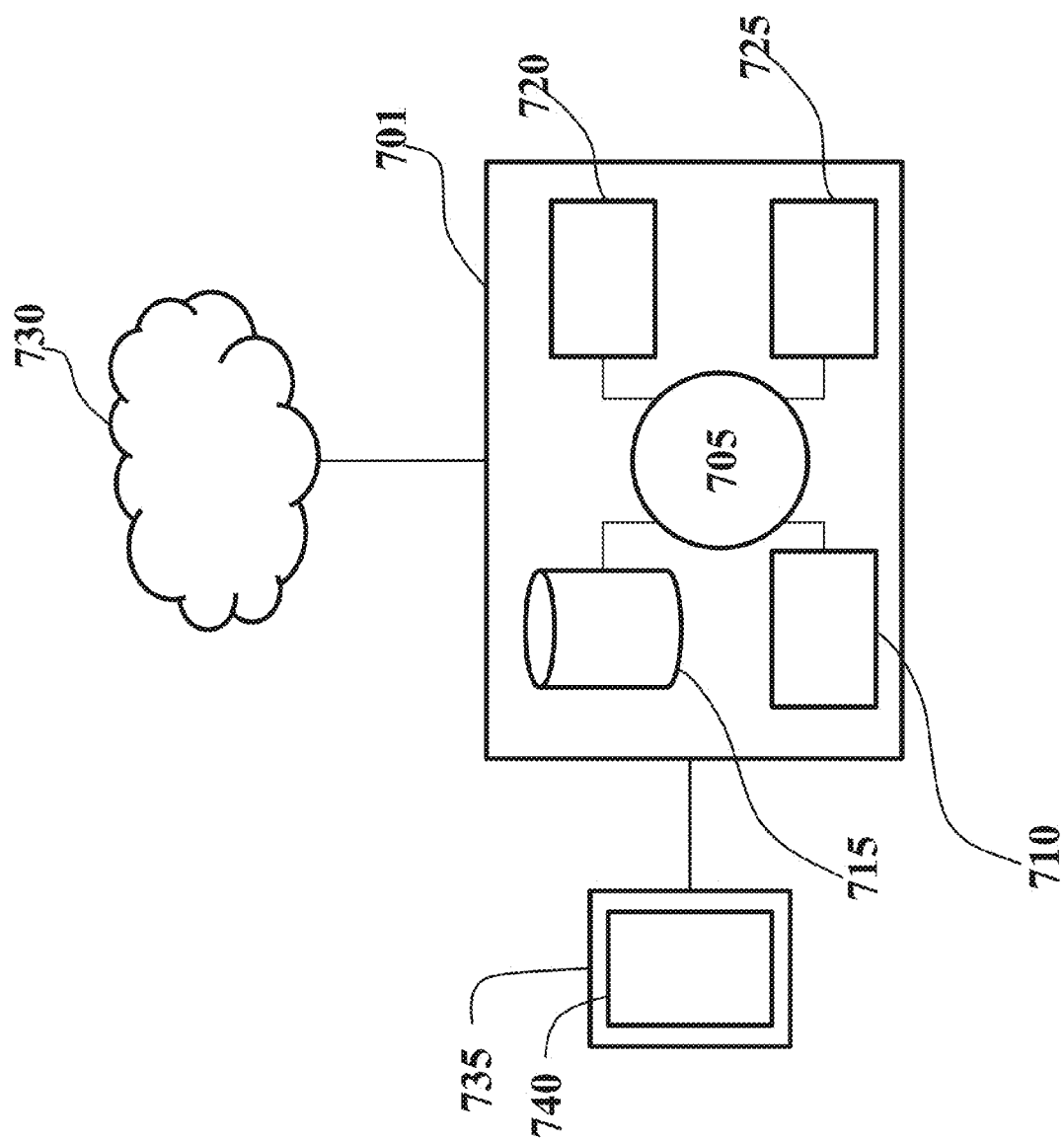
FIG. 7 shows a computer control system that is programmed or otherwise configured to implement methods provided herein.

The present disclosure provides computer control systems that are programmed to implement methods of the disclosure. FIG. 7 shows a computer system 701 that is programmed or otherwise configured to implement methods of the present disclosure.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback.

The CPU 705 can be part of a circuit, such as an integrated circuit. One or more other components of the system 701 can be included in the circuit. In some cases, the circuit is an application specific integrated circuit (ASIC).

The storage unit 715 can store files, such as drivers, libraries and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 730. For instance, the computer system 701 can communicate with a remote computer system of a user (e.g., healthcare provider). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 701 via the network 730.

Methods as described herein can be implemented by way of machine (e.g., computer processor) executable code stored on an electronic storage location of the computer system 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for providing, an output of a report, which may include a diagnosis of a subject or a therapeutic intervention for the subject. Examples of UI's include, without limitation, a graphical user interface (GUI) and web-based user interface. The analysis can be provided as a report. The report may be provided to a subject, to a health care professional, a lab-worker, or other individual.

Methods and systems of the present disclosure can be implemented by way of one or more algorithms. An algorithm can be implemented by way of software upon execution by the central processing unit 705. The algorithm can, for example, facilitate the enrichment, sequencing and/or detection of pathogen or other target nucleic acids.

Information about a patient or subject can be entered into a computer system, for example, patient background, patient medical history, or medical scans. The computer system can be used to analyze results from a method described herein, report results to a patient or doctor, or come up with a treatment plan.

Reagents and Kits

Also provided are reagents and kits thereof for practicing one or more of the methods described herein. The subject reagents and kits thereof may vary greatly. Reagents of interest include reagents specifically designed for use in identification, detection, and/or quantitation of one or more pathogen or other target nucleic acids in a sample obtained from a subject. The kits may comprise reagents necessary to perform nucleic acid extraction and/or nucleic acid detection using the methods described herein such as PCR and sequencing. The kit may further comprise a software package for data analysis, which may include reference profiles for comparison with the test profile, and in particular may include reference databases. The kits may comprise reagents such as buffers and water.

Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such kits may also include instructions to access a database. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

This disclosure also provides kits for generating a sequencing library. The kits may comprise at least one synthetic nucleic acid described herein and a reagent for a sequencing library reaction. In some cases, the kits comprise one or more sequencing adapters and one or more carrier nucleic acids. The carrier nucleic acids in the kits may comprise: i) one or more carrier nucleic acids that resist end-repair; ii) one or more carrier nucleic acids that resist ligation; iii) one or more carrier nucleic acids that resist amplification; iv) one or more carrier nucleic acids comprising a immobilization tag; v) one or more carrier nucleic acids with a size that allows for size-based depletion; and/or vi) any combination thereof. For example, the kits may comprise one or more sequencing adapters and one or more carrier nucleic acids that resist end-repair.

The amount of the sequencing library adapter and the amount of the one or more carrier nucleic acids in a kit may be at certain ratio. In some cases, the ratio of the amount of the sequencing library adapter to the amount of one or more carrier nucleic acid is no more than 1:10, 1:5, 1:1, 5:1, 10:1, 20:1, 50:1, 100:1, 500:1, or 1000:1. For example, the ratio of the amount of the sequencing library adapter to the amount of one or more carrier nucleic acid may be no more than 1:1.

Carrier Nucleic Acids (CNAs)

This disclosure provides carrier nucleic acids (CNAs), particularly surreptitious CNAs that contain features designed to exclude them from one or more steps of a sequencing assay. This disclosure also provided methods of using CNAs capable of evading one or more steps of a sequencing assay. Although the CNAs provided herein may behave surreptitiously, they are generally still capable of increasing the total nucleic acid quantity in a sample, thereby acting as a typical "carrier" nucleic acid. Carrier nucleic acids in general boost nucleic acid quantity in order to improve yield and/or efficiency when preparing a sequencing library from a sample and may ultimately improve the accuracy and/or sensitivity of a sequencing assay. Addition of carrier nucleic acids, including the modified CNAs provided herein, may be particularly useful when a sample contains a low amount of target nucleic acids, e.g., less than 1 ng, because low quantities of nucleic acids may reduce the efficiency and/or yield of one or more steps of library generation (e.g., nucleic acid extraction, nucleic acid purification, nucleic acid end-repair, adapter ligation, and the like) or later steps in a sequencing assay such as amplification. DNA- and/or RNA-based nucleic acids, in any of their structural forms and/or with or without one or more chemical modifications, can be added as CNAs to a sample of nucleic acids of interest. Typically, the CNAs do not interfere with nucleic acid sequencing, for example, by inhibition or by taking up a prohibitive portion of the sequencing throughput. In some cases, DNA CNAs are added to a DNA sample and/or an RNA sample. In some cases, RNA CNAs are added to a DNA sample and/or an RNA sample.

TABLE 6

Exemplary Carrier Nucleic Acid Sequences

| SEQ ID NO | Sequence (5'-3') |
|---|---|
| SEQ ID NO: 170 | CTG TTG GGC CGC CAC TGC GTG AGC CTC GGC CC |
| SEQ ID NO: 171 | GAC CTA TTT TGA CGG CAC CGT TGG rCrGrG rArArG TTG CTG GGC CTG CGC ACC GCG G |
| SEQ ID NO: 172 | GCG TCC CGG CGC GCG TTT AGG GAT AAC AGG GTA ATG GCG CAA GGG TGC TGG C |

TABLE 6-continued

Exemplary Carrier Nucleic Acid Sequences

| SEQ ID NO | Sequence (5'-3') |
|---|---|
| SEQ ID NO: 173 | /5InvddT/GC GTC CCG GCG CGC GTT TAG GGA TAA CA/idSp//idSp//idSp//idSp/ GGG TAA TGG CGC AAG GGT GCT GGC/ 3InvdT/ |

Figure 8:
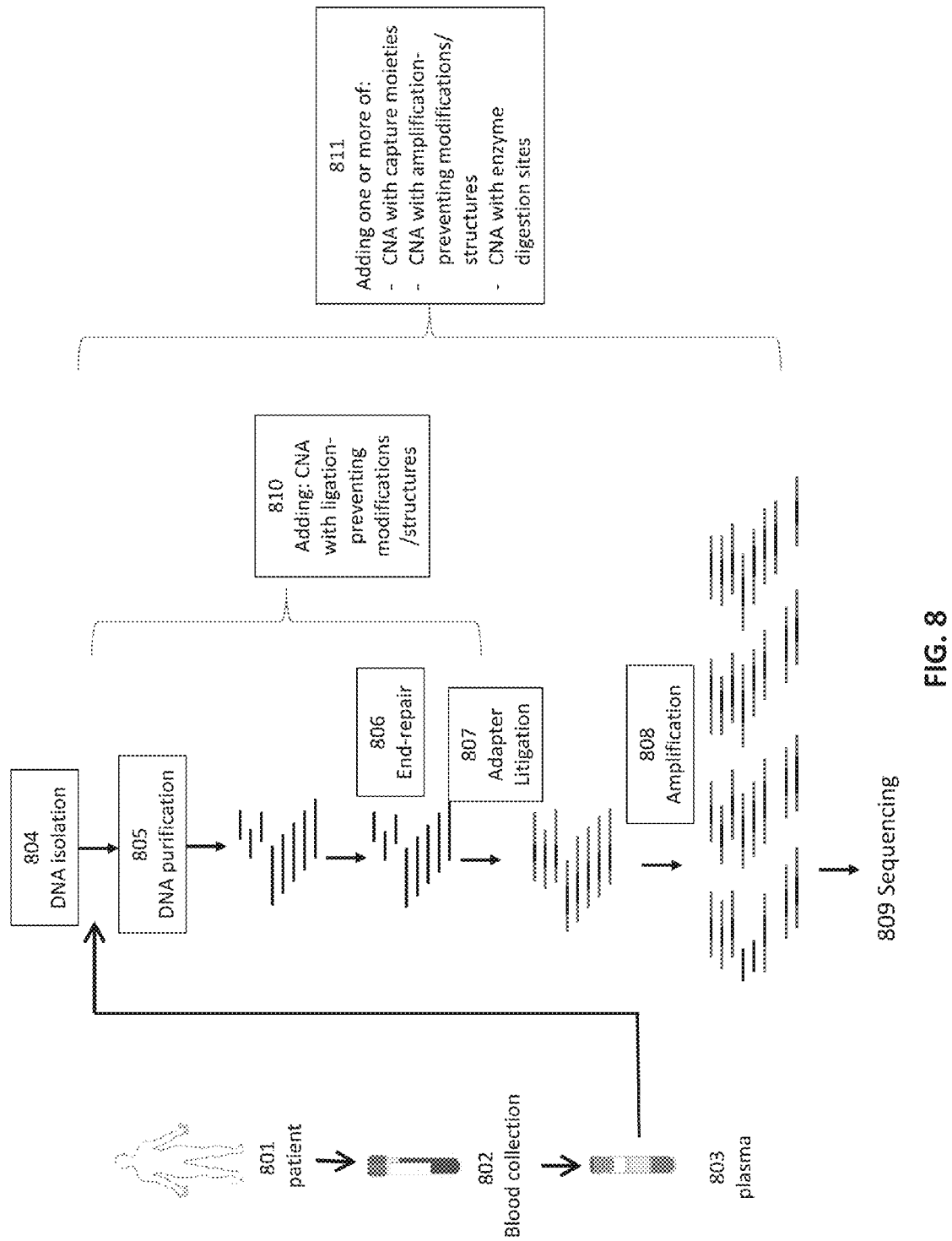
FIG. 8 shows the steps in a sequencing library preparation where carrier nucleic acids may be added.

The CNAs provided herein may be designed or modified to evade one or more steps of sequencing library generation, such as end-repair, fragmentation, amplification, ligation, and sequencing. The CNAs may be added to one or more steps in a sequencing library preparation. For example, as shown in FIG. 8, the CNAs may be added during or directly after sample collection 802, during or after sample preparation, such as isolation of plasma 803; before, during or after nucleic acid isolation 804 or extraction 805, before, during, or after nucleic acid purification, before, during or after end repair of the nucleic acids 806, before, during or after ligation 807 or other procedure to attach adapters to the nucleic acids, and/or before or during amplification 808. In certain cases, the CNAs can be removed from a step in a sequencing assay, e.g., by enzyme digestion, affinity-based depletion, and/or size-based depletion. For example, the CNAs provided herein may be physically removed from a step in a sequencing assay in such a manner as to exclude them from being included in a sequencing library. In some cases, the CNAs may be physically removed from a sequencing library itself.

CNAs that Resist Attachment

The CNAs provided herein may resist being attached or ligated to one or more sequencing adapters and/or to other molecules such as target nucleic acids. In some cases, the CNAs may be designed so that adapters preferentially ligate to target nucleic acids over the CNAs. By avoiding ligation or attachment to adapters or the target nucleic acids, the CNAs may also avoid being sequenced.

In some cases, particularly when ligation is used to attach adapter to nucleic acids in a sample, the CNAs may be designed to resist being including in a ligation reaction. Generally, a ligation reaction involves linking two nucleic acids via a phosphodiester bond. In some cases, the CNAs may be designed to have a secondary structure (e.g., single-stranded structure, hairpin structure) that resists a ligation reaction. The secondary structure may contain RNA, DNA, ssDNA, dsDNA, DNA-RNA hybrid, and/or other features. In some cases, the CNAs may contain a blocking group or other structure designed to impede ligation.

The CNAs provided herein may contain single-stranded and/or double-stranded secondary structures designed to resist or diminish attachment or ligation. The CNA may contain one or more single-stranded regions, or may be entirely single-stranded. The single-stranded region may occur at any location of the CNA, but in some preferred cases, the CNA contains single-stranded regions near or at one or both of its ends. For example, the CNA may contain single-stranded regions within 50 nucleotides from one or both ends, e.g., within 50 nt, 45 nt, 40 nt, 35 nt, 30 nt, 25 nt, 20 nt, 15 nt, 10 nt, or 5 nt from one or both ends. In some preferred cases, the CNA may contain single-stranded regions at one or both of its ends (e.g., at the 5' end, at the 3' end). In some cases, the CNA may be entirely double-stranded or simply contain regions that are double-stranded. Secondary structures (particularly hairpin loops) may prevent the binding and/or recognition of the CNAs by a ligase.

In some cases, the CNAs may contain Y-shaped double-stranded nucleic acids, such that the Y-shape portion of the CNAs is not able to be ligated or attached to another nucleic acid.

Hairpin structures that may be present in a CNA provided herein generally possess a loop and a hybridization region, e.g., hairpin stem. For example, a hairpin may comprise two complementary regions that form a double-stranded hybridization region and a loop that links the two complementary regions. A complementary region may comprise at least 5, 10, 15, 20, 30, 40, 50 nucleotides. A loop region may comprise at least 3, 4, 5, 10, 15, 20, 30, 40, 50 nucleotides. Generally, hairpin structures may be relatively easy to manufacture as they often are merely single-stranded nucleic acids, without attachments. The hairpins may contain RNA or DNA.

The CNAs provided herein may contain a circular structure that resists or diminishes attachment or ligation. The circular structure may be circular DNA, circular RNA, or circular DNA-RNA hybrid. In some cases, the circular structure is circular DNA. The circular structure may be double-stranded or single-stranded. The circular structure may be of certain length, e.g., at least 5 nt, 10 nt, 20 nt, 30 nt, 32 nt, 40 nt, 50 nt, 60 nt, 70 nt, 80 nt, 90 nt, 100 nt, 120 nt, 140 nt, 160 nt, 180 nt, 200 nt, 250 nt, 300 nt, 400 nt, 500 nt, or 1000 nt. In some cases, the circular structure comprises from about 30 to about 100 nucleotides. In some cases, the circular structure may have a size within the range from about 10 nucleotides to about 10,000 nucleotides, such as within the range from about 100 nucleotides to about 1,000 nucleotides. In the cases where the circular structure is double-stranded, the circular structure may have a size of at least 10 bp, 20 bp, 30 bp, 40 bp, 50 bp, 60 bp, 70 bp, 80 bp, 90 bp, 100 bp, 120 bp, 140 bp, 160 bp, 180 bp, 200 bp, 250 bp, 300 bp, 400 bp, 500 bp, or 1000 bp. In some cases, the double-stranded circular structure comprises from about 30 bp to 100 bp. In some cases, the double-stranded circular structure may have a size within the range from about 10 base pairs to about 10,000 base pairs, such as within the range from about 100 base pairs to about 1,000 base pairs. In some cases, the circular structure may enable the CNA to resist digestion from a certain enzyme, e.g., endonuclease. For example, the CNA may contain a double-stranded circular structure and may resist digestion by endonucleases, such as endonucleases that digest double-stranded linear, but not double-stranded circular, DNA. In some cases, the CNA is primarily or entirely circular, e.g., circular double-stranded DNA, circular single-stranded DNA. In some cases, the CNA comprises a secondary structure that resists digestion by an endonuclease, e.g., an endonuclease that does not bind and/or recognize the CNA's secondary structure. For example, the CNA may comprise double-stranded DNA that resists digestion by an endonuclease recognizing single-stranded DNA but not double-stranded DNA. For another example, the CNA may comprise single-stranded DNA that resists digestion by an endonuclease recognizing double-stranded DNA but not single-stranded DNA.

In some cases, a CNA is double-stranded with one or more nicks. A nick may be a discontinuity in a double-stranded nucleic acid molecule where there is no phosphodiester bond between adjacent nucleotides of one of the strands. A nick may be generated by an enzyme, e.g., a nicking endonuclease. In some cases, a nick may be ligated by an enzyme, e.g., a ligase. In certain cases, a nick is protected against exonuclease digestion and/or ligation.

The CNAs may comprise one or more modifications (e.g., modified nucleotides) that resist a ligation reaction. In some cases, a modification may be a blocking group that prevents the CNAs from ligating to a nucleic acid. For example, the CNA may have a blocking group at the 3' end, the 5' end, or both ends. The blocking group may comprise an inverted deoxy-sugar. The inverted deoxy-sugar may be an inverted deoxy-sugar, an inverted dideoxy-sugar, or other inverted deoxy sugar. The inverted deoxy-sugar may be a 3' inverted deoxy-sugar or a 5' inverted dideoxy-sugar. For example, a blocking group may be a 3' inverted thymidine (dT), a 3' inverted adenosine (dA), a 3' inverted guanosine (dG), a 3' inverted cytidine (dC), a 3' inverted deoxyuracil (dU), a 5' inverted dideoxythymidine (ddT), a 5' inverted dideoxyadenosine (ddA), a 5' inverted dideoxyguanosine (ddG), a 5' inverted dideoxycytidine (ddC), a 5' inverted dideoxyuracil (ddU), or any analog thereof. In some cases, a CNA comprises a 3' inverted thymidine. In some cases, a CNA comprises a 5' inverted dideoxythymidine. In some cases, a CNA comprises 3' inverted thymidine and/or a 5' inverted dideoxythymidine. In some cases, the blocking group comprises dideoxycytidine. In some cases, modifications include a uracil (U) base, 2'OMe modified RNA, C3-18 spacers (e.g., structures with 3-18 consecutive carbon atoms), biotin, di-deoxynucleotide triphosphate, ethylene glycol, amine, and/or phosphate.

Carrier Nucleic Acids that Resist Amplification

The CNAs may comprise one or more nucleic acid modifications that inhibit nucleic acid amplification, thereby preventing the CNAs from being amplified in a sequencing reaction. In some cases, the modifications may prevent a nucleic acid polymerase from functioning, e.g., by stalling or inhibiting (e.g., slowing down) the polymerase. In some cases, the modifications may comprise one or more abasic sites. An abasic site may refer to a location in a nucleic acid that does not have a base. For example, an abasic site in a nucleic acid may be at a 1'-end without a base. An abasic site may have an apurine or apyrimidine structure, a base analog, or an analogue of a phosphate backbone. In some cases, an abasic site has a backbone of N-(2-aminoethyl)-glycine linked by amide bonds, tetrahydrofuran, or 1',2'-Dideoxyribose (dSpacer). In some cases, a modification may comprise an abasic site and a modified sugar residue, e.g., a sugar residue with 3 carbon atoms, such as a partial ribose structure (e.g., only 3', 4', 5' end carbon atoms are retained) to retain the connectivity along the backbone.

The abasic sites may prevent a polymerase from amplifying the CNA. In some cases, the abasic sites in a CNA may inhibit a polymerase (e.g., Taq polymerase) by one order of magnitude per abasic site.

The CNAs provided herein may comprise multiple abasic sites, e.g., multiple internal abasic sites and one or more other features. The CNAs may also contain features that prevent participation in one or more library preparation reactions. For example, the CNAs may comprise one or more internal abasic sites, 3' inverted dT, and/or 5' inverted ddT in any combination.

In some cases, the CNAs may contain other modifications that inhibit nucleic amplification. In some cases, the modifications that inhibit nucleic acid amplification include a uracil (U) base, 2'OMe modified RNA, C3-18 spacers (e.g., structures with 3-18 consecutive carbon atoms, such as C3 spacer), ethyleneglycol multimer spacers (e.g., spacer 18 (hexa-ethyleneglycol spacer), biotin, di-deoxynucleotide triphosphate, ethylene glycol, amine, and/or phosphate.

Modifications

A CNA may comprise at least one, two, three four, five, six, seven, eight, nine, ten, or higher numbers of modifications (e.g., abasic sites). In cases where a CNA comprises multiple modifications (e.g., modifications that inhibit nucleic acid amplification), the modifications may be clustered (e.g., the modifications locate consecutively next to each other). In some cases, the one or more modifications are at the 5' end of the CNA. In some cases, the one or more modifications are at the 3' end of the CNA. In some cases, the one or more modifications are at both the 3' end and the 5' end of the CNA. In some cases, the one or more modifications are at an internal position of the CNA. For example, a CNA may comprise one or more internal dspacers (idsp).

The modifications described herein may include 2-Aminopurine, 2,6-Diaminopurine, 5-Bromo dU, deoxyUridine, Inverted dT, Inverted Dideoxy-T, Dideoxy-C, 5-Methyl dC, deoxyInosine, Universal base such as 5-Nitroindole, 2'-O-Methyl RNA bases, Iso-dC, Iso-dG, Ribonucleotide, Morpholino, Protein nucleitide analogues, Glycoic nucleotide analogues, Locked nucleotide analogues, Threose nucleotide analogues, Chain terminating nucleotide analogues, Thiouridine, Pseudouridine, Dihydrouridine, Queuosine, Wyosine nucleotides, abasic sites, functional groups, e.g., alkyne functional group, azide functional group such as azide (NHS Ester, unnatural bonds, e.g., phosphorothioate bonds, spacers, e.g., 2'-Dideoxyribose (dSpacer), Hexanediol, photo-cleavable spacer, different length spacers with different number of carbon atoms, e.g., C3 spacer phosphoramidite, C9 spacer, e.g., a triethylene glycol spacer, CI8 an 18-atom hexa-ethyleneglycol spacer. Such spacers can be incorporated at the 5'-end or 3'-end of a CNA or an adapter or internally. Furthermore, at least one strand of a CNA may be modified by phosphorylation, e.g., comprising either 5' phosphate, or 3' phosphate (e.g., on the complementary strand), or both.

Enzyme Recognition Site

The CNAs may comprise characteristics that allow the CNAs to be removed from a sequencing library. Such characteristics may include an enzyme recognition site. For example, a CNA may comprise one or more enzyme recognition site, so that the synthetic nucleic may be degraded by the enzyme. In some cases, the CNAs may comprise one or more enzyme recognition sites that are not present in the target nucleic acids and adapters. Thus, the carrier nucleic acids may be removed by enzymes targeting the recognition sites without resulting in enzymatic degradation of the target nucleic acids or the adapters.

In some cases, a CNA may comprise a nuclease recognition site. For example, the nuclease recognition site may be an endonuclease recognition site. The endonuclease can be type I, type II (including type IIS, type IIG), type III or type IV endonuclease. In some cases, the endonuclease recognition site is a restriction nuclease recognition site. For example, the endonuclease recognition site may be a recognition site for AatII, Acc65I, AccI, AclI, AatII, Acc65I, AccI, AclI, AfeI, AflIII, AgeI, ApaI, ApaLI, ApoI, AscI, AseI, AsiSI, AvrII, BamHI, BclI, BglII, Bme1580I, BmtI, BsaHI, BsiEI, BsiWI, BspEI, BspHI, BsrGI, BssHII, BstBI, BstZ17I, BtgI, ClaI, DraI, EaeI, EagI, EcoRI, EcoRV, FseI, FspI, HaeII, HincII, HindIII, HpaI, KasI, KpnI, MfeI, MluI, MscI, MspA1I, MfeI, MluI, MscI, MspA1I, NaeI, NarI, NcoI, NdeI, NgoMIV, NheI, NotI, NruI, NsiI, NspI, PacI, PciI, PmeI, PmlI, PsiI, PspOMI, PstI, PvuI, PvuII, SacI, SacII, SalI, SbfI, ScaI, SfcI, SfoI, SgrAI, SmaI, SmlI, SnaBI, SpeI, SphI, SspI, StuI, SwaI, XbaI, XhoI, or XmaI. The enzyme recognition site may be a site for a DNase not mentioned above, e.g., an exodeoxyribonuclease. The enzyme recognition site may be a site for Uracil DNA glycosylase (UDG), DNA glycosylase-lyase (Endonuclease VIII), or a mixture thereof (e.g., Uracil-Specific Excision Reagent (USER) Enzyme). For example, the CNAs may comprise one or more uracils (e.g., internal uracil). The enzyme recognition site may be a site for a RNA-guided DNase, e.g., CRISPR-associated protein nuclease, e.g., Cas9. In certain cases, nuclease recognition site may be a recognized site for RNase, e.g., an endoribonuclease, such as RNase A, RNase H, RNase III, RNase L, RNase P, RNase PhyM, RNase T1, RNase T2, RNase U2, RNase V, or an exoribonuclease, such as polynucleotide phosphorylase, RNase PH, RNase R, RNase D, RNase T, oligoribonuclease, exoribonuclease I, or exoribonuclease II. In some specific instances, the CNA may contain a restriction enzyme recognition site and a method provided herein may comprise digesting the CNA with the restriction enzyme that recognizes such site. In some cases, the CNA comprises a secondary or tertiary structure that may be recognized by an enzyme (e.g., an enzyme that binds and/or degrades the CNA), ribozymes, aptamers, and DNA-based catalytic or binding polymers. In some cases, the CNA comprises one or more specific binding nucleic acid sequences that can be recognized by an enzyme.

In some cases, the CNAs may comprise a DNA-RNA hybrid that can be degraded by a DNase or RNase. In some cases, a CNA comprises DNA-RNA-DNA hybrid. Such a molecule may be double-stranded. The terminal regions of the CNA may comprise deoxyribonucleotides. The internal regions may comprise ribonucleotides. In some cases, the DNA-RNA hybrid is able to ligate to the target nucleic acids or adapters; the DNA-RNA hybrid may then be digested by RNase prior to sequencing (e.g., prior to the amplification step). In some particular cases, the DNA-RNA hybrid is digested (e.g., by RNase), while the target nucleic acids (e.g., DNA, such as cell-free DNA) are not digested by the RNase.

In cases where the DNA section of the CNAs are long enough to resist amplification, an RNase digestion step may not be needed to remove the DNA-RNA hybrid before sequencing. Alternatively, in cases where the DNA-RNA hybrid molecules are degraded by enzymatic digestion before amplification, the DNA-RNA hybrid may not need to have a size or length that resists amplification.

CNAs for Size-Based Depletion

The CNAs may have a size so that they can be separated from the sequencing library by size-based depletion. In some cases, the CNAs have a length greater than a length of the target nucleic acids, or than the average length of the target nucleic acids. For example, the CNAs may have a length at least 1.5, 2, 3, 4, 5, 10, 20, or 50 times greater than a length of the target nucleic acids, or the average length of the target nucleic acids. The CNAs may have a length of at least 150 bp, 200 bp, 300 bp, 400 bp, 500 bp, 600 bp, 800 bp, 1 kb, 2 kb, 5 kb or 10 kb. For example the CNAs may have a length of at least 500 bp. In some cases, CNAs may have a size within the range from about 150 bp to about 1000 bp. In some cases, CNAs may have a size up to 2 kb. In some cases, the length of CNAs is shorter length than a length of the target nucleic acids, or than the average length of the target nucleic acids. For example, the CNAs may have a length that is at most 99%, 95%, 90%, 80%, 60%, 50%, 40%, 20%, or 10% of a length of the target nucleic acids, or the average length of the target nucleic acids. In some cases, the CNAs may have a size that is at most 50% of a size of a target nucleic acid, or the average size of the target nucleic acids. In certain cases, the CNA has a length that is substantially the same as the target nucleic acids, or the average length of the target nucleic acids.

CNAs with a size or length allowing for size-based depletion may also contain any modification described in the disclosure, e.g., modifications for preventing ligation, amplification, end-repair, or a combination thereof. In some cases, one or both ends of the CNA may contain one or more of the modifications. In some cases, the modifications may be internal modifications, e.g., internal abasic sites or a combination of end modifications and internal modifications.

In some specific examples, a CNA may have a longer length that enables size-based depletion as well as a modification (e.g., an end modification) such as an inverted base that discourages ligation. Other combinations of structures that prevent or discourage ligation are also possible (e.g., hairpin loops, hairpin loops combined with end modifications). In some cases, the CNA may comprise one or more hairpin structures and one or more abasic sites. In some specific cases, a CNA may have a size or length more than 500 bp and have a 3' inverted dT, 5' inverted ddT, C3 spacer, or spacer 18, or a hairpin structure on one end. In some specific cases, a CNA may have a size or length more than 600 bp and have a 3' inverted dT, 5' inverted ddT on one end at one or more internal abasic sites.

Immobilization Tags

The CNAs may comprise one or more immobilization tags. The immobilization tags may be used to remove the CNAs from a solution (e.g., a solution of sequencing library) by affinity-based depletion. For example, the immobilization tags may attach to a solid support, e.g., a bead or a plate. The CNA may be removed from a solution when contacting the solution with the solid support. The CNAs comprising one or more immobilization tags may be shorter than the target nucleic acids. Alternatively, the CNAs molecule may be longer than the target nucleic acids, e.g., to minimize carryover of the CNAs into the sequencing reaction.

The immobilization tags may include biotin, digoxigenin, Ni-Nitrilotriacetic acid, desthiobiotin, histidine, polyhistidine, myc, hemagglutinin (HA), FLAG, fluorescence tag, tandemaffinity purification (TAP) tags, glutathione S transferase (GST), polynucleotide, aptamer, polypeptide (e.g., antigen or antibody), or derivatives thereof. For example, the CNAs may comprise biotin, e.g., internally or terminally biotinylated strands. In some cases, the immobilization tags may comprise magnetically susceptible material, e.g., a magnet, or magnetically susceptible metal. In some particular examples, biotinylated CNA may enable magnetic bead-based depletion (e.g., via avidin-magnetic beads) of CNA from a sample or sequencing library prior to the amplification step. In some cases, the CNAs comprise a secondary or tertiary structure that may attach to a solid support or bind to an immobilization tag.

In some cases, the target nucleic acids and/or the sequencing library nucleic acids comprise one or more immobilization tags. In these cases, the CNAs comprise no immobilization tags or different immobilization tags compared to the target nucleic acids. Thus, the CNAs may be separated from the target nucleic acids and/or the sequencing library nucleic acids by affinity-based depletion using different immobilization tags. For example, the target nucleic acids and/or the sequencing library nucleic acids may be immobilized on a solid support while the CNAs may be washed away. In some cases, the CNAs are linked directly or indirectly to the immobilization tags. In some cases, the CNAs are cleaved from the immobilization tags.

The CNAs may comprise a combination of the characteristics and structures disclosed herein. In some cases, the CNAs comprise one or more modifications that inhibit nucleic acid amplification and one or more modifications that resist a ligation reaction. For example, the CNAs comprise may comprise one or more abasic sites (e.g., internal dspacer) and an inverted deoxy-base (e.g., 3' inverted thymidine). The CNAs comprising the modifications may further comprise an enzyme recognition site and/or an immobilization tag. In certain cases, the CNAs comprise a DNA-RNA hybrid with one or more immobilization tags, e.g., a biotinylated DNA-RNA-DNA hybrid molecule. The CNAs may also have secondary and/or tertiary structures of nucleic acids with high affinity for a specific enzyme or protein, or any non-amino-acid-based catalytic or affinity unit, e.g., ribozymes, DNA-based catalytic polymers, and molecularly imprinted polymers.

Ratio of Carrier Nucleic Acids to Nucleic Acids in a Sample

Certain amount of CNAs may be added to a sample comprising nucleic acids, e.g., for preparing a sequencing library from the nucleic acids in the sample. In some cases, the ratio of the amount of the total nucleic acids in the sample to the amount of CNAs added to the sample is at least 1:100, 1:50, 1:10, 1:1, 10:1, 50:1, 100:1, 500:1, 1000:1, 2000:1, or 5000:1. In some cases, the ratio of the amount of the target nucleic acids in the sample to the amount of CNAs added to the sample is at least 1:100, 1:50, 1:10, 1:1, 10:1, 50:1, 100:1, 500:1, 1000:1, 2000:1, or 5000:1. In some cases, the ratio of the amount of the total nucleic acids in the sample to the amount of CNAs added to the sample is at most 10:1, 1:1, 1:10, 1:50, 1:100, 1:500, 1:1000, 1:2000, or 1:5000. In some cases, the ratio of the amount of the target nucleic acids in the sample to the amount of CNAs added to the sample is at most 10:1, 1:1, 1:10, 1:50, 1:100, 1:500, 1:1000, 1:2000, or 1:5000. In some cases, the ratio of the amount of the total nucleic acids in the sample to the amount of CNAs added to the sample is within the range from about 1:1 to about 1:100. In some cases, the ratio of the amount of the target nucleic acids in the sample to the amount of CNAs added to the sample is within the range from about 1:1 to about 1:100. In some cases, the ratio is a molar ratio.

Methods for Using CNAs when Generating a Sequencing Library

Disclosed herein include methods for preparing a sequencing library. The methods may include adding the CNAs disclosed herein to improve the efficiency and/or yield of sequencing library generation. A sequencing library may refer to a population of nucleic acid molecules subject to sequencing. The methods may involve obtaining a sample comprising target nucleic acids and/or adapters (e.g., sequencing adapters), and one or more CNAs. The methods may further comprise one or more steps for generating a sequencing library. The methods may also comprise sequencing one or more nucleic acids in the sequencing library. The CNAs may not be sequenced, e.g., the CNAs may be physically removed from the library or may be designed such that they do not participate in one or more steps in sequencing library generation.

The methods may comprise adding the CNAs in a sample comprising target nucleic acids and/or adapters. The amount of CNAs added in a sample may be at least 0.1 ng, 0.5 ng, 1 ng, 5 ng, 10 ng, 20 ng, 30 ng, 40 ng, 50 ng, 60 ng, 70 ng, 80 ng, 90 ng, 100 ng, 150 ng, 200 ng, 300 ng, 400 ng, or 500 ng. In some cases, the amount of CNA may be from 0.1 ng to 200 ng, from 1 ng to 100 ng, from 5 ng to 80 ng, from 10 to 60 ng, or from 20 ng to 50 ng. The concentration of the CNAs in the sample may be at least 0.1 ng/mL, 0.5 ng/mL, 0.6 ng/mL, 0.8 ng/mL, 1 ng/mL, 2 ng/mL, 5 ng/mL, 10 ng/mL, 0.01 ng/µL, 0.05 ng/µL, 0.1 ng/µL, 0.2 ng/µL, 0.4 ng/µL, 0.8 ng/µL, 1 ng/µL, 1.2 ng/µL, 1.5 ng/µL, 2 ng/µL, 5 ng/µL, or 10 ng/µL. In some cases, the amount of CNAs added in a sample may be within the range from about 1 ng per 15 µL to about 5 ng per 15 µL. In some cases, the amount of CNAs added in a sample may be within the range from about 0.05 ng/µL to about 0.5 ng/µL.

The methods herein may comprise adding any types of synthetic nucleic acids described throughout the disclosure. For example, the methods may comprise adding one or more of the following synthetic nucleic acids: synthetic nucleic acids for sequencing library generation, synthetic nucleic acids for normalizing relative abundance of target nucleic acids (e.g., synthetic nucleic acids of known concentration), and/or synthetic nucleic acids for determining diversity loss of nucleic acids in a sample.

Nucleic Acids Extraction

The method may comprise extracting nucleic acids (e.g., target nucleic acids, cell-free nucleic acids) from a sample. The extraction may comprise separating the nucleic acids from other cellular components and contaminants that may be present in the sample, e.g., biological fluid or tissue sample. In some cases, the extraction is performed by phenol chloroform extraction or precipitation by organic solvents (e.g., ethanol, or isopropanol). In some cases, the extraction is performed using nucleic acid-binding columns. In some cases, the extraction is performed using commercially available kits such as the Qiagen Qiamp Circulating Nucleic Acid Kit Qiagen Qubit dsDNA HS Assay kit, Agilent™ DNA 1000 kit, TruSeq™ Sequencing Library Preparation, or nucleic acid-binding spin columns (e.g., Qiagen DNA miniprep kit). In some cases, extraction of cell-free nucleic acids may involve filtration or ultra-filtration.

The CNAs may be added to the sample before or during the extraction. For example, the carrier nucleic acids may be added to the sample before it is mixed with an extraction reagent, e.g., an extraction buffer. Alternatively, the carrier nucleic acids may be added to an extraction reagent, e.g., an extraction buffer that is then mixed with the sample. In certain cases, the CNAs may also be added to the mixture of the sample and an extraction reagent, e.g., an extraction buffer. In these cases, the target nucleic acids and the CNAs may be extracted simultaneously.

Adding the CNAs to a sample may increase the yield of nucleic acid extraction. The yield of extracting the target nucleic acids together with the CNAs may be higher than the yield of extracting the target nucleic acids without the CNAs, e.g., by at least 10%, 20%, 40%, 60%, 80%, 100%, 2-fold, 4-fold, 6-fold, 8-fold, or 10-fold. In some cases, the CNAs may be added to the sample comprising target nucleic acid after the nucleic acids extraction. The extraction may yield at least 10 ng, 50 ng, 100 ng, 200 ng, 300 ng, 400 ng, 500 ng, 600 ng, 700 ng, 800 ng, 900 ng, or 1000 ng nucleic acids.

Nucleic Acid Purification

The method may comprise purifying the target nucleic acids. Exemplary purification methods include ethanol precipitation, isopropanol precipitation, phenol chloroform purification, and column purification (e.g., affinity-based column purification), dialysis, filtration, or ultrafiltration.

The CNAs may be added to the sample before or during the purification. For example, the carrier nucleic acids may be added to the sample before it is mixed with a purification reagent, e.g., a purification buffer. Alternatively, the carrier nucleic acids may be added to purification reagent, e.g., a purification buffer that is then mixed with the sample. In certain cases, the CNAs may also be added to the mixture of the sample and a purification reagent, e.g., a purification buffer. In these cases, the target nucleic acids and the CNAs may be purified simultaneously.

Adding the CNAs to a sample may increase the yield of nucleic acid purification. The yield of purifying the target nucleic acids together with the CNAs may be higher than the yield of purifying the target nucleic acids without the CNAs, e.g., by at least 10%, 20%, 40%, 60%, 80%, 100%, 2-fold, 4-fold, 6-fold, 8-fold, or 10-fold. In some cases, the CNAs may be added to the sample comprising target nucleic acid after the nucleic acids purification. In some cases, the purification of nucleic acids in a sample with CNA added yield at least 1 pg, 10 pg, 50 pg, 100 pg, 500 pg, 1 ng, 5 ng, 10 ng, 50 ng, 100 ng, 200 ng, 300 ng, 400 ng, 500 ng, 600 ng, 700 ng, 800 ng, 900 ng, or 1000 ng of the total nucleic acids in a sample. In some cases, the purification of nucleic acids in a sample with CNA added yield at least 1 pg, 10 pg, 50 pg, 100 pg, 500 pg, 1 ng, 5 ng, 10 ng, 50 ng, 100 ng, 200 ng, 300 ng, 400 ng, 500 ng, 600 ng, 700 ng, 800 ng, 900 ng, or 1000 ng of the target nucleic acids in a sample.

Fragmentation

The method may comprise fragmenting the target nucleic acids. Fragmenting of the target nucleic acids may be performed by e.g., mechanical shearing, passing the sample through a syringe, sonication, heat treatment, or a combination thereof. In some cases, fragmenting of the target nucleic acids is performed by using an enzyme, including a nuclease, or a transposase. Nucleases used for fragmenting may comprise restriction endonucleases, homing endonucleases, nicking endonucleases, high fidelity restriction enzymes, or any enzyme disclosed herein. The methods may comprise fragmenting the target nucleic acids into fragments of certain length, e.g., at least 50, 60, 80, 100, 120, 140, 160, 180, 200, 300, 400, 500, 1000, 2000, 4000, 6000, 8000, or 10000 bp in length. The CNAs may be added to the sample before the fragmentation of the target nucleic acids. The CNAs may be added to the sample after the fragmentation of the target nucleic acids.

A-Tailing

The method may comprise performing A-tailing on the target nucleic acids. An A-tailing reaction may be performed by using one or more A-tailing enzymes. For example, an adenine (A) residue can be added by incubating a DNA fragment with dATP and a non-proofreading DNA polymerase, which will add a single 3' A residue. The CNAs may be added to the sample comprising target nucleic acid before the A-tailing. Alternatively, the CNAs may be added to the sample comprising target nucleic acid after the A-tailing.

End Repair

The method may comprise performing end repair on the target nucleic acids. For example, end repair may be performed on the target nucleic acids so they may be suitable for other steps of the sequencing library preparation. The end repair reaction may be performed by using one or more end repair enzymes. Enzymes for repairing DNA may include polymerase and exonuclease. For example, a polymerase may fill in the missing bases for a DNA strand from 5' to 3' direction. The resulting double-stranded DNA may have substantially the same length as the original longest DNA strand. Exonuclease may remove the 3' overhangs. The resulting double-stranded DNA may have substantially the same length as the original shortest DNA strand.

The CNAs may be added to the sample comprising target nucleic acids before the end repair. In some cases, adding the CNAs increases the efficiency of the end repair reaction, e.g., by at least 10%, 20%, 40%, 60%, 80%, or 100%. In some cases, CNAs may be added to the sample comprising target nucleic acid after the end repair. In certain cases, adding the CNA may preserve the activity and/or function of an enzyme, e.g., an end-repair enzyme. For example, an enzyme may have decreased activity and/or abnormal function in a sample with low amount of nucleic acids, and adding CNAs may increase the total nucleic acid amount in the sample so that the enzyme may function normally in the sample.

Adapter Attachment

The methods may comprise attaching one or more adapters to the target nucleic acids. Adapters may be attached to a target nucleic acid by primer extension, reverse transcription, or hybridization. In some cases, an adapter is attached to a target nucleic acid by ligation. For example, an adapter maybe attached to a target nucleic acid by a ligase. For example, an adapter may be attached to a target nucleic acid by sticky-end ligation or blunt-end ligation. In some cases, an adapter may be attached to a target nucleic acid by a transposase. A target nucleic acid may be attached an adapter at the 3' end, the 5' end, or both ends. In some cases, a target nucleic acid is attached the same adapter or different adaptors at both ends. In some cases, a target nucleic acid may be attached one or more adapters on one end.

The CNAs may be added before the attaching step. Alternatively, CNAs may be added after the attaching step. The CNAs may resist a ligation reaction. For example, the CNAs may resist ligating to a target nucleic acid and/or an adapter. In these cases, when the CNAs are added before the attaching step, they do not ligate to either the target nucleic acids or the adapters, and are not sequenced in the sequencing step. In further cases, the CNAs may be removed from the sample before the attaching step. Alternatively, the CNAs may be removed after sample extraction and before the attaching step.

Before attaching the adapter to the target nucleic acids in a sample, the sample may be treated with an enzyme. For example, the sample may be treated with an endonuclease to create ligation site, e.g., a sticky end or a blunt end. Alternatively, a sample may be treated with an enzyme after the adapter attaches to the target nucleic acids.

Amplification

The methods may comprise amplifying the target nucleic acids. Amplification may refer to any method for increasing the number of copies of a nucleic acid sequence. For example, the amplification may be performed with a polymerase, e.g., in one or more polymerase chain reactions. Amplification may be performed using methods known in the art. These methods often depend on the product catalyzed formation of multiple copies of a nucleic acid or its complement. One of such methods is polymerase chain reaction (PCR), including AFLP (amplified fragment length polymorphism) PCR, allele-specific PCR, Alu PCR, assembly, asymmetric PCR, colony PCR, helicase dependent PCR, hot start PCR, inverse PCR, in situ PCR, intersequence-specific PCR or IS SR PCR, digital PCR, droplet digital PCR, linear-after-the-exponential-PCR or Late PCR, long PCR, nested PCR, real-time PCR, duplex PCR, multiplex PCR, quantitative PCR, or single cell PCR. Other amplification methods may also be used, including ligase chain reaction (LCR), nucleic acid sequence based amplification (NASBA), linear amplification, isothermal linear amplification, Q-beta-replicase method, 3 SR, Transcription Mediated Amplification (TMA), Strand Displacement Amplification (SDA), or Rolling Circle Amplification (RCA).

The CNAs may be added before the amplification. Alternatively, the CNAs may be added after the amplification. The CNAs may not be amplified. For example, the CNAs may comprise modifications that inhibit the amplification. In these cases, when the CNAs are added before the amplification, they are not amplified. Thus, the CNAs may not be in the sequencing library or sequenced.

Removal of CNAs

The methods may further comprise removing the CNAs from a sample, which often prevents the CNAs from being sequenced. In some cases, the methods comprise removing some or all of the CNAs from a sample to make a sequencing sample. The resulting sequencing sample may not contain the CNAs and may be ready for sequencing. In some cases, the methods comprise preferentially removing the at least one CNA over other nucleic acids in the sample, e.g., the target nucleic acids, the adapters, or multimers of the adapters.

Removing the CNAs may be performed using an enzyme. For example, the CNAs may be degraded by an enzyme, e.g., by enzyme digestion. In some cases, the method comprises removing the CNAs using a nuclease. For example, the method may comprise removing the CNAs using an endonuclease, e.g., type I, type II (including type IIS, type IIG), type III or type IV endonuclease. The method may comprise removing the CNAs using a restrictive endonuclease, e.g., AatII, Acc65I, AccI, AclI, AatII, Acc65I, AccI, AclI, AfeI, AflII, AgeI, ApaI, ApaLI, ApoI, AscI, AseI, AsiSI, AvrII, BamHI, BclI, BglII, Bme1580I, BmtI, BsaHI, BsiEI, BsiWI, BspEI, BspHI, BsrGI, BssHII, BstBI, BstZ17I, BtgI, ClaI, DraI, EaeI, EagI, EcoRI, EcoRV, FseI, FspI, HaeII, HincII, HindIII, HpaI, KasI, KpnI, MfeI, MluI, MscI, MspA1I, MfeI, MluI, MscI, MspA1I, NaeI, NarI, NcoI, NdeI, NgoMIV, NheI, NotI, NruI, NsiI, NspI, PacI, PciI, PmeI, PmlI, PsiI, PspOMI, PstI, PvuI, PvuII, SacI, SacII, SalI, SbfI, ScaI, SfcI, SfoI, SgrAI, SmaI, SmlI, SnaBI, SpeI, SphI, SspI, StuI, SwaI, XbaI, XhoI, XmaI, or any combination thereof. The method may comprise removing the CNAs using a DNase not mentioned above, e.g., an exodeoxyribonuclease. The method may comprise removing the CNAs using Uracil DNA glycosylase (UDG), DNA glycosylase-lyase (Endonuclease VIII), or a mixture thereof (e.g., Uracil-Specific Excision Reagent (USER) Enzyme). The method may comprise removing the CNAs using RNA-guided DNase, e.g., CRISPR-associated protein nuclease, e.g., Cas9. RNase, The method may comprise removing the carrier synthetic nucleic acids using an RNase, e.g., an endoribonuclease, such as RNase A, RNase H, RNase III, RNase L, RNase P, RNase PhyM, RNase T1, RNase T2, RNase U2, RNase V, or an exoribonuclease, such as polynucleotide phosphorylase, RNase PH, RNase R, RNase D, RNase T, oligoribonuclease, exoribonuclease I, or exoribonuclease II, or any combination thereof. In some cases, the method comprises removing the CNAs using any a nucleic acid-degrading reagent known in the art. In some cases, the method may comprise removing the CNAs by subjecting the CNAs to a physical treatment, e.g., heating, cooling, or shearing. In some cases, the methods for removing the CNAs do not remove the target nucleic acids, adapters, or any other molecules in the sequencing library from the sample. In certain cases, the removal of the CNAs is not performed by enzyme degradation, e.g., an endonuclease digestion.

For removing the CNAs, the methods may comprise incubating the CNAs with the enzyme at a temperature under which the enzyme is functional. For example, the methods may comprise incubating the CNAs with an enzyme at a temperature of from 10° C. to 80° C., e.g., from 20° C. to 60° C., from 20° C. to 40° C., from 30° C. to 40° C., or from 20° C. to 25° C. The methods may comprise incubating the CNAs with an enzyme at a temperature of at least 10° C., 20° C., 25° C., 30° C., 31° C., 32° C., 33° C., 34° C., 35° C., 36° C., 37° C., 38° C., 39° C., 40° C., 50° C., 60° C., or 70° C. In some cases, the methods may comprise incubating the CNAs with an enzyme at a temperature of about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., or 42° C.

For removing the CNAs, the methods may comprise incubating the CNAs with an enzyme for a period of time for the enzyme to be functional. In some cases, the methods may comprise incubating the CNAs with the enzyme for at least 1 minute, 5 minutes, 10 minutes, 15 minutes, 20 minutes, 30 minutes, 40 minutes, 50 minutes, 1 hour, 2 hours, 5 hours, 12 hours, 24 hours, 48 hours, or 72 hours.

The method may comprise removing the carrier synthetic nucleic acids by affinity-based depletion. The affinity-based depletion may be performed on carrier synthetic nucleic acids may comprise one or more immobilization tags. In these cases, the method may comprise removing the CNAs by attaching the immobilization tags to a solid support. Such solid support may be paper, glass (e.g., controlled pore glass (CPG)), plastic (e.g., polymethylacrylic, polyethylene, polypropylene, polyacrylate, polymethylmethacrylate, polyvinylchloride, polytetrafluoroethylene, polystyrene, polycarbonate macroporoous polystyrene (MPPS), or nylon), polyacrylamide, cellulose acetate, cellulose nitrate, nitrocellulose, silicon or other metals, or optical fiber.

A solid support for affinity-based depletion may be molded into any shape and form. In some cases, a solid support may be fabricated in the form of a planar device having discrete isolated areas in the form of wells, troughs, pedestals, hydrophobic or hydrophilic patches, die-cut adhesive reservoirs or other physical barriers to fluid flow. Examples of such solid supports include slides, microplates, sheets, films, dipsticks, and the like.

In other cases, a solid support may be in the form a bead or pellet containing a coated cationic surface. Beads may provide a means for increasing probe density on the coated solid support. Beads may provide a variety of surface chemistries or functionalities (e.g., amine, carboxyl, or hydrox) suitable for rendering the bead cationic by e.g., amination. Suitable bead compositions include, for example, plastics, such as polystyrene, methylstyrene, acrylic polymers, ceramics, glass, polymeric materials, such as cross-linked dextrans, cellulose, nylon, and latex, paramagnetic materials, titanium dioxide, latex. Beads may encompass any type of solid or hollow sphere, ball, bearing, cylinder, or other solid configuration. The beads may be porous or non-porous in nature. The use of porous beads may increase the surface area of the bead available for nucleic acid detection. Bead sizes may range from 100 nm to 5 mm, for example, from 0.2 µm to 200 µm, or from 0.5 µm to 5 µm. In some cases, the solid support may be magnetic or magnetically susceptible. The solid support may be coated. The coating may bind to the immobilization tags. For example, the solid support may be coated with a binding partner of the immobilization tag, e.g., streptavidin, antigen, antibody (e.g., anti-polyhistidine antibody), glutathione S transferase, or an analogue thereof.

The methods may comprise removing the CNAs by size-based depletion. For example, the size-based depletion may be performed using porous beads (e.g., Solid Phase Reversible Immobilization (SPRI) Magnetic Beads, electrophoresis gel purification (e.g., agarose gel purification), and/or gel filtration. In some cases, the method may comprise removing the synthetic nuclei acids that have a length of at least 50 bp, 100 bp, 200 bp, 300 bp, 400 bp, 500 bp, 600 bp, 700 bp, 800 bp, 900 bp, 1 kb, 2 kp, 5 kb, or 10 kb. For example, the method may comprise removing the synthetic nuclei acids that have a length of at least 500 bp.

Sequencing

The methods may comprise sequencing the target nucleic acids and/or adapters in the sequencing library. Sequencing may be performed by basic sequencing methods, including Maxam-Gilbert sequencing, chain-termination sequencing, shotgun sequencing or Bridge PCR. Sequencing may also be performed by massively parallel sequencing methods (e.g., next generation sequencing), including high-throughput sequencing, pyro-sequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Maxam-Gilbert or Sanger sequencing, primer walking, sequencing using Illumina, PacBio, SOLiD, Ion Torrent, 454, or nanopore platforms. In the cases where the sequencing is performed by a next generation sequencing method, the sequencing library generated herein is a next generation sequencing library.

As used throughout the specification herein, the term "about" when referring to a number or a numerical range means that the number or numerical range referred to is an approximation within experimental variability (or within statistical experimental error), and the number or numerical range may vary from, for example, from 1% to 15% of the stated number or numerical range. In examples, the term "about" refers to ±10% of a stated number or value.

As used herein, the term "or" is used to refer to a nonexclusive or, such as "A or B" includes "A but not B," "B but not A," and "A and B," unless otherwise indicated.

EXAMPLES

Example 1: Diagnosis by a Cell-Free DNA Sequencing Assay

A cell-free plasma sample is prepared. DNA libraries for next-generation sequencing are prepared as previously described (De Vlaminck I, Khush K K, Strehl C, et al. Temporal response of the human virome to immunosuppression and antiviral therapy. Cell 2013; 155(5): 1178-87; De Vlaminck I, Martin L, Kertesz M, et al. Noninvasive monitoring of infection and rejection after lung transplantation. Proceedings of the National Academy of Sciences of the United States of America 2015; 112(43): 13336-41; each of which is hereby incorporated by reference in its entirety). Sequencing is performed on an Illumina NextSeq instrument and analyzed. Briefly, after removing low-quality reads, reads are mapped to a human reference genome (e.g., hg19). Remaining reads are mapped to a curated reference database of viral, bacterial, fungal, and other eukaryotic pathogens. Abundances of individual pathogens are expressed as genome copies per volume, an absolute measure of the amount of nucleic acid from a specific pathogen per 1 ml of plasma. Further analysis can be performed to identify sequences known to confer resistance.

Direct Next-Generation Sequencing (NGS) of Patient Plasma

Plasma sample is spiked with a known concentration of synthetic DNA molecules prior to DNA extraction. DNA is extracted using a modified magnetic bead-based method (Omega Biotek, Norcross, Ga.). NGS libraries are constructed using a modified library preparation kit (NuGEN, San Carlos, Calif.). Negative (containing buffer but no plasma) and positive (containing plasma from a healthy donor(s) plus known concentrations of sheared, laboratory-derived pathogen DNA) control samples are processed alongside the sample. All three DNA library types are multiplexed and sequenced on an Illumina NextSeq using a 75-cycle, single-end, dual-index sequencing kit.

Bioinformatics Analysis

Pathogen reads are quantified from NGS read sets. Briefly, after low quality reads are discarded, human reads are removed by aligning to a human reference sequence (e.g., hg19). Synthetic spike-in reads are identified by aligning to the database of the full spike-in sequences. The remaining reads are aligned to a curated database of over 8000 reference sequences of viruses, prokaryotes, and eukaryotes including fungi, protozoa, and parasites. Duplicate reads, assumed to be derived from PCR duplication or sequencing instrument error, are identified based on alignment and removed. Relative abundance of organisms is expressed as estimated deduped reads (EDR), or reads per million (RPM, normalized to total reads for the sample), or reads per volume of sample (MPM, molecules per microliter). MPM is a normalized quantity that calculates the estimated number of nucleic acid fragments represented for each organism in 1 microliter of plasma. This calculation is derived from the number of sequences present for each organism normalized to the known quantity of synthetic DNA spiked into plasma at the beginning of the extraction.

A description of the processing of two patient samples is as follows: Plasma is spiked with a mixture of Spank-75B (SEQ ID NO: 120), Spark-32/52/75/100/125/150/175/350 (SEQ ID NOs: 111-118), and an ID-Spike ($3 \times 10^5$ molecules of each spike-in per microliter of plasma). Each sample receives the same Spank/Spark mixture but a different ID-Spike. Spiked plasma is centrifuged for 10 minutes at 16,000 g, and the supernatants consisting of cell-free plasma are transferred to fresh tubes. Following cell-free DNA extraction and library preparation to add dual-indexed Illumina adapters, samples are pooled along with the negative and positive control samples processed in parallel and then sequenced on an Illumina NextSeq. Typically, approximately 400 million reads are distributed among the samples in a batch, with the number of reads for any individual sample being proportional to the fraction of the total library pool that sample comprises, and this fraction being in turn proportional to the amount of DNA in the cell-free plasma.

Computational Analysis: The reads for an individual sample were identified based on the corresponding adapter barcode sequence ("demuxing"). Following removal of adapter dimer sequences and quality-based read trimming, the likely origin of the read sequences was determined by alignment to human genome, spike-in and pathogen genome reference sequences. The number of ID-spike and SPANK-75B reads were counted using the spike-in alignments; SPANK-75B reads were de-duplicated ("deduped") using the randomized sequence tags embedded within each spiked molecule. Pathogen alignments were deduped based on genome position, and the most likely taxonomic origin of each read was determined using a machine learning approach, to arrive at estimated deduped reads attributed to specific pathogens. The normalized pathogen abundance is expressed in terms of concentration as pathogen molecules per microliter (MPM-Spank), and is calculated as follows: MPM-Spank=(Estimated deduped reads/Number of SPANK-75B reads)×c, where c is the concentration of SPANK-75B reads as spiked into the sample, namely $3 \times 10^5$ reads per microliter.

An ID-spike may be a type of spike-in that is unique for each sample in a sequencing batch. SPANK molecules may be spiked in at a constant concentration across all libraries. Thus, the number of deduped SPANK molecules detected in a particular library may be a proxy for the minimum concentration detectable in that library. More generally, it may be proportional to the efficiency with which that library converted nucleic acid (e.g., DNA) molecules in the original sample to reads in the nucleic acid sequencing data. A purpose of the SPANK molecules may be to help establish the relative abundance of the target (e.g., pathogen or disease-associated) molecules within the mixture represented in a sample.

| Metric | Sample A | Sample B, Pathogen 1 | Sample B, Pathogen 2 |
|---|---|---|---|
| Number of reads | 58,078,895 | 35,045,795 | 35,045,795 |
| Number of ID-spike reads | 344,677 | 45,785 | 45,785 |
| Number of deduped SPANK-75B reads | 194,124 | 55,040 | 55,040 |
| Estimated deduped reads attributed to pathogen | 178,758.561 | 74,324.581 | 16,866.832 |
| MPM-Spank | 276,254.189 | 405,112.18 | 91,934.042 |

Figure 9:
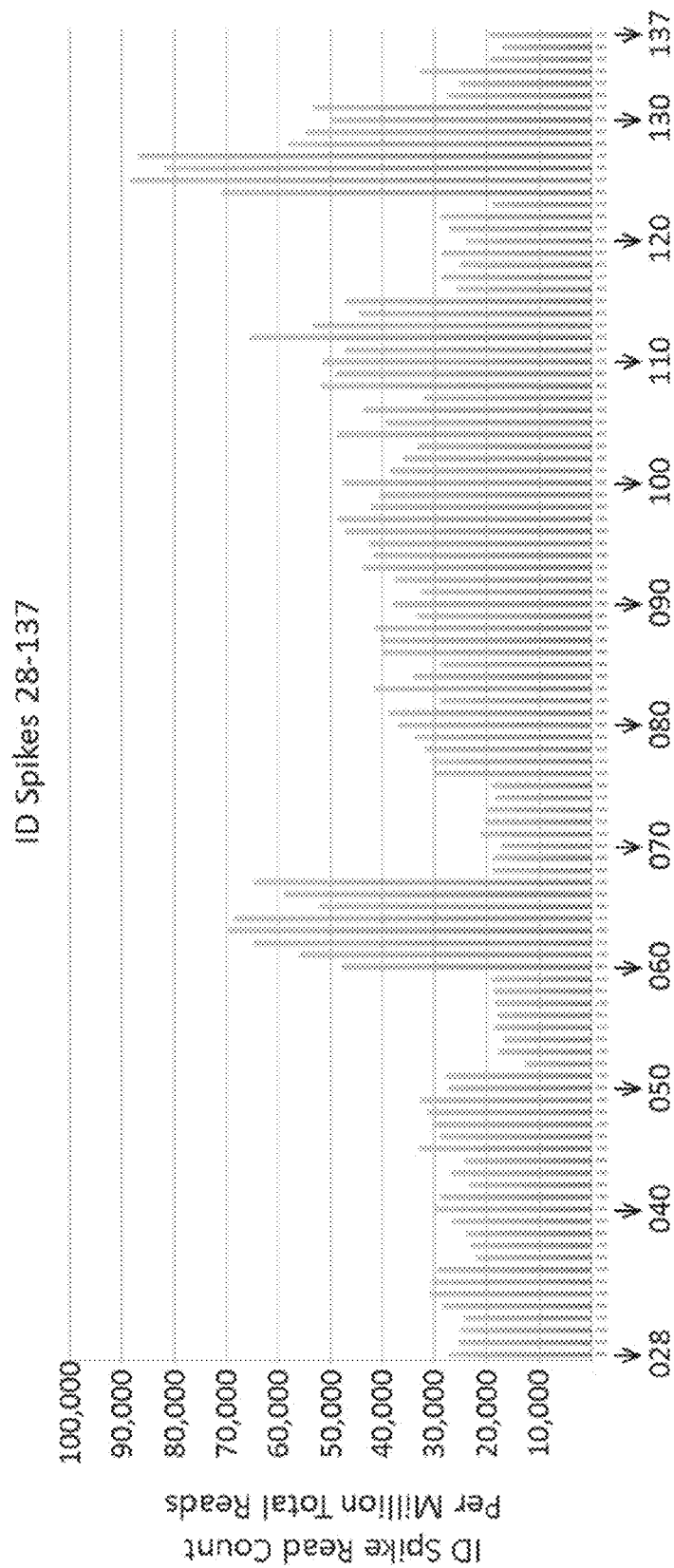
FIG. 9 depicts a normalized read count for 110 exemplary ID Spikes.

Example 2: Synthesis and Processing of ID Spikes 110 exemplary ID Spikes (ID Spikes 28-137, sequences are listed in Table 1) were constructed by annealing pairs of complementary 100 mer oligonucleotides synthesized by Integrated DNA Technologies. These sequences were then sub-pooled into 4 groups, added to 4 aliquots of human plasma, extracted and processed into sequencing libraries along with the plasma's cell-free DNA, and sequenced on an Illumina NextSeq500 instrument. The number of reads mapping to each of the 110 ID Spikes was determined and then normalized per million total reads. A plot demonstrating a minimum of ~12,000 and a maximum of ~88,000 per million total reads is shown in FIG. 9.

Figure 10:
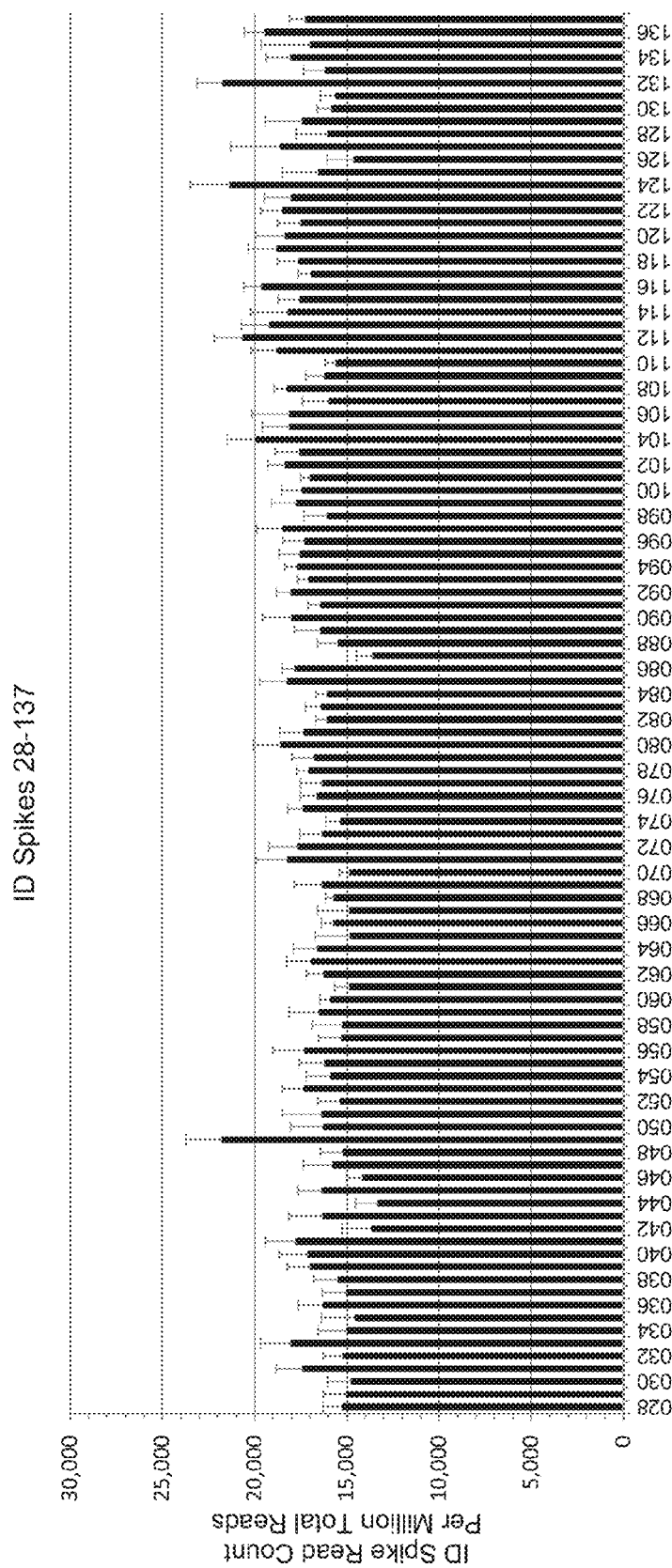
FIG. 10 depicts a normalized read count for 110 signal-normalized exemplary ID Spikes.
Figure 11:
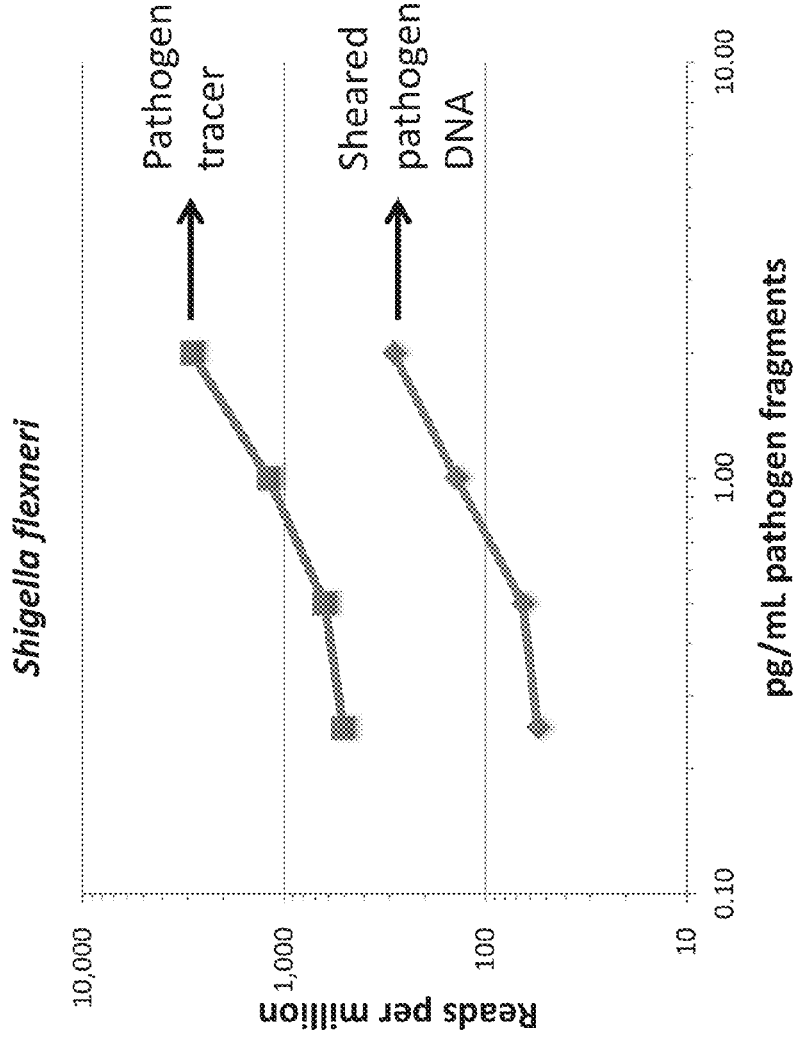
FIG. 11 shows the results from a method for identifying cross-contamination from a positive control of *Shigella flexneri* using a pathogen tracer.
Figure 12:
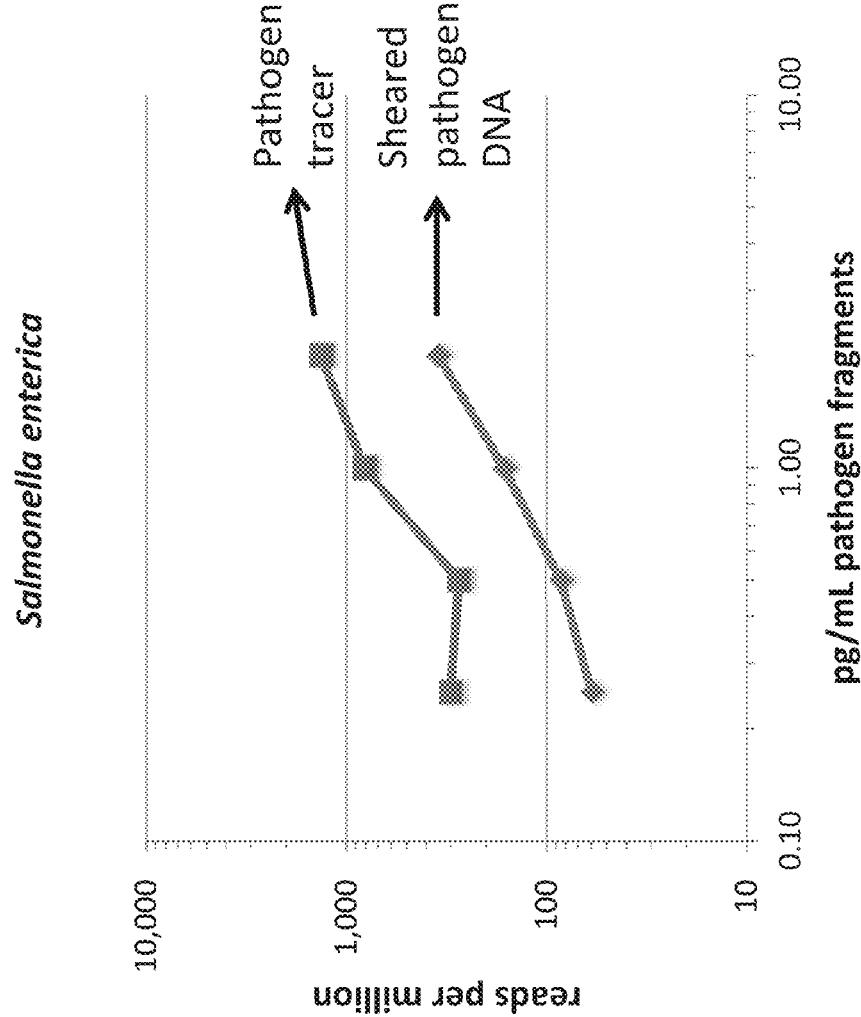
FIG. 12 shows the results from a method for identifying cross-contamination from a positive control of *Salmonella enterica* using a pathogen tracer.
Figure 13:
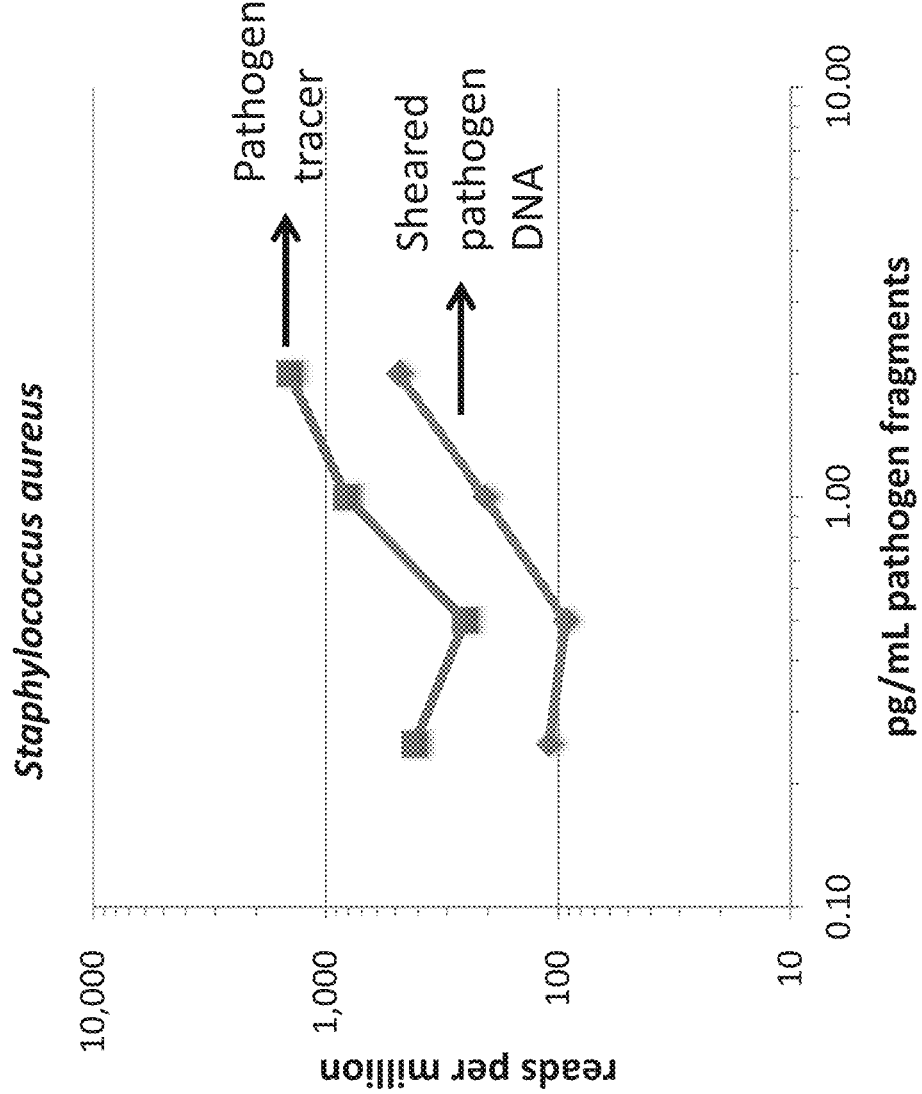
FIG. 13 shows the results from a method for identifying cross-contamination from a positive control of *Staphylococcus aureus* using a pathogen tracer.
Figure 14:
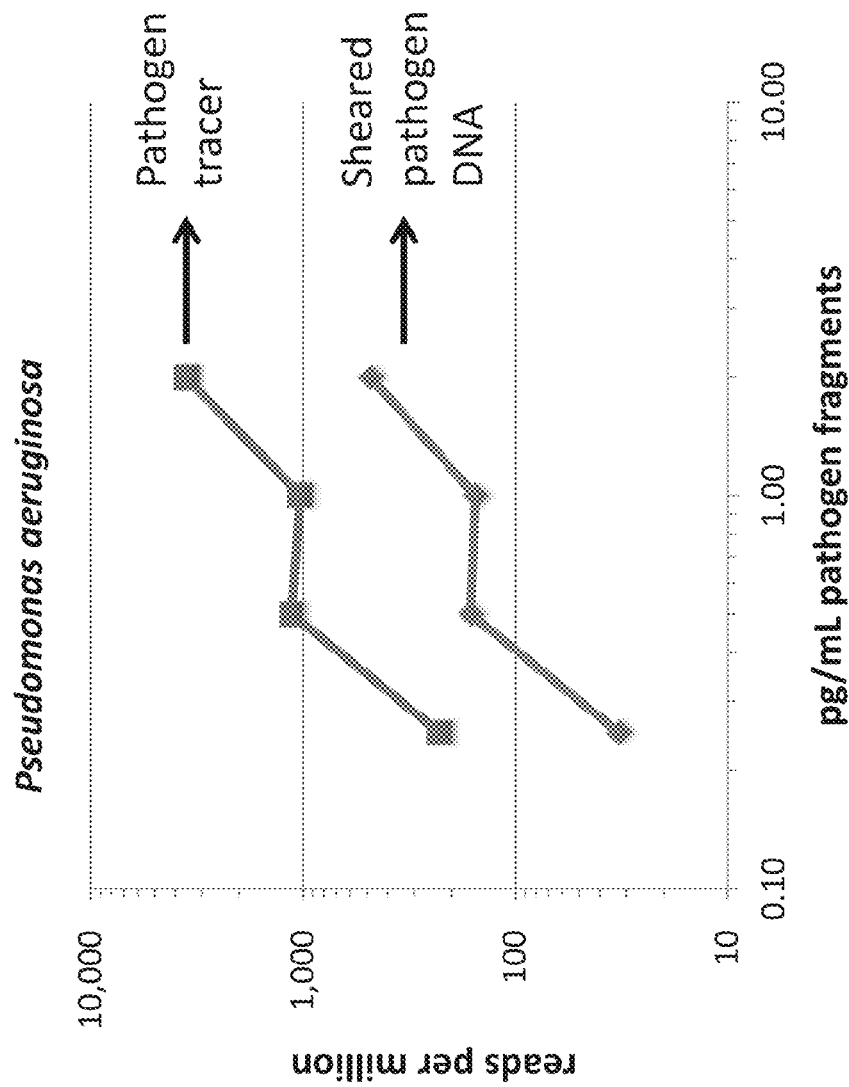
FIG. 14 shows the results from a method for identifying cross-contamination from a positive control of *Pseudomonas aeruginosa* using a pathogen tracer.
Figure 15:
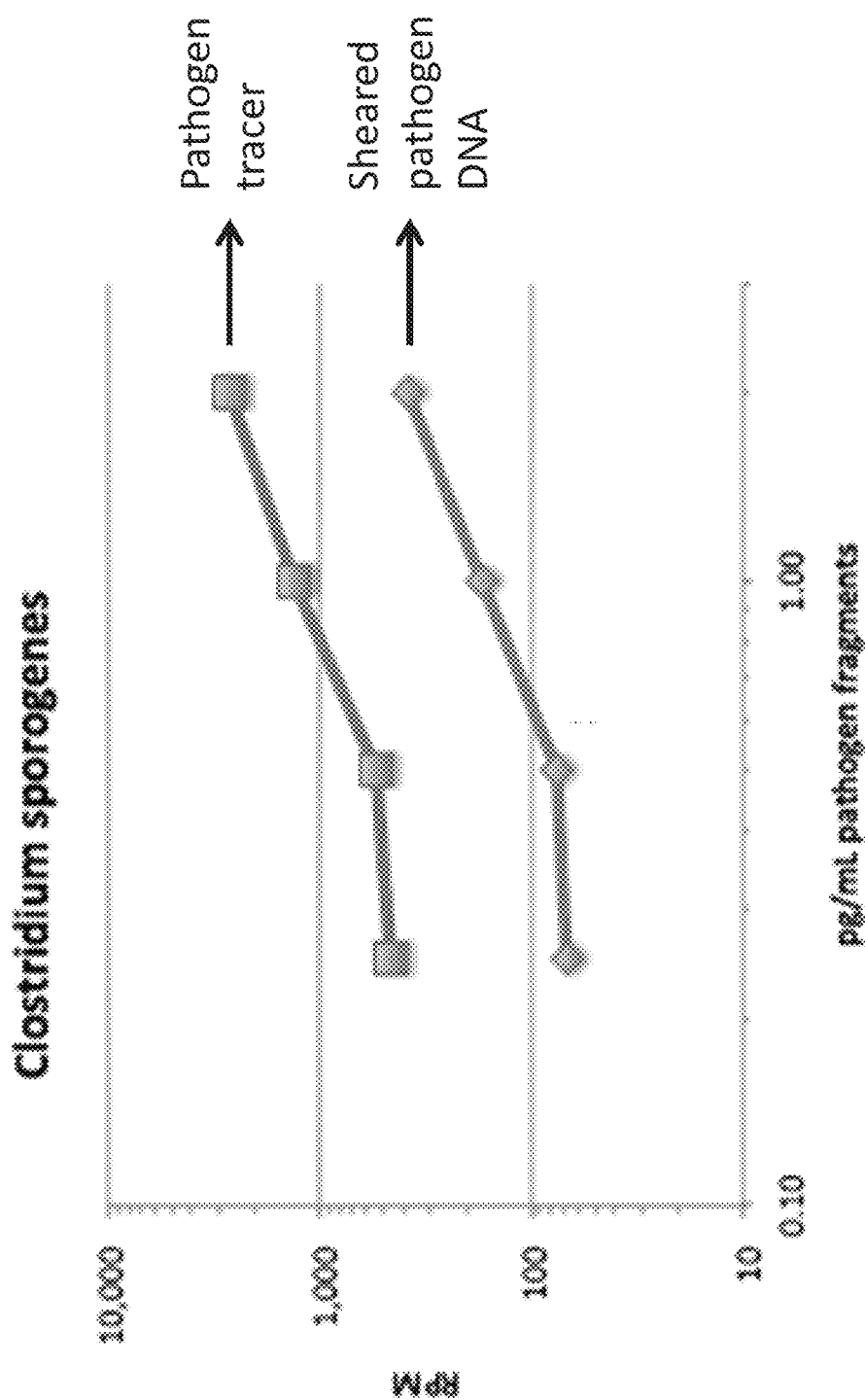
FIG. 15 shows the results from a method for identifying cross-contamination from a positive control of *Clostridium sporogenes* using a pathogen tracer.

The signal from the ID Spikes can be adjusted. The ID Spikes can be signal-normalized by, for example, adjusting the input amount of each ID Spike based on the median signal shown in FIG. 9. Re-testing the signal-normalized ID Spikes results in a more uniform read count, as shown in FIG. 10. In this case, the number of reads mapping to each ID Spike is within the range of 10,000 to 25,000 per million total reads, and most ID Spikes have a number of reads within the range of 15,000 to 20,000 per million total reads. A benefit of equalizing or normalizing the signal of different ID Spikes is that it can improve the precision of cross-contamination detection. For example, if one ID Spike typically gives 70,000 reads per million and another ID Spike gives 19,000, the latter may be a less sensitive cross-contamination tracer; normalizing the signal between the two ID Spikes can provide more uniformity.

Example 3: Measurement of Cross-Contamination of Samples Using ID Spikes

Four samples are prepared. ID Spikes 124-127 are added to Sample 1. ID Spikes 128-131 are added to Sample 2. ID Spikes 132-134 are added to Sample 3. ID Spikes 135-137 are added to Sample 4. The four samples are processed and sequenced. Cross-contamination (e.g., a read attributed to an ID Spike in a sample in which the ID Spike was not intentionally added) is demonstrated to be less than 1:10,000, as shown for a subset of the ID Spikes in Table 7.

TABLE 7

| | sample 1 | sample 2 | sample 3 | sample 4 |
|---|---|---|---|---|
| ID Spike 124 | 70,896 | 1 | 1 | 2 |
| ID Spike 125 | 88,403 | 2 | 2 | 2 |
| ID Spike 126 | 81,767 | 2 | 1 | 2 |
| ID Spike 127 | 86,878 | 2 | 2 | 2 |
| ID Spike 128 | 1 | 58,131 | 1 | 1 |
| ID Spike 129 | 1 | 54,839 | 1 | 1 |
| ID Spike 130 | 1 | 49,834 | 1 | 1 |
| ID Spike 131 | 1 | 53,491 | 1 | 1 |
| ID Spike 132 | 0 | 0 | 27,537 | 1 |
| ID Spike 133 | 0 | 0 | 25,055 | 0 |
| ID Spike 134 | 1 | 0 | 32,739 | 0 |
| ID Spike 135 | 1 | 0 | 1 | 19,459 |
| ID Spike 136 | 0 | 0 | 0 | 17,030 |
| ID Spike 137 | 0 | 1 | 0 | 19,644 |

Example 4: Identification of Cross-Contamination of Samples Using ID Spikes

Four samples are prepared. ID Spike 124 is added to Sample A. ID Spike 123 is added to Sample B. ID Spike 122 is added to Sample C. ID Spike 119 is added to Sample D. The four samples are processed and sequenced. A significant number of reads from both ID Spike 123 and ID Spike 124 in Samples A and B indicates cross-contamination either between the two ID Spike stocks or between Samples A and B, as shown in Table 8.

TABLE 8

| | sample A | sample B | sample C | sample D |
|---|---|---|---|---|
| ID Spike 119 | 0 | 0 | 0 | 20,804 |
| ID Spike 122 | 0 | 0 | 7,291 | 0 |
| ID Spike 123 | 21 | 23,451 | 0 | 0 |
| ID Spike 124 | 5,990 | 13 | 0 | 0 |

Example 5: Identification of Cross-Contamination Source Using ID Spikes

In some samples essentially only 1 ID Spike is identified, but in others several contaminating ID Spikes are observed at significant levels. In such situations, the identity of the contaminating ID Spikes may inform the source of the cross-contamination, for example, from adjacent wells of a microtiter plate, as shown in Table 9.

TABLE 9

| | RD-1819-Lib144-1 | RD-1819-Lib133-1 | RD-1819-Lib137-1 | EC-1991-Lib2-1 | EC-1997-Lib2-1 | RD-1819-Lib148-1 |
|---|---|---|---|---|---|---|
| ID Spike 052 | | 38,541 | | | | |
| ID Spike 053 | | 65 | | 5 | | |
| ID Spike 054 | | | | 156,813 | | |

TABLE 9-continued

| | RD-1819-Lib144-1 | RD-1819-Lib133-1 | RD-1819-Lib137-1 | EC-1991-Lib2-1 | EC-1997-Lib2-1 | RD-1819-Lib148-1 |
|---|---|---|---|---|---|---|
| ID Spike 055 | | | | 40 | | |
| ID Spike 056 | | | | | 2 | |
| ID Spike 057 | | | | | | |
| ID Spike 058 | | | 57,163 | 0 | | |
| ID Spike 059 | | | | | | 0 |
| ID Spike 060 | 1 | 15 | | | | |
| ID Spike 061 | | | | | | |
| ID Spike 062 | | | | | 0 | |
| ID Spike 063 | | | | 0 | | |
| ID Spike 064 | | | | | 0 | |
| ID Spike 065 | | | | | | |
| ID Spike 066 | | | 419 | | | 2 |
| ID Spike 067 | | | | | | 1 |
| ID Spike 068 | 42,351 | 3 | | | | |
| ID Spike 069 | | 19 | | | | |
| ID Spike 070 | | | | | | |
| ID Spike 071 | | | | | | |
| ID Spike 072 | | | 6 | | 145,380 | 6 |
| ID Spike 073 | | | 11 | | 1,516 | 3 |
| ID Spike 074 | | | 221 | | 2,270 | 210 |
| ID Spike 075 | | | 46 | | 388 | 58,921 |

Example 6: Tracer Sequences for Identifying Cross-Contamination from Positive Controls of Pathogen DNA Laboratory pathogen DNA samples are used as positive controls but carry the risk of cross-contaminating clinical samples and generating false positive reads or diagnoses. A tracer is added to a laboratory pathogen DNA sample to enable cross-contamination detection. In the case of NGS detection of cell-free pathogen DNA fragments from blood, relatively short tracers can be used because the cell-free pathogen fragments are relatively short, e.g., 20-120 bp and often averaging about 75 bp. Here, a set of 75 bp synthetic DNA duplexes is used as tracers, with one unique tracer sequence per pathogen control. The pathogen fragments were produced by shearing laboratory-produced genomic DNA (ATCC or NIST) with DNaseI (New England Biolabs) or Fragmentase nuclease mixture (New England Biolabs).

Genomic DNAs from 11 different pathogens, as listed in Tables 10-12, were sheared individually to approximately 75 bp average fragment length, purified, and quantified (Qubit, Thermo Fisher). To each fragment pool, a separate 75-bp synthetic DNA duplex (Integrated DNA Technologies) was added at approximately 10× higher mass quantity (Qubit, Thermo Fisher), thus providing each fragmented pathogen with a unique tracer. Preferably, at least about 5× higher signal is achieved for the tracer relative to the genomic DNA. Pathogen/tracer pairs were mixed together in three various combinations to simulate co-infections (Mix 1 contained 4 pathogens, Mix 2 contained 4 pathogens, and Mix 3 contained 3 pathogens, as listed in Tables 10-12), added to human plasma, diluted further in human plasma to provide a concentration series, and then subjected to cell-free DNA extraction, library preparation, and NGS. Alignments to databases calculated the detected concentrations of all 11 tracers and all 11 pathogens in all samples.

The results shown in Tables 10-12 and in FIG. 11-FIG. 15 demonstrate a 1:1 pairing of tracer and pathogen. In each case, the tracer is detected at a higher concentration than the pathogen, and the concentration difference remains consistent throughout the dilution series. Extrapolation to very low concentrations, such as one would expect from a low-level cross-contamination event, strongly suggests that the tracer would be detected before the pathogen. Tables 10-12 shows data from all samples, and FIG. 11-FIG. 15 plot representative tracer:pathogen pairs for *Shigella flexneri, Salmonella enterica, Staphylococcus aureus, Pseudomonas aeruginosa,* and *Clostridium sporogenes,* respectively. Tracers were observed only in samples to which they were intentionally added. Only one pathogen, *E. coli,* was observed in non-spiked samples. Because the *E. coli* tracer #143 was not observed in those samples, one can conclude that the *E. coli* was present at a low level in human plasma, which is a common occurrence for this commensal organism.

TABLE 10

Pathogen Tracer Mix 1

| Pathogen SPIKE | Mix 1-2 pg/mL | Mix 1-1 pg/mL | Mix 1-0.5 pg/mL | Mix 1-0.25 pg/mL |
|---|---|---|---|---|
| | READS PER MILLION | | | |
| *Salmonella enterica* | 348 | 163 | 85 | 60 |
| Tracer_138 | 1339 | 814 | 274 | 303 |
| *Clostridium sporogenes* | 387 | 170 | 75 | 68 |
| Tracer_141 | 2616 | 1318 | 541 | 463 |
| *Shigella flexneri* | 286 | 139 | 65 | 55 |
| Tracer_144 | 2865 | 1195 | 628 | 508 |
| *Aspergillus fumigatus* | 150 | 73 | 31 | 25 |
| Tracer_147 | 1205 | 742 | 269 | 274 |
| *Staphylococcus aureus* | 0 | 0 | 0 | 0 |
| Tracer_139 | 0 | 0 | 0 | 0 |
| *Mycobacterium tuberculosis* | 0 | 0 | 0 | 0 |
| Tracer_142 | 0 | 0 | 0 | 0 |
| *Bordetella pertussis* | 0 | 0 | 0 | 0 |
| Tracer_145 | 0 | 0 | 0 | 0 |
| *Leishmania major* | 0 | 0 | 0 | 0 |
| Tracer_148 | 0 | 0 | 0 | 0 |
| *Pseudomonas aeruginosa* | 0 | 0 | 0 | 0 |
| Tracer_140 | 0 | 0 | 0 | 0 |
| *Escherichia coli* | 2 | 0 | 0 | 1 |
| Tracer_143 | 0 | 0 | 0 | 0 |
| *Staphylococcus epidermidis* | 0 | 0 | 0 | 0 |
| Tracer_146 | 0 | 0 | 0 | 0 |

TABLE 11

Pathogen Tracer Mix 2

| Pathogen SPIKE | Mix 2-2 pg/mL | Mix 2-1 pg/mL | Mix 2-0.5 pg/mL | Mix 2-0.25 pg/mL |
|---|---|---|---|---|
| | READS PER MILLION | | | |
| Salmonella enterica | 0 | 0 | 0 | 0 |
| Tracer_138 | 0 | 0 | 0 | 0 |
| Clostridium sporogenes | 0 | 0 | 0 | 0 |
| Tracer_141 | 0 | 0 | 0 | 0 |
| Shigella flexneri | 0 | 0 | 0 | 0 |
| Tracer_144 | 0 | 0 | 0 | 0 |
| Aspergillus fumigatus | 0 | 0 | 0 | 0 |
| Tracer_147 | 0 | 0 | 0 | 0 |
| Staphylococcus aureus | 484 | 207 | 93 | 109 |
| Tracer_139 | 1435 | 816 | 252 | 416 |
| Mycobacterium tuberculosis | 256 | 172 | 60 | 62 |
| Tracer_142 | 3942 | 1767 | 626 | 1327 |
| Bordetella pertussis | 207 | 152 | 52 | 45 |
| Tracer_145 | 3149 | 1667 | 632 | 1093 |
| Leishmania major | 138 | 76 | 31 | 45 |
| Tracer_148 | 1261 | 605 | 249 | 363 |
| Pseudomonas aeruginosa | 0 | 0 | 0 | 0 |
| Tracer_140 | 0 | 0 | 0 | 0 |
| Escherichia coli | 1 | 7 | 1 | 0 |
| Tracer_143 | 0 | 0 | 0 | 0 |
| Staphylococcus epidermidis | 0 | 0 | 0 | 0 |
| Tracer_146 | 0 | 0 | 0 | 0 |

TABLE 12

Pathogen Tracer Mix 3

| Pathogen SPIKE | Mix 3-2 pg/mL | Mix 3-1 pg/mL | Mix 3-0.5 pg/mL | Mix 3-0.25 pg/mL |
|---|---|---|---|---|
| | READS PER MILLION | | | |
| Salmonella enterica | 0 | 0 | 0 | 0 |
| Tracer_138 | 0 | 0 | 0 | 0 |
| Clostridium sporogenes | 0 | 0 | 0 | 0 |
| Tracer_141 | 0 | 0 | 0 | 0 |
| Shigella flexneri | 0 | 0 | 0 | 0 |
| Tracer_144 | 0 | 0 | 0 | 0 |
| Aspergillus fumigatus | 0 | 0 | 0 | 0 |
| Tracer_147 | 0 | 0 | 0 | 0 |
| Staphylococcus aureus | 0 | 0 | 0 | 0 |
| Tracer_139 | 0 | 0 | 0 | 0 |
| Mycobacterium tuberculosis | 0 | 0 | 0 | 0 |
| Tracer_142 | 0 | 0 | 0 | 0 |
| Bordetella pertussis | 0 | 0 | 0 | 0 |
| Tracer_145 | 0 | 0 | 0 | 0 |
| Leishmania major | 0 | 0 | 0 | 0 |
| Tracer_148 | 0 | 0 | 0 | 0 |
| Pseudomonas aeruginosa | 480 | 154 | 162 | 33 |
| Tracer_140 | 3544 | 1031 | 1132 | 227 |
| Escherichia coli | 363 | 104 | 133 | 24 |
| Tracer_143 | 5020 | 1202 | 1359 | 295 |
| Staphylococcus epidermidis | 265 | 69 | 80 | 25 |
| Tracer_146 | 5399 | 1506 | 1820 | 361 |

Figure 16:
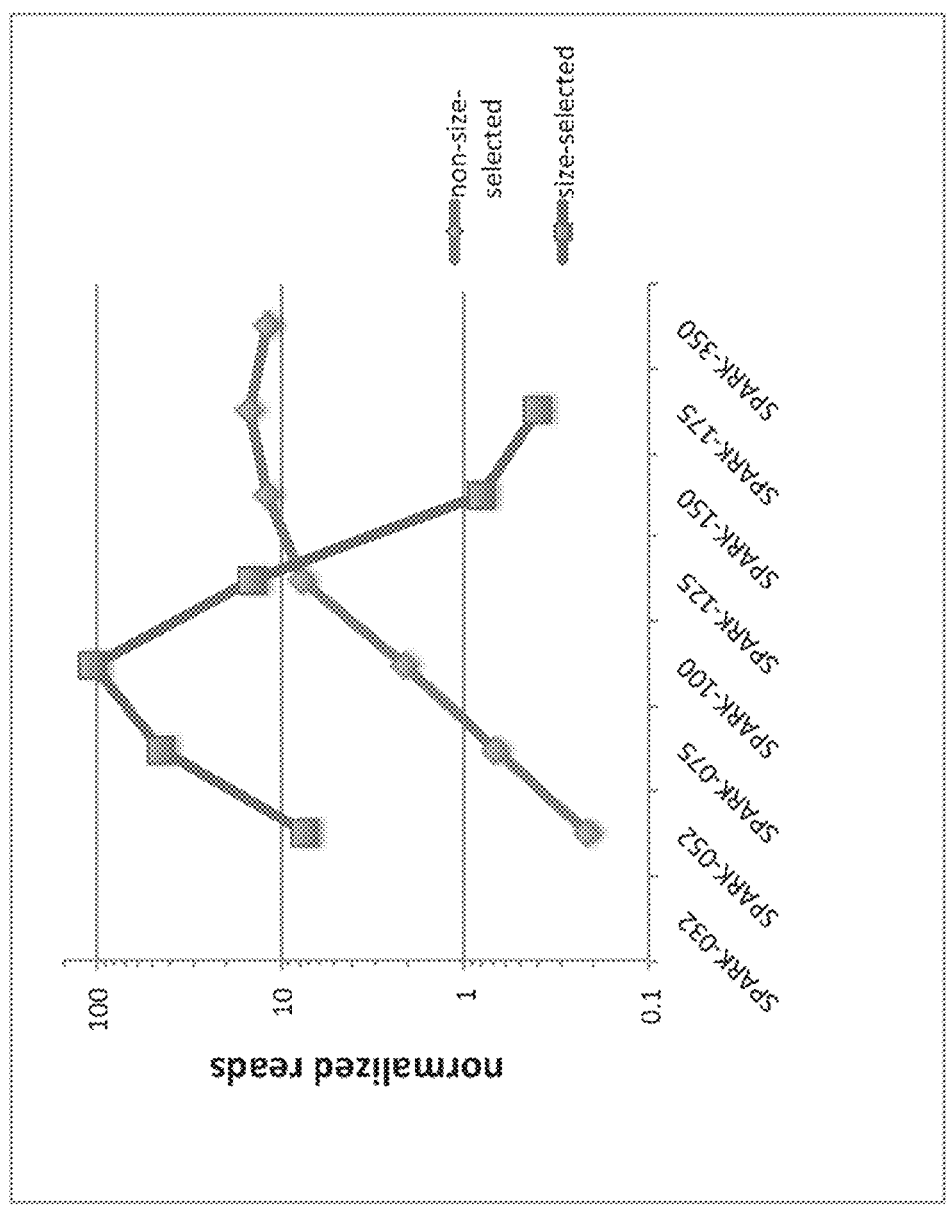
FIG. 16 depicts effect of size selection library processing methods on relative yields of exemplary Spark size spike-ins.

Example 7: Determination of Relative Yields of Nucleic Acids with Different Lengths Using Spark Sequences 8 Sparks were added in equimolar amounts to human plasma, extracted and processed into sequencing libraries along with the plasma's cell-free DNA, and sequenced on an Illumina NextSeq500 instrument. Different processing methods, such as selecting subsets of libraries with different size ranges as shown in FIG. 16, can be monitored by determining the relative yields of the different Sparks. Furthermore, if all samples are spiked with the same quantity of Sparks, for example 100 million molecules of each of the 8 Sparks added to each mL of plasma, the number of reads of a given Spark can be used to infer the starting concentration of other similarly sized fragments in the sample, such as cell-free DNA from infectious agents.

Example 8: Preparation of Sequencing Library Using Synthetic Nucleic Acids with Various GC Content Cell-free pathogen nucleic acids may vary in their GC content and may have very different $T_m$'s at short fragment lengths. Due to the relatively short lengths of cell-free pathogen fragments (e.g., 20-120 bp and often averaging about 75 bp), shorter fragments may be more susceptible to denaturation during processing for NGS, for example, and therefore may not be sequenced or detected, even if present in the sample. Methods for tracking the recovery of low $T_m$ fragments (e.g., short fragments from low GC genomes), particularly in the range from 32 to 75 bp, can be used to optimize nucleic acid processing to retain a greater percentage of low $T_m$ fragments.

Each of the 28 duplexes was made by annealing 2 oligonucleotides. Concentrations of duplex DNA were determined by Qubit (Thermo Fisher), and equal molar amounts of the 28 were combined into one mixture. Eight replicate samples of the mixture were processed with standard library preparation method 1 (containing enzyme heat-kill steps), and another 8 with modified library preparation method 2 (lacking enzyme heat-kill steps). After library preparation, the 16 samples were combined in a single sequencing run, and the yield of each of the 28 spikes for each sample was calculated and normalized to reads per million for each library.

Figure 17:
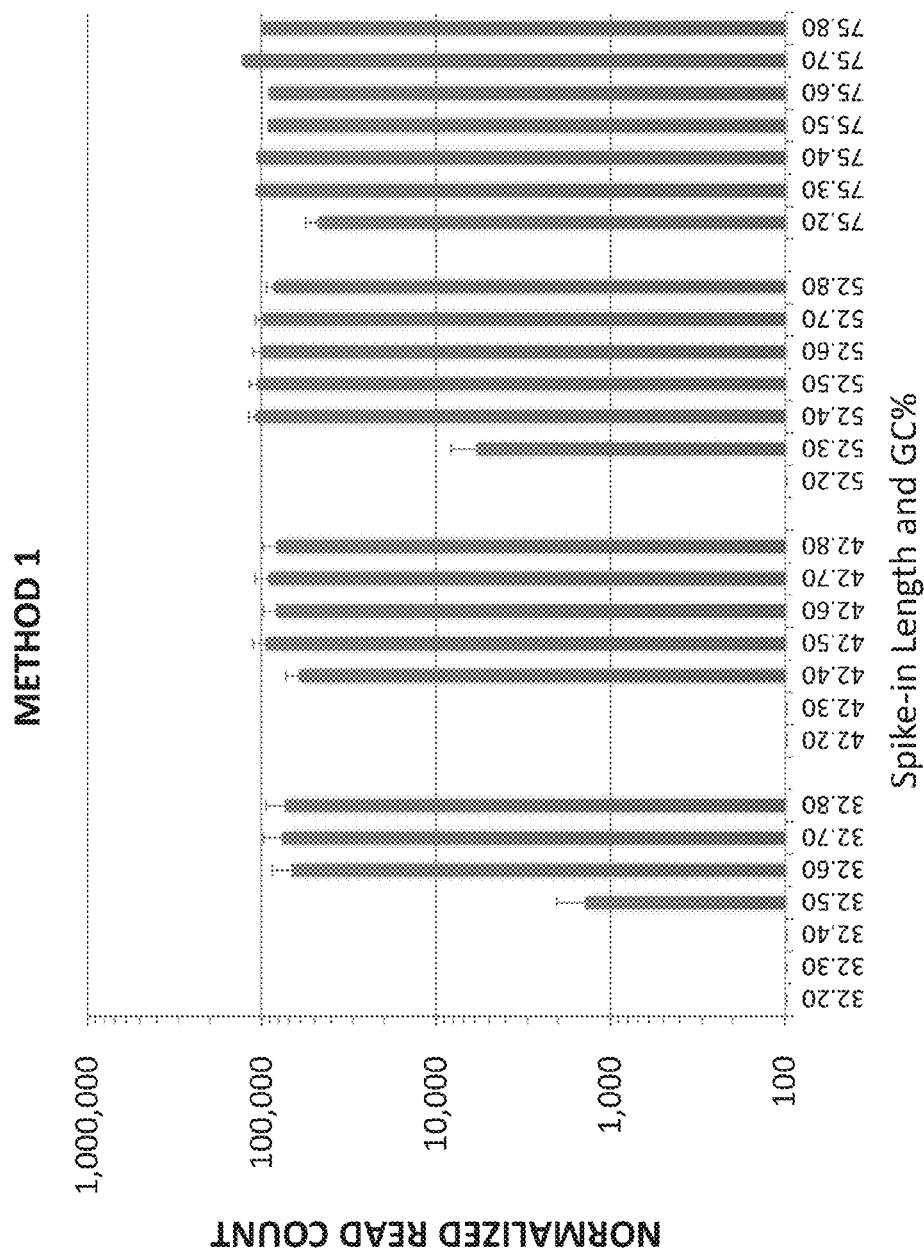
FIG. 17 shows the results from a method for preparing a sequencing library, containing enzyme heat-kill steps, using nucleic acids of varying GC content.
Figure 18:
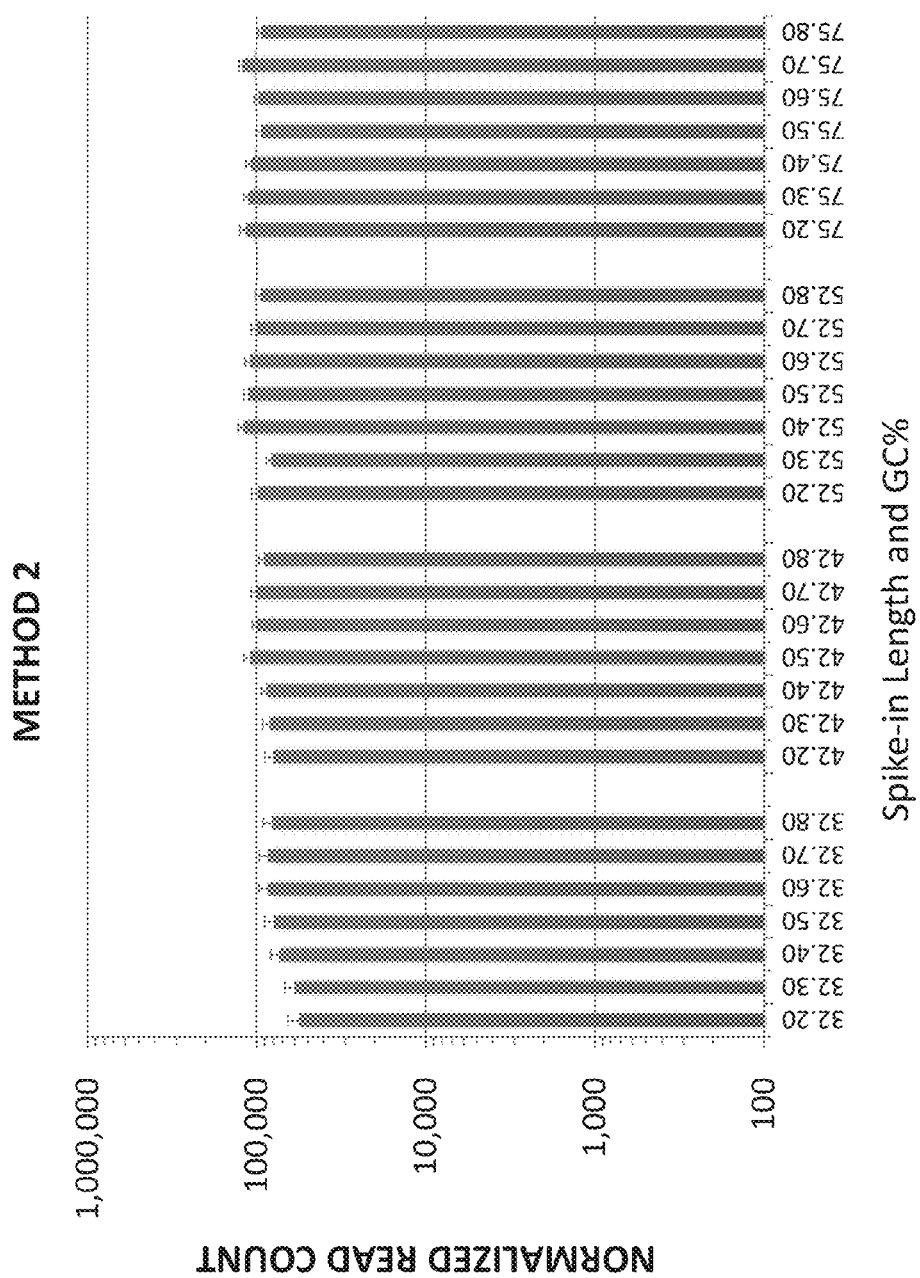
FIG. 18 shows the results from a method for preparing a sequencing library, lacking enzyme heat-kill steps, using nucleic acids of varying GC content.

The normalized read count shows an increase in recovery of low $T_m$ species in modified method 2 (shown in FIG. 18) compared to standard method 1 (shown in FIG. 17), e.g., for spike-ins that are 32 bp in length with 20% GC content, 32 bp in length with 30% GC content, 32 bp in length with 40% GC content, 42 bp in length with 20% GC content, 42 bp in length with 30% GC content, or 52 bp in length with 20% GC content. Without this granularity of the GC panel, the differences would have been much less clear; for example, at 50% GC content, only the 32 bp length shows a difference in recovery levels among the four tested lengths.

Example 9: Preparation of Sequencing Library Using Carrier Synthetic Nucleic Acids with a Long Length that Allows for Size-Based Depletion This example shows an exemplary method for generating a sequencing library using synthetic DNA (e.g., DNA synthesized by PCR) longer than the target nucleic acids in the sample. The synthetic DNA may have a length that allows size-based separation from the target nucleic acids in the sample. One or both ends of the synthetic DNA may have modifications that resist ligation. The modifications may include one or more internal abasic sites and/or inverted nucleotides at one or more ends. After being added to a sequencing library, the synthetic DNA can be depleted from the library at any time using size-based depletion methods that capitalize on the relatively long length of the synthetic DNA.

Plasma sample comprising cell-free DNA is obtained from a subject. The synthetic DNA is added to the library DNA input solution (e.g., cell-free DNA extract) at the concentration for the minimum required amount of DNA for a library generation kit. The synthetic DNA is added to the plasma DNA extraction, before end repair steps, or after end repair steps but before adapter ligation step.

Then DNA-concentration-sensitive ligation is performed following the kit manufacturer's instruction. The synthetic DNA is not PCR amplified. Rather, the synthetic DNA is size-selected and depleted from the sequencing library during the enrichment for short fragments (e.g., fragments <110 bp). Also, if the synthetic DNA was modified to resist end repair or ligation, or if it was added after end repair so that it resists ligation, it will lack adapters at both ends and will thus not be sequenced.

Figure 19:
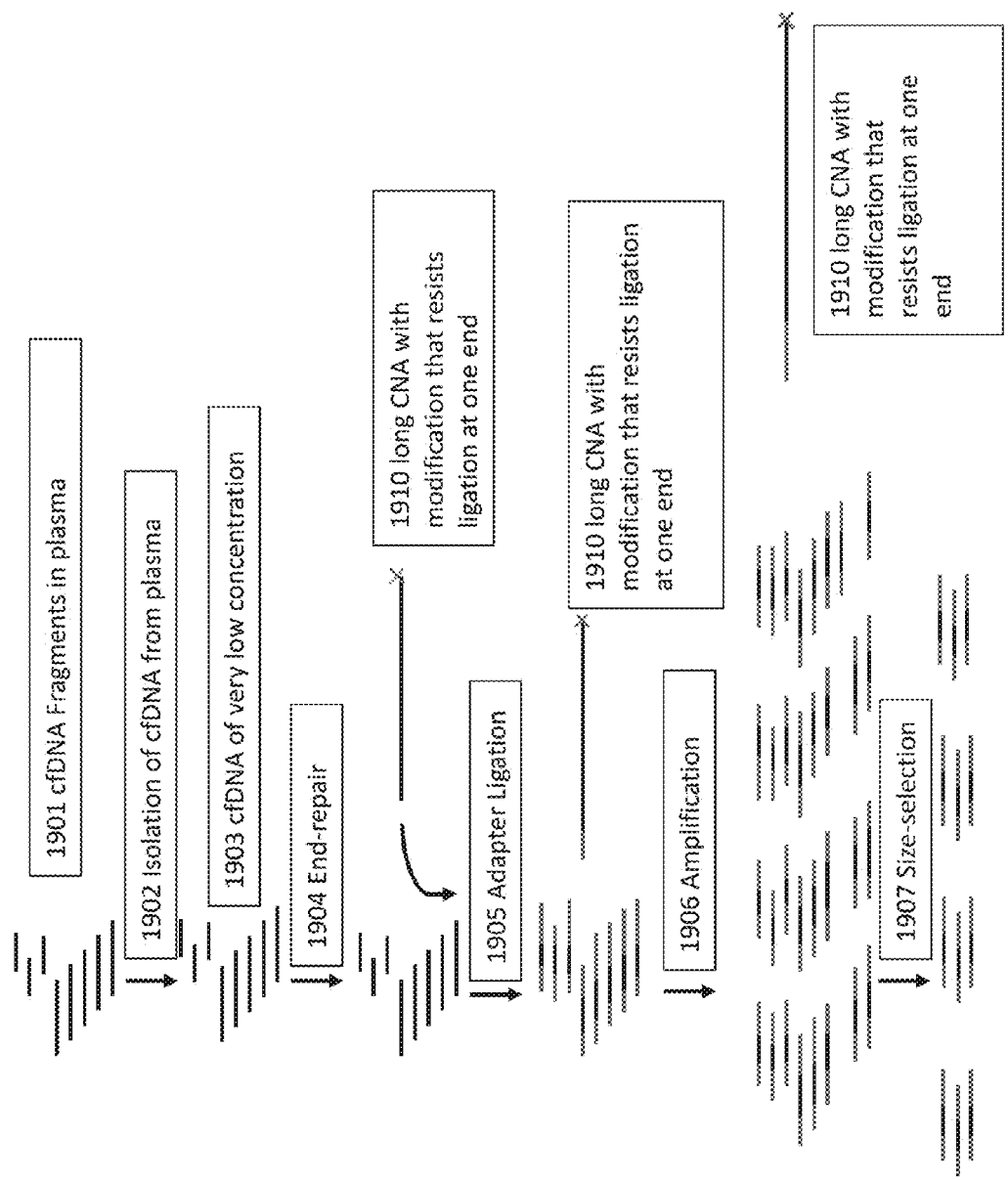
FIG. 19 shows an exemplary method for preparing a sequencing library using carrier synthetic nucleic acids with a great size that prevent ligation on both ends.

FIG. 19 shows the steps in the sequencing library generation. Cell-free DNA fragments 1901 in a sample (e.g., plasma) may be isolated in step 1902 to obtain cell-free DNA of very low concentration 1903. The fragments may be subjected to an end repair in step 1904. Long carrier nucleic acids 1910 with modification that resists ligation at one end can then be added. The nucleic acids may then undergo an adapter ligation step 1905, in which the end-repaired fragments have adapters ligated to both ends but the carrier nucleic acids only have an adapter ligated to one end. During amplification step 1906, the ligated fragments are amplified but not the carrier nucleic acids. A size selection step 1907 can then occur.

One end of the synthetic DNA comprises modifications or structures that prevent the synthetic DNA from participating reactions in library preparation. If an adapter is ligated to the 3' end of the synthetic DNA, the synthetic DNA is double digested with two restriction enzymes to yield a molecule greater than 500 bp with two different overhangs, or with an overhang at one end and blunt end at the other. Next, a hairpin is ligated to the overhang or blunt end specifically using complementary overhang or blunt ended hairpin, respectively. If an adapter is expected to ligate to the 5'end of the synthetic DNA, the synthetic DNA is synthesized using a pair of PCR primers, one of which has deactivated 5'-end (e.g., 5' Inverted dideoxy-T, C3 Spacer, Spacer 18 etc.).

Example 10: Preparation of Sequencing Library Using Carrier Synthetic Nucleic Acids with Abasic Sites and Modifications A carrier synthetic nucleic acid was designed to serve as carrier nucleic acids during cfDNA extraction step and to provide the minimum library input amount during the library preparation. The carrier synthetic nucleic acid contained central abasic stretch and had both ends comprising modifications. The sequence of the carrier synthetic nucleic acid is shown below (5InvddT indicates 5' inverted ddT; 3invdT indicates 3' inverted dT; idSp indicates internal abasic sites):

5'-/5InvddT/GCGTCCCGGCGCGCGTTTAGGGATAACA/idSp/
idSp/idSp/idSp/GGGTAATGGCGCAAGGGTGCTGGC/
3InvdT/-3' (SEQ ID NO: 173)

3'-/3InvdT/CGCAGGGCCGCGCGCAAATCCCTATTGT/idSp/
idSp/idSp/idSp/CCCATTACCGCGTTCCCACGACCG/
5InvddT/-5' (SEQ ID NO: 174)

Figure 20A:
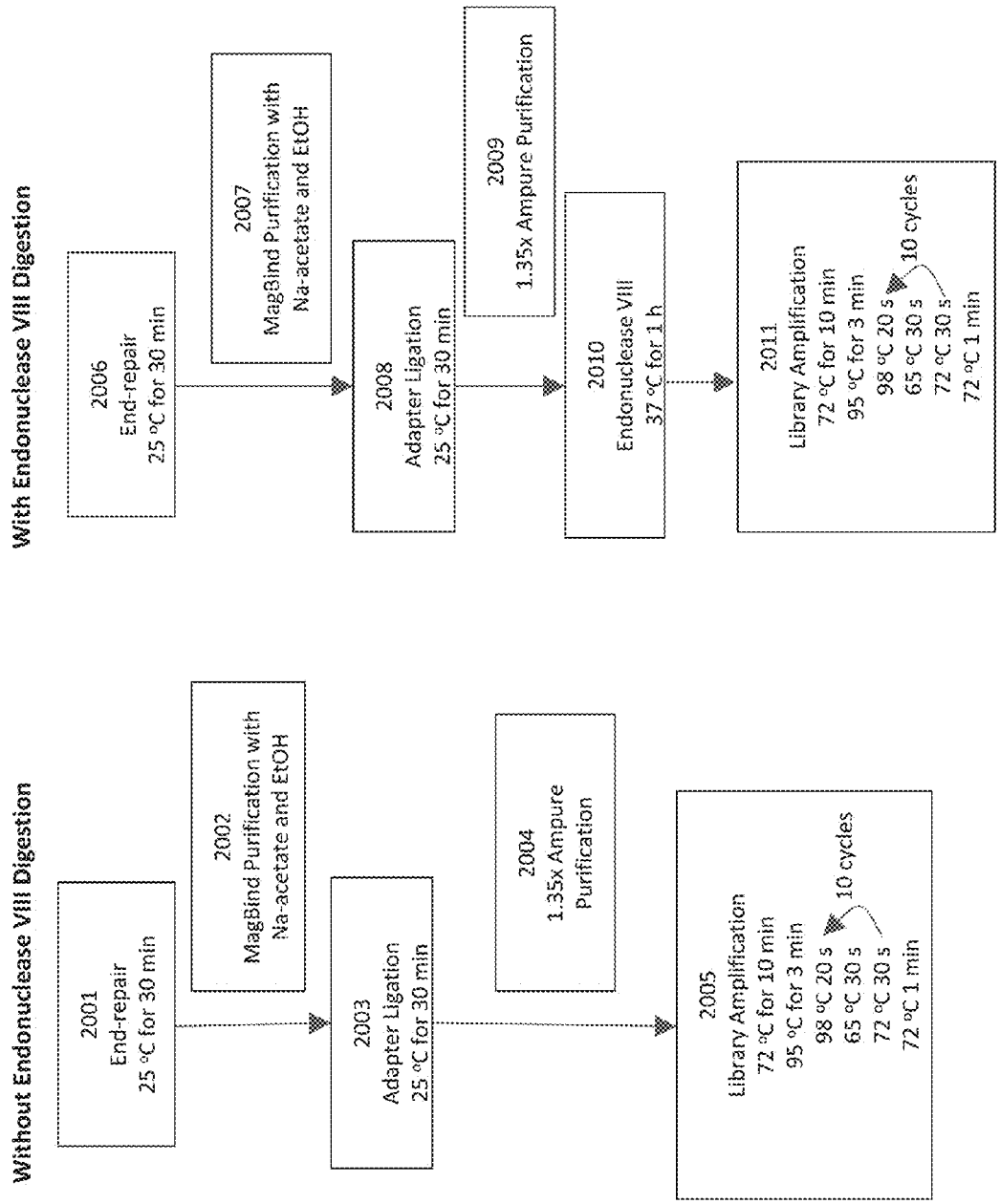
FIG. 20A shows an exemplary method for preparing a sequencing library using carrier synthetic nucleic acids with abasic sites and modifications.

The steps of the protocol are shown in FIG. 20A. Two parallel experiments were carried out. Endonuclease VIII digestion was performed in one of the two experiments. In the experiment without endonuclease VIII digestion, the protocol includes end-repair (step 2001), MagBind purification with sodium acetate and ethanol (step 2002), adapter ligation (step 2003), Ampure purification (step 2004), and library amplification (step 2005). In the experiment with endonuclease VIII digestion, the protocol includes end-repair (step 2006), MagBind purification with sodium acetate and ethanol (step 2007), adapter ligation (step 2008), Ampure purification (step 2009), endonuclease VIII digestion (step 2010), and library amplification (step 2011).

Endonuclease VIII digestion was carried out at 37° C., and allowed to proceed for 1 hour. No depletion of the carrier synthetic nucleic acid was required after adapter ligation because abasic sites already efficiently inhibited amplification of the templates. In addition, the modifications prevented adapter ligation, all preventing the carrier synthetic nucleic acid from being sequenced. Endonuclease VIII may be used to deplete adapter-dimers in the library.

Figure 20B:
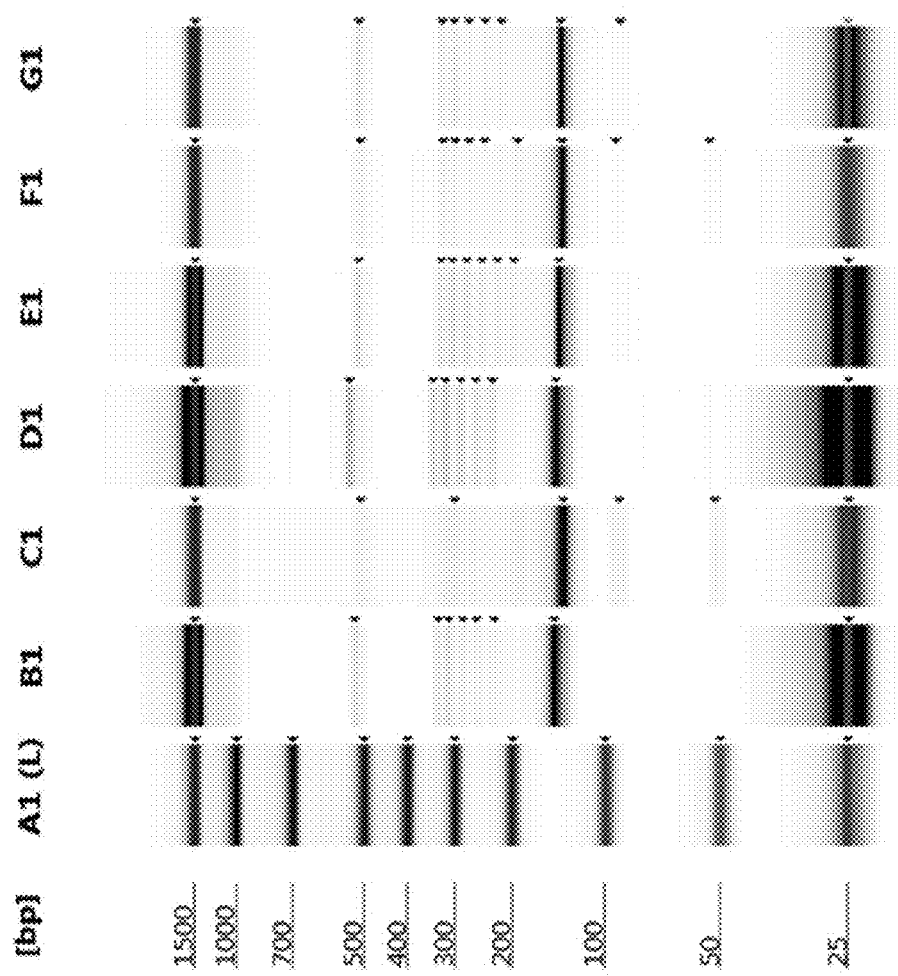
FIG. 20B shows the results from sequencing library generation using carrier synthetic nucleic acids without Endonuclease VIII digestion. Lane A1: TapeStation Ladder. Lane B1: No CNA, 1st replicate. Lane C1: No CNA, 2nd replicate. Lane D1: No CNA, 3rd replicate. Lane E1: 10 ng CNA, 1st replicate. Lane F1: 10 ng CNA, 2nd replicate. Lane G1: 10 ng CNA, 3rd replicate.
Figure 20C:
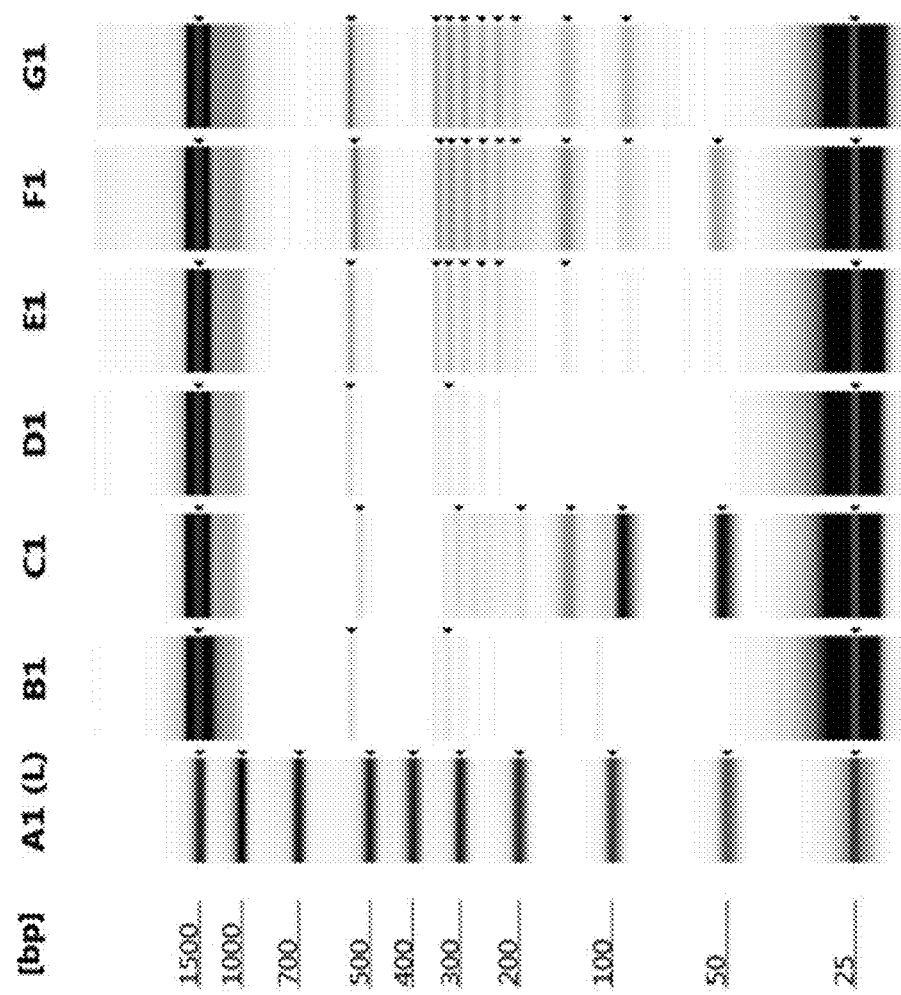
FIG. 20C shows the results from sequencing library generation using carrier synthetic nucleic acids with Endonuclease VIII digestion. Lane A1: TapeStation Ladder. Lane B1: No CNA, 1st replicate. Lane C1: No CNA, 2nd replicate. Lane D1: No CNA, 3rd replicate. Lane E1: 10 ng CNA, 1st replicate. Lane F1: 10 ng CNA, 2nd replicate. Lane G1: 10 ng CNA, 3rd replicate.

FIGS. 20B and 20C show sequencing library generation with or without Endonuclease VIII digestion. Digestion with Endonuclease VIII after adapter ligation in libraries containing the carrier synthetic nucleic acid resulted in improved reproducibility and higher spike-in signal as compared to the libraries without the carrier synthetic nucleic acid.

Example 11: Preparation of Sequencing Library Using Synthetic Nucleic Acids with Abasic Sites Abasic-containing carrier synthetic nucleic acid was designed to serve as carrier nucleic acids during cfDNA extraction step and to provide the minimum library input amount during library preparation. The method of sequencing library generation was the substantially same as used in Example 8. Different types of abasic-containing carrier synthetic nucleic acids were designed. The sequence of the carrier synthetic nucleic acid molecules are shown below:

Partially active abasic-carrier synthetic nucleic acid (Partial ab-CNA) with one end of the duplex comprising modifications that resist ligation (leaving one end of the duplex for ligation helped mediate any concentration effects on the end-repair and adapter ligation reaction) (5Invddt indicates 5' inverted ddT; 3invdT indicates 3' inverted dT; idSp indicates internal abasic sites):

5'-GCGTCCCGGCGCGCGTTTAGGGATAACA/idSp/idSp/idSp/
idSp/GGGTAATGGCGCAAGGGTGCTGGC/3InvdT/-3'
(SEQ ID NO: 175)

3'-CGCAGGGCCGCGCGCAAATCCCTATTGT/idSp/idSp/idSp/
idSp/CCCATTACCGCGTTCCCACGACCG/5InvddT/-5'
(SEQ ID NO: 176)

Active abasic-carrier synthetic nucleic acid (active ab-CNA) with both ends of the duplex were ligatable (leaving both ends for ligation was useful for reducing the amount of carrier synthetic nucleic acids input in case the ends were required for efficient reduction of the concentration effect) (idSp indicates internal abasic sites):

5'-GCGTCCCGGCGCGCGTTTAGGGATAACA/idSp//idSp//
idSp//idSp/GGGTAATGGCGCAAGGGTGCTGGC-3'
(SEQ ID NO: 177)

3'-CGCAGGGCCGCGCGCAAATCCCTATTGT/idSp//idSp//
idSp//idSp/CCCATTACCGCGTTCCCACGACCG-5'
(SEQ ID NO: 178)

Single abasic-carrier synthetic nucleic acid (Single ab-CNA) with only one abasic site per strand (single abasic site was more efficiently digested with Endonuclease VIII) (idSp indicates internal abasic sites):

```
5'-GCGTCCCGGCGCGCGTTTAGGGATAACAGT/idSp/
GGGTAA T GGCGCAAGGGTGCTGGC-3'
(SEQ ID NO: 179)

3'-CGCAGGGCCGCGCGCAAATCCCTATTGTCA T
CCCATT/idSp/CCGCGTTCCCACGACCG-5'
(SEQ ID NO: 180)
```

Figure 21A:
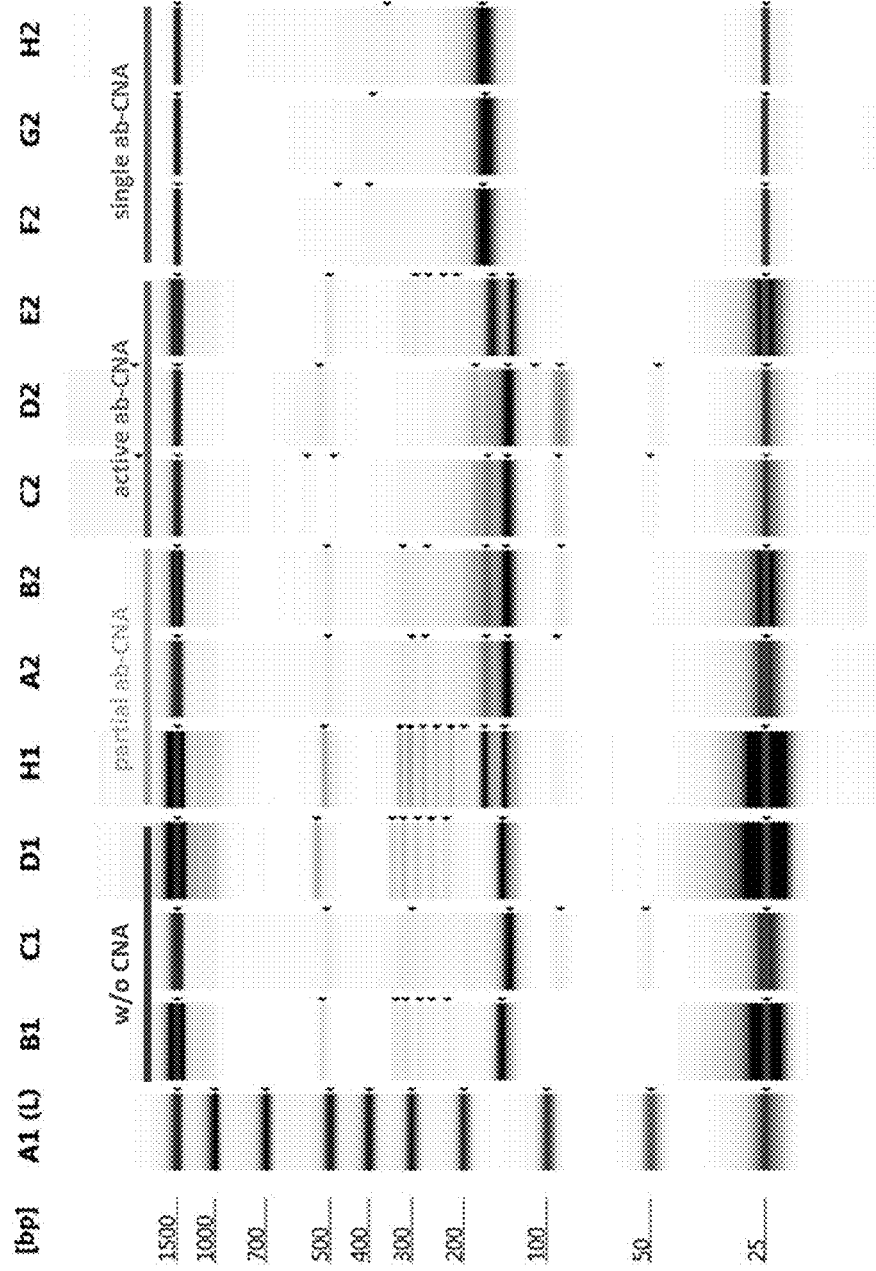
FIG. 21A shows results for preparing a sequencing library using carrier synthetic nucleic acids with abasic sites without Endonuclease VIII digestion.
Figure 21B:
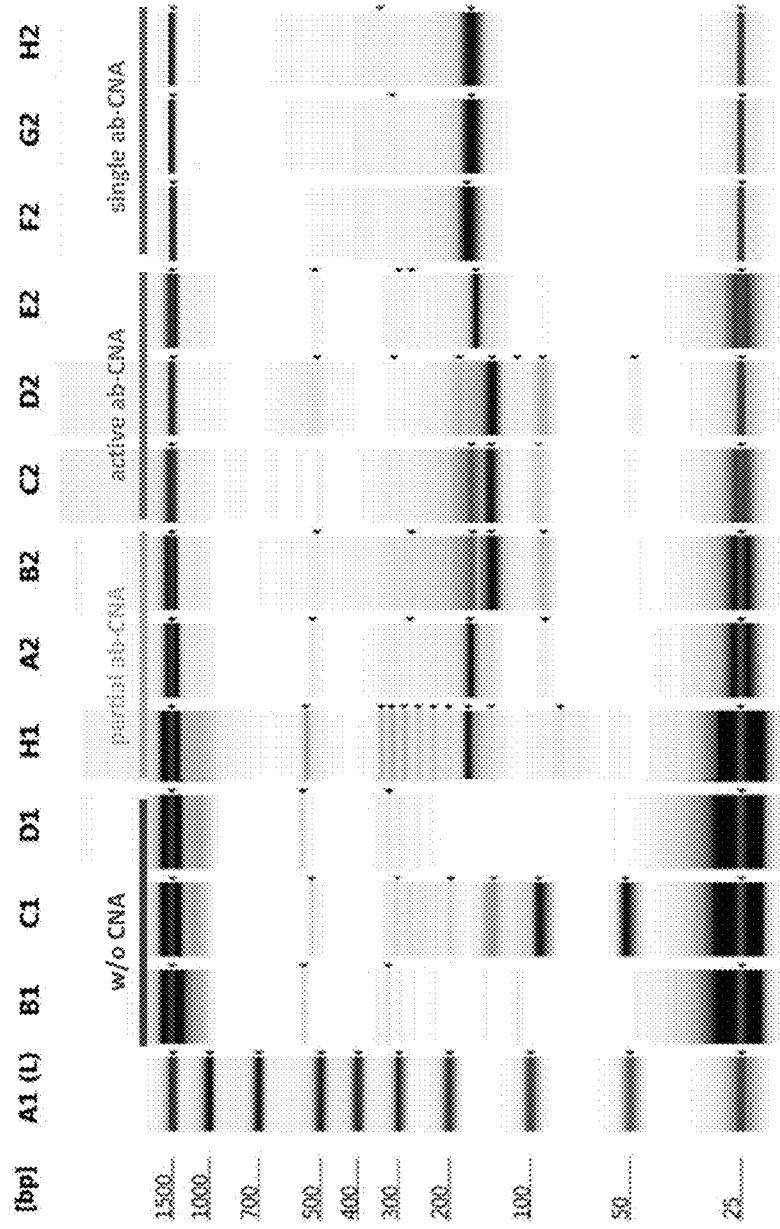
FIG. 21B shows results for preparing a sequencing library using carrier synthetic nucleic acids with abasic sites with Endonuclease VIII digestion.

All libraries were prepared and each variation was made in three replicates. In addition, making the duplex ends for ligation also diffused the bands for spike-in molecules (e.g. SPARKs), suggesting that the reduction in the diversity may be significant under this experimental conditions. FIGS. 21A and 21B show the result of sequencing library generation. The Endonuclease VIII digestion caused the disappearance of the adapter dimer band in some of the replicates. More non-adapter dimer templates were made available for amplification when Endonuclease VIII digest was employed.

Figure 22:
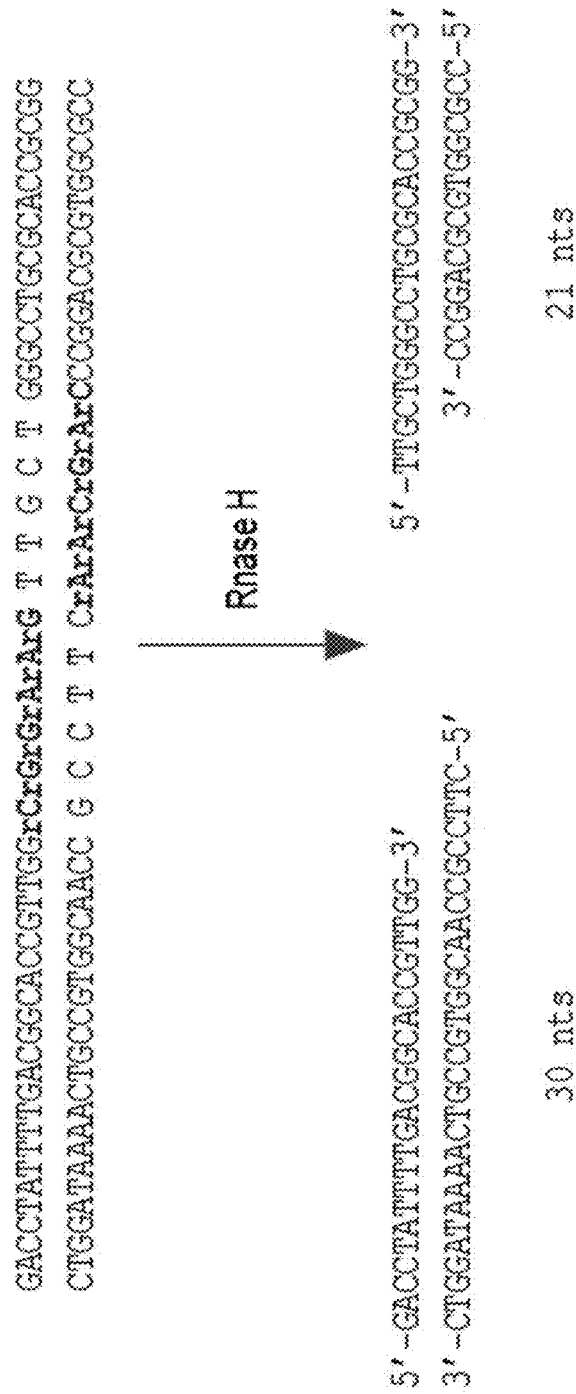
FIG. 22 shows an exemplary sequence of carrier synthetic nucleic acids with DNA-RNA hybrid. The letters "rX" (e.g., rG, rC, rA) indicate RNA sequence. The figure discloses SEQ ID NOS 182-187, respectively, in order of appearance.

Example 12: Preparation of Sequencing Library Using Synthetic Nucleic Acids with DNA-RNA Hybrid Carrier synthetic nucleic acids with DNA-RNA hybrid (RnD-CNA) were designed to serve as carrier nucleic acids during cfDNA extraction step and to provide the minimum library input amount during the library preparation. RnD-CNA depletion in the final pool of the sequencable molecules was achieved by Rnase H digestion after adapter ligation but before library amplification, as shown in FIG. 22. RNase H-based depletion was carried out in a library amplification buffer at 37° C., and allowed to proceed for 1 hour.

Figure 23A:
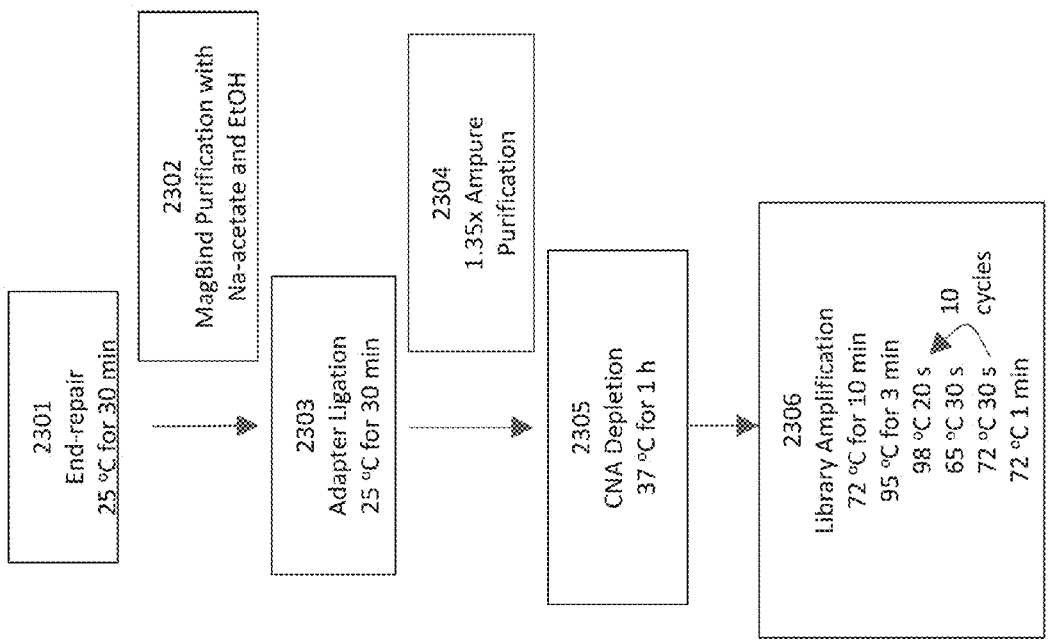
FIG. 23A shows an exemplary method for preparing a sequencing library using carrier synthetic nucleic acids with DNA-RNA hybrid.
Figure 23B:
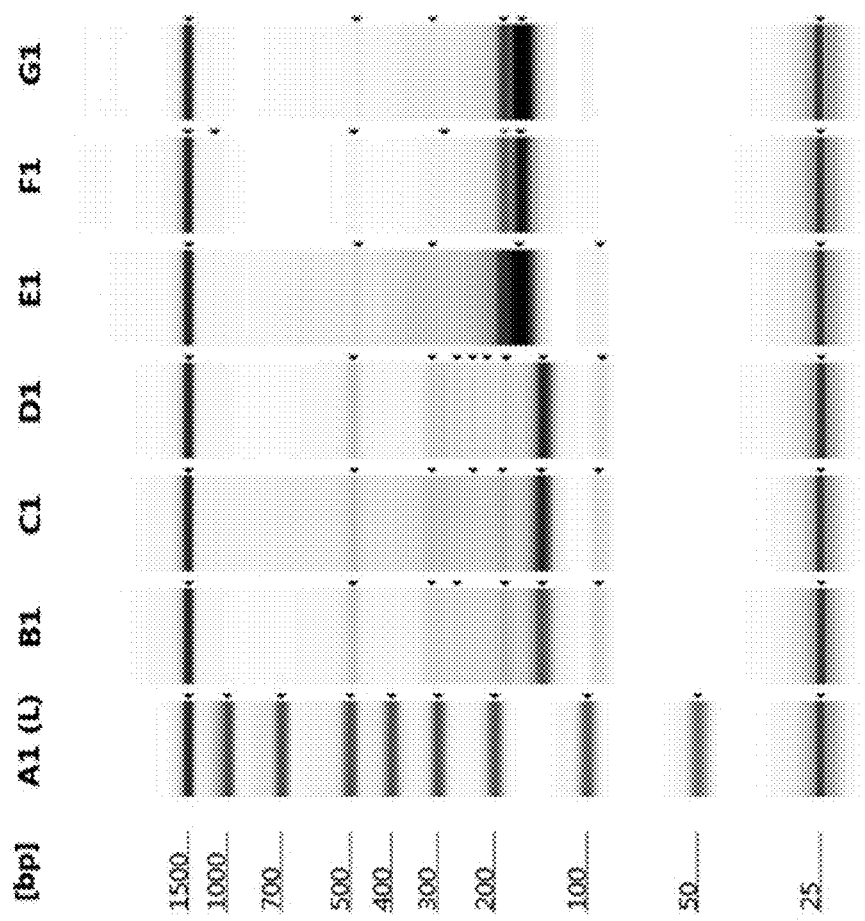
FIG. 23B shows the results from sequencing library generation using carrier synthetic nucleic acids with DNA-RNA hybrid.

The steps of the protocol are shown in FIG. 23A. In a typical experiment, the protocol includes end-repair (step 2301), MagBind purification with sodium acetate and ethanol (step 2302), adapter ligation (step 2303), Ampure purification (step 2304), carrier nucleic acid depletion (step 2305), and library amplification (step 2306). RnD-CNA in these experiments did not have ends that prevent ligation or amplification. FIG. 23B shows the library generation results. Adapter dimer bands disappeared when RnD-CNA was introduced as part of the library input material.

FIGS. 23A and 23B show RnD-CNA after RNase H Digestion. The fragments resulting from RNase H digestion yielded fragments of 175 bp and 166 bp, if both sides were ligated to an adapter, assuming 145 bp total length of 2× adapter. This ligation was possible if the 3'-recessed ends were filled in first by the polymerase in the amplification buffer. This was prevented by designing the locations of the ribonucleotides within the RnD-CNA so that the fragments after digestion both contained 3'-overhangs and that the amplification polymerase did not exhibit 3'-end exonuclease activity.

While preferred embodiments of the present disclosed subject matter have been shown and described herein, it will be obvious to those skilled in the art that such embodiments are provided by way of example only. Numerous variations, changes, and substitutions will now occur to those skilled in the art without departing from the disclosed subject matter. It should be understood that various alternatives to the embodiments of the disclosed subject matter described herein may be employed in practicing the disclosed subject matter. It is intended that the following claims define the scope of the disclosed subject matter and that methods and structures within the scope of these claims and their equivalents be covered thereby.

What is claimed is:

1. A method for determining abundance of nucleic acids in an initial sample comprising target nucleic acids, the method comprising:
   (a) adding a starting quantity of at least 1,000 unique synthetic nucleic acids to the initial sample, wherein each of the at least 1,000 unique synthetic nucleic acids comprises (i) an identifying tag and (ii) a variable region comprising at least 5 degenerate bases;
   (b) performing a sequencing assay on a portion of the target nucleic acids and on a portion of the at least 1,000 unique synthetic nucleic acids, thereby obtaining target and synthetic nucleic acid sequence reads; and
   (c) calculating a diversity loss value for the portion of the at least 1,000 unique synthetic nucleic acids, wherein abundance of the target nucleic acids in the initial sample is determined using the diversity loss value.

2. The method of claim 1, wherein the target nucleic acids comprise pathogen nucleic acids.

3. The method of claim 2, wherein the pathogen nucleic acids are from at least five different pathogens.

4. The method of claim 1, wherein the at least 1,000 unique synthetic nucleic acids comprise DNA.

5. The method of claim 1, wherein each of the at least 1,000 unique synthetic nucleic acids is less than 500 base pairs or nucleotides in length.

6. The method of claim 1, wherein the initial sample is blood, plasma, serum, cerebrospinal fluid, synovial fluid, bronchial-alveolar lavage, urine, stool, saliva, or a nasal sample.

7. The method of claim 1, wherein the initial sample is a sample of isolated nucleic acids.

8. The method of claim 1, further comprising generating a sequencing library from the initial sample, wherein the at least 1,000 unique synthetic nucleic acids are added to the sample before the generating of the sequencing library.

9. The method of claim 1, wherein the diversity loss value for the portion of the at least 1,000 unique synthetic nucleic acids indicates a loss of one or more nucleic acids during sample processing of the initial sample.

10. The method of claim 1, wherein the identifying tag of each of the at least 1,000 unique synthetic nucleic acids comprises a common sequence.

11. The method of claim 1, wherein the initial sample is from a human subject.

12. The method of claim 1, wherein the at least 1,000 unique synthetic nucleic acids comprise at least $10^4$ unique synthetic nucleic acids.

13. The method of claim 1, further comprising adding additional synthetic nucleic acids to the initial sample, wherein the additional synthetic nucleic acids have at least three different lengths.

14. The method of claim 1, further comprising adding to the initial sample a first group of additional synthetic nucleic acids with a first length, a second group of additional synthetic nucleic acids with a second length, and a third group of additional synthetic nucleic acids with a third length, wherein the first group of additional synthetic nucleic acids, the second group of additional synthetic nucleic acids and third group of additional synthetic nucleic acids each comprises synthetic nucleic acids with at least three different GC contents.

15. The method of claim 13, further comprising using the additional synthetic nucleic acids to calculate abundance of the target nucleic acids in the initial sample.

16. The method of claim 13, further comprising using the additional synthetic nucleic acids to calculate abundance of the target nucleic acids in the initial sample based on lengths, GC contents, or both lengths and GC contents of the additional synthetic nucleic acids.

17. The method of claim 1, wherein the at least 1,000 unique synthetic nucleic acids are added to the initial sample at a first sample processing step.

18. The method of claim 17, further comprising adding an additional pool of at least 1,000 unique synthetic nucleic acids to the initial sample at a second sample processing step, wherein the second sample processing step is different from the first sample processing step.

19. The method of claim 18, further comprising calculating a diversity loss value for the additional pool of at least 1,000 unique synthetic nucleic acids.

20. The method of claim 18, further comprising identifying a sample processing step with relatively high diversity loss by comparing the diversity loss value for the at least 1,000 unique synthetic nucleic acids with the diversity loss value for the additional pool of at least 1,000 unique synthetic nucleic acids.

21. The method of claim 18, wherein each of the unique synthetic nucleic acids in the additional pool of at least 1,000 unique synthetic nucleic acids comprises a domain identifying the synthetic nucleic acid as a member of the additional pool of at least 1,000 unique synthetic nucleic acids.

22. The method of claim 1, further comprising adding a sample identifier nucleic acid to the initial sample.

23. The method of claim 1, wherein (a) further comprises adding non-unique synthetic nucleic acids to the initial sample.

24. The method of claim 1, further comprising: reporting a result of the method to a caregiver, patient, or other person.

25. The method of claim 1, wherein the determined abundance is a relative abundance.

26. The method of claim 1, wherein the determined abundance is absolute abundance.

27. The method of claim 1, further comprising determining a number of synthetic nucleic acid sequence reads comprising different variable regions.

28. The method of claim 27, wherein the diversity loss value is calculated by comparing the starting quantity of the at least 1,000 unique synthetic nucleic acids with the number of synthetic nucleic acid sequence reads comprising different variable regions.

29. The method of claim 27, wherein the number of different synthetic nucleic acid sequence reads comprising different variable regions are detected by aligning the synthetic nucleic acid sequence reads with a reference sequence.

30. The method of claim 28, wherein the number of different synthetic nucleic acid sequence reads comprising different variable regions is quantified by aligning the synthetic nucleic acid sequence reads with each other and throwing out duplicate reads.

* * * * *

SEQUENCE LISTING

```
<160> NUMBER OF SEQ ID NOS: 187

<210> SEQ ID NO 1
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
acgttgtctg cgagtcagct aatcctatcc tggtgcatgc ttgacttgtc accgaggtaa     60
tcatcgaatc ctggatgagg acgcaagaga tgtatggtca                          100

<210> SEQ ID NO 2
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
acgtcgaatc ctacgcgact gcgcgtgact aggtgaaggt gaacttagag gctctcaacc     60
tcatccactc ggtatcatcc tgtgtgtatc aagagagtca                          100

<210> SEQ ID NO 3
```

```
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
acgtgagtga gagtactcaa tcaatcttct ccgcaccgtg aatgcgtgag tgtggccaat    60
gccgccatca acgattctac tgagcgagtg ctcgcagtca                          100

<210> SEQ ID NO 4
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
acgttggtct caatgcctgt gacggacata acgcattaag gaccgatatg gtagaactgt    60
tcctcatgtg actaggaggt aatcctggcg cataacgtca                          100

<210> SEQ ID NO 5
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
acgtacaact atggtatgtc cactgagcgg caaccaggtt ctcatcatcg ctgcggagaa    60
gtcacgtaat attctgaagg tagtggcgtg tagacggtca                          100

<210> SEQ ID NO 6
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
acgtcgtatg caacgtatat ggaattatct gtgtacgtgc atacgtgacc aacaaccaga    60
cggcaccgat catcttagtc gccgagagat ctaattgtca                          100

<210> SEQ ID NO 7
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
acgtacggca ttgttctcag gaacgtgtgt tcatacgatc ttcgactcta gcatatccaa    60
cgtcgaagtt atcattaccg agccggaaca acgtcggtca                          100

<210> SEQ ID NO 8
<211> LENGTH: 100
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 8
acgtaccgtt aagtgctgtt gaagaatatg agtctatagg ttccggacct gttgcgacgt    60
gcgatggcta cttacgcatt aaccagtgtt gtataggtca                         100

<210> SEQ ID NO 9
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9
acgttgacca agaggacgat acttggataa gttcttgcta tatgagcgcg gtcaacgtga    60
aggccgatat cgcgccaatc ttcacgatgg agcttcgtca                         100

<210> SEQ ID NO 10
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
acgtcctgaa tcatcgactg aaccggctta ctaggaatta gtcagcgcat aatatactcc    60
aatgaatgtt ctgagctcga cgctcttgcc ggagtggtca                         100

<210> SEQ ID NO 11
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 11
acgttctgtc tatacgtata tgctaagcgc aatatgattc aatggtagtc acttcgtccg    60
acggcgagta acgcaccacg tgtccattct ctggaggtca                         100

<210> SEQ ID NO 12
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12
acgttactgg tgacggatgc ctctcctgac cgagtatcta ggcaccacac ggacgttgac    60
aggcatgctt aatccggtga tgaacggatc ggtcctgtca                         100

<210> SEQ ID NO 13
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13

```
acgtgaggcg tctcgcgatg tcaagtgaat atgatgcagt tctgactgca caccacacga    60
ggtcgcttga agtcgatgac tccgcatagt cattcagtca                         100
```

<210> SEQ ID NO 14
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
acgtcgcacg tatgacgtgc gaggttagag ttggcctact acttagataa tcttgccgca    60
tgcttattaa ctagaacggt tgccgaattg cacctggtca                         100
```

<210> SEQ ID NO 15
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
acgtcactta tgcacgactc aacttgaggt aagcgtgtag agaagccttg atagtcttgt    60
cgtcgcggcg gagatctccg ttaccttcac acttgggtca                         100
```

<210> SEQ ID NO 16
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
acgttccgat agataagcac aagtcagcga agccttgtcc gctgtgtaac atatatcatc    60
gaatgcgata gtcggttgga acgcgatctg acgtacgtca                         100
```

<210> SEQ ID NO 17
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
acgtccagca ttcaataagc atcgactctt agtgcggtgt ggagtgtact tccatgtgac    60
aactcgagta gaccgattag gctgctgaca agttaggtca                         100
```

<210> SEQ ID NO 18
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
acgtggaata gagatggtaa gccaccggct tcggtgcctt ggcacgtgag acctatagct    60
tagtgctcat ccatcgttat ctacgacgaa catcgcgtca                         100
```

<210> SEQ ID NO 19
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
acgtgccgcg tgttgtgtac cgtacagtgt tctagaagtc tattggattg gctagctagc       60
gagattaccg acgctactca acagagtgga gctcatgtca                            100

<210> SEQ ID NO 20
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
acgtaactag cgatcgcaga ggctaaggcg tacagttcgt ggttcgcgtc cacgtaggcc       60
gttatctgct tacttccgta ggtactgaga gattcagtca                            100

<210> SEQ ID NO 21
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
acgtaggccg gatgtgactg atgattcatc tcagcagcat agccttcacg tgtagcggct       60
tatcacgctg agttcgttcc aacagctgga tagtaggtca                            100

<210> SEQ ID NO 22
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
acgttatgta cacgtgaagc tggcgcgtgc gcgctactta tattacggag gttagttcat       60
caatatcaga gaagttcctc atgtatacat gaattcgtca                            100

<210> SEQ ID NO 23
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
acgtctggta cagacggatg ctgcttgtcc aattatggtg actaactcct aatcatcagc       60
aatcgcgagt ccggtaagcg tccgcgactg atcgccgtca                            100

<210> SEQ ID NO 24
<211> LENGTH: 100

-continued

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
acgtgttata ccgtaccggt aggaacacaa gtgtacctgg tgagataggt tccatgcttc    60
tggcgacctg acaatctaca gcagactagt atgcgggtca                         100

<210> SEQ ID NO 25
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
acgttgcggc caggacaatc atatcgcaat gatcatgact gtgattcaac ggactcgcgt    60
catgagatga atctgccaga gtatgtcggc tctggagtca                         100

<210> SEQ ID NO 26
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
acgttgagag ataattgagc gatactgtta tcgcggctat acatagctct cacctcatgg    60
acagcgtagg attgtgaata gctgctccac tcgtccgtca                         100

<210> SEQ ID NO 27
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
acgtacggaa gacggcaagt tcttgatctt cacgcatctg ccgctattgc aatatgtggt    60
atgacgtgat aactagccgg cgtccgacgt aacatggtca                         100

<210> SEQ ID NO 28
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
acgtcatcga tcgtaggcgc ttccggcaag gacctagtag acttccagat tggacttcta    60
cggctcggat attataccgt ctcaaggaac ggtgctgtca                         100

<210> SEQ ID NO 29
<211> LENGTH: 100
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 29
acgtcctgcg ccttaaggcg catcgcttgt taccaggatt aaggatacgt cgtcgaatgc    60
gcaggtctag gattgttgtt gctatagaac taatacgtca                         100

<210> SEQ ID NO 30
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
acgtcaggcg tacatcgaac tgcttactct cacgtctgtc cgtatcaggt tgacctaacg    60
cgtctggtgg caagctaata ctgagcatag cagtaggtca                         100

<210> SEQ ID NO 31
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
acgttacgca atgtgtcata cgcgcatctg agttcagact gcaatcacgc tgacgcacga    60
ctatatggtt gcctccgagt acttggtact aggtcggtca                         100

<210> SEQ ID NO 32
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
acgtttgaca gcgcgctagc aatctgatgc agttgacgtg ttccgtattc ctagttgaca    60
catacaacgt cctcacgtgt cgaagaccgt attcgtgtca                         100

<210> SEQ ID NO 33
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
acgtttctgc ctcttaagct gtgaagcaag ccgcttagtc aggactgtat tccaactgtt    60
ccagcttccg gttgaacact gtatcaggca acgagcgtca                         100

<210> SEQ ID NO 34
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
acgtactact caccaattgg ccaatacagt tagtatcagc tggagccgtg agacttatgc    60
ttcggatgac ttcagttggc taattggagg cgaccagtca                         100
```

<210> SEQ ID NO 35
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
acgtgattag ataatgagtc cacacgcatc ttgtgttgga ctgcagcgtt aacaatgacg    60
atgccttgcg ttacggcgct atcttcatta ggactcgtca                         100
```

<210> SEQ ID NO 36
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
acgtgagata cgcgcctgac ggataccgtg accgtatatg tccaggttat gagagaacat    60
gacttgagag agtctggcac ttccttgacg tgtccggtca                         100
```

<210> SEQ ID NO 37
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
acgtcagcgg cgttggtcac acgtcaacac ctctcgtaga atctgctgca gctcctgtcg    60
ttcagtaggc taagcactga ggtagtaagg ctcagtgtca                         100
```

<210> SEQ ID NO 38
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
acgtacttcc tactccttcg tgtgaggaag gtgccacggt gatgtgtcac gtagtctcgg    60
aatatatggc cacactactt ccatgcaact gcggatgtca                         100
```

<210> SEQ ID NO 39
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
acgtgtggcc tctaggaagg aaggtgcaac cagctacttg atagacgtcg actagcatac    60
tactcctcac gtgtgctgtg cgagtatgag ttcctagtca                         100
```

<210> SEQ ID NO 40
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
acgtattcga attgatgcgg actaccacta gcaacgccgt tgataatagc aagatggaac    60
gtacttgtac cttgcctgag gcgctcgatt aacgcggtca                         100

<210> SEQ ID NO 41
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
acgtagcaac gtgttaagac ttgcgacaac ggtcctgcgg aaggtactga tacttacatt    60
attagactgc agttgactac cgtgtaagtg gacgtcgtca                         100

<210> SEQ ID NO 42
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
acgtaattcg agcaggctac actggcttaa gtaggctgtg ttcagtagcg tacacattct    60
acaacgtccg agccacatcg atatgtgcct aagtcggtca                         100

<210> SEQ ID NO 43
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
acgttaggaa ttggctgtgg ttcattcggc tgaatctcgc caacaactct cgattgttaa    60
ggcacttaag aagcagagtc ggccgccaat ctggtagtca                         100

<210> SEQ ID NO 44
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
acgttcttga accagtgaga agtcagcata gtaactctct ggtcaattaa catagaccat    60
cgtctcggat tgcgtggtcg acgcctgcca gaatgagtca                         100

<210> SEQ ID NO 45
<211> LENGTH: 100
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 45
acgtggaatg aggaatagga tgctaagaca ggacagaact ctgaccatag gctcctcatt    60
gtggcttgag atcttcttcc acgaaccgtc cggcacgtca                          100

<210> SEQ ID NO 46
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
acgtctgacg actactgaga tcacctagtt cggatgaatg cgccattcat gcggaggtat    60
acgagcttac gtcggatcct agcgcgtact gacgtggtca                          100

<210> SEQ ID NO 47
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
acgtaggcac tattctaact attcttaagg cagaggcgaa cggttagtta tccgcgctca    60
gataagcctc cttacagatc cgatatcaat gctggcgtca                          100

<210> SEQ ID NO 48
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
acgtcgcttc atggacaatt agttactgct tacagccagc acagtggtac taacgatcgc    60
cgttagcgca acgcctgaga ttatcgtagt tgaatggtca                          100

<210> SEQ ID NO 49
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
acgtgagtca gtagtctcca gtcatcacga gcgaatcgag ctcggtgaac agtcgtgaac    60
aatatacctg gttcagatac gtatatagtc agtgccgtca                          100

<210> SEQ ID NO 50
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 50
acgtagaatt ccacgttact gatgaccggt agatgaagtt agagagtagc gctcactgtc    60
gaacatcgac gcaattgtac tgtgtaacgt gccatggtca                          100

<210> SEQ ID NO 51
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
acgtctcttg cgccgatatc cactctaaga tgtgccacgc gtaatctaat agaaggagcc    60
ggagccgtag tggtaccatc aacttgactg gtactagtca                          100

<210> SEQ ID NO 52
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
acgtcctaag tgcggaagtc ctaattgttg gtacggtatg caagcttgta cgaccttctg    60
ctaccttata tagaagtaca cagtcggaag cgtcgggtca                          100

<210> SEQ ID NO 53
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
acgtgtgaac aagatgatcc ggtatccagt aggaccgtca taagatcacg agttaccacg    60
tagagtcaat tggatagtcc tggcggttat gctagtgtca                          100

<210> SEQ ID NO 54
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
acgtcggccg taatcgcttg tatctgctac agtgcattgt ggcgcactag agtaatacgg    60
atataggttc tcacacatgc gcatccaggc gcatgggtca                          100

<210> SEQ ID NO 55
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
acgtggcaac taccgacctg taattgctag tcgacgcata cggtgtccgt gctggttctt    60
ggtgcgatca tatcaccagt tgaagcagtg atctgagtca                          100

<210> SEQ ID NO 56
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
acgtcaatcg taccgctcta agtccacgtg aacttgctct ccacaatgta ataagaagtt     60
cgccgctgcg gacggagaag gttgctagat taggctgtca                          100

<210> SEQ ID NO 57
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
acgtcagcct tattagcaac atacacatcg ctcgcgatat gtaagaatgg tactcttgct     60
ccaaggtgga gcgtgtaaga accgttggtt gctgacgtca                          100

<210> SEQ ID NO 58
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
acgtgctcct tggaggagca tgatatagta accttcagtt ctaacagtct tataccgctt     60
cgagctagct cgcaatggca acaacttcat cggaaggtca                          100

<210> SEQ ID NO 59
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
acgtagctgg taacgtggtt agccaccaga tctcgcagga gccataggtg tattcgcata     60
tgaatcttcg gcgacatacg tcggatatgc agagtcgtca                          100

<210> SEQ ID NO 60
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
acgtcatagc tgccgatcac ctatggcata actcattcta ccaattagtc ggcaggtggc     60
atgtacgcag tgtgatgctc caatggcttc tgagtggtca                          100

```
<210> SEQ ID NO 61
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
acgtcaagcg agtgttaact gtctactcca ccgatgcatg agtcaacaag ccatcctgtc    60
tgcgctggtg attactctta agagtccata ggcgaggtca                         100

<210> SEQ ID NO 62
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
acgtccatat agcgcgctgc gaagctacac tacagcgcat gattgaatca ggccttctta    60
attcaggagt cagatattca gtggcgcggc gaggacgtca                         100

<210> SEQ ID NO 63
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
acgtgatcag cggtatctcg tcatacgaat atcgtgaacg ttacgcctaa ttccatggta    60
gactcgatgg cgcaagaagc gaccgagtat ctgttcgtca                         100

<210> SEQ ID NO 64
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
acgttcttgt taatggttga tagcaacaag gcgagtagtc cgaatagctc cggaatcaca    60
ctgttctcca cgacggtagc catcttgcgt cttagcgtca                         100

<210> SEQ ID NO 65
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
acgtagctgg agagacaact agatcggcgt caatatctga gcggtataat atgcttggaa    60
tgctagctgt attggctctc tctcaatctg gtagtggtca                         100

<210> SEQ ID NO 66
<211> LENGTH: 100
<212> TYPE: DNA
<213> ORGANISM: Artificial Sequence
```

<220> FEATURE:
<223> OTHER INFORMATION: Description of Artificial Sequence: Synthetic
polynucleotide

<400> SEQUENCE: 66
acgttcatca acagaaggag agactgatac gattagcgcc atcctgttag tggctcttaa    60
caggccggta gcgattctgg ccatggtatt ccgatggtca                         100

<210> SEQ ID NO 67
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 67
acgtgtgtgc ttagcactac gtgtcgtgag tccgtgatag tccgttggta tgtcactcac    60
ttggctaacg ccaagatacg ttcagcatta atccaagtca                         100

<210> SEQ ID NO 68
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 68
acgtgaaggc actcttatgg tagtcgcagc gtgatattgt ccgaccattg tgaggatcgc    60
acggtactca tcttactgcc aatagtgctc cagtaggtca                         100

<210> SEQ ID NO 69
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 69
acgtgaatct ctgcaacgcg gagactgcct cggttgtaag ctaccacgta gtcagaactc    60
cgcgtcgcat attggctatg atattacgga agaccggtca                         100

<210> SEQ ID NO 70
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 70
acgttgtagc accgtccgtc caactagagt tatacgaagt gctcgccagt tcatgatcgc    60
tgcactgcca ggctgtcacc tgtagctaca gtgcttgtca                         100

<210> SEQ ID NO 71
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 71
acgtactgta tctgtagctg cggtagtgct gacattgtac aagagcgtcc gtgccacaga       60
tacatcgaca cgcatgcgtt cgccaggtta agcgtggtca                            100

<210> SEQ ID NO 72
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
acgtcgcgtc tcgtcgtagg tagtcaatcc ttgcaaccgc gcataaggac agcatgaggt       60
gtctatctta taagatagac tagaggttac gtgagagtca                            100

<210> SEQ ID NO 73
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
acgttgcggc aagcaagtag cattgagact gttcacagga cgactacaga tggctcgtac       60
acctccatac ctggttgccg ttagcttgga cagcgtgtca                            100

<210> SEQ ID NO 74
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
acgtgatgtg cgtcatccgg aaccaacgca ttgtatgata acatacggct tgcgaccaga       60
cgttatctca tagacgtcgc ggcctccgca aggtaggtca                            100

<210> SEQ ID NO 75
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
acgtaccagg tgttgaccgg agtacggcaa ctcgcgcagg tgtgcacgta cctatcacgg       60
tagtaatact agtaacacgt cgatactgta tagatcgtca                            100

<210> SEQ ID NO 76
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
acgtatacac tctgcgcgca ccacgatacg gctaacgtgc gatatcagtc catgtcacaa       60
ctctggcgtg gtaatgtagc ttcttggagt cgcttagtca                            100

<210> SEQ ID NO 77
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
acgtaacatc gtggacgtgt ctaagctcct ggagaataga ctcgttattg gcatcacgtc       60
acttgcacgc gatattccgt ctgccgatat ggtcctgtca                            100

<210> SEQ ID NO 78
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
acgtctagcg tgtagttgtc ggctcctcaa gtactcaaga ccgcctctgg tgcgtcgaga       60
gctcactgcg taggacatat gctgacacgt tagttagtca                            100

<210> SEQ ID NO 79
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
acgtagataa gtccgtacta agcgtattct cactggattc atgctgaacg tagaactgct       60
atagtccacg tgctacgccg ttgaccgacg tacgaagtca                            100

<210> SEQ ID NO 80
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
acgtctctgt cgatcacacg ccggacgcac tgttacttga ctggaggtga ccttcgcacc       60
aataacgttg aagagctaga ttagatggta gaacgagtca                            100

<210> SEQ ID NO 81
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
acgtggacct gctcgccata acgcggatcg gtcctgcgat gtatcaactg atgattgaca       60
cacagcgcaa gtatgaccgt tagataattc agctcggtca                            100

<210> SEQ ID NO 82

```
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
acgtaccaac cacgcgtcgg tgagccgtga tactcgatct acctaggata ttgcacttcc      60
tggcggtatg cgaccgatct tcgtgttcaa ggaatcgtca                           100

<210> SEQ ID NO 83
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
acgttactaa cgtggccgag gcaacttcat ggtgaattgc tctaggccta ctatgtaccg      60
ccagtgactc ggcagaccga cagaaccgca atacgggtca                           100

<210> SEQ ID NO 84
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
acgtagacca gctggcgcga cgtctgcgag cagtctcctg agaggtgtgt gtctcactac      60
tcaagtactc tggcacaggc cgcattaatt ggattggtca                           100

<210> SEQ ID NO 85
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
acgttactat gcttgccgta cggttgtcga tgaggtcggt acagcagaat cgactaggta      60
taagaccgac atgctcaatt agtctgtcac ctcatagtca                           100

<210> SEQ ID NO 86
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
acgttactag gagaccgtaa ttagtagtgt aacctagcga cagccgcgta ccgcaacttc      60
acttggtatt gctgctatcc attaggtgtc acgcgagtca                           100

<210> SEQ ID NO 87
<211> LENGTH: 100
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 87

```
acgtctaagt ccgccgaagg catatgtgaa ttcacctgga gactgccatt cactccgttg    60
aagtactagt tacggagctg ctagtgcaca gaggaagtca                         100
```

<210> SEQ ID NO 88
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 88

```
acgtcacaga ccggattacg gtattagttg ctggaggcgc acgcacgtcg ccgtatcagt    60
aaggtgattc ctgcgtatac tggccggaag cagaatgtca                         100
```

<210> SEQ ID NO 89
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 89

```
acgtgcagtc gcgatgacgg ctcgatcgcg aactaattct gagctgtaga ccgatgatct    60
ggtggtaagg ctatcactgt cagtgcatcg agcactgtca                         100
```

<210> SEQ ID NO 90
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 90

```
acgtattgga tatacaagga ttattggcac gtagtcatac gcacagtgcc atggcaagtt    60
ggcttcttac cacctggcca ccgtcgatca gtgcaagtca                         100
```

<210> SEQ ID NO 91
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 91

```
acgtcgccgt caaggaatat ggccattcat gacagacgga actcgtcgca tctgtgttca    60
taaggaggac gaatctgcat cgacgtggtc ctcgcagtca                         100
```

<210> SEQ ID NO 92
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 92
acgtacagcg ctgacaggac tggcgcaact aggaatgtca gcacctggat cggcttagag    60
gtgtgtcgat gtatctgctg ctagtgtaac tcctctgtca                        100

<210> SEQ ID NO 93
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
acgtgcggcc tgtgcgatta gtcttaagcg gatcgagtta tccgcaagca gattacaaga    60
agcgttccta catgagtatt cctgcatcgt atggtagtca                        100

<210> SEQ ID NO 94
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
acgttgtatt cactcgagct ccgctgcacc ttcggaattg agagagtggc aatctcatgg    60
acagtcgtcg tcgtgcgcta aggtacagta ttagacgtca                        100

<210> SEQ ID NO 95
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
acgtagtgcc gaacatgcgt gagctcgcct cggaattagg ccttggctaa gaactactaa    60
ggtataggca ctaatacgcg gctgtggcaa catgatgtca                        100

<210> SEQ ID NO 96
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
acgtaaggcg gcatcattcc tctgaggtga ctcaagtgcc aacctcattg tatagtggct    60
taagttcatg cggcactctg agaggaacac gtataagtca                        100

<210> SEQ ID NO 97
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
acgtgtcata tgacgaggat tcgcacggtc ggtacacatg ccgtctctcc aggttacatt    60
attcgaagtg tgtccatgcg gaagacggat gtctccgtca                        100

<210> SEQ ID NO 98
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
acgtttggac agtgacggaa ctaatagtta tgtcgcgtaa ctctccgctg ataatacatg      60
ctaacgagcc acgagttctt ggcgaggtcc acaagggtca                           100

<210> SEQ ID NO 99
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
acgtagagcc actctccata tcgatctcct ctatagtcgt aggtcggcta ctgtgagcag      60
gtggagtgac tgaagcttgc aaggacgaga ttcatagtca                           100

<210> SEQ ID NO 100
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
acgtaagcga taggatagca gtatccgacc agcctagcgt ggcacattcc gcattctcag      60
gcagttacca tgtatatctc tcaagaatgc ggttgagtca                           100

<210> SEQ ID NO 101
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
acgttggtac ataggaggtt gacgcgcgac catctgcagt taccactccg actgtatgtt      60
ctgtcggcgg caatgcggaa tgtacatgcg gatgatgtca                           100

<210> SEQ ID NO 102
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
acgtagtgtt gttgttctgg cctctaggag aagattcata cttgcaagac cgtactacta      60
gacgagttac agtcatccag taatcggcgt gccacagtca                           100

<210> SEQ ID NO 103
<211> LENGTH: 100

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
acgtcttcct aggagtcgag gtatgagttg tccagttcgt tctagatcct caaggtccta     60
taaggctcca acgaccgagc agcggaatat gaccgtgtca                          100

<210> SEQ ID NO 104
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
acgtggctct atcgagttgt cgactacaag aatgcgactt ggtatcggcc tacgagactc     60
aacgtggaag taaggagcca caaggtatca ctcgtagtca                          100

<210> SEQ ID NO 105
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
acgttatgag atataacgtc gcagcgtgct tccgcatcgc gcagaccatt aatggtaatc     60
ctagacctgg tacttagtcc gcaggttgtg tgaatagtca                          100

<210> SEQ ID NO 106
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
acgtccagga ggaccttatg tgtcgaatat ggtctgtagg agcatccgtc cacatctgat     60
actgagttag cgccaacatc ggccggcgat ctagacgtca                          100

<210> SEQ ID NO 107
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
acgtgtctaa ctgatcagag gaggtgtagt gctcgtgtcc taaccgcacc acacgattcg     60
gtgccagcac gtagatcgga cgtgtcggta catatagtca                          100

<210> SEQ ID NO 108
<211> LENGTH: 100
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108
acgtgattgc tgataacgag ttctcacaag gacagttata tggcgaactg tctgtcgtca    60
ctcagtcggc attgaactcg cgcatcggcg taagacgtca                         100

<210> SEQ ID NO 109
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
acgtgaggac actagtgtac gtgctcgtac cattcctgtt aggtgatgcc taataacctg    60
taatgcagat agagttacag cttctaccgc cgacaagtca                         100

<210> SEQ ID NO 110
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
acgtcgttcc tgaccgtaca tagagcggct accgagctca ctgttggtag catagtagtc    60
cagtaatgtc gagcggatcg cataacaagg cttgatgtca                         100

<210> SEQ ID NO 111
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tagtcagtac agctgctgca cgatacgtgt ac                                  32

<210> SEQ ID NO 112
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tagtcagtac agctgcgtct acagtctgcc tgctgttgca cgatacgtgt ac            52

<210> SEQ ID NO 113
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tagtcagtac agctgcagtg caagtctgcc ttcatcctaa gtcaccgtca ttagatgagt    60
gcacgatacg tgtac                                                     75

<210> SEQ ID NO 114
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
tagtcagtac agctgccgca taagtctgcc ttcatcctaa gtcaccgtca ttaggttcac      60
gtgcacttca ggatctgcac tcagtgcacg atacgtgtac                          100

<210> SEQ ID NO 115
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
tagtcagtac agctgcctca gtagtctgcc ttcatcctaa gtcaccgtca ttaggttcac      60
gtgcacttca ggatctgcta ttacagcgcg aagatgcct gcgctgtcat gcacgatacg     120
tgtac                                                                125

<210> SEQ ID NO 116
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
tagtcagtac agctgccatc tgagtctgcc ttcatcctaa gtcaccgtca ttaggttcac      60
gtgcacttca ggatctgcta ttacagcgcg aagatgcct gcgaccaacg atctaacact     120
tatattgaga catctgcacg atacgtgtac                                     150

<210> SEQ ID NO 117
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
tagtcagtac agctgctcgc taagtctgcc ttcatcctaa gtcaccgtca ttaggttcac      60
gtgcacttca ggatctgcta ttacagcgcg aagatgcct gcgaccaacg atctaacact     120
tatattgatc cgaatcaatc atatgagtgt tgatctgctt gcacgatacg tgtac         175

<210> SEQ ID NO 118
<211> LENGTH: 350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
tagtcagtac agctgcgcta caagtctgcc ttcatcctaa gtcaccgtca ttaggttcac      60

```
gtgcacttca ggatctgcta ttacagcgcg aagatgcct gcgaccaacg atctaacact      120
tatattgatc cgaatcaatc atatgagtgt tgaccggaca tcggcgtgtg gtggccgtgg     180
aatcacttat tccatggctc ctgccgcgat gtatatgtcg acagcgagtt agatacgaca     240
gataagtcga cgcgtgcctt gtagccgtac aacgcatatg tcttcattcc tgatagagtg    300
tcggtactca taggagtgaa cctatacggt atcgtgcacg atacgtgtac                350
```

```
<210> SEQ ID NO 119
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(29)
<223> OTHER INFORMATION: a, c, t, g, unknown or other
<220> FEATURE:
<221> NAME/KEY: modified_base
<222> LOCATION: (34)..(41)
<223> OTHER INFORMATION: a, c, t, g, unknown or other

<400> SEQUENCE: 119
cctgtgctct agagtagagt annnnnnnna gctnnnnnnn ngagcgatct gtatagatag      60
ctacacgctg agtga                                                      75
```

```
<210> SEQ ID NO 120
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(29)
<223> OTHER INFORMATION: a, c, t, g, unknown or other
<220> FEATURE:
<221> NAME/KEY: modified_base
<222> LOCATION: (34)..(41)
<223> OTHER INFORMATION: a, c, t, g, unknown or other

<400> SEQUENCE: 120
cctgactctc gatgatagta cnnnnnnnna gctnnnnnnn ngtctatagc tctagcgaca      60
tacgtactgt gtcgt                                                      75
```

```
<210> SEQ ID NO 121
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
acgcggagtg aacgctgtat aatccagtgt cgtatgattc gtctatcctg ttcggatgaa      60
ggcacctgcg acgaaggtat gaagcattgc cacgcacatt                          100
```

```
<210> SEQ ID NO 122
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 122
gtctccaatt agaggtccta ccacgacact tattggcgat cgatatagac tggtgacgct    60
gaccggcacc tccagtccgg ctgatcagga ctatcgtgaa gcggttctag ttccgtaact   120
gtgtt                                                               125

<210> SEQ ID NO 123
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
tgctatacgg aacggtctct aggcgaacaa gtgaggaatg tcaacagaga ctaacatcga    60
tattctcctc gtcattactg ttgacgtaat tgctccgatg tcgcgcgcgg tcatgccagc   120
tatactggct aagagttact atccatatac                                    150

<210> SEQ ID NO 124
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
agctgatgga caatatcgcc acctgcgact gctaggcatg ctgctataag cgaggctcct    60
actaagcgct cgctgtactg gtgcggagga ctaggagttc aatacgtgcg ccattaacgg   120
acgtatcgag cagacggaac tgcttggatc accacttcat gttagttctt ggaga        175

<210> SEQ ID NO 125
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
agtcatatta ttatattaat ttaactatca cg                                  32

<210> SEQ ID NO 126
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
agtcacgtta tttcttttgt aaaatacaca cg                                  32

<210> SEQ ID NO 127
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
```
agtctaaagt cctaactctt tgatcacaca cg                                    32

<210> SEQ ID NO 128
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
agtcggttac tttctggaga atccttggca cg                                    32

<210> SEQ ID NO 129
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
agtccttgcc aagaggctcc gtaagcacca cg                                    32

<210> SEQ ID NO 130
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
agtccggctg aggctcggga ccttggctca cg                                    32

<210> SEQ ID NO 131
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
agtcccaccg gctcggggcg gcagcggcca cg                                    32

<210> SEQ ID NO 132
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
agtcttatat attaatacta ttttctttta aagataatca cg                         42

<210> SEQ ID NO 133
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
agtcactata tatatttaga gacgaatatc aagtaaagca cg                42

<210> SEQ ID NO 134
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
agtctacact actcgggctt taaacgaaat tcaacattca cg                42

<210> SEQ ID NO 135
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
agtctggata cgataacggg agcccttatt gacggataca cg                42

<210> SEQ ID NO 136
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
agtctgttta gcggggcggc ccaagagacg tagtcgtaca cg                42

<210> SEQ ID NO 137
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
agtccaggga tccacccgtc aggctgctag ccgccagcca cg                42

<210> SEQ ID NO 138
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
agtccggtgg ctccgcgtgc gggcgcggca ccggccacca cg                42

<210> SEQ ID NO 139
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
agtcaaatat cgatacaaat taaaatattt tactatttta aagattatca cg        52

<210> SEQ ID NO 140
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
agtcatgttt aattactgag aacgttatgt aatatatgtc ctgtaaatca cg                52

<210> SEQ ID NO 141
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
agtcggtgta gttgtgagtt aatctaagga ataccttgt tcctatgtca cg                 52

<210> SEQ ID NO 142
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
agtctaggct gcttggcttc ttctagctca cttggttatc ccgacataca cg                52

<210> SEQ ID NO 143
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
agtctcctag cggtacagct actgtcattc ctcgggccct ctagtcgcca cg                52

<210> SEQ ID NO 144
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
agtcggcgcg ccgttatatg gcagagcggc ggtcgcccgt ctgcggaaca cg                52

<210> SEQ ID NO 145
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
agtcgccaac ggactcgcgc cccggggcgc gccgcgcagc cggctcgtca cg                52

<210> SEQ ID NO 146
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
agtcattaat atattatggt ttattatgaa acgataaaag tatctttgta taaaatttag    60
agtttaaatt acacg                                                    75

<210> SEQ ID NO 147
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
agtcgaaagc ttatttataa gcatactaaa atattaactt cttgattggc atcgaatata    60
tactttcaca acacg                                                    75

<210> SEQ ID NO 148
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
agtcgaaatg aaaaggttta ggatgaatcc ttaaataaat ctaccttagg tcgtgtacta    60
ccgagtggac tcacg                                                    75

<210> SEQ ID NO 149
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
agtcaggagg aaggacaata tagaatgcgc gttatctcct tgtctccaac cggctcaatg    60
cttagttggc ccacg                                                    75

<210> SEQ ID NO 150
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
agtctcgcac ttttgcttcc gctgagatac tcgccgcctg gaccgattga ggtcgggagc    60
ccacctcttg acacg                                                    75

<210> SEQ ID NO 151
<211> LENGTH: 75
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 151
agtctgatag cacgccgccc acgggctcag ccttccaccc ggccgacgtt gccgtacctc    60
tccctgcgga gcacg                                                    75

<210> SEQ ID NO 152
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
agtcggggac tcacccgtgg cctgctgagg gcccgcgcgg cgccccggcc ctctggcgaa    60
ggcggcgagc ccacg                                                    75

<210> SEQ ID NO 153
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gcgttggccg agatgaagac ctcgtgctca cgttaccacg catgagttaa tcagttggca    60
cgaaggtcgg catta                                                    75

<210> SEQ ID NO 154
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gcgccacagc ctgtgctact atggctaaca gcgtatgccg tccggatagt gacctgtccg    60
cgtcggatac ttggc                                                    75

<210> SEQ ID NO 155
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
acgtcggttg ttacatatga cgcaacgctt gattgaaggc gttgtgaatc gcgcagtacc    60
gtgctcgctc agagc                                                    75

<210> SEQ ID NO 156
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
gacaattgaa ttgtggccgc ttacttcgca ctaccgcacg cggcaatgct atgatgtgag    60
aacttgattc ttggc                                                    75

<210> SEQ ID NO 157
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gtaatggaat cctacagaca tgtgtaagta tgctgattga tccgacttac atcagtcagt    60
cagaggccgc catat                                                    75

<210> SEQ ID NO 158
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
cgctagtcct ctcctcggtt ccgaacttcg tcgtcacgag gtggctaacc atggcattag    60
tgctctaagt cctat                                                    75

<210> SEQ ID NO 159
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
ctagatgaag gcaggcgagc aaccggatag atggctccgt accgctgcga ggtattctcc    60
gatatattgt actct                                                    75

<210> SEQ ID NO 160
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
atgtcctgaa ggaatagaga atcactctgc cagcgacaag acggcctggt tcagtagatc    60
tagagatcag aatct                                                    75

<210> SEQ ID NO 161
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tacgagtatg acgattggcg acaacgtggc atctgcttaa ttattatgtc gcctgcgacc    60
acagcacgcg agact 75

<210> SEQ ID NO 162
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
agttgtgact gcagatgcca taacagcacc gaaccatatg tgactgcggt ggcgagcgag    60
ctaatgcttg cgtgg    75

<210> SEQ ID NO 163
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
aactgtaaga agaatattcc ggctgccagc cttgaatgtc tagcgaagcc gaacgcatag    60
aggatgcatg tgcgg    75

<210> SEQ ID NO 164
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
gattccgagg cctagtgcga cagcagctcc gtcaactgat attccactgg cagtccacga    60
atagaggtgg tgaca    75

<210> SEQ ID NO 165
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ttcggtaccg agcacgcata tgaactcgtc gtagatacta gtagatcacc gtaagacctt    60
gctgtgcgcg ccgta    75

<210> SEQ ID NO 166
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
agagcgcact taatgtctct ggaatgttgc gtgaatcgca gcggcgtaag tatgagcaat    60
cgtacctcgg accgt    75

```
<210> SEQ ID NO 167
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
cttaaggtag atcttgtatc atgaatcacc aattatgtat gcatgcggcg cgcacctaag      60
agcctgtgag atgtc                                                      75

<210> SEQ ID NO 168
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
agcgctgtcg gaacacgcaa cggtgtatgt ccactcattg ttccgcagtt gcgaagtaga      60
caggatccta ctaac                                                      75

<210> SEQ ID NO 169
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tcgctcaata cacttggacc agaattatgt cctattcaga accttgccgc gcggcagtcg      60
cgcagatggt cctga                                                      75

<210> SEQ ID NO 170
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ctgttgggcc gccactgcgt gagcctcggc cc                                   32

<210> SEQ ID NO 171
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 171
gacctatttt gacggcaccg ttggcggaag ttgctgggcc tgcgcaccgc gg             52

<210> SEQ ID NO 172
<211> LENGTH: 52
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 172
gcgtcccggc gcgcgtttag ggataacagg gtaatggcgc aagggtgctg gc            52

<210> SEQ ID NO 173
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (30)..(33)
<223> OTHER INFORMATION: Any abasic nucleotide

<400> SEQUENCE: 173
tgcgtcccgg cgcgcgttta gggataacan nnngggtaat ggcgcaaggg tgctggct      58

<210> SEQ ID NO 174
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(29)
<223> OTHER INFORMATION: Any abasic nucleotide

<400> SEQUENCE: 174
tgccagcacc cttgcgccat tacccnnnnt gttatccctc aacgcgcgcc gggacgct      58

<210> SEQ ID NO 175
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(32)
<223> OTHER INFORMATION: Any abasic nucleotide

<400> SEQUENCE: 175
gcgtcccggc gcgcgtttag ggataacann nngggtaatg gcgcaagggt gctggct       57

<210> SEQ ID NO 176
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(29)
<223> OTHER INFORMATION: Any abasic nucleotide

<400> SEQUENCE: 176
tgccagcacc cttgcgccat tacccnnnnt gttatccctc aacgcgcgcc gggacgc       57

<210> SEQ ID NO 177
<211> LENGTH: 56
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(32)
<223> OTHER INFORMATION: Any abasic nucleotide

<400> SEQUENCE: 177
gcgtcccggc gcgcgtttag ggataacann nngggtaatg cgcaagggt gctggc        56

<210> SEQ ID NO 178
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: Any abasic nucleotide

<400> SEQUENCE: 178
gccagcaccc ttgcgccatt acccnnnntg ttatccctaa acgcgcgccg ggacgc        56

<210> SEQ ID NO 179
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: Any abasic nucleotide

<400> SEQUENCE: 179
gcgtcccggc gcgcgtttag ggataacagt ngggtaatgg cgcaagggtg ctggc         55

<210> SEQ ID NO 180
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: Any abasic nucleotide

<400> SEQUENCE: 180
gccagcaccc ttgcgccntt accctactgt tatccctaaa cgcgcgccgg gacgc         55

<210> SEQ ID NO 181
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
cagaagctca tggcctcagt gcagttgcaa ggatgcgcct gcatctcgac tagcaactgt    60
tcatacgtca tggtc                                                    75
```

<210> SEQ ID NO 182
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 182
gacctatttt gacggcaccg ttggcggaag ttgctgggcc tgcgcaccgc gg     52

<210> SEQ ID NO 183
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 183
ccgcggtgcg caggcccagc aacttccgcc aacggtgccg tcaaaatagg tc     52

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 184
gacctatttt gacggcaccg ttgg     24

<210> SEQ ID NO 185
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 185
ttgctgggcc tgcgcaccgc gg     22

<210> SEQ ID NO 186
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 186
cttccgccaa cggtgccgtc aaaataggtc     30

```
<210> SEQ ID NO 187
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
ccgcggtgcg caggcc                                                         16
```